United States Patent [19]

Martel et al.

[11] Patent Number: 5,686,426
[45] Date of Patent: Nov. 11, 1997

[54] DICARBOXYMETHYLATED GLYCOLIPID DERIVATIVES AS CELL ADHESION INHIBITORS

[75] Inventors: Alain Martel, Delson, Canada; John J. Wright, North Guilford, Conn.

[73] Assignee: Bristol-Myers Squibb Company, Princeton, N.J.

[21] Appl. No.: 340,951

[22] Filed: Nov. 17, 1994

[51] Int. Cl.$^6$ .............................. A61K 31/70; C07H 15/04
[52] U.S. Cl. ............................. 514/25; 514/886; 536/17.9
[58] Field of Search ....................... 514/25, 886; 536/17.9

[56] References Cited

U.S. PATENT DOCUMENTS

| | | | |
|---|---|---|---|
| 4,937,328 | 6/1990 | Schmidt et al. | 536/18.6 |
| 4,952,683 | 8/1990 | Tschannen et al. | 536/18.6 |
| 5,211,937 | 5/1993 | Brandley et al. | 424/1.73 |

FOREIGN PATENT DOCUMENTS

| | | |
|---|---|---|
| WO 92/01718 | 2/1992 | WIPO. |
| WO 93/05803 | 4/1993 | WIPO. |
| WO 93/10796 | 6/1993 | WIPO. |

OTHER PUBLICATIONS

Needham et al. *Proc. Natl. Acad. Sci.* 1993, 90, 1359–1363 months not available.
Green et al. *Biochem. Biophys. Res. Commun.* 1992, 188(1), 244–251 months not available.
Springer *Nature* 1990, 346, 425–434 months not available.
Hsu-Lin, S., et al., *J. Biol. Chem.*, 259, 9121–9126 (1984) months not available.
Stenberg, P.E., *J. Cell Biol.*, 101, 880–886 (1985) months not available.
McEver, R.P., et al., *J. Clin. Invest.*, 84, 92–99 (1989) months not available.
Bonfanti, R., et al., *Blood*, 73, 1109–1112 (1989) months not available.
Hattori, R., et al., *J. Biol. Chem.*, 264, 7768–7771 (1989) months not available.
Hattori, R., et al., *J. Biol. Chem.*, 264, 9053–9060 (1989) months not available.
Patel, K.D., et al., *J. Cell Biol.*, 112, 749–759 (1991) months not available.
Larsen, E., et al., *Cell*, 63, 467–474 (1990) months not available.
Erbe, V.E., et al., *J. Cell Biol.*, 119, 215–217 (1992) months not available.
Skinner, M.P., et al., *Biochem. Biophys. Res. Commun.*, 164, 1373–1379 (1989) months not available.
Skinner, M.P., et al., *J. Biol. Chem.*, 266, 5371–5374 (1991) months not available.
Aruffo, A., et al., *Cell*, 67, 35–44 (1991) months not available.
Y. Suzuki, et al., *Biochem. Biophys. Res. Commun.*, 190, 426–434 (1993) months not available.
M.S. Mulligan, et al., *Nature*, 364, 149–151 (1993) months not available.
Radin, N.S., *Handbook of Neurochemistry*, 3, 415–424 (1969) months not available.
Sweeley, C.C., *Pure and Appl. Chem.*, 61(7) 1307–1312 (1989) months not available.

*Primary Examiner*—Kathleen K. Fonda
*Attorney, Agent, or Firm*—Aldo A. Algieri

[57] ABSTRACT

There is provided a novel series of O-carboxymethylated α- and β-glycolipid compounds of the formula

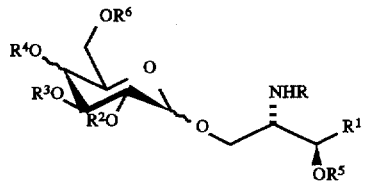

wherein
R is an acyl residue of a fatty acid;
$R^1$ is —(CH=CH)$_m$—(CH$_2$)$_n$—CH$_3$;
$R^2$, $R^3$, $R^4$ $R^5$ and $R^6$ each are independently hydrogen, unsubstituted or substituted alkanoyl, arylalkyl or arylcarbonyl wherein said substituent is selected from halogen, $C_{1-4}$ alkyl, trifluoromethyl, hydroxy and $C_{1-4}$ alkoxy;
$R^3$, $R^4$ and $R^6$ each are independently —CH$_2$COOR$^7$, provided at least two of the $R^3$, $R^4$ and $R^6$ substituents are —CH$_2$COOR$_7$;
m is an integer of 0 or 1;
n is an integer of from 5 to 14, inclusive; and
$R^7$ is hydrogen, a hydrolyzable ester group or a cation to form a non-toxic pharmaceutically acceptable salt;
or a solvate or hydrate thereof which are inhibitors of selectin-mediated cellular adhesion and are useful in the treatment or prevention of inflammatory diseases and other pathological conditions in mammals.

45 Claims, No Drawings

DICARBOXYMETHYLATED GLYCOLIPID DERIVATIVES AS CELL ADHESION INHIBITORS

FIELD OF THE INVENTION

The present invention provides a novel series of O-carboxy-methylated glycolipid compounds, pharmaceutically acceptable salts and pharmaceutical compositions thereof as inhibitors of selectin-mediated cellular adhesion which are useful in the treatment or prevention of inflammatory disease processes and other pathological conditions mediated by the binding of selectins involved in intercellular adhesion.

BACKGROUND OF THE INVENTION

P-selectin (CD62, GMP140, PADGEM) is a membrane glycoprotein of ~140 kDa expressed by activated platelets and vascular endothelial cells. In resting platelets and vascular endothelial cells P-selectin is sequestered in α granules [Hsu-Lin, S., et al., *J. Biol. Chem.*, 259, 9121–9126 (1984); and Stenberg, P. E., *J. Cell Biol.*, 101, 880–886 (1985)] and Weibel-Palade bodies [McEver, R. P., et al., *J. Clin. Invest.*, 84, 92–99 (1989); and Bonfanti, R., et al., *Blood*, 73, 1109–1112 (1989)], respectively. In response to inflammatory mediators such as thrombin [Hsu-Lin, S., et al., *J. Biol. Chem.*, 259, 9121–9126 (1984); and Stenberg, P. E., *J. Cell Biol.*, 101, 880–886 (1985)], histamine [Hattori, R., et al., *J. Biol. Chem.*, 264, 7768–7771 (1989)], complement components [Hattori, R., et al., *J. Biol. Chem.*, 264, 9053–9060 (1989)], or peroxides [Patel, K. D., et al., *J. Cell Biol.*, 112, 749–759 (1991)] and cytokines such as interleukin-1 and tumor necrosis factor, P-selectin is rapidly mobilized from these intracellular stores to the cell surface where it mediates the initial binding interactions of activated platelets with leukocytes and the vascular wall, and of leukocytes with activated vascular endothelial cells. P-selectin is a member of a family of adhesion molecules which includes E-selectin (ELAM-1), which is expressed by activated vascular endothelial cells, and L-selectin (Leu 8, LAM-1, LECAM), which is expressed by leukocytes. These proteins are type I membrane proteins and are composed of an amino terminal lectin domain followed by an epidermal growth factor (EGF) like domain, a variable number of complement receptor related repeats (CR), a hydrophobic membrane spanning region and a cytoplasmic domain. As indicated by high sequence homology, these proteins are not only structurally but also functionally related, modulating the trafficking of peripheral blood leukocyte by permitting adhesive interactions between leukocytes and endothelial cells. These binding interactions are predominantly mediated by contacts between the lectin domain of the selectin and various carbohydrate ligands.

Although it is now widely accepted that a lectin domain/carbohydrate interaction is primarily responsible for mediating P-selectin/myeloid cell binding, the exact molecular nature of the P-selectin ligand is not known. Binding of P-selectin to myeloid cells is $Ca^{2+}$ dependent as well as neuraminidase and protease sensitive. The binding of P-selectin to myeloid cell lines can be inhibited by growing the cells in the presence of sodium selenate and inhibitor of sulfation. P-selectin has been shown to bind to the carbohydrate Le$^x$ (CD15) [Larsen, E., et al., *Cell*, 63, 467–474 (1990)] and its sialylated form, sialyl-Lewis$^x$ (sLe$^x$) [Erbe, V. E., et al., *J. Cell Biol.*, 119, 215–217 (1992)], and there is evidence that these carbohydrates and/or others like them are presented to P-selectin by a discrete number of cell surface proteins including L-selectin. Various anionic polymers, including heparin, fucoidan, and dextran sulfate have also been shown to inhibit P-selectin mediated adhesion [Skinner, M. P., et al., *Biochem. Biophys. Res. Commun.*, 164, 1373–1379 (1989); and *J. Biol. Chem.*, 266, 5371–5374 (1991)]. In addition, P-selectin has been shown to bind 3-sulfated galactosyl ceramides (sulfatides) [Aruffo, A., et al., *Cell*, 67, 35–44 (1991)]. Although the physiological relevance of this interaction remains to be elucidated, it is known that myeloid cells can excrete large quantities of sulfatides on activation. This suggests that sulfatides might participate in leukocyte extravasation at sites of inflammation by displacing the adhesion-mediating leukocyte surface ligand(s), thereby permitting the efficient exit of leukocytes from the blood stream at sites of inflammation.

A number of publications have appeared which describe new agents as inhibitors of cellular adhesion. Some of these publications, but not limited to, include the use of peptides and carbohydrate structures in International patent application WO 92/01718 published Feb. 6, 1992; the use of substituted lactose and lactosamine derivatives in International patent application WO 93/10796 published Jun. 10, 1993; the use of glycoconjugates in International patent application WO 93/05803 published Apr. 1, 1993; the use of sulfated glycolipid derivatives by Y. Suzuki, et al., *Biochem. Biophys. Res. Commun.*, 190, 426–434 (1993) and the use of oligosaccharides by M. S. Mulligan, et al., *Nature*, 364, 149–151 (1993).

However, there am many situations in which the recruitment of leukocytes by adhesion to the endothelial cells is abnormal or in excess, and the end result is tissue damage instead of repair. Thus, there is a need to develop specific and potent compounds which can inhibit the initial cellular adhesion process. It is the object of the present invention to provide new carboxymethylated glycolipids which are inhibitors of cell adhesion and, therefore, useful in man for the treatment and/or prevention of acute or chronic inflammatory diseases such as rheumatoid arthritis, asthma, allergy conditions, psoriasis, septic shock and other indications such as reperfusion injury, adult respiratory distress syndrome, ischemia, ulcerative colitis, vasculitides, atherosclerosis and inflammatory bowel disease, chemical and thermal burn injuries, multiple sclerosis and tumor metastases.

SUMMARY OF THE INVENTION

The present invention provides novel O-carboxymethylated glycolipids having the formula

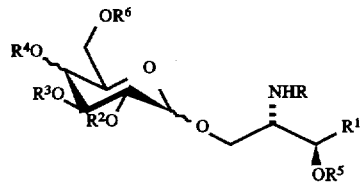

wherein R, $R^1$, $R^2$, $R^3$, $R^4$, $R^5$ and $R^6$ are as defined below, or a solvate or hydrate thereof which are inhibitors of selectin-mediated cellular adhesion. The present invention also provides pharmaceutical compositions comprising said carboxymethylated glycolipids and to the method of treatment or prevention of conditions characterized by selectin-mediated cellular adhesion such as inflammatory diseases and other pathological conditions in mammals.

DESCRIPTION OF THE INVENTION

The present invention provides novel O-carboxymethylated α- and β-glycolipid compounds which are inhibitors of selectin-mediated cellular adhesion and which have the formula

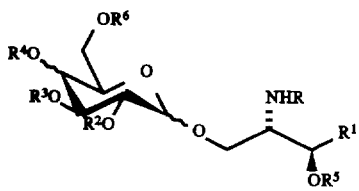

wherein

R is an acyl residue of a fatty acid;

$R^1$ is —$(CH=CH)_m$—$(CH_2)_n$—$CH_3$;

$R^2$, $R^3$, $R^4$ $R^5$ and $R^6$ each are independently hydrogen, unsubstituted or substituted alkanoyl, arylalkyl or arylcarbonyl wherein said substituent is selected from halogen, $C_{1-4}$ alkyl, trifluoromethyl, hydroxy and $C_{1-4}$ alkoxy;

$R^3$, $R^4$ and $R^6$ each are independently —$CH_2COOR^7$, provided at least two of the $R^3$, $R^4$ and $R^6$ substituents are —$CH_2COOR^7$;

m is an integer of 0 or 1;

n is an integer of from 5 to 14, inclusive; and $R^7$ is hydrogen, a hydrolyzable ester group or a cation to form a non-toxic pharmaceutically acceptable salt;

or a solvate or hydrate thereof.

The present invention also provides a method for the treatment or prevention of inflammatory diseases and other pathological conditions characterized by selectin-mediated cellular adhesion, which comprises administering a therapeutically effective amount of a compound of formula I or in combination with a pharmaceutical carrier or diluent.

The terms "$C_{1-4}$ alkyl", "$C_{1-4}$ alkoxy", "(lower) alkyl" and "(lower) alkoxy" as used herein and in the claims (unless the context indicates otherwise) mean straight or branched chain alkyl or alkoxy groups such as methyl, ethyl, propyl, isopropyl, butyl, isobutyl, t-butyl. Preferably, these groups contain from 1 to 2 carbon atoms. The term "arylalkyl" as used herein and in the claims means a phenyl group attached via an alkyl moiety containing from 1 to 4 carbon atoms such as methyl, ethyl, propyl, butyl and the like, and most preferably means benzyl or phenylethyl. Unless otherwise specified, the term "halogen" as used herein and in the claims is intended to include bromine, chlorine, iodine and fluorine while the term "halide" is intended to include bromide, chloride and iodide anion. Preferably, halogen is chlorine or fluorine. The term "alkanoyl" as used herein and in the claims means acetyl, propionyl and the like.

The term "provided at least two of the $R^3$, $R^4$ and $R^6$ substituents are —$CH_2CO_2R^7$" as used herein and in the claims means than a minimum of any two substituents selected from $R^3$, $R^4$ and $R^6$ must be —$CH_2CO_2R^7$ to provide a di-O-carboxymethylated glycolipid. The wavy bond "〜" in the structural formula to which the bond to the anomeric carbon and $R^4O$ is attached as used herein and in the claims means that the bond may be either in the axial or equatorial configuration as occurs in the monosaccharides selected from galactose and glucose.

The term "a cation to form a non-toxic pharmaceutically acceptable salt" as used herein and in the claims is intended to include non-toxic base addition salts with inorganic and organic bases. Suitable inorganic bases such as alkali and alkaline earth metal bases include metallic cations such as sodium, potassium, magnesium, calcium and the like. Suitable organic bases include amines such as ammonium, trialkylamines, pyridine, dibenzylamine, ethanolamine, N-methylglucamine, N-methylpiperidine, N-methylmorpholine, lysine, arginine and other amines which have been used to form salts of carboxylic acids.

Unless otherwise specified, the term "a hydrolyzable ester group" as used herein and in the claims is intended to include an ester group which is physiologically acceptable and hydrolyzable such as $C_{1-6}$ alkyl, benzyl, 4-methoxybenzyl, (lower)-alkanoyloxy(lower)alkyl, e.g., acetoxymethyl, propionyloxymethyl or pivaloyloxymethyl, (lower)alkoxycarbonyloxy(lower)alkyl, e.g., methoxycarbonyloxymethyl or ethoxycarbonyloxymethyl, (lower)-alkoxycarbonyl(lower)alkyl, e.g., methoxycarbonylmethyl or t-butoxycarbonylmethyl, 2-methoxycarbonyloxyethyl, (5-methyl-2-oxo-1,3-dioxol-4-yl)methyl, dihydroxypropyl and the like.

Certain of the compounds of the present invention can exist in unsolvated forms as well as solvated forms including hydrated forms such as monohydrate, dihydrate, hemihydrate, trihydrate, tetrahydrate and the like. The products may be true solvates, while in other cases, the products may merely retain adventitious solvent or be a mixture of solvate plus some adventitious solvent. It should be appreciated by those skilled in the art that solvated forms are equivalent to unsolvated forms and are intended to be encompassed within the scope of the present invention.

The compounds of the present invention contain a monosaccharide selected from galactose and glucose. The natural occurring sulfatides from brain tissue are part of a class of compounds known as sulfated cerebrosides [N. S. Radin *Handbook of Neurochemistry*, Vol. 3 415–424 (1969)]. The commercially available sulfatides are a mixture of compounds in which the hexose moiety is mainly galactose and the configuration of the hexose in the natural sulfatides is in the β-anomeric form. [C. C. Sweeley, *Pure and Appl. Chem.*, 61 (7) 1307–1312 (1989)].

In the method of the present invention, the term "therapeutically effective amount" means the total amount of each active component of the method that is sufficient to show a meaningful patient benefit, i.e., healing of chronic conditions characterized by selectin-mediated cellular adhesion or increase in the rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases, tissue damage and/or symptoms associated with selectin-mediated cellular adhesion.

The term "acyl residue of a fatty acid" as used herein and in the claims means the acyl residue of a naturally occurring saturated or unsaturated fatty acid or a fatty acid derived therefrom such as 9-methoxycarbonyl nonanoic acid. Suitable saturated fatty acids are those described herein and other known fatty acids such as butyric, isovaleric, caproic, caprylic, capric, lauric, myristic, palmitic, stearic, arachidic, behenic, lignoceric, cerotic and the like. Suitable unsaturated fatty acids include the cis and trans isomers of fatty acids such as $\Delta^9$-decylenic, stillingic, $\Delta^9$-dodecylenic, palmitoleic, oleic, ricinoleic, petroselinic, vaccenic, linoleic, linolenic, eleostearic, punicic, licanic, parinaric, gadoleic, arachidonic, 5-eicosenic, 5-docosenic, cetoleic, erucic, 5,13-docosadienic, nervonic and the like.

Hydroxy-protecting groups which can be employed in the present invention to block or protect the hydroxyl group are well-known to those skilled in the art and, preferably, said groups can be removed, if desired, by methods which do not result in any appreciable destruction of the remaining portion of the molecule, for example, by chemical or enzymatic hydrolysis, treatment with chemical reducing agents under mild conditions, irradiation with ultraviolet light or catalytic hydrogenation. Hydroxy-protecting (blocking) groups which are advantageously used are those which are common in carbohydrate chemistry especially for primary alcohols, secondary alcohols and vicinal cis and trans diols.

Suitable hydroxy-protecting groups may be, for example, acyl groups such as acetyl, trichloroacetyl, phenoxycarbonyl, benzyloxycarbonyl, benzhydryloxycarbonyl, trityloxycarbonyl and 2,2,2-trichloroethoxycarbonyl, ether groups such as methoxymethyl, benzyloxymethyl, allyl, benzyl, p-methoxybenzyl, p-nitrobenzyl, benzhydryl, trityl or triorganosilyl groups such as tri($C_1$-$C_6$) alkylsilyl (e.g., trimethylsilyl, triethylsilyl, triisopropylsilyl, isopropyldimethylsilyl, t-butydimethylsilyl, methyldiisopropylsilyl or methyldi-t-butylsilyl), t-butyl-diphenylsilyl, triarylsilyl (e.g. triphenylsilyl, tri-p-xylylsilyl) or triaralkylsilyl (e.g. tribenzylsilyl). Examples of these and other suitable hydroxy-protecting groups and methods for their formation and removal are known in the art, e.g., see *Protective Groups in Organic Synthesis*, second ed., T. W. Greene and P. G. M. Wuts, John Wiley & Sons, New York, 1991, Chapter 2 and references therein.

The compounds of Formula I may be prepared by various procedures such as those illustrated herein in the examples, in the Reaction Schemes 5, 6 and 7 and variations thereof which would be evident to those skilled in the art. The various O-carboxymethyl substituted glycolipids of Formula I wherein the carbohydrate moiety is galactose and glucose are advantageously prepared from the intermediates of Formula Va, Vb, Vc, Vd, Ve or Vf which are prepared by various procedures such as those illustrated in Reaction Schemes 2, 3 and 4 and the azido alcohol of Formula III illustrated in Reaction Scheme I.

The preparation of a generic azido diol lipid of Formula II (occasionally referred to as azidosphingosine) wherein $R^1$ is as previously defined is illustrated in the process shown in Reaction Scheme 1. Thus, 2,4-O-benzylidene-D-threose is advantageously reacted with the desired phosphonium salt in a Wittig reaction by the general procedures described by P. Zimmerman, et al., *Liebigs Ann. Chem.*, 663–667 (1988) to produce the desired trans olefin wherein n=5–14. The olefin moiety may be retained in the process to provide compounds of Formula I wherein m=1 in the definition of $R^1$ or, if desired, the olefin may be reduced by conventional hydrogenation procedures to eventually provide compounds of Formula I wherein m=0 in the definition of $R^1$. The hydroxy function of the intermediate is treated with triflic anhydride and sodium azide to produce the cyclic azido intermediate with inversion of configuration followed by acid treatment to remove the benzylidene blocking group to produce the desired azido diol intermediate of Formula II wherein $R^1$ is —(CH=CH)$_m$—(CH$_2$)$_n$—CH$_3$. It is advantageous in the present process to block (protect) the secondary alcohol or allylic alcohol as the case may be in the compound of Formula Ii by first readily blocking the primary alcohol by conventional blocking (protecting) groups with an organosilyl group such as t-butyldimethylsilyl followed by the reaction with the desired $R^5$ substituent, as previously defined and wherein X is a conventional leaving group well-known in the art such as chloro, bromo, iodo, fluorosulfonyl and the like. After the displacement is completed, the silyl blocking group may readily be removed such as with tetrabutylammonium fluoride to give the desired compound of Formula III which is now suitable for use in the coupling reaction with a carbohydrate moiety, as illustrated in Reaction Schemes 5, 6 and 7.

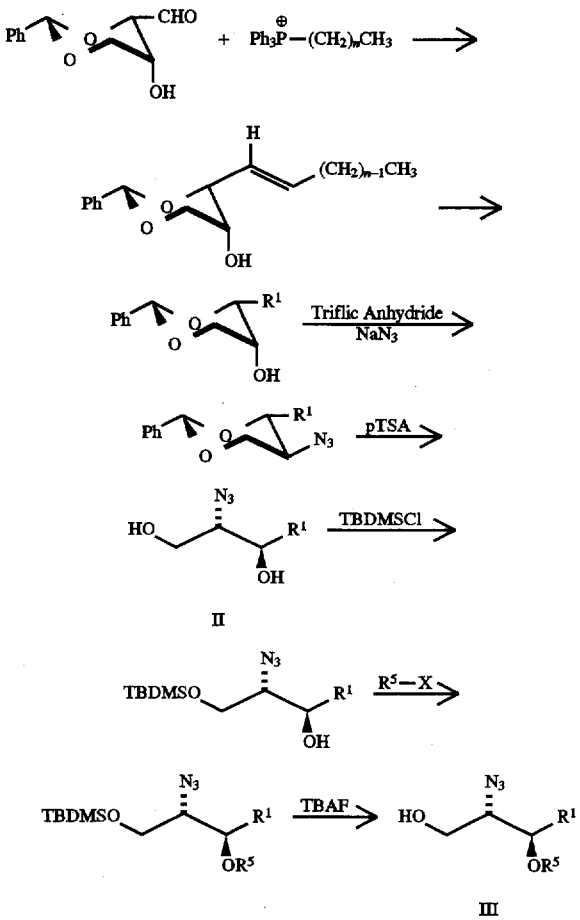

There are various processes which am useful for the preparation of the pyranoside compounds of Formula Va, Vc and Ve having the galactose configuration and compounds of Formula Vb, Vd and Vf having the glucose configuration. It should be appreciated by those skilled in the art that selective blocking and deblocking of carbohydrates which are used to prepare the various positional carboxymethylated isomers are well-known in the art such as those illustrated herein and in *Protective Groups* in *Organic Synthesis*, second ed., T. W. Greene and P. G. M. Wuts, John Wiley & Sons, New York, 1991, Chapter 2 and references therein. It Should further be appreciated by those skilled in the art that the specific blocking group to be used will vary with the axial or equatorial position of the hydroxyl groups in the preferred carbohydrate moiety of the instant invention. Thus, Reaction Schemes 2, 3 and 4 exemplify the preparation of 4,6-dicarboxymethylated galacto- and glucopyranosides of Formula Va and Vb, respectively, the 3,4-dicarboxymethylated galacto- and glucopyranosides of Formula Vc and Vd, respectively, and the 3,6-dicarboxymethylated galacto- and glucopyranosides of Formula Ve and Vf, respectively. Some of the processes for the preparation of compounds of Formula Va to Vf are exemplified in the examples described herein, some are illustrated in the Reaction Schemes and other processes will be evident to those skilled in the art.

The process for the preparation of O-carboxymethylated α- and β-glycolipids of Formula I are conveniently illustrated and summarized in Reaction Schemes 5, 6 and 7. When it is desired to prepare a dicarboxymethylated glycolipid of Formula I, the possible combinations of the instant invention are set forth in Reaction Schemes 5, 6 and 7. The sequence in Reaction Scheme 5 exemplifies the preparation of both the α-anomers of Formula Ia and Ib and the β-anomers of Formula Ic and Id of 4,6-dicarboxymethylated glycolipids of galacto- and glucopyranosides of Formula I, respectively from the corresponding pyranoside intermediates of Formula Va and Vb. The reaction sequence in Reaction Schemes 6 exemplifies the preparation of both the α-anomers of Formula Ie and If and the β-anomers of Formula Ig and Ih of 3,4-dicarboxymethylated glycolipids of galacto- and glucopyranosides of Formula I, respectively from the corresponding pyranoside intermediates of Formula Vc and Vd. The process in Reaction Scheme 7 exemplifies the preparation of both the α-anomers of Formula Ii and Ij and the β-anomers of Formula Ik and Il of 3,6-dicarboxymethylated glycolipids of galacto- and glucopyranosides of Formula I, respectively from the corresponding pyranoside intermediates of Formula Ve and Vf.

In the process for the preparation of carboxymethylated α- and β-glycolipids of Formula I several known procedures are contemplated which generally follow the sequence of reaction steps as illustrated in Reaction Schemes 2, 3, 4, 5, 6 and 7. Each reaction step is generally well-known to those skilled in the art and, advantageously, the appropriate use of protecting (blocking) groups are used when necessary to effect the desired results. In the compounds of Formula I, the $R^2$, $R^3$, $R^4$, $R^5$ and $R^6$ substituents may also be changed by standard well-known procedures to achieve a different but desirable modification of the compounds of Formula I. This is conveniently illustrated in the reaction scheme by the double arrows indicating that the chemical structures may be interchanged by well-known hydrolysis and esterification or etherification procedures. It should be understood by those skilled in the art that the selection and therefore the result will depend on the nature, number and position of the substituents. It should also be understood that the illustration in the schemes is not intended to be limiting since slight modifications are often deemed desirable or necessary to achieve a particular result.

As used herein and in the reaction schemes the term "reduction" is intended to include well-known reduction procedures for the azido group such as reducing metals, i.e., activated zinc; hydrogenolysis with hydrogen and palladium; hydrogen transfer reactions with cyclohexane/formic acid/palladium; and preferably with hydrogen sulfide in aqueous pyridine.

As used herein and in the reaction schemes the term "acylation" is intended to include conventional and well-known acylation procedures for the preparation of amides such as the use of leaving groups and activating groups on the acyl portion of the fatty acid. For example, the use of acid chlorides and carbodiimide as activating groups in an organic solvent such as tetrahydrofuran, dichloromethane or mixture of aqueous-organic solvents in the presence of a base such as triethylamine, pyridine, dimethylaminopyridine and 50% sodium acetate.

As used herein and in the reaction schemes the term "alkylation" is intended to include conventional and well-known alkylation procedures. Thus, in one method, the desired hydroxy groups which are to be alkylated are treated with an alkylating agent such as an ester of bromoacetate [P. Westerduin, et al, *Carbohydrate Research*, 234, 131–140, (1992)], i.e., t-butyl ester or any other suitable carboxy-protecting group in the presence of an organic or inorganic base such as sodium hydride, potassium hydride, lithium diisopropylamine or lithium bis(trimethylsilyl)amide in an inert organic solvent such as dimethylformamide, hexamethylphosphoramide, dimethylsulfoxide, N-methylpyrolidinone and the like. In a second method, the alkylation may be carried out under phase transfer catalysis conditions [T. H. Keller, et al, *Helvica Chim. Acta*, 76, 884 (1993)]. This method is well-known to those skilled in the art and the alkylation reaction proceeds at the interface of the aqueous solution and the immisible solvent such as methylene chloride, diethyl ether, diisopropyl ether, and other similar water-immisible solvents. The alkylation reaction proceeds with the addition of a phase-transfer catalyst which are well-known and are readily available from commercial sources such as tetraorganoammonium salts, i.e., tetrabutylammonium chloride, tetrabutylammonium bromide, and tributylbenzylammonium chloride. Advantageously, an excess of alkylating agent is utilized in the two methods described above to carboxymethylate the desired hydroxy groups while the hydroxy groups to be retained are blocked (protected).

As used herein and in the reaction schemes the terms "blocking" and "protecting" are intended to include conventional and well-known protecting groups in the art such as those illustrated herein and in *Protective Groups In Organic Synthesis*, second ed., T. W. Greene and P. G. M. Wuts, John Wiley and Sons, New York, 1991, Chapter 2 and references therein. For example, the use of acetals and ketals with an acid catalyst; the use of trisubstituted organosilyl reagents such as tert-butyldimethylsilyl chloride and triethylsilyl chloride; methoxymethyl bromide; benzyl bromide; benzoyl chloride and the like. The reaction may be carried out in tetrahydrofuran, dichloromethane, dimethyl formamide and the like in the presence of a base such as triethylamine, dimethylaminopyridine, pyridine, sodium hydride and the like, and optionally with imidazole or 4-dimethylaminopyridine as a catalyst.

As used herein and in the reaction schemes, the term "hydrolysis" is intended to include conventional hydrolysis procedures well-known to those skilled in the art. For example, the hydrolysis of benzylidene, isopropylidene, p-methoxybenzyl (PMB), methoxymethyl (MOM) and the like may be carried out under acidic conditions such as 90% trifluoroacetic acid, 3N hydrochloric acid, p-toluene sulfonic acid and the like in solvents such as dichloromethane and tetrahydrofuran. Also, p-methoxybenzyl may be removed with the use of dichlorodihydroxyquinone. Furthermore, organosilyl blocking groups such as tert-butyldimethylsilyl and triethylsilyl may advantageously be removed by the use of tetrabutylammonium fluoride (TBAF) in tetrahydrofuran and acetic acid. Still further, benzoate and acetate blocking groups may also be removed by the use of sodium or potassium alkoxides.

The preparation of the 4,6-dicarboxymethylated intermediates of the galactopyranoside of Formula Va or the glucopyranoside of Formula Vb is advantageously carried out from the corresponding ethyl 1-thio-β-galacto- or β-glucopyranoside as shown in Reaction Scheme 2. When it is desired to prepare the 4,6-dicarboxymethylated galactopyranoside of Formula Va, the corresponding ethy 1-thio-β-galactopyranoside of Formula IVa is selectively treated with two different blocking groups. It is advantageous to first block the 4- and 6-hydroxy groups with benzaldehyde or benzaldehyde dimethylacetal and the partially blocked intermediate is then selectively blocked with a different blocking group such as p-methoxybenzyl. The fully protected pyranoside compound is subjected to conventional hydrolysis to remove the benzylidene blocking group. The resulting unblocked 4- and 6-hydroxy groups are then alkylated and preferably with t-butyl ester of bromoacetate under conditions described herein to produce the 4,6-dicarboxymethylated galactopyranoside of Formula Va. It should be appreciated by those skilled in the art that by following the general synthetic steps outlined above the 4,6-dicarboxymethylated glucopyranosides of Formula Vb may be produced from the corresponding compound of Formula IVb.

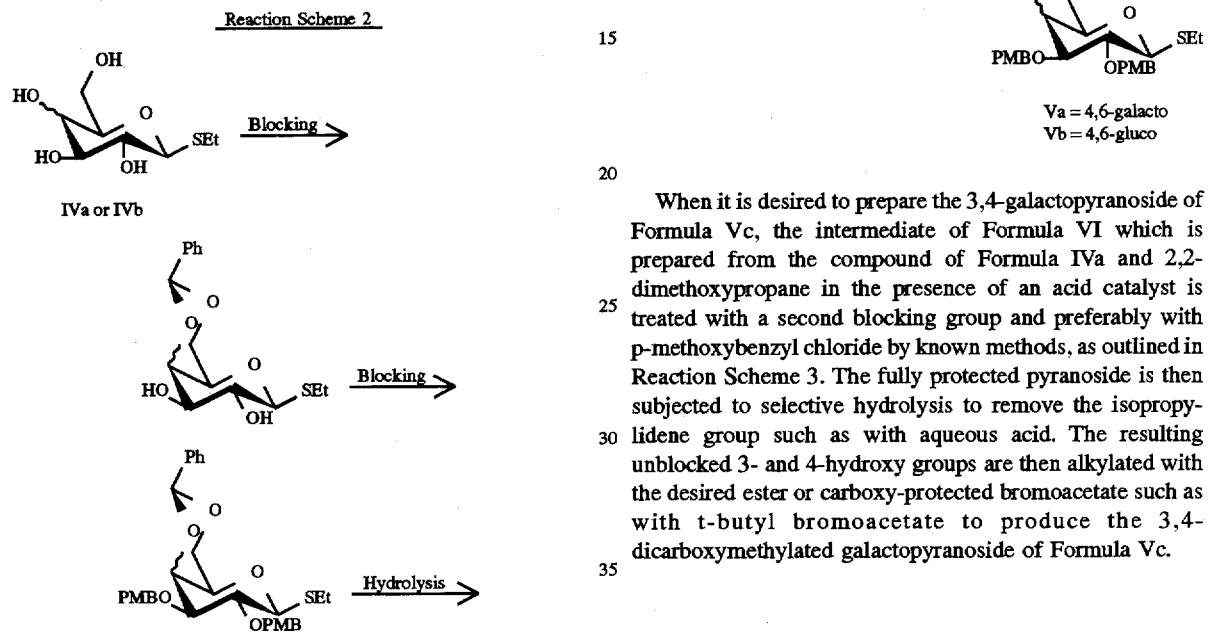

When it is desired to prepare the 3,4-galactopyranoside of Formula Vc, the intermediate of Formula VI which is prepared from the compound of Formula IVa and 2,2-dimethoxypropane in the presence of an acid catalyst is treated with a second blocking group and preferably with p-methoxybenzyl chloride by known methods, as outlined in Reaction Scheme 3. The fully protected pyranoside is then subjected to selective hydrolysis to remove the isopropylidene group such as with aqueous acid. The resulting unblocked 3- and 4-hydroxy groups are then alkylated with the desired ester or carboxy-protected bromoacetate such as with t-butyl bromoacetate to produce the 3,4-dicarboxymethylated galactopyranoside of Formula Vc.

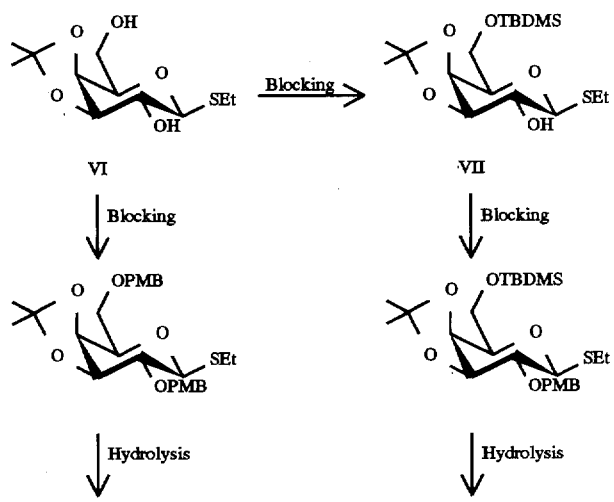

-continued
Reaction Scheme 3

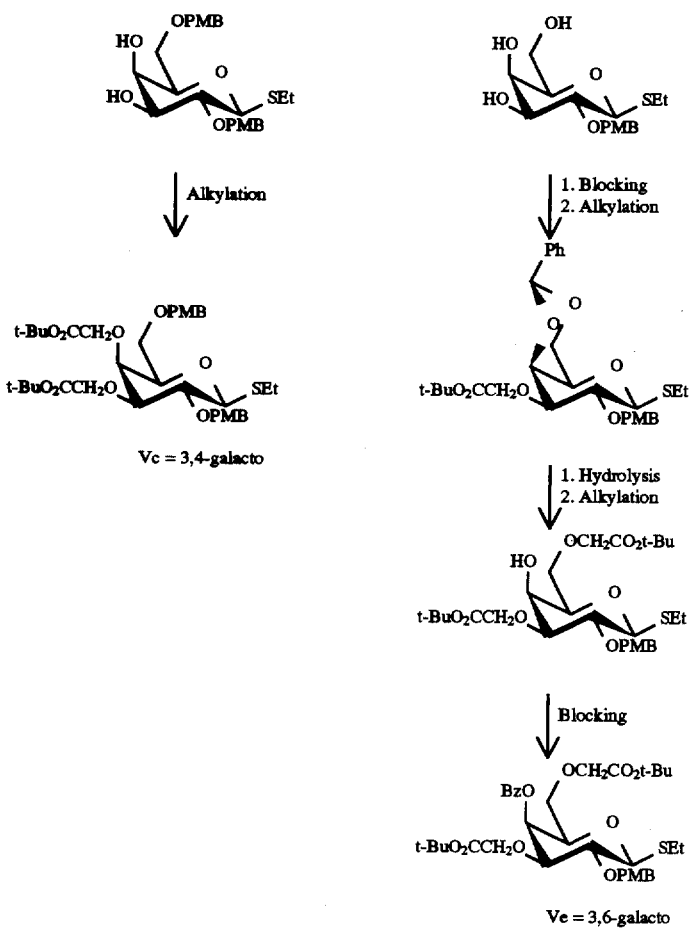

When it is desired to prepare the 3,6-galactopyranoside of Formula Ve, as outlined in Reaction Scheme 3, the intermediate of Formula VI is selectively treated with two different blocking groups. It is advantageous to first block the primary alcohol in the 6-position with a triorganosilyl group such as tri ($C_1$–$C_6$) alkylsilyl and triarylsilyl, and preferably with t-butyldimethylsilyl group. The remaining secondary hydroxy group may then be advantageously blocked with other conventional groups and, preferably with a p-methoxybenzyl group. The resulting fully protected pyranoside is selectively hydrolyzed to remove both the isopropylidene and the t-butyldimethylsilyl protecting groups and then treated with new blocking groups and advantageously with benzaldehyde dimethylacetal to temporarily block the 4- and 6-hydroxy groups. The 3-hydroxy group is advantageously alkylated with t-butyl bromoacetate and then selectively hydrolyzed to remove the benzylidene group. The primary 6-hydroxy group is first alkylated with the desired ester of bromoacetate and then the remaining 4-hydroxy group is treated with a blocking group and preferably with a benzoyl moiety by known methods to produce the 3,6-dicarboxymethylated galactopyranoside of Formula Ve.

The preparation of 3,6- and 3,4-dicarboxymethylated glucopyranosides of Formula Vf and Vd, respectively may be carried out from the compound of Formula IVb following the reaction sequences outlined in Reaction Scheme 4. To elaborate on the processes of Reaction Scheme 4, the ethyl 1-thio-β-D-glucopyranoside of Formula IVb is treated with a blocking group and advantageously with benzaldehyde dimethylacetal to block the 4- and 6-hydroxy groups. The partially blocked intermediate is then selectively blocked with a different protecting group and preferably with p-methoxybenzyl group by well-known methods to give the compound of Formula VIII.

Reaction Scheme 4

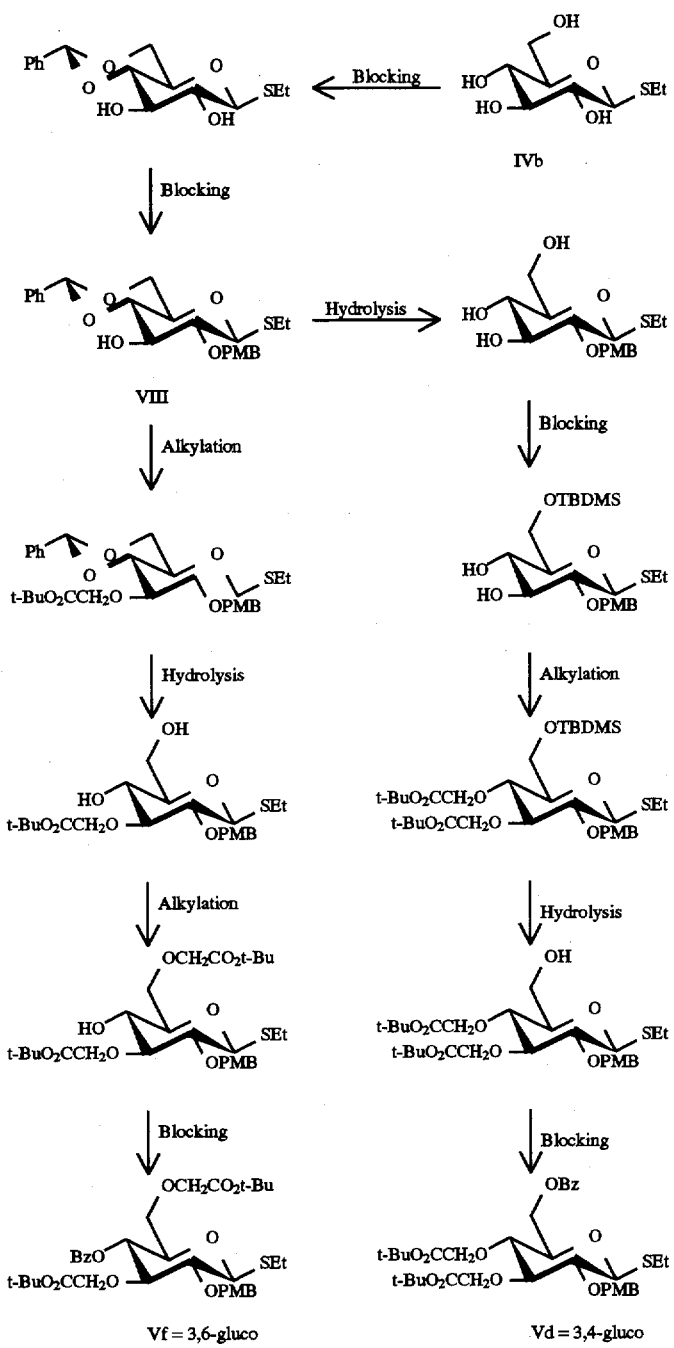

To prepare the 3,6-dicarboxymethylated glucopyranoside of Formula Vf, the intermediate of Formula VIII is alkylated with an ester of bromoacetate and preferably with t-butyl bromoacetate and then hydrolyzed to remove the benzylidene group. The resulting 4,6-dihydroxy compound is selectively alkylated in the primary 6-hydroxy group as described previously and then the remaining 4-hydroxy group is treated with a blocking group and preferably with a benzoyl moiety by known methods to produce the 3,6-dicarboxymethylated glucopyranoside of Formula Vf.

To prepare the 3,4-dicarboxymethylated glucopyranoside of Formula Vd, the intermediate of Formula VIII is selectively hydrolyzed to remove the benzylidene group. It is advantageous to block the primary 6-alcohol group with a triorganosilyl group such as with a t-butyldimethylsilyl group. The secondary 3- and 4-hydroxy groups may now be alkylated and preferably with t-butyl bromoacetate. The 6-position silyl protecting group is removed by standard procedures such as with tetrabutylammonium fluoride and then treated with another blocking group and preferably with a benzoyl moiety by known methods to produce the 3,4-dicarboxymethylated glucopyranoside of Formula Vd.

In the process for the preparation of O-carboxymethylated α- and β-glycolipids of Formula I several known procedures are contemplated which generally follow the sequence of reaction steps as illustrated in Reaction Schemes 5, 6 and 7.

Each reaction step is generally well-known to those skilled in the art and, advantageously, the appropriate use of protecting (blocking) groups are used when necessary to effect the desired results. In the compounds of Formula I, the $R^2$, $R^3$, $R^4$, $R^5$ and $R^6$ substituents may also be changed by standard well-known procedures to achieve a different but desirable modification of the compounds of Formula I. This is conveniently illustrated in the reaction schemes by the double arrows indicating that the chemical structures may be interchanged by well-known hydrolysis and esterification or etherification procedures. It should be understood by those skilled in the art that the selection and therefore the result will depend on the nature, number and position of the substituents. It should also be understood that the illustration in the schemes is not intended to be limiting since slight modifications are often deemed desirable or necessary to achieve a particular result.

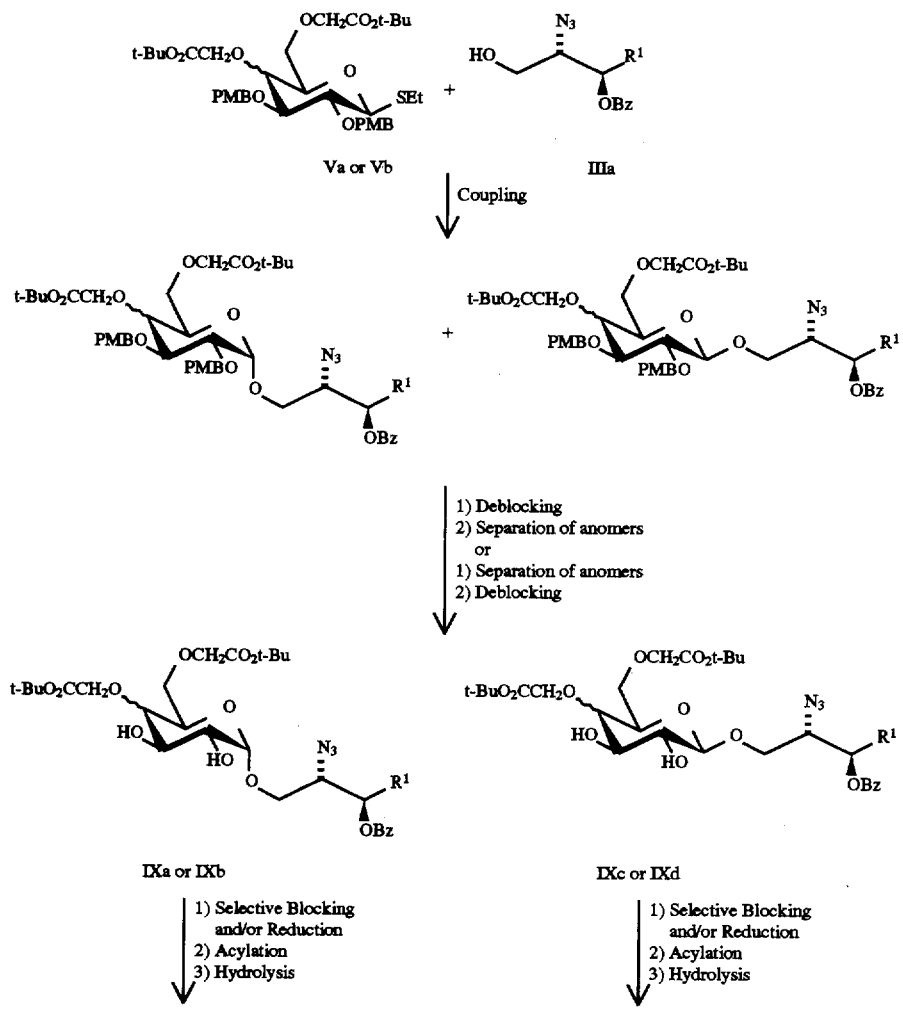

-continued
Reaction Scheme 5

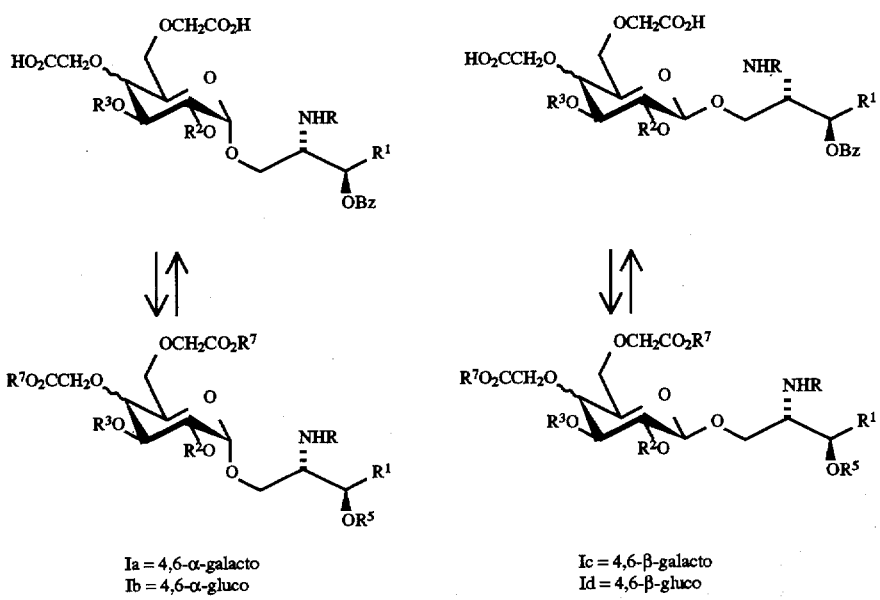

Ia = 4,6-α-galacto
Ib = 4,6-α-gluco

Ic = 4,6-β-galacto
Id = 4,6-β-gluco

When it is desired to prepare the 4,6-dicarboxymethylated α- and β-anomer compounds of Formula Ia and Ic, respectively, the fully protected galactopyranoside of Formula Va is reacted with the azido alcohol of Formula IIIa under well-known coupling procedures as shown in Reaction Scheme 5. Procedures which may be used are described by H. Paulsen, *Angew. Chem. Int. Ed. Engl.*, 21, 155–173 (1982) and K. Toshima et al, *Chem. Rev.*, 93 1503–1531 (1993). Preferably, dimethyl(methylthio) sulfonium triflate is used in the coupling procedure in an inert organic solvent in the presence of an organic base. Inert organic solvents, such as dioxane, dimethylformamide, methylene chloride, benzene, or mixtures thereof may be used in the coupling reaction and the selection of solvent will depend on the desired ratio of anomeric products to be produced. It should be understood that the selection of solvents for the reaction will influence whether an α-anomeric or a β-anomeric product is obtained as described in the above references and illustrated in the examples herein. It should also be understood by those skilled in the art that if the β-anomer is preferred then it is advantageous to have a participating blocking group in the 2-position of the compounds of Formula Va to Ve. It is well known that protecting groups such as the benzoyl group participate in the coupling procedure and thus lead to mostly β-anomeric products. However, it is also well-known that an α-anomeric product is desired, then no participating blocking group should be utilized in the 2-position. Thus, the choice of blocking group to be used is dependent on the anomeric product which is desired. In a preferred embodiment, the azido alcohol of Formula IIIa wherein $R^5$ is benzoyl is illustrated in Reaction Scheme 5 and in subsequent Reaction Schemes 6 and 7. The use of $R^5$ being benzoyl is for illustration purposes only and is not intended to be limiting. The resulting azido glycolipid from the reaction of the pyranoside of Formula Va and the alcohol of Formula IIIa is a mixture of α- and β-anomers of the desired azido glycolipid compound. It should be appreciated by those skilled in the art that the mixture of anomers produced in the coupling reaction can be readily separated by methods such as fractional crystallization and preferably, chromatography as described herein. It should further be appreciated by those skilled in the art that the separation may be carried out at this step while the glycolipid compound is fully protected (blocked) or, if desired, after the blocking groups on the 2- and 3-hydroxy groups have been removed, i.e., with 2,3-dichloro-5,6-dicyano-1,4-benzoquinone when the blocking group is p-methoxybenzyl. It should be understood by those skilled in the art that if the separation is not complete at this step, then the separation can be completed in the next step. The choice of when the separation of anomers is carried out is dependent on the nature of the substituents, the ratio of anomers and the ease of separation based on the relative differences between the anomers and the desired anomer.

To prepare the 4,6-dicarboxymethylated α-galacto type glycolipids of Formula Ia, the corresponding separated α-anomer of the azido glycolipid of Formula IXa is subjected to reduction of the azido group followed by acylation of the resulting amino group with the desired activated acyl residue of a fatty acid having the definitions of R as defined herein. The resulting glycolipid is subjected, if desired, to conventional hydrolysis of the carboxylic acid ester to produce the carboxylic acid of the compound of Formula Ia or a non-toxic pharmaceutically acceptable salt thereof. It should be appreciated by those skilled in the art that the removal and insertion of the desired $R^2$, $R^3$, $R^5$ and $R^7$ moieties in the compound of Formula Ia can be interchanged, or left untouched depending on the particular substituent which is desired in the preparation of compounds having the carboxymethylated moiety in the 4- and 6-position of the α-galacto type glycolipids of Formula Ia.

Similarly, to prepare the 4,6-dicarboxymethylated β-galacto type glycolipids of Formula Ic, the corresponding separated β-anomer of the azido glycolipid of Formula IXc is subjected to selective blocking and/or reduction followed by acylation of the resulting amino group and, if desired, hydrolysis of the carboxylic ester group. The substituents may then be interchanged or converted to the desired compounds of Formula Ic having the carboxymethylated moiety in the 4- and 6-position of the β-galacto type glycolipids of Formula Ic.

It should be understood that by following the general sequence steps outlined above and in Reaction Scheme 5 starting from the glucopyranoside of the Formula Vb, the 4,6-dicarboxymethylated gluco type glycolipids of Formula Ib and Id may be prepared from the corresponding α-gluco compound of Formula IXb and β-gluco compound of Formula IXd, respectively.
Reaction Scheme 6
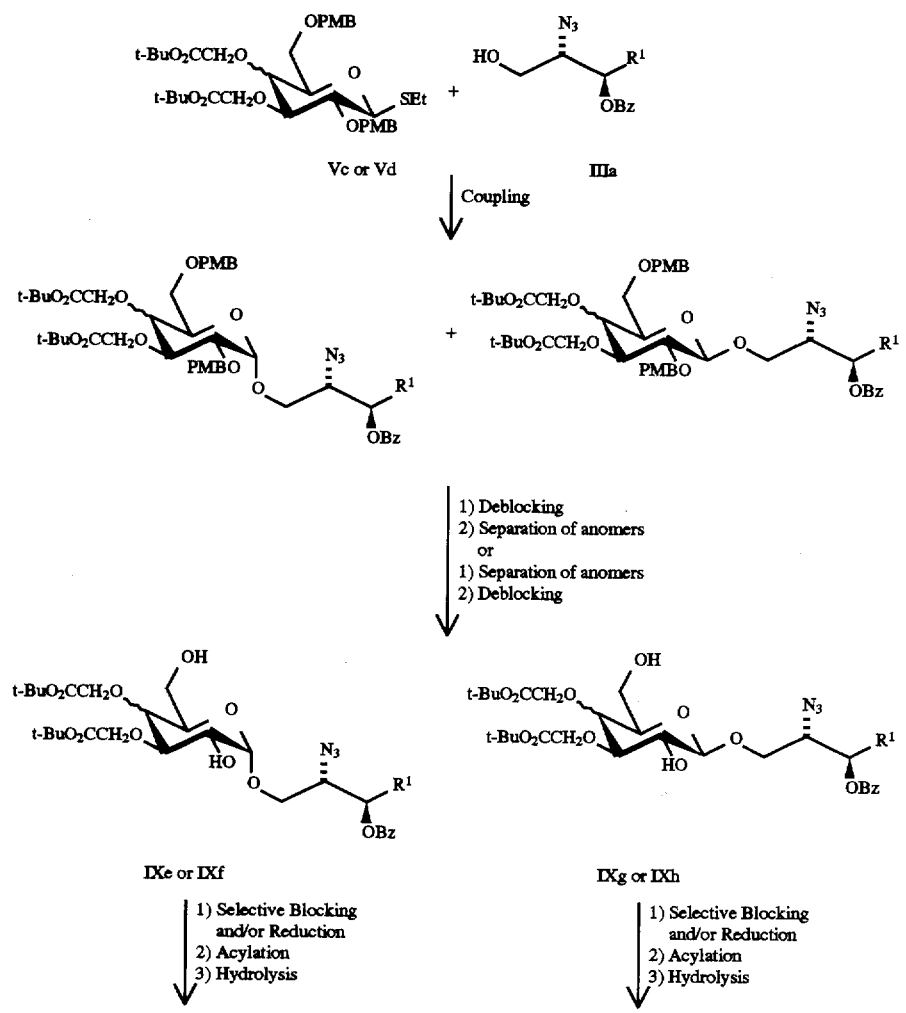

-continued
Reaction Scheme 6

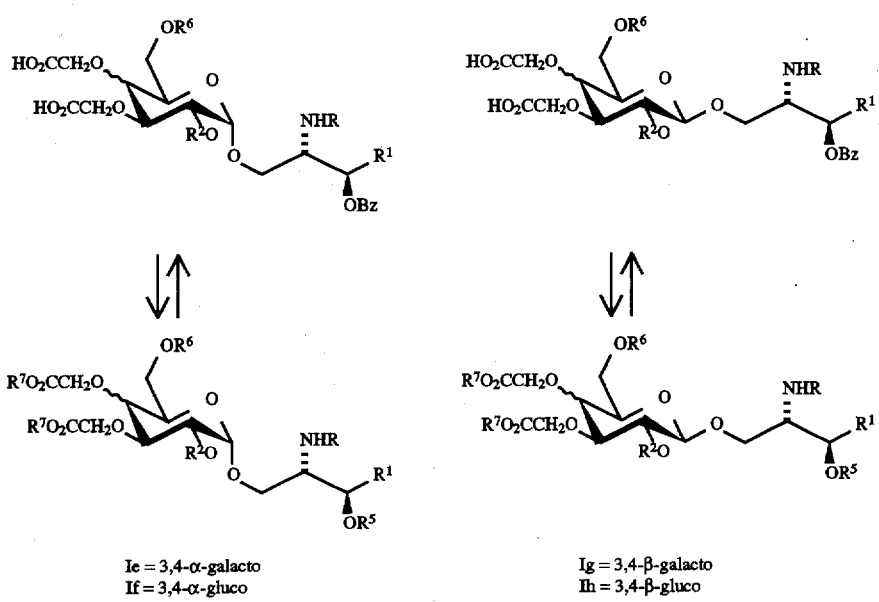

Ie = 3,4-α-galacto
If = 3,4-α-gluco

Ig = 3,4-β-galacto
Ih = 3,4-β-gluco

When it is desired to prepare the 3,4-dicarboxymethylated α- and β-anomer compounds of Formula Ie and Ig, respectively, the fully protected galactopyranoside of Formula Vc is reacted with the azido alcohol of Formula IIIa under well-known coupling procedures as shown in Reaction Scheme 6 and as previously described. The resulting azido glycolipid from the reaction of the pyranoside of Formula Vc and the alcohol of Formula IIIa is a mixture of α- and β-anomers of the desired azido glycolipid compound. It should be appreciated by those skilled in the art that the mixture of anomers produced in the coupling reaction can be readily separated by methods such as fractional crystallization and preferably, chromatography as described herein. It should further be appreciated by those skilled in the art that the separation may be carried out at this step while the glycolipid compound is fully protected (blocked) or, if desired, after the blocking groups on the 2- and 6-hydroxy groups have been removed, i.e., with 2,3-dichloro-5,6-dicyano-1,4-benzoquinone when the blocking group is p-methoxybenzyl. It should be understood by those skilled in the art that if the separation is not complete at this step, then the separation can be completed in the next step. The choice of when the separation of anomers is carried out is dependent on the nature of the substituents, the ratio of anomers and the ease of separation based on the relative differences between the anomers and the desired anomer.

To prepare the 3,4-dicarboxymethylated α-galacto type glycolipids of Formula Ie, the corresponding separated α-anomer of the azido glycolipid of Formula IXe is subjected to reduction of the azido group followed by acylation of the resulting amino group with the desired activated acyl residue of a fatty acid having the definitions of R as defined herein. The resulting glycolipid is subjected, if desired, to conventional hydrolysis of the carboxylic acid ester to produce the carboxylic acid of the compound of Formula Ie or a non-toxic pharmaceutically acceptable salt thereof. It should be appreciated by those skilled in the art that the removal and insertion of the desired $R^2$, $R^5$, $R^6$ and $R^7$ moieties in the compound of Formula Ie can be interchanged, or left untouched depending on the particular substituent which is desired in the preparation of compounds having the carboxymethylated moiety in the 3- and 4-position of the α-galacto type glycolipids of Formula Ie.

Similarly, to prepare the 3,4-dicarboxymethylated β-galacto type glycolipids of Formula Ig, the corresponding separated β-anomer of the azido glycolipid of Formula IXg is subjected to selective blocking and/or reduction followed by acylation of the resulting amino group and, if desired, hydrolysis of the carboxylic ester group. The substituents may then be interchanged or converted to the desired compounds of Formula Ig having the carboxymethylated moiety in the 3- and 4-position of the β-galacto type glycolipids of Formula Ig.

It should be understood that by following the general sequence steps outlined above and in Reaction Scheme 6 starting from the glucopyranoside of the Formula Vd, the 3,4-dicarboxymethylated gluco type glycolipids of Formula If and Ih may be prepared from the corresponding α-gluco compound of Formula IXf and β-gluco compound of Formula IXh, respectively.

Reaction Scheme 7

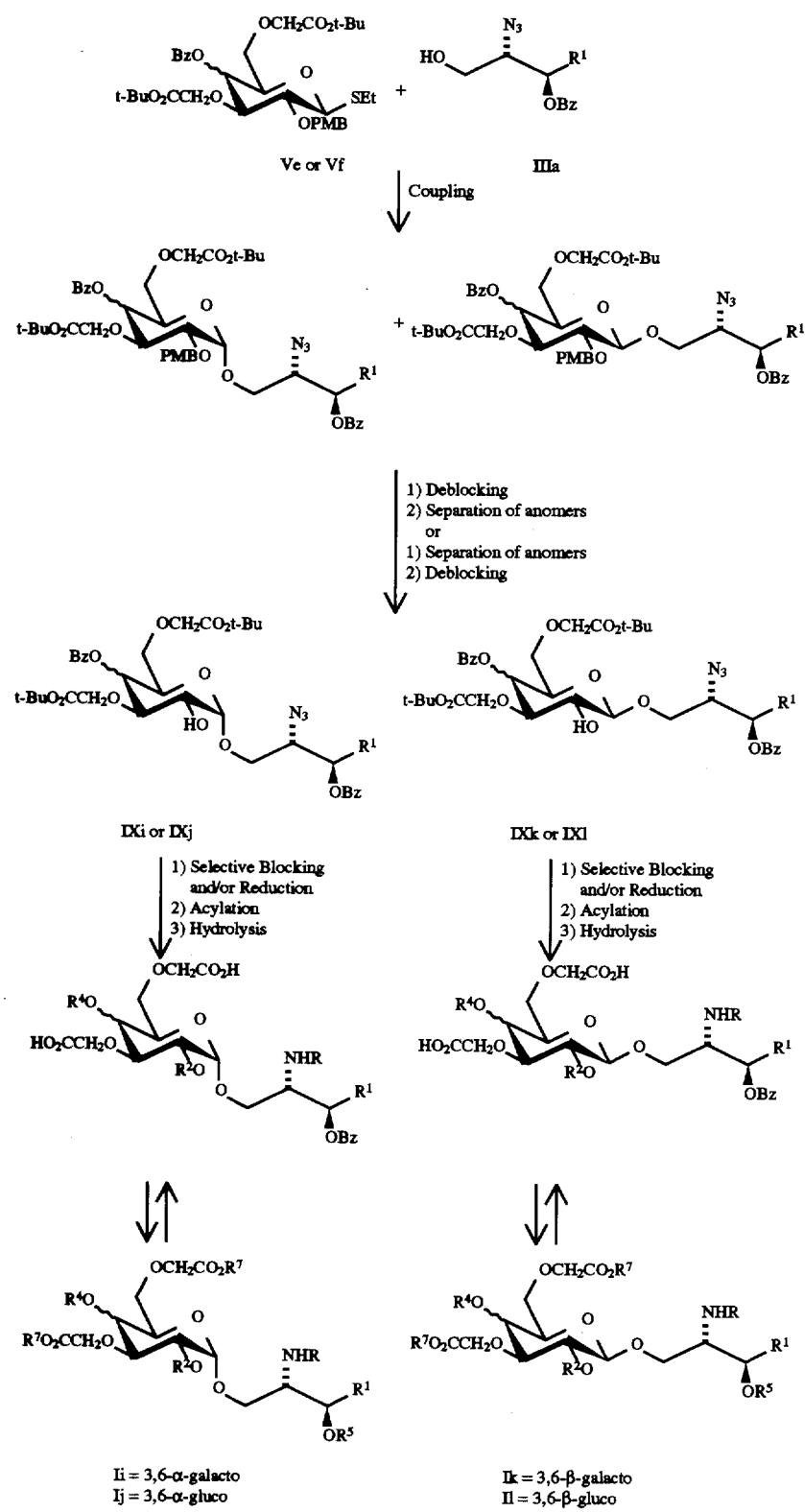

Ii = 3,6-α-galacto
Ij = 3,6-α-gluco

Ik = 3,6-β-galacto
Il = 3,6-β-gluco

When it is desired to prepare the 3,6-dicarboxymethylated α- and β-anomer compounds of Formula Ii and Ik, respectively, the fully protected galactopyranoside of Formula Ve is reacted with the azido alcohol of Formula IIIa under well-known coupling procedures as shown in Reaction Scheme 7 and as previously described. The resulting azido glycolipid from the reaction of the pyranoside of Formula Ve and the alcohol of Formula IIIa is a mixture of α- and β-anomers of the desired azido glycolipid compound. It should be appreciated by those skilled in the art that the mixture of anomers produced in the coupling reaction can be readily separated by methods such as fractional crystallization and preferably, chromatography as described herein. It should further be appreciated by those skilled in the art that the separation may be carried out at this step while the glycolipid compound is fully protected (blocked) or, if desired, after the blocking groups on the 2- and 4-hydroxy groups have been removed, i.e., with 2,3-dichloro-5,6-dicyano-1,4-benzoquinone when the blocking group is p-methoxybenzyl. It should be understood by those skilled in the art that if the separation is not complete at this step, then the separation can be completed in the next step. The choice of when the separation of anomers is carried out is dependent on the nature of the substituents, the ratio of anomers and the ease of separation based on the relative differences between the anomers and the desired anomer.

To prepare the 3,6-dicarboxymethylated α-galacto type glycolipids of Formula Ii, the corresponding separated α-anomer of the azido glycolipid of Formula IXi is subjected to reduction of the azido group followed by acylation of the resulting amino group with the desired activated acyl residue of a fatty acid having the definitions of R as defined herein. The resulting glycolipid is subjected, if desired, to conventional hydrolysis of the carboxylic acid ester to produce the carboxylic acid of the compound of Formula Ii or a non-toxic pharmaceutically acceptable salt thereof. It should be appreciated by those skilled in the art that the removal and insertion of the desired $R^2$, $R^4$, $R^5$ and $R^7$ moieties in the compound of Formula Ii can be interchanged, or left untouched depending on the particular substituent which is desired in the preparation of compounds having the carboxymethylated moiety in the 3- and 6-position of the α-galacto type glycolipids of Formula Ii.

Similarly, to prepare the 3,6-dicarboxymethylated β-galacto type glycolipids of Formula Ik, the corresponding separated β-anomer of the azido glycolipid of Formula IXk is subjected to selective blocking and/or reduction followed by acylation of the resulting amino group and, if desired, hydrolysis of the carboxylic ester group. The substituents may then be interchanged or converted to the desired compounds of Formula Ik having the carboxymethylated moiety in the 3- and 6-position of the β-galacto type glycolipids of Formula Ik.

It should be understood that by following the general sequence steps outlined above and in Reaction Scheme 7 starting from the glucopyranoside of the Formula Vf, the 3,6-dicarboxymethylated gluco type glycolipids of Formula Ij and Il may be prepared from the corresponding α-gluco compound of Formula IXj and β-gluco compound of Formula IXl, respectively.

In a preferred embodiment of the invention, the compounds of Formula I have the formula

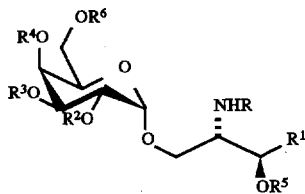

wherein R is an acyl residue of a fatty acid; $R^1$ is —(CH=CH)$_m$—(CH$_2$)$_n$—CH$_3$; $R^3$, $R^4$ and $R^6$ each are independently —CH$_2$COOR$^7$, provided at least two of the $R^3$, $R^4$ and $R^6$ substituents are —CH$_2$COOR$^7$; $R^2$, $R^3$, $R^4$, $R^5$ and $R^6$ each are independently hydrogen, unsubstituted or substituted alkanoyl, arylalkyl or arylcarbonyl wherein said substituent is selected from halogen, $C_{1-4}$ alkyl, trifluoromethyl, hydroxy and $C_{1-4}$ alkoxy; m is an integer of 0 or 1; n is an integer of from 5 to 14, inclusive; $R^7$ is hydrogen, a hydrolyzable ester group or a cation to form a non-toxic pharmaceutically acceptable salt; or a solvate or hydrate thereof. In a particularly preferred embodiment, $R^4$ and $R^6$ are —CH$_2$COOR$^7$ and $R^2$, $R^3$, and $R^5$ each are independently hydrogen or benzoyl. In another particular preferred embodiment $R^3$ and $R^4$ are —CH$_2$CO$_2$R$^7$ and $R^2$, $R^5$ and $R^6$ each are independently hydrogen or benzoyl. In still another particularly preferred embodiment $R^3$ and $R^6$ are —CH$_2$COOR$^7$ and $R^2$, $R^4$ and $R^5$ each are independently hydrogen or benzoyl.

In another preferred embodiment of the invention, the compounds of Formula I have the formula

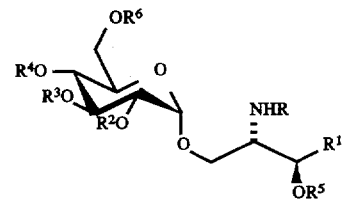

wherein R is an acyl residue of a fatty acid; $R^1$ is —(CH=CH)$_m$—(CH$_2$)$_n$—CH$_3$; $R^3$, $R^4$ and $R^6$ each are independently —CH$_2$COOR$^7$, provided at least two of the $R^3$, $R^4$ and $R^6$ substituents are —CH$_2$COOR$^7$; $R^2$, $R^3$, $R^4$, $R^5$ and $R^6$ each are independently hydrogen, unsubstituted or substituted alkanoyl, arylalkyl or arylcarbonyl wherein said substituent is selected from halogen, $C_{1-4}$ alkyl, trifluoromethyl, hydroxy and $C_{1-4}$ alkoxy; m is an integer of 0 or 1; n is an integer of from 5 to 14, inclusive; $R^7$ is hydrogen, a hydrolyzable ester group or a cation to form a non-toxic pharmaceutically acceptable salt; or a solvate or hydrate thereof. In a particularly preferred embodiment, $R^4$ and $R^6$ are —CH$_2$COOR$^7$ and $R^2$, $R^3$, and $R^5$ each are independently hydrogen or benzoyl. In another particularly preferred embodiment $R^3$ and $R^4$ are —CH$_2$CO$_2$R$^7$ and $R^2$, $R^5$ and $R^6$ each are independently hydrogen or benzoyl. In still another particularly preferred embodiment $R^3$ and $R^6$ are —CH$_2$COOR$^7$ and $R^2$, $R^4$ and $R^5$ each are independently hydrogen or benzoyl.

In still another preferred embodiment of the invention, the compounds of Formula I have the formula

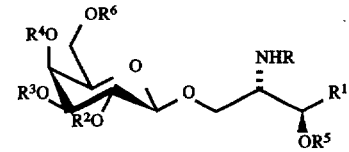

wherein R is an acyl residue of a fatty acid; $R^1$ is —(CH=CH)$_m$—(CH$_2$)$_n$—CH$_3$; $R^3$, $R^4$ and $R^6$ each are independently —CH$_2$COOR$^7$, provided at least two of the $R^3$, $R^4$ and $R^6$ substituents are —CH$_2$COOR$^7$; $R^2$, $R^3$, $R^4$, $R^5$ and $R^6$ each are independently hydrogen, unsubstituted or substituted alkanoyl, arylalkyl or arylcarbonyl wherein said substituent is selected from halogen, $C_{1-4}$ alkyl, trifluoromethyl, hydroxy and $C_{1-4}$ alkoxy; m is an integer of 0 or 1; n is an integer of from 5 to 14, inclusive; $R^7$ is hydrogen, a hydrolyzable ester group or a cation to form a non-toxic pharmaceutically acceptable salt; or a solvate or hydrate thereof. In a particularly preferred embodiment, $R^4$ and $R^6$ are —$CH_2COOR^7$ and $R^2$, $R^3$, and $R^5$ each are independently hydrogen or benzoyl. In another particularly preferred embodiment $R^3$ and $R^4$ are —$CH_2CO_2R^7$ and $R^2$, $R^5$ and $R^6$ each are independently hydrogen or benzoyl. In still another particularly preferred embodiment $R^3$ and $R^6$ are —$CH_2COOR^7$ and $R^2$, $R^4$ and $R^5$ each are independently hydrogen or benzoyl.

In still yet another preferred embodiment of the invention, the compounds of Formula I have the formula

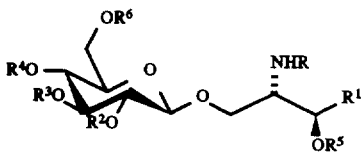

wherein R is an acyl residue of a fatty acid; $R^1$ is —$(CH=CH)_m$—$(CH_2)_n$—$CH_3$; $R^3$, $R^4$ and $R^6$ each are independently —$CH_2COOR^7$, provided at least two of the $R^3$, $R^4$ and $R^6$ substituents are —$CH_2COOR^7$; $R^2$, $R^3$, $R^4$, $R^5$ and $R^6$ each are independently hydrogen, unsubstituted or substituted alkanoyl, arylalkyl or arylcarbonyl wherein said substituent is selected from halogen, $C_{1-4}$ alkyl, trifluoromethyl, hydroxy and $C_{1-4}$ alkoxy; m is an integer of 0 or 1; n is an integer of from 5 to 14, inclusive; $R^7$ is hydrogen, a hydrolyzable ester group or a cation to form a non-toxic pharmaceutically acceptable salt; or a solvate or hydrate thereof. In a particularly preferred embodiment, $R^4$ and $R^6$ are —$CH_2COOR^7$ and $R^2$, $R^3$, and $R^5$ each are independently hydrogen or benzoyl. In another particularly preferred embodiment $R^3$ and $R^4$ are —$CH_2CO_2R^7$ and $R^2$, $R^5$ and $R^6$ each are independently hydrogen or benzoyl. In still another particularly preferred embodiment $R^3$ and $R^6$ are —$CH_2COOR^7$ and $R^2$, $R^4$ and $R^5$ each are independently hydrogen or benzoyl.

In another aspect, this invention provides novel intermediates of the Formula X

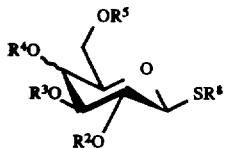 (X)

wherein $R^2$, $R^3$, $R^4$ and $R^6$ each are independently hydrogen, unsubstituted or substituted alkanoyl, arylalkyl or arylcarbonyl wherein said substituent is selected from halogen, $C_{1-4}$ alkyl, trifluoromethyl and $C_{1-4}$ alkoxy;

$R^3$, $R^4$ and $R^6$ each are independently —$CH_2COOR^{7a}$, provided at least two of the $R^3$, $R^4$ and $R^6$ substituents are —$CH_2COOR^{7a}$;

$R^{7a}$ is a hydrolyzable ester group; and $R^8$ is (lower)alkyl, unsubstituted or substituted aryl, or aryl(lower)alkyl wherein said substituent is selected from halogen, $C_{1-4}$ alkyl, trifluoromethyl and $C_{1-4}$ alkoxy.

In a preferred embodiment of the invention, the compounds of Formula X have the formula

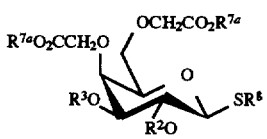

wherein $R^2$ and $R^3$ each are independently hydrogen, unsubstituted or substituted alkanoyl, arylalkyl or arylcarbonyl wherein said substituent is selected from halogen, $C_{1-4}$ alkyl, trifluoromethyl and $C_{1-4}$ alkoxy; $R^{7a}$ is a hydrolyzable ester group; and $R^8$ is (lower)alkyl, unsubstituted or substituted aryl, or aryl(lower)alkyl wherein said substituent is selected from halogen, $C_{1-4}$ alkyl, trifluoromethyl and $C_{1-4}$ alkoxy. In a more preferred embodiment, $R^2$ and $R^3$ each are unsubstituted or substituted arylalkyl or arylcarbonyl wherein said substituent is selected from halogen, $C_{1-4}$ alkyl, trifluoromethyl and $C_{1-4}$ alkoxy; $R^{7a}$ is a hydrolyzable ester group; and $R^8$ is (lower)alkyl, unsubstituted or substituted aryl, or aryl(lower)alkyl wherein said substituent is selected from halogen, $C_{1-4}$ alkyl, trifluoromethyl and $C_{1-4}$ alkoxy. In a most preferred embodiment, $R^2$ and $R^3$ are p-methoxybenzyl; $R^{7a}$ is t-butyl and $R^8$ is (lower)alkyl or phenyl.

In yet another aspect, this invention provides a method for the treatment or prevention of diseases mediated by the inhibition of selectin-mediated cellular adhesion in a mammal in need thereof, which comprises administering to said mammal a therapeutically effective amount of a compound of Formula I or a non-toxic pharmaceutically acceptable salt, solvate or hydrate thereof. In a particularly preferred embodiment, this invention provides a method for the treatment of inflammatory related diseases or other pathological conditions in a mammal in need thereof, which comprises administering to said mammal a therapeutically effective amount of a compound of Formula I or a non-toxic pharmaceutically acceptable salt, solvate or hydrate thereof.

In still yet another aspect, this invention provides pharmaceutical compositions comprising at least one compound of Formula I in combination with a pharmaceutical carrier or diluent.

CELL ADHESION ACTIVITY

1. P-Selectin Adhesion Receptor Binding

P-selectin (GMP140, granule membrane protein-140, PADGEM, or CD62) is a calcium-dependent transmembrane protein found in alpha granules of endothelial cells and platelets. It is an inducible selectin produced on activated endothelium and platelets which recognize alpha(2-3)sialylated and alpha(1-3)fucosylated lactosaminoglycans which include the sequence, Lewis x (Zhou et al., *J. Cell. Biol.*, (1991) 115 (2): 557–564) and sulfatides (3-sulfated galactosyl ceramides, Aruffo, et al., *Cell* (1991) 67: 35–44). P-selectin may be responsible for the initial adhesion events between endothelium and neutrophils as evidenced by leukocyte rolling induced by P-selectin in flow cells (Lawrence, M., and T. Springer, *Cell* (1991) 65: 859–873).

Based on the availability of soluble forms of P-selectin prepared as described by Aruffo, A., et al., *Cell*, 67, 35–44 (1991), a binding ELISA based assay modified from Foxall, et al., *J., Cell Biol.*, 117, 895–902 (1992) was developed to measure inhibitors of P-selectin binding to immobilized sulfatides. Such inhibitors were tested in the assay described below.

0.1 ml of sulfatide (SIGMA) at 1 μg/ml in MeOH was added to 48 wells of a 96-well ELISA plate (ProBind, Falcon) and allowed to dry overnight at room temperature. Another set of 48 wells were incubated with the solvent (methanol, Fisher Scientific). The next day the antigen/solvent coated plates were blocked for 1.5 hours at room temperature with 5% BSA (ICN) in buffer containing 20 mM Hepes, 1 mM $CaCl_2$ and 0.15M NaCl, pH 8.0. Wild type P-selectin was first mixed with HRP-conjugated goat anti-human IgG (1:5000 dilution, Fisher Scientific), and incubated for 30 minutes at 37° C. in buffer containing 20 mM Hepes, 0.15M NaCl, 1% BSA and 1 mM $CaCl_2$, pH 8.0 prior to addition to the BSA blocked plates. Following the 30 minute preincubation, the fusion protein-HRP conjugate immunocomplexes were incubated on the blocked antigen coated plates for 45 minutes at 37° C. in the presence or absence of the test compounds and then washed to remove any unbound proteins. Bound complexes were detected by addition of substrate buffer (95 mM $NaOAc.3H_2O$, 5 mM citric acid monohydrate, 1.4 mM $urea/H_2O_2$) containing 3, 3', 5, 5' Tetramethylbenzidine (SIGMA). Reactions were stopped by the addition of 3N sulfuric acid and the absorbance read on an ELISA reader at dual wavelengths 450 and 630 nm. The efficacy of these compounds was compared to that of sulfatide (positive control) or to MeOH (negative control). The data is obtained as percent inhibition of specific binding $$\% \text{ Inhibition} = \left[ 1 - \left( \frac{\text{Specific binding: Test Compound}}{\text{Specific binding: Vehicle}} \right) \right] \times 100$$

and a plot of dose vs. percent inhibition of Rg binding is generated in which $IC_{50}$ (µM) is calculated and reported as cell free data in Table 1.

2. HL-60 Platelet Cell Adhesion Assay

HL-60 cells, obtained from American Type Culture Collection, were cultured in RPMI 1640 medium (GIBCO) supplemented with 20% fetal calf serum (Sigma) and 50 µg/ml gentamicin (GIBCO). Cells in log phase growth were harvested, washed and resuspended in Tyrodes buffer containing 5 mM HEPES and 0.2% bovine serum albumin and were fixed with 1% buffered formalin.

Blood from normal human donors was anticoagulated with citrate, layered over 1-Step Platelets (Accurate Chemical Co.), and centrifuged at 350 g for 20 minutes at room temperature. The platelet band was collected, diluted in 2 volumes of Tyrode's Buffer with 5 mM HEPES, 10 mM EDTA, and 0.2% BSA (pH 7.4) (THEB) and centrifuged at 600 g for 10 minutes. The platelet pellet was resuspended in THEB and incubated at room temperature for 1 hour. Calcein-acetoxy methylester (Calcein-Am, Molecular Probes) was added to the platelets at a final concentration of 10 µM and incubated for 10 minutes at 37° C. to label the platelets. Without washing, the platelets were counted on a Coulter counter model ZM, and the concentration was adjusted to $1\times10^7$/ml. The platelets were activated with 2 U/ml of human thrombin for 10 minutes in Tyrode's containing 2 mM $CaCl_2$, 5 mM HEPES, and 0.2% BSA (pH 7.4) (THB) at 37° and immediately fixed with 1% buffered formalin for 1 to 2 hours at room temperature. A small aliquot of labeled platelets was removed before activation and designated as non-activated.

Both platelets and HL-60 were washed in a $\geq 5$ fold excess volume of Hanks Balanced Salt Solution (HBSS), resuspended in THB and counted. Cell concentrations were adjusted to $2\times10^7$/ml for platelets and $4\times10^6$/ml for HL-60, this ratio determined to be optimum for platelet: HL-60 cell adhesion. Compounds were incubated with 50 µl of platelets for 30 minutes at room temperature before addition of 50 µl of HL-60. This ratio of 5:1 platelets to HL-60 was incubated for 30 minutes at room temperature before addition of 0.2 ml of THB to increase the volume so the samples could be analyzed on a FACScan cytometer (Becton Dickinson). Non-activated platelets, and activated platelets with 10 mM EDTA were included as controls. Data were collected within a region set for the forward scatter channel corresponding to HL-60 size events.

The HL-60 cells were present in two populations: one was non-fluorescent and did not contain platelets; the other was fluorescent due to bound platelets. The percent HL-60 cells which contained bound platelets was determined for each test condition. The inhibition of binding was determined by comparison to standards which were treated with vehicle alone (representing 0% inhibition) and standards whose specific binding had been blocked by the use of EDTA (representing 100% inhibition), by the following formula:

$$\left\{ 1 - \frac{x-b}{a-b} \right\} \times 100 = z$$

where x=HL-60 cells containing bound platelets in the presence of the compound;

b=HL-60 cells containing bound platelets in the presence of EDTA;

a=HL-60 cells containing bound platelets in presence of compound vehicle;

z=% inhibition of platelet: HL-60 cell adhesion

3. Reverse Passive Arthus Reaction in Rats

The reverse passive Arthus reaction in rats is a modification of the method by Mulligan et al., as described in *J. Clin. Invest.*, (1991) 88: 1396–1406. This is an experimental model in which the interaction of antigen-antibody complexes and complement leads to a severe vasculitis that is associated with edema, induration, erythema and hemorrhage. The interaction between the antigen-antibody complexes and complement leads to a localized influx of neutrophils. These neutrophils release a variety of mediators that are associated with tissue damage and vascular permeability. The localized inflammatory reaction is measured using different techniques i.e., vascular permeability and neutrophil influx which is evaluated both biochemically and microscopically.

Male Sprague Dawley specific pathogen-free rats with jugular vein cannulae (280–320 g, Hill Top Labs, Pa.) are used in these studies. Animals are acclimated for at least 1 day and individually housed in stainless steel cages. The dorsal region of the rats is closely clipped 2 days prior to the experiments and divided into 4 sites on each side of the midline. Prior to all injections the rats are sedated with 0.4 ml per 300 gm rat of ketamine/rompun [1000 mg (10 ml) of ketamine HCL is mixed with 40 mg (2.0 ml) Rompun] administered IP and or inhalation anesthesia with metafane (methoxyflurane).

Bovin Serum Albumin (BSA) and rabbit polyclonal IgG rich in anti-BSA are purchased from Sigma Chemical Co. (St. Louis, Mo.). Radiolabelled $^{125}$I-BSA (spAct 1-5 µCi/µg) is purchased from Dupont NEN (Boston, Mass.).

Each rat is administered intradermal (ID) injection of (0.4 mg, 0.6 mg and 0.8 mg) anti-BSA in a volume of 100 µl per injection in normal saline. The ID injections are randomized near the mid dorsal region on both sides of the back bone. Immediately after the ID injections of the anti-BSA, the rats are administered intravenous (IV) injections of BSA (10 mg in 1.0 ml) in normal saline containing $^{125}$I labeled BSA (1 µCi/ml BSA or 5.0 µCi/kg body wt) for quantification of dermal vascular injury. Anti-inflammatory agents such as inhibitors of adhesion molecules of the present invention are administered IV at a single dose of 3 mg immediately after BSA. Four (4) hours after the IV injection of BSA, the rats are anesthetized with metafane and 2 to 3 ml of blood is withdrawn via the cannula into an anticoagulant containing (EDTA or Heparin) tube and plasma separated and saved for neutrophil and albumin quantitation. The rats are killed and the skin surrounding the injection site (15 mm diameter) is punched out and weighed. The skin samples and a fixed volume of plasma (0.1 to 1.0 ml) is analyzed in a gamma-counter for $^{125}I$ content. Skin samples from the contralateral side are processed and analyzed for myeloperoxidase activity (MPO) as a measure of neutrophil accumulation. As needed, samples are also processed for histological evaluation of the reacted sites.

Vascular Permeability (VP)

The calculation of the plasma protein exudation into skin is made by determining the radioactivity in the tissue and relating this to the level of radioactive albumin in the blood at the time of sacrifice. The equation below shows the calculation for microliter plasma extravasated (Issekutz and Issekutz, Pharmacological methods in the control of inflammation, (1989) 129-150).

$$\mu l \text{ plasma extravasated} = \frac{CPM \text{ in tissue}}{CPM/\mu l \text{ plasma}}$$

Percent inhibition of the test compound at 3 mg was determined as follows:

% Inhibition =

$$\left[1 - \left(\frac{\mu l \text{ plasma extravasated with test compound}}{\mu l \text{ plasma extravasated with vehicle}}\right)\right] \times 100$$

Myeloperoxidase (MPO)

MPO is located in the azurophil granules of polymorphonuclear leukocytes (PMN). Because of its abundance in these cells (5% dry weight), this enzyme is used as a marker for tissue neutrophil content. For tissue MPO content, the method of Bradley, et al., was used as described in *J. Invest. Dermatol.* (1982) 78: 206–209. Biopsies from each treatment group were placed in plastic tubes (15×100 mm) containing 10 ml of 0.5% hexadecyltrimethylammonium bromide (HTAB)in 0.05M potassium phosphate buffer pH 6.0. The tissue was then homogenized with a Brinkmann Polytron homogenizer (10s). The supernatant (0.05 ml) was assayed by mixing with 0.150 ml o-dianisidine (0.334 mg/ml) and 0.0005% hydrogen peroxide in 0.05M potassium phosphate buffer pH 6.0 in a 96-well microtiter plate. Change in absorbance at 450 nm was measured at room temperature using a $V_{max}$ kinetic plate reader (Molecular Devices, Palo Alto, Calif., USA). Percent inhibition of the test compound at 3 mg dose was determined as follows:

% Inhibition =

$$\left[1 - \left(\frac{\text{Absorbance of test compound treated Biopsies}}{\text{Absorbance of vehicle treated Biopsies}}\right)\right] \times 100$$

The in vivo experimental results as measured by vascular permeability (VP) and myeloperoxidase (MPO) at a single dose of the test compound are shown in Table 1.

TABLE 1

| Example No. | P-Selectin | | RPA | |
|---|---|---|---|---|
| | Cell Free $IC_{50}$ (μM) | HL-60 Platelets | VP % Inhib.* | MPO % Inhib.* |
| 2 | 0.92 | 32 | >73 | >99 |
| 8 | >50 | >100 | 9 | 22 |
| 10 | NA** | >100 | 54 | 65 |
| 14 | 0.7 | 20 | 32 | 13 |
| 16 | 3.5 | 10.1 | NS*** | NS |
| 18 | <0.03 | 7 | 73.6 | 98 |

*% Inhibition at 3 mg
**not available
***no significant inhibition at 3 mg

The biological results of representative compounds according to this invention are shown in Table 1. Both the cell and cell-free in vitro assays and the in vivo tests carried out in the RPA rat model show that the compounds of Formula I are inhibitors of P-selectin mediated binding and, more importantly, confirm that the compounds of the instant invention are selectin inhibitors useful to treat inflammatory conditions in a mammal.

Therefore, the compounds of Formula I or pharmaceutical compositions thereof are useful in the treatment and/or prevention of diseases or other pathological conditions which are mediated by the binding of selectins in cellular adhesion. Such diseases and conditions include acute or chronic inflammatory diseases such as rheumatoid arthritis, asthma, allergy conditions, psoriasis, septic shock, adult respiratory distress syndrome, inflammatory bowel disease and opthalmic inflammatory diseases; autoimmune diseases; thrombosis or inappropriate platelet aggregation conditions, and cardiovascular disease; reperfusion injury; multiple sclerosis; chemical and thermal burn injuries and neoplastic disease including metastasis conditions.

In another embodiment, this invention includes pharmaceutical compositions comprising at least one compound of Formula I in combination with a pharmaceutical carrier or diluent.

In still another embodiment, this invention relates to a method of treatment or prevention of diseases or other pathological conditions characterized by selectin-mediated cellular adhesion in a mammal in need thereof, which comprises administering to said mammal a therapeutically effective amount of a compound of Formula I or a non-toxic pharmaceutically acceptable salt, solvate or hydrate thereof.

In yet another embodiment, this invention relates to a method for inhibiting or reducing inflammatory disease processes in a mammal in need thereof, which comprises administering to said mammal a therapeutically effective amount of a compound of Formula I or a non-toxic pharmaceutically acceptable salt, solvate or hydrate thereof.

For therapeutic use, the pharmacologically active compounds of Formula I will normally be administered as a pharmaceutical composition comprising as the (or an) essential active ingredient at least one such compound in association with a solid or liquid pharmaceutically acceptable carrier and, optionally, with pharmaceutically acceptable adjuvants and excipients employing standard and conventional techniques.

The pharmaceutical compositions include suitable dosage forms for oral, parenteral (including subcutaneous, intramuscular, intradermal and intravenous), transdermal, bronchial, rectal, topical, ophthalmic, intraarticular or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. Particularly useful is the administration of a compound of Formula I directly in transdermal formulations with permeation enhancers such as DMSO and iontophoresis. Other topical compositions well-known in the art can be administered to treat dermal inflammation. The pharmaceutical compositions are prepared by conventional techniques appropriate to the desired preparation containing appropriate amounts of the active ingredient, that is, the compound of Formula I according to the invention. See, for example, *Remington's Pharmaceutical Sciences*, Mack Publishing Company, Easton, Pa., 17th edition, 1985.

The dosage of the compounds of Formula I to achieve a therapeutic effect will depend not only on such factors as the age, weight and sex of the patient and mode of administration, but also on the degree of cell adhesion inhibition desired and the potency of the particular compound being utilized for the particular disorder of disease concerned. It is also contemplated that the treatment and dosage of the particular compound may be similar to the treatment and dosage used with dexamethasone phosphate and that the dosage would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention for the satisfactory inhibition or reduction of selectin-mediated cell adhesion.

A suitable dose of a compound of Formula I or pharmaceutical composition thereof for a mammal suffering from, or likely to suffer from any condition as described herein is an amount of active ingredient from 0.1 µg/kg to 100 mg/kg body weight. For systemic administration, the dose may be in the range of 0.1 to 100 mg/kg body weight to the active ingredient, and preferably, in the range of 0.1 to 50 mg/kg body weight. For topical administration, for example to the skin or eye, a suitable dose of active ingredient may be in the range of 0.1 µg to about 100 mg/ml of liquid carrier or excipient, and preferably, about 0.1 mg to 10 mg/ml. For oral dosing including the treatment or prophylaxis of inflammatory diseases or conditions, a suitable dose may be in the range of about 1 mg to 100 mg/kg of mammal body weight, and preferably, from about 1 mg to about 50 mg/kg body weight. The active ingredient will preferably be administered in equal doses from one to four times a day. However, usually a small dosage is administered, and the dosage is gradually increased until the optimal dosage for the host under treatment is determined.

The following examples are given by way of illustration and are not to be construed as limiting the invention in any way inasmuch as many variations of the invention are possible within the spirit of the invention.

DESCRIPTION OF SPECIFIC EMBODIMENTS

EXAMPLE 1

(2S,3R,4E)-3-Benzoyloxy-2-hexadecanoylamino-1-(2,3-di-O-benzoyl-4,6-di-O-tert-butyloxycarbonylmethyl-α-D-galactopyranosyloxy)-4-octadecene A. Ethyl 4,6-O-benzylidene-2,3-di-O-para-methoxybenzyl-1-thio-β-D-galactopyranoside

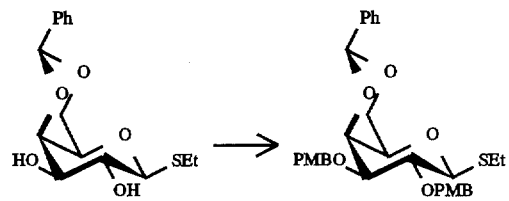

A solution of ethyl 4,6-O-benzylidene-1-thio-β-D-galactopyranoside [Nilsson, et al., *J. Carbohy. Chem.* 10(6) 1023 (1991)] (2.0 g, 6.4 mmol) in dimethylformamide (25 mL) was added under argon to a suspension of sodium hydride (2.0 g, 8.33 mmol, previously washed with hexane). The mixture was allowed to stir for 1.5 h after which para-methoxybenzyl chloride (4.75 mL, 29.0 mmol) was added in slowly. The reaction mixture was allowed to react at ~22° C. for 18 hours, cooled down to 5° C. and treated slowly with cold 1M aqueous sodium bicarbonate solution. The crude aqueous mixture was extracted with ethyl acetate (4×100 mL). The organic extracts were combined, washed with 1M aqueous sodium bicarbonate (2×100 mL), water (3×100 mL), brine (100 mL) and dried over anhydrous magnesium sulfate. The residue upon solvent evaporation was crystallized from ethyl acetate and hexane to give the title compound (2.69 g, 75%).

IR (CH$_2$Cl$_2$) v$_{max}$ (cm$^{-1}$): 3060–2860 (C—H).

$^1$H NMR 200 MHz (CDCl$_3$) δ(ppm): 1.33 (3H, t, J=7.3 Hz, —CH$_3$), 2.60–2.91 (2H, m, —SCH$_2$—), 3.34 (1H, br s, H-5), 3.55 (1H, dd, J=9.2 and 3.5 Hz, H-3), 3.805 (6H, s, 2×—OCH$_3$), 3.856 (1H, t, J=9.4 Hz, H-2), 3.956 (1H, dd, J=12.4 and 1.6 Hz, H-6), 4.110 (1H, d, J=3.2 Hz, H-4), 4.302 (1H, dd, J=12.3 and 1.4 Hz, H-6), 4.414 (1H, d, J=9.6 Hz, H-1), 4.70 (1H, d, J$_{AB}$=11.9 Hz, —OCH$_2$Ar), 4.72 (1H, d, J$_{AB}$=11.9 Hz, —OCH$_2$Ar), 4.77 (1H, d, J$_{AB}$=9.8 Hz, —OCH$_2$Ar), 4.82 (1H, d, J$_{AB}$=9.8 Hz, —OCH$_2$Ar), 5.469 (1H, s, —OCHO—), 6.82–6.90, 7.26–7.40, 7.51–7.56 (13H, 3 sets of m, aromatic H).

B. Ethyl 2,3-di-O-para-methoxybenzyl-1-thio-β-D-galactopyranoside

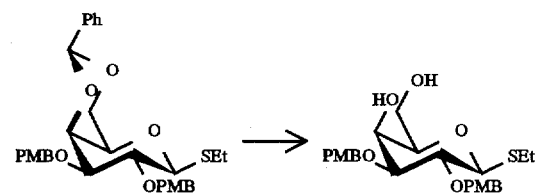

A solution of ethyl 4,6-O-benzylidene-2,3-di-O-para-methoxybenzyl-1-thio-β-D-galactopyranoside (2.6 g, 4.8 mmol) in tetrahydrofuran (80 mL) was treated with 3N aqueous hydrochloric acid (20 mL). The mixture was allowed to react for 30 hours after which it was neutralized with solid sodium bicarbonate and diluted with ethyl acetate. The aqueous layer was saturated with sodium chloride and removed. The organic layer was dried over anhydrous magnesium sulfate and the solvent removed under vacuum to give a solid that was triturated in ethyl acetate and hexane and afforded the title material (2.0 g, 90%).

IR ($CH_2Cl_2$) $v_{max}$ ($cm^{-1}$): 3600–3200 (OH), 3000–2820 (C—H).

$^1$H NMR 400 MHz (CDCl$_3$) δ(ppm): 1.32 (3H, t, J=7.4 Hz, —CH$_3$), 2.05–2.13 (1H, m, —OH—6), 2.60 (1H, br s, —OH—4), 2.68–2.84 (2H, m, —SCH$_2$—), 3.476 (1H, t, J=5.5 Hz, H-5), 3.530 (1H, dd, J=8.9 and 3.3 Hz, H-3), 3.635 (1H, t, J=9.3 Hz, H-2), 3.76–3.82 (1H, m, H-6), 3.815 and 3.818 (6H, 2s, 2×—OCH$_3$), 3.934–3.996 (1H, m, H-6), 4.011 (1H, br t, J=1.5 Hz, H-4), 4.416 (1H, d, J=9.7 Hz, H-1), 4.633, 4.663, 4.692 (2H, ABq, J=11.7 Hz, —OCH$_2$Ar), 4.70 (1H, d, J$_{AB}$=9.9 Hz, —OCH$_2$Ar), 4.81 (1H, d, J$_{AB}$=11.7 Hz, —OCH$_2$Ar), 6.86–6.90, 7.26–7.35 (8H, 3 sets of m, aromatic H).

C. Ethyl 4,6-di-O-tert-butyloxycarbonylmethyl-2,3-di-O-para-methoxybenzyl-1-thio-β-D-galactopyranoside

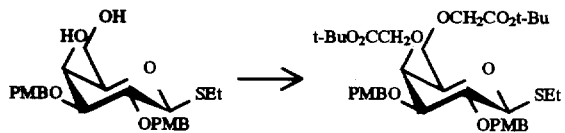

Procedure 1

A solution of ethyl 2,3-di-O-para-methoxybenzyl-1-thio-β-D-galactopyranoside (2.0 g, 4.4 mmol) in dimethylformamide (40 mL) was added to a suspension of sodium hydride (2.1 g, 65% in mineral oil, 59.4 mmol), previously washed with hexane (3×20 mL), in dimethylformamide (10 mL). The mixture was allowed to react for 30–45 minutes and tert-butyl bromoacetate (6 mL, 5 g, 26 mmol) was added in. The exothermic reaction was then stirred for ~30 minutes after which it was cooled down (5° C.) and quenched carefully with cold saturated aqueous sodium bicarbonate. It was diluted with ethyl acetate (250 mL) and ether (50 mL), washed with aqueous sodium bicarbonate (3×100 mL), water (4×100 mL), brine (100 mL) and dried over anhydrous magnesium sulfate. The residue upon evaporation was passed through a silica gel column (200 g, 20–30% ethyl acetate/hexane) to give the title material (2.3 g, 76.6%) as an oil.

Procedure 2

An aqueous sodium hydroxide solution (10N, 280 mL) was added to a stirred solution of ethyl 2,3-di-O-tert-butyloxycarbonylmethyl-2,3-di-O-para-methoxybenzyl-1-thio-β-D-galactopyranoside (43.4 g, 93.4 mmol) in methylene chloride (560 mL) at 22° C. followed by tert-butylbromoacetate (150 mL, 934 mmol) and tetrabutylammonium chloride (131 g, 0.471 mmol). This mixture was vigorously stirred for 18 hours (the temperature of the reaction mixture raised to 30°–35° C.). The mixture was diluted with cold water (1 L) and ethyl ether (~1.5 L) and the aqueous phase was extracted with ethyl ether (1×500 mL). The combined organic layers were washed with water (4×1 L) and brine, dried over anhydrous magnesium sulfate, filtered and concentrated. The residue was passed through a silica gel pad (11.5×18 cm, 5% to 30% ethylacetate/hexane) and the resulting solid was triturated in hexane to give the title compound (50.28 g, 77%) as a white solid.

IR (film) $v_{max}$ ($cm^{-1}$): 3200–2850 (CH) and 1750 $cm^{-1}$ (C=O).

$^1$H NMR 400 MHz (CDCl$_3$) δ(ppm): 1.307 (3H, t, J=7.4 Hz, —CH$_3$) 1.464 and 1.483 (18H, 2s, 2×tert-butyl), 2.68–2.81 (2H, m, —SCH$_2$—), 3.510 (1H, dd, J=9.3 and 2.5 Hz, H-3), 3.605 (1H, br t, J=6.0 Hz, H-5), 3.732 (1H, dd, J=9.8 and 6.0 Hz, H-6), 3.811 and 3.822 (6H, 2s, 2×—OCH$_3$), 3.822 (1H, t, J=9.3 Hz, H-2), 3.909 (1H, d, J=1.9 Hz, H-4), 3.985 (1H, dd, J=9.7 and 5.8 Hz, H-6), 4.043 and 4.048 (2H, part of ABq, —OCH$_2$CO—), 4.28 (1H, d, J$_{AB}$=16.4 Hz, —OCH$_2$CO—), 4.35 (1H, d, J$_{AB}$=16.4 Hz, —OCH$_2$CO—), 4.404 (1H, d, J=9.7 Hz, H-1), 4.652 (2H, part of ABq, —CH$_2$Ar), 4.68 (1H, d, J$_{AB}$=9.8 Hz, —OCH$_2$Ar), 4.80 (1H, d, J$_{AB}$=11.7 Hz, —OCH$_2$Ar), 6.84–6.88, 7.26–7.33 (8H, 3 sets of m, aromatic H).

D. (2S,3R,4E)-2-Azido-3-benzoyloxy-1-(4,6-O-tert-butyloxycarbonylmethyl-2,3-di-O-para-methoxybenzyl-α-D-galactopyranoside)-4-octadecene and (2S,3R,4E)-2-azido-3-benzoyloxy-1-(4,6-di-O-tert-butyloxycarbonylmethyl-2,3-di-O-para-methoxybenzyl-β-D-galactopyranoside)-4-octadecene

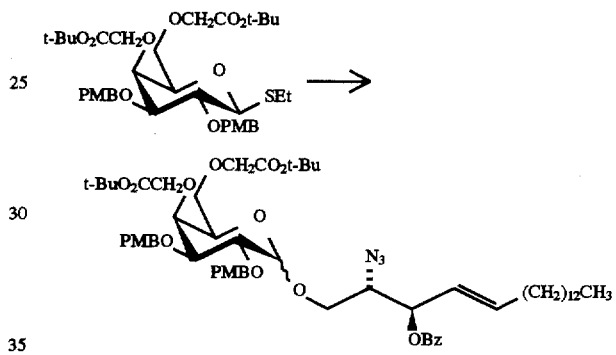

Procedure 1

A solution of ethyl 4,6-di-O-tert-butyloxycarbonylmethyl-2,3-di-O-para-methoxybenzyl-1-thio-β-D-galactopyranoside (26.44 g, 38.16 mmol), (2S,3R,4E)-2-azido-3-benzoyloxy-4-octadecen-1-ol [P. Zimmermann and R. R. Schmidt. Liebigs Ann. Chem. 1988, 663–667] (14.26 g, 33.18 mmol) and 2,6-tert-butyl-4-methyl pyridine (13.6 g, 66.36 mmol) in dioxane (500 mL) was stirred over 4A molecular sieves (50 g, previously heated with a Bunsen flame) for 1 hour at room temperature (ca 22° C.). Then dimethyl(methylthio)sulfonium triflate (16.3 g, 63.04 mmol) [P. Fugedi, et al., Carbohydr. Res., 149 (1986) C9–C12] was added in and stirring was continued for 1.5–2 hours. Then triethylamine (75 mL) was added followed by a 30 minutes stirring period after which the solid was removed by filtration and then washed with ethyl acetate (200 mL). The organic fraction was washed with saturated aqueous sodium bicarbonate (3×1 L), water (4×1 L), brine (500 mL) and dried over anhydrous magnesium sulfate. The residue was passed through a silica gel pad (17×18 cm, 0 to 75% ethyl acetate/toluene) to give the α-anomer (17.55 g, 50%) and the β-anomer (17.59 g, 50%) of the title material as oils.

Procedure 2

The same procedure as described above was repeated using ethyl 4,6-di-O-tert-butyloxycarbonylmethyl-2,3-di-O-para-methoxybenzyl-1-thio-β-D-galactopyranoside (59.4 g, 85.8 mmol), (2S,3R,4E)-2-azido-3-benzoyloxy-4-octadecen-1-ol (24.8 g, 60 mmol) and dimethylformamide (distilled over CaO, 900 mL) was used instead of dioxane. These conditions afforded the title compound (58.8 g, 92%)

as a 8:2 (α:β) mixture of anomers as determined by ¹H NMR (400 MHz). The mixture of anomers obtained from the method of procedure 2 was used directly in the next reaction step (Step E) and the resulting two anomeric products were separated at this later stage.

α-anomer:

$[\alpha]_D^{22}$: +7.5° (c=1.0, CHCl₃).

IR (film) $v_{max}$ (cm⁻¹): 3200–2800 (CH), 2095 (N₃), 1740 and 1720 (C=O).

¹H NMR 400 MHz (CDCl₃) δ(ppm): 0.890 (3H, t, J=6.8 Hz, —CH₃) 1.20–1.40 (22H, 2 sets of m, —(CH₂)₁₁—), 1.448 and 1.464 (18H, 2s, 2×tert-butyl), 2.04–2.10 (2H, m, =CH—CH₂—), 3.531 (1H, dd, J=10.8 and 7.9 Hz, H-6'), 3.667 (1H, dd, J=9.3 and 6.3 Hz, H-1), 3.778 and 3.822 (6H, 2s, 2×—OCH₃), 3.790 and 3.807 (1H, 2s, part of H-5'), 3.877 (1H, dd, J=9.4 and 2.6 Hz, H-3'), 3.861 (1H, br s, H-4'), 3.9–4.0 (3H, m, H-2', H-6', H-2), 3.948, 3.979, 3.992 (2H, ABq, J=12.5 Hz, —OCH₂CO—), 3.042 (1H, dd, J=9.3 Hz and 3.6Hz, H-1), 4.28 (1H, d, $J_{AB}$=16.7 Hz, —OCH₂CO—), 4.29 (1H, d, $J_{AB}$=16.7 Hz, —OCH₂CO—), 4.61 (1H, d, $J_{AB}$=11.7 Hz, —OCH₂Ar), 4.61 (1H, d, $J_{AB}$=11.3 Hz, —OCH₂Ar), 4.70 (1H, d, $J_{AB}$=11.7 Hz, —OCH₂Ar), 4.73 (1H, d, $J_{AB}$=11.3 Hz, —OCH₂Ar), 4.816 (1H, d, J=3.6 Hz, H-1'), 5.573 (1H, dd, J=14.9 and 7.8 Hz, H-4), 5.629 (1H, dd, J=7.8 and 4.2 Hz, H-3), 5.918 (1H, dd, J=14.9 and 6.7 Hz, H-5), 6.80–6.897, 7.274, 7.305 (8H, 3 sets of m, aromatic H), 7.44–7.48, 7.559–7.560, 8.06–8.086 (5H, 3 sets of m, aromatic H).

Anal. Calcd. for C₅₉H₈₅N₃O₄: C, 66.83; H, 8.08; N, 3.96. Found: C, 66.49; H, 7.92; N, 4.04.

β-anomer:

IR (CH₂Cl₂) $v_{max}$ (cm⁻¹): 3055, 2930, 2855 (CH), 2105 (N₃), 1735 and 1720 (C=O).

¹H NMR 400 MHz (CDCl₃) δ(ppm): 0.89 (3H, t, J=6.8 Hz, —CH₃), 1.24–1.42 (22H, m, —(CH₂)₁₁—), 1.46 and 1.48 (18H, 2s, 2×tert-butyl), 2.03 (2H, qa, J=6.8 Hz, =CH—CH₂—), 3.46 (1H, d, J=9.7 and 2.6 Hz, H-3'), 3.56–3.59 (1H, m overlapped by H-5', H-1), 3.58 (1H, br t, H-5'), 3.72 (1H, dd, J=9.7 and 6.0 Hz, H-6'), 3.79 and 3.82 (6H, 2s, 2×—OCH₃), 3.77–3.84 and 3.94–4.04 (6H, m, —OCH₂CO—, H-1, H-6', H-2' and H-2), 3.87 (1H, br d, H-4'), 4.27 (1H, d, $J_{AB}$=16.5 Hz, —OCH₂CO—), 4.34 (1H, d, $J_{AB}$=16.5 Hz, —OCH₂CO—), 4.34 (1H, d, J=6.7 Hz, H-1'), 4.63 (1H, d, $J_{AB}$=11.3 Hz, —OCH₂Ar), 4.65 (1H, d, $J_{AB}$=11.3 Hz, —OCH₂Ar), 4.70 (1H, J=10.5 Hz, —OCH₂Ar), 4.85 (1H, d, J=10.5 Hz, —OCH₂Ar), 5.56 (1H, dd, J=15.4 and 7.9 Hz, H-4), 5.69 (1H, dd, J=7.9 and 3.5 Hz, H-3), 5.90 (1H, dt, J=15.4 and 6.8Hz, H-5), 6.83–6.88, 7.24–7.33, 7.44–7.48, 7.55–7.59 and 8.07–8.09 (13H, 5 sets of m, aromatic H).

E. (2S,3R,4E)-2-Azido-3-benzoyloxy-1-(4,6-di-O-tert-butyloxycarbonylmethyl-α-D-galactopyranosyloxy)-4-octadecene

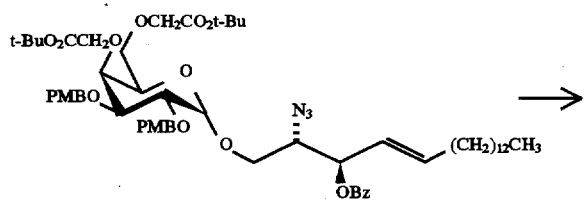

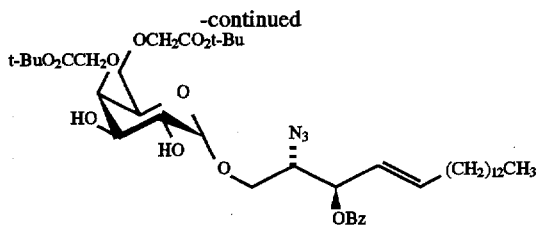

A solution of (2S,3R,4E)-2-azido-3-benzoyloxy-1-(4,6-di-O-tert-butyloxycarbonyl-methyl-2,3-di-O-para-methoxybenzyl-α-D-galactopyranosyloxy)-4-octadecene (472 mg, 0.450 mmol) in dichloromethane/water (18 mL/2 mL) was treated with 2,3-dichloro-5,6-dicyano-1,4-benzoquinone (DDQ) (306 mg, 1.35 mmol) and was allowed to stir at ~22° C. for 2 hours (reaction progression monitored by TLC). The reaction was then quenched with cold 10% aqueous sodium bicarbonate and cold 10% aqueous sodium thiosulfate and diluted with ethyl acetate. The organic layer was washed with the mixture until complete decoloration, then washed with 10% aqueous sodium bicarbonate, water (3×50 mL), brine (50 mL) and dried over anhydrous magnesium sulfate. The residue was passed through a silica gel column (25 g, 30–40% ethyl acetate/hexane) to give the title material (360 mg, >90%) as an oil.

$[\alpha]_D^{22}$: 36° (c=1.0, CHCl₃).

IR (film) $v_{max}$ (cm⁻¹): 3420 (bp, OH), 3000–2860 (CH), 2110 (N₃), 1750 and 1730 (C=O).

¹H NMR 400 MHz (CDCl₃) δ(ppm): 0.891 (3H, t, J=6.9 Hz, —CH₃) 1.253–1.46 (22H, m, —(CH₂)₁₁—), 1.489 (18H, s, tert-butyl), 2.05–2.11 (2H, m, =CH—CH₂—), 2.304 (1H, d, J=8.4 Hz, —OH), 3.572 (1H, dd, J=10.6 and 7.4 Hz, H-1), 3.615 (1H, dd, J=9.4 and 6.0 Hz, H-6'), 3.76–3.90 (3H, m, H-6', H-2' and H-3'), 3.850 (1H, d, J=3.3 Hz, H-4'), 3.895 (1H, dd, J=10.6 and 4.1 Hz, H-1), 3.93–3.97 (1H, m, H-2), 3.99, (1H, d, $J_{AB}$=16.3 Hz, —OCH₂CO—), 4.04 (1H, d, $J_{AB}$=16.4 Hz, —OCH₂CO—), 4.075 (1H, br t, J=6.7 Hz, H-5), 4.10 (1H, d, J=17.2 Hz, —OCH₂CO—), 4.37 (1H, d, J=17.2, Hz, —OCH₂CO—), 4.654 (1H, d, J=8.4 Hz, —OH), 4.925 (1H, d, J=3.8 Hz, H-1'), 5.593 (1H, dd, J=15.0 and 8.0 Hz, H-4), 5.656 (1H, dd, J=8.0 and 4.7 Hz, H-3), 5.953 (1H, dt, J=14.9 and 6.8 Hz, H-5), 7.44–7.48, 7.56–7.60, 8.05–8.07 (5H, 3 sets of m, aromatic H).

Anal. Calcd. for C₄₃H₆₉N₃O₁₂: C, 62.98; H, 8.48; N, 5.12. Found: C, 62.92; H, 8.30; N, 5.19.

F. (2S,3R,4E)-2-Azido-3-benzoyloxy-1-(2,3-di-O-benzoyl-4,6-di-O-tert-butyloxycarbonylmethyl-α-D-galactopyranosyloxy)-4-octadecene

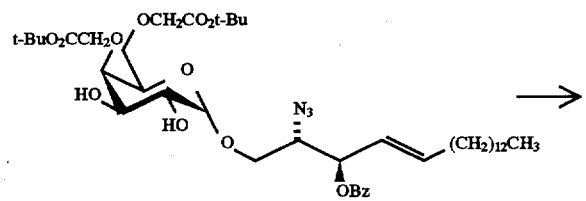

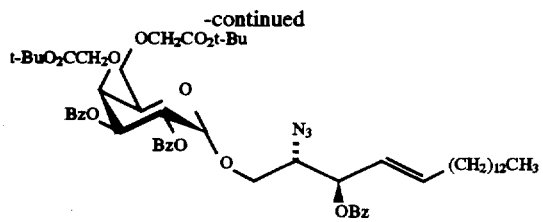
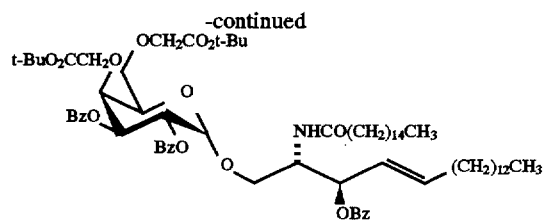

A solution of (2S,3R,4E)-2-azido-3-benzoyloxy-1-(4,6-di-O-tert-butyloxycarbonyl-methyl-α-D-galactopyranosyloxy)-4-octadecene (320 mg, 0.396 mmol) in pyridine (6 mL) was treated with dimethylaminopyridine (200 mg, 1.63 mmol) and benzoyl chloride (400 mg, 2.85 mol) at 5° C. (ice bath). The bath was removed and the mixture was allowed to stir for a 5 hours period after which it was treated again with benzoyl chloride (400 mg, 1.63 mmol). It was stirred for 16 hours, then treated with methanol (4 mL) and allowed to react for ~3-4 hours until complete reaction of benzoyl chloride. The reaction mixture was then diluted with ethyl acetate (100 mL), washed with water (5×50 mL) saturated aqueous sodium bicarbonate (50 mL) and dried over anhydrous magnesium sulfate. The residue was passed through a silica gel column (25 g, 10-15% ethyl acetate/hexane) to give the title material (367 mg, 91%) as an oil.

$[\alpha]_D^{22}$: +40° (c=1.0, CHCl$_3$).

IR (film) $v_{max}$ (cm$^{-1}$): 3000-2860 (C—H), 2100 (N$_3$), 1750 and 1725 cm$^{-1}$ (C=O).

$^1$H NMR 400 MHz (CDCl$_3$) δ(ppm): 0.841 (3H, t, J=6.8 Hz, —CH$_3$) 1.24-1.39 (22H, m, —(CH$_2$)$_{11}$—), 1.415 and 1.488 (18H, 2s, tert-butyl), 2.02-2.08 (2H, m, =CH—C H$_2$—), 3.48-3.54 (1H, m, H-1), 3.816 (1H, dd, J=9.6 and 6.5 Hz, H-6'), 3.965 (1H, dd, J=9.3 and 3.5 Hz, H-1), 3.95-4.005 (1H, m, H-2), 4.028, 4.034 (2H, part of ABq, —OCH$_2$CO—), 4.068 (1H, dd, J=9.7 and 3.8 Hz, H-6'), 4.07 (1H, d, J=16.1 Hz, —OCH$_2$CO—), 4.238 (1H, br s, H-4'), 4.30 (1H, d, J=16.1 Hz, —OCH$_2$CO—), 4.300 (1H, dd, J=11.3 and 4.9 Hz, H-6'), 5.332 (1H, d, J=3.3 Hz, H-1'), 5.539 (1H, dd, J=16.6 and 7.8 Hz, H-4), 5.558, 5.562, 5.579 (1H, m, H-3), 5.745 (1H, dd, J=10.8 and 3.3 Hz, H-2'), 5.790 (1H, dd, J=10.8 and 2.4 Hz, H-3'), 5.905 (1H, dt, J=14.3 and 6.6 Hz, H-5), 7.320-7.582, 7.98-8.02 (15H, 2 sets of m, aromatic H).

Anal. Calcd. for C$_{57}$H$_{77}$N$_3$O$_{14}$: C, 66.58; H, 7.55; N, 4.09. Found: C, 66.53; H, 7.41; N, 4.17.

G. (2S,3R,4E)-3-Benzoyloxy-2-hexadecanoylamino-1-(2,3-di-O-benzoyl-4,6-di-O-tert-butyloxycarbonylmethyl-α-D-galactopyranosyloxy)-4-octadecene

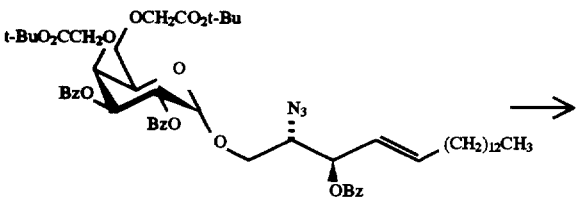

A solution of (2S,3R,4E)-2-azido-3-benzoyloxy-1-(2,3-di-O-benzoyl-4,6-di-O-tert-butyloxycarbonylmethyl-α-D-galactopyranosyloxy)-4-octadecene (367 mg, 0.361 mmol) in pyridine/water (18 mL/2 mL) was treated with a stream of H$_2$S for 5 minutes. The mixture was allowed to stir for 72 hours at c.a. 22° C. and the solvent was removed under vacuum. The last traces of pyridine were removed by co-evaporation with toluene (2×20 mL) and the residue was taken up in tetrahydrofuran (20 mL) and a 50% aqueous sodium acetate solution (2 mL). The well stirred mixture was then treated dropwise with palmitoyl chloride (0.11 mL, 0.35 mmol) in tetrahydrofuran (1 mL). After a 1 hour stirring period, the mixture was treated again with palmitoyl chloride (0.05 mL, 0.17 mmol) in tetrahydrofuran (0.5 mL) and was allowed to react for a 45 minutes period. The reaction mixture was then diluted with ethyl acetate (50 mL), washed with water (20 mL), 1M aqueous sodium bicarbonate (2×20 mL), water (20 mL), brine (20 mL) and dried over anhydrous magnesium sulfate. The residue was then passed twice on a silica gel column (40 g and 50 g, 16% to 28% ethyl acetate/hexane) to give the pure title compound (398 mg, 92%).

$[\alpha]_D^{22}$: +46° (c=1.0, CHCl$_3$).

IR (CH$_2$Cl$_2$) $v_{max}$ (cm$^{-1}$): 3440, 3370 (NH), 3060-2860 (C—H), 1745, 1725 and 1675 (C=O).

$^1$H NMR 400 MHz (CDCl$_3$) δ(ppm): 0.892 (6H, t, J=6.8 Hz, 2×CH$_3$) 1.22-1.33 (48H, m, —(CH$_2$)$_{11}$— and —(CH$_2$)$_{13}$—), 1.411 (9H, s, tert-butyl), 1.490 (9H, s, tert-butyl), 1.94-2.0 (2H, m, =CH—CH$_2$—), 2.11-2.20 (2H, m, —CH$_2$CONH—), 3.80-3.89 (3H, m, H-1 and H-6'), 3.995-4.008 (1H, d, J=5.3 Hz, part of H-1), 4.01 (1H, d, J$_{AB}$=16.4 Hz, —OCH$_2$CO—), 4.04 (1H, d, J$_{AB}$=16.4 Hz, —OCH$_2$CO—), 4.07 (1H, d, J$_{AB}$=16.1 Hz, —OCH$_2$CO—), 4.29 (1H, d, J$_{AB}$=16.1 Hz, —OCH$_2$CO—), 4.227 (1H, br s, H-4'), 4.347 (1H, br t, J=6.1 Hz, H-5'), 4.43-4.48 (1H, m, H-2), 5.240 (1H, d, J=3.0 Hz, H-1'), 5.491 (1H, dd, J=15.2 and 7.7 Hz, H-4), 5.573 (1H, br t, J=7.6 Hz, H-3), 5.69-5.75 (2H, m, H-2' and H-3), 5.771 and 5.788 (1H, two lines, J=7.0 Hz, part of dt from H-5), 6.091 (1H, d, J=9.3 Hz, —NH—), 7.28-7.33, 7.38-7.55, 7.90-8.02 (15H, 3 sets of m, aromatic H).

Anal. Calcd. for C$_{73}$H$_{109}$NO$_{15}$: C, 70.67; H, 8.86; N, 1.13. Found: C, 70.68; H, 8.72; N, 1.26.

EXAMPLE 2

(2S,3R,4E)-3-Benzoyloxy-2-hexadecanoylamino-1-
[2,3-di-O-benzoyl-4,6-di-O-carboxymethyl-α-D-
galactopyranosyloxy]-4-octadecene

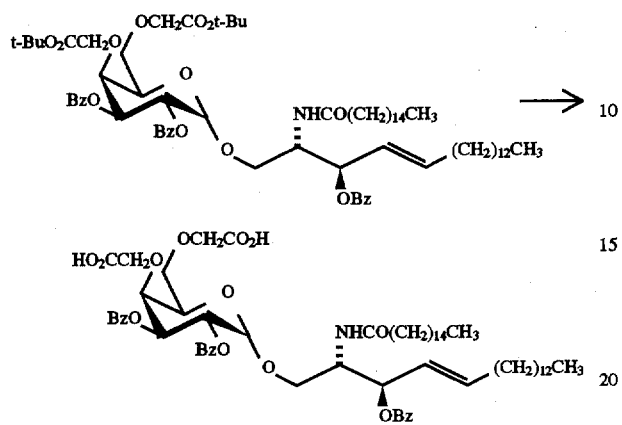

(2S,3R,4E)-3-Benzoyloxy-2-hexadecanoylamino-1-(2,3-di-O-benzoyl-4,6-di-O-tert-butyloxycarbonylmethyl-α-D-galactopyranosyloxy)-4-octadecene (248 mg, 0.200 mmol) (from Example 1) was stirred at 22° C. with a 9/1 trifluoroacetic acid/water solution (2 mL) for 2-3 minutes. The solvent was removed under high vacuum and the process was repeated again. Then the last traces of trifluoroacetic acid were azeotropically removed with toluene (2×5 mL) under high vacuum and the residue was passed through a silica gel column (35 g, 2% to 17.5% methanol/dichloromethane and 20% methanol/dichloromethane+2% water to 25% methanol/dichloromethane+4% water) to give the title material. The residue upon solvent evaporation was redissolved in dichloromethane/methanol (8:2, 20 mL) and treated at 0° C. (ice bath) with Dowex 50W8 (H⁺) resin for 1 hour to give the title material as the free carboxylic acid (172 mg, 76%) as a solid.

On a larger scale:

(2S,3R,4E)-3-Benzoyloxy-2-hexadecanoylamino-1-(2,3-di-O-benzoyl-4,6-di-O-tert-butyloxycarbonylmethyl-α-D-galactopyranosyloxy)-4-octadecene (12.1 g, 9.75 mmol) was stirred at 22° C. with a 9/1 trifluoroacetic acid/water solution (100 mL) for 15 minutes. The solution was diluted with toluene (100 mL) and concentrated under vacuum. The residue was diluted in acetonitrile (100 mL) and this mixture was evaporated to dryness. This process was repeated again three more times to give a pink solid which was recrystallized from acetonitrile and afforded the diacid of the title material (7.78 g, 71%) as a white solid.

Diacid of title compound: m.p.: 91°–92° C.

$[\alpha]_D^{22}$: +53° (c=1.0, CHCl₃).

IR (Nujol) $v_{max}$ (cm⁻¹): 3320 (NH), 1720, 1695 and 1650 (C=O).

¹H NMR 400 MHz (pyridine-d₅) δ(ppm): 0.850 (6H, t, J=6.8 Hz, 2×—CH₃) 1.23–1.35 (46H, m, —(CH₂)₁₁— and —(CH₂)₁₀—), 1.75–1.88 (2H, m, —CH₂—), 2.03–2.09 (2H, m, =CH—CH₂—), 2.400 (2H, t, J=7.3 Hz, —CH₂CONH—), 4.121 (1H, dd, J=10.7 and 7.1 Hz, H-1), 4.348 (1H, dd, J=9.5 and 6.5 Hz, H-6'), 4.439 (1H, dd, J=10.7 and 3.9 Hz, H-1), 4.54 (1H, d, $J_{AB}$=16.4 Hz, —OCH₂CO—), 4.57 (1H, d, $J_{AB}$=16.4 Hz, —OCH₂CO—), 4.632 (1H, dd, J=9.6 and 6.5 Hz, H-6'), 4.78 (1H, d, $J_{AB}$=16.2 Hz, —OCH₂CO—), 4.766 (1H, br s, H-4'), 4.818, 4.848 (1H, 2 lines of H-5'), 4.85 (1H, d, $J_{AB}$=16.2 Hz, —OCH₂CO—), 5.16–5.23 (1H, m, H-2), 5.754 (1H, br s, H-1'), 5.945 (1H, dd, J=15.5 and 7.2 Hz, H-4), 6.078 (1H, dt, J=15.4 and 6.6 Hz, H-5), 6.26 (1H, br t, H-3), 6.368 (2H, br s, H-2' and H-3'), 7.21–7.49, 8.16–8.25 (15H, 2 sets of m, aromatic H) and 8.835 (1H, d, J=8.7 Hz, —NH—).

Anal. Calcd. for C₆₅H₉₃NO₁₅: C, 69.18; H, 8.31; N, 1.24. Found: C, 68.83; H, 8.19; N, 1.30.

Preparation of sodium salt of title compound:

The diacid (10.0 g, 8.86 mmol) from the above procedure was dissolved in freshly distilled dioxane (200 mL) and water (100 mL) was added followed by an aqueous sodium bicarbonate solution (1.8 g in 30 mL). This unclear solution was stirred for 15 minutes (pH~8.5) and concentrated. The residue was diluted in hexane (100 mL) and evaporated to dryness. This process was repeated two more times to give a solid which was dissolved in hexane (~200 mL). The solution was filtered (excess sodium bicarbonate) and concentrated. The residue was dissolved in dioxane and lyophilized to afford the sodium salt of the title compound (10.3 g, 99%) as a white fluffy solid.

$[\alpha]_D^{22}$: +72° (C=1.0, CHCl₃).

IR (film) $v_{max}$ (cm⁻¹): 3700–3100 (NH), 1920,1850 (C—H), 1720, 1605 (C=O).

¹H NMR 400 MHz (pyridine-d₅) δ(ppm): 0.85–0.88 (6H, m, 2×—CH₃), 1.25 (46H, br s, —(CH₂)₁₁— and —(CH₂)₁₂—), 1.77–1.89 (2H, m, —CH₂—), 2.05 (2H, m, =CH—CH₂—), 2.36 (2H, m, —NHCOCH₂—), 3.57–3.60 (1H, m, H-1), 3.73 (1H, d, J=13.4 Hz, —OCH₂CO—), 4.03–4.31 (7H, m, H-4', H-5', H-6', H-1 and —OCH₂CO—), 4.62 (1H, d, J=13.3 Hz, —OCH₂CO—), 5.08 (1H, m, H-2), 5.91 (1H, dd, J=15.3 and 7.4 Hz, H-4), 6.01 (1H, d, J=3.9 Hz, H-1'), 6.06 (1H, dt, J=15.3 and 6.8 Hz, H-5), 6.14 (1H, br d, J=10.6 Hz, H-3'), 6.21 (1H, br t, H-3), 6.42 (1H, br d, H-2'), 7.16–7.19, 7.28–7.32, 7.39–7.43, 7.91–7.93, 8.18–8.25 (15H, 5 sets of m, 3×—C₆H₅), 8.97 (1H, d, J=8.1 Hz, —NH—).

EXAMPLE 3

(2S,3R,4E)-3-Benzoyloxy-2-azido-1(2,3-di-O-benzoyl-4,6-di-O-carboxymethyl-α-D-galactopyranosyloxy)-4-octadecene

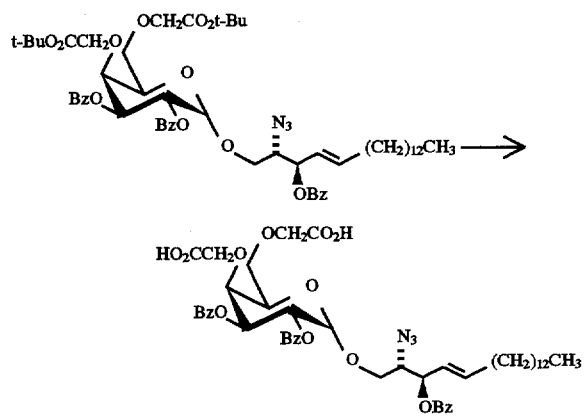

A solution of (2S,3R,4E)-2-Azido-3-benzoyloxy-1-(2,3-di-O-benzoyl-4,6-di-O-tert-butyloxycarbonylmethyl-α-D-galactopyranosyloxy)-4-octadecene described in Example 1-F (0.145 g, 0.14 mmol) in aqueous trifluoroacetic acid (90%, 3 mL) was stirred at 22° C. during 5 minutes. The solvents were evaporated under vacuum and the residue was co-evaporated with toluene (3×5 mL) and then dissolved in a mixture of dioxane/water (1:1, 10 mL). This mixture was stirred at 22° C. for 30 minutes. The solvents were evaporated under vacuum and the residue was co-evaporated again with toluene (4×10 mL). The residue was purified by silica gel plates (chloroform/methanol/water 75:25:2). The residue upon solvent evaporation was redissolved in methylene chloride/methanol (1:1, 40 mL) and treated at 0° C. (ice bath) with Dowex 50W X8 ($H^+$) resin for 40 minutes to give the title compound (0.076 g, 59%).

IR ($CH_2Cl_2$) $v_{max}$ ($cm^{-1}$): 2910, 2850 (C—H), 2100 ($N_3$), 1720 (C=O).

$^1$H NMR 400 MHz (pyridine-$d_5$) δ(ppm): 0.85 (3H, t, J=6.8 Hz, —$CH_3$), 1.23–1.36 (22H, m, —($CH_2)_{11}$—), 2.06 (2H, qa, J=6.9 Hz, =CH—$CH_2$—), 3.89 (1H, dd J=8.3 and 10.6 Hz, H-1), 4.33–4.38 (2H, m, H-1 and H-6'), 4.42 (1H, qi, J=4.0 Hz, H-2), 4.52 (1H, d, $J_{AB}$=16.4 Hz, —$OCH_2$CO—), 4.56 (1H, d, $J_{AB}$=16.4 Hz, —$OCH_2$CO—), 4.65 (1H, dd, J=9.6 and 6.0 Hz, H-6'), 4.80 (1H, d, $J_{AB}$=16.1 Hz, —$OCH_2$CO—), 4.78–4.83 (1H, m, H-5'), 4.83 (1H, br s, H-4'), 4.88 (1H, d, $J_{AB}$=16.1 Hz, —$OCH_2$CO—), 5.80 (1H, d, J=3.2 Hz, H-1'), 5.84 (1H, dd, J=15.4 and 7.6 Hz, H-4), 6.04 (1H, dd, J=7.6 and 4.0 Hz, H-3), 6.08 (1H, dt, J=15.4 and 6.9 Hz, H-5), 6.41 (1H, dd, $J_{AB}$=10.8 and $J_{AX}$=3.2 Hz, H-2'), 6.45 (1H, dd, $J_{AB}$=10.8 and $J_{BX}$=2.3 Hz, H-3'), 7.22–7.29, 7.34–7.42, 7.46–7.51 and 8.21–8.27 (15H, 4 sets of m, 3×—$C_6H_5$).

EXAMPLE 4

(2S,3R,4E)-2-Hexadecanoylamino-3-benzoyloxy-1-(4,6-di-O-tert-butyloxycarbonylmethyl-2,3-di-O-benzyl-α-D-galactopyranosyloxy)-4-octadecene A. Ethyl 4,6-di-O-benzylidene-2,3-di-O-benzyl-1-thio-β-D-galactopyranoside

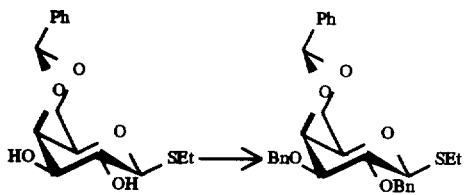

A solution of ethyl 4,6-di-O-benzylidene [Nilsson, et al., J. Carbohy. Chem. 10(6), 1023 (1991)] (3.00 g, 9.60 mmol), in tetrahydrofuran (25 mL) was added under argon to a suspension of sodium hydride (50% in mineral oil, 1.8 g, 37.5 mmol, previously washed with hexane). The mixture was allowed to stir for ~15 minutes after which benzyl bromide (5.2 mL, 43.7 mmol) followed by dimethylformamide (20 mL) were added in slowly. The reaction mixture was allowed to react at 22° C. for ~1 hour, cooled down to 5° C. and treated slowly with cold 1M aqueous sodium bicarbonate solution. The crude aqueous mixture was extracted with ethyl acetate (4×100 mL). The organic extracts were combined, washed with 1M aqueous sodium bicarbonate (2×100 mL), water (3×100 mL), brine (100 mL) and dried over anhydrous magnesium sulfate. The residue upon solvent evaporation was crystallized form ethyl acetate/hexane to give the title compound (3.50 g, 75%).

$^1$H NMR 200 MHz (CDCl$_3$) δ(ppm): 1.33 (3H, t, J=6.4 Hz, —$CH_3$), 2.69–2.88 (2H, m, —$CH_2$S—), 3.36 (1H, br s, H-5), 3.59 (1H, dd, J=9.1 and 3.4 Hz, H-3), 3.89 (1H, t, J=9.4 Hz, H-2), 3.96 (1H, dd, J=12.3 and 1.8 Hz, H-6), 4.16 (1H, d, J=3.4 Hz, H-4), 4.31 (1H, dd, J=12.3 and 1.4 Hz, H-6), 4.44 (1H, d, J=9.6 Hz, H-1), 4.76 (2H, br s, —$CH_2$Ph), 4.83 (1H, d, $J_{AB}$=10.2 Hz, —$CH_2$Ph), 4.87 (1H, d, $J_{AB}$=10.2 Hz, —$CH_2$Ph), 5.48 (1H, s, —O—CH—O—), 7.28–7.57 (15H, m, 3×—$C_6H_5$).

B. Ethyl 2,3-di-O-benzyl-1-thio-β-D-galactopyranoside

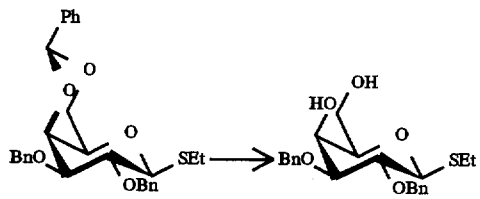

A solution of ethyl 4,6-di-O-benzylidene-2,3-di-O-benzyl-1-thio-β-D-galactopyranoside (0.625 g, 1.28 mmol) in dichloromethane (25 mL) was treated with trifluoroacetic acid (50% aqueous, 0.2 mL) and (90% aqueous, 0.2 mL) at 22° C. This mixture was stirred for ~1 hour and trifluoroacetic acid (90% aqueous, 0.2 mL) was added again. The same procedure was repeated with trifluoroacetic acid (50% aqueous, 0.2 mL) until reaction completion by TLC. Solid sodium bicarbonate was added to this mixture (pH~7) and the solution was filtered and washed with methylene chloride (~50 mL). After addition of triethylamine, the solution was evaporated under vacuum. The residue was purified by silica gel column chromatography (30 g, 30% to 100% ethyl acetate/hexane) and gave the title compound (0.430 g, 83%).

$^1$H NMR 400 MHz (CDCl$_3$) δ(ppm): 1.33 (3H, t, J=7.5 Hz, —$CH_3$), 2.35 (2H, br s, 2×—OH), 2.77 (2H, m, —$SCH_2$—), 3.49 (1H, br t, H-5), 3.57 (1H, dd, J=9.0 and 3.3 Hz, H-3), 3.68 (1H, t, J=9.4 Hz, H-2), 3.81 (1H, dd, J=11.8 and 4.4 Hz, H-6), 3.97 (1H, dd, J=11.8 and 6.7 Hz, H-6), 4.06 (1H, br d, J=3.3 Hz, H-4'), 4.44 (1H, d, J=9.6 Hz, H-1), 4.73 (2H, s, —$CH_2$Ph), 4.78 (1H, d, $J_{AB}$=10.3 Hz, —$CH_2$Ph), 4.90 (1H, d, $J_{AB}$=10.3 Hz, —$CH_2$Ph), 7.28 (10H, m, 2×—$C_6H_5$).

C. Ethyl 2,3di-O-benzyl-4,6-di-O-tert-butyloxycarbonylmethyl-1-thio-β-D-galactopyranoside

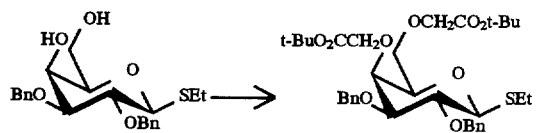

Ethyl 2,3-di-O-benzyl-1-thio-β-D-galactopyranoside (1.30 g, 3.21 mmol) was reacted by the general procedure as described in Example 1-C and afforded the title compound (1.50 g, 77%).

$^1$H NMR 400 MHz (CDCl$_3$) δ(ppm): 1.31 (3H, t, J=7.4 Hz, —$CH_3$), 1.46 and 1.49 (18H, 2s, 2×tert-butyl), 2.76 (2H, m, —$SCH_2$—), 3.55 (1H, dd, J=9.3 and 2.5 Hz, H-3), 3.63 (1H, t, J=6.0 Hz, H-5), 3.74 (1H, dd, J=9.8 and 6.0 Hz, H-6), 3.88 (1H, t, J=9.5 Hz, H-2), 3.97 (1H, br d, J=2.5 Hz, H-4), 4.00 (1H, dd, J=9.8 and 6.0 Hz, H-6), 4.05 (2H, br s, —$OCH_2$CO—), 4.28 (1H, d, $J_{AB}$16.6 Hz, —$OCH_2$CO—), 4.36 (1H, d, $J_{AB}$=16.6 Hz, —$OCH_2$CO—), 4.43 (1H, d, J=9.6 Hz, H-1), 4.73 (2H, s, —$CH_2$Ph), 4.76 (1H, d, $J_{AB}$=10.2 Hz, —$CH_2$Ph), 4.90 (1H, d, $J_{AB}$=10.2 Hz, —$CH_2$Ph), 7.29–7.40 (10 H, 2×—$C_6H_5$).

D. (2S,3R,4E)-2-Azido-3-benzoyloxy-1-(4,6-di-O-tert-butyloxy-carbonylmethyl-2,3-di-O-benzyl-α-D-galactopyranosyloxy)-4-octadecene and (2S,3R,4E)-2-azido-3-benzoyloxy-1-(4,6-di-O-tert-butyloxycarbonylmethyl-2,3-di-O-benzyl-β-D-galactopyranosyloxy)-4-octadecene

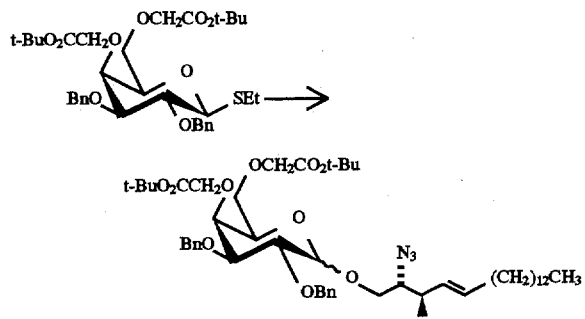

Ethyl 2,3-di-O-benzyl-4,6-di-O-tert-butyloxycarbonylmethyl-1-thio-β-D-galactopyranoside (0.555 g, 0.88 mmol) and (2S,3R,4E)-2-azido-3-benzoyloxy-4-octadecenol (0.239 g, 0.55 mmol) were reacted by the general procedure as described in Example 1-D using methylene chloride/benzene (1:1) as solvents instead of dioxane and afforded the α-anomer (0.174 g, 31%) and the β-anomer (0.365 g, 66%) of the title compound as yellow oils.

α-anomer:

IR (CH$_2$Cl$_2$) ν$_{max}$ (cm$^{-1}$) 3060, 2990, 2930 (CH), 2100 (N$_3$), 1745 and 1720 (C=O).

$^1$H NMR 400 MHz (CDCl$_3$) δ(ppm) (α-anomer): 0.89 (3H, t, J=6.9 Hz, —CH$_3$), 1.25–1.42 (22H, m, —(CH$_2$)$_{11}$—), 1.44 and 1.47 (18H, 2s, 2×tert-butyl), 2.07 (2H, qa, J=6.9 Hz, =CH—CH$_2$—), 3.53 (1H, dd, J=10.8 and 8.0 Hz, H-1), 3.68 (1H, dd, J=9.5 and 6.4 Hz, H-6'), 3.81 (1H, dd, J=10.8 and 4.1 Hz, H-1), 3.90–4.04 (7H, m, —OCH$_2$CO—, H-6', H-5', H-4', H-3' and H-2), 4.09 (1H, dd J=10.2 and 3.6 Hz, H-2'), 4.28 (1H, d, J$_{AB}$=16.5 Hz, —OCH$_2$CO—), 4.32 (1H, d, J$_{AB}$=16.5 Hz, —OCH$_2$CO—), 4.68 (1H, d, J$_{AB}$=11.9 Hz, —CH$_2$Ph), 4.70 (1H, d, J=11.7 Hz, —CH$_2$Ph), 4.78 (1H, d, J$_{AB}$=11.9 Hz, —CH$_2$Ph), 4.83 (1H, d, J$_{AB}$=11.7 Hz, —CH$_2$Ph), 4.87 (1H, d, J=3.6 Hz, H-1'), 5.57 (1H, dd, J=14.7 and 7.8 Hz, H-4), 5.62 (1H, dd, J=7.8 and 4.1 Hz, H-3), 5.92 (1H, dt, J=14.7 and 6.9 Hz, H-5), 7.22–7.38, 7.44–7.48, 7.56–7.60, 8.06–8.08 (15H, 4 sets of m, 3×—C$_6$H$_5$).

β-anomer:

IR (CH$_2$Cl$_2$) ν$_{max}$ (cm$^{-1}$): 3060, 2990, 2930 (CH), 2100 (N$_3$), 1745 and 1720 C=O).

$^1$H NMR 400 MHz (CDCl$_3$) δ(ppm): 0.89 (3H, t, J=6.8 Hz, —CH$_3$), 1.24–1.33 (22H, m, —(CH$_2$)$_{11}$—), 1.46 and 1.48 (18H, 2s, 2×tert-butyl), 2.03 (2H, qa, J=6.8 Hz, =CH—CH$_2$—), 3.51 (1H, dd, J=9.7 and 2.7 Hz, H-3'), 3.58–3.62 (2H, m, H-2 and H-1), 3.73 (1H, dd, J=9.6 and 6.0 Hz, H-6'), 3.87 (1H, dd, J=9.7 and 7.6 Hz, H-2'), 3.93 (1H, br d, H-4'), 3.95–4.06 (5H, m, —OCH$_2$CO—, H-5', H-6' and H-1), 4.30 (1H, d, J$_{AB}$=16.5 Hz, —OCH$_2$CO—), 4.36 (1H, d, J$_{AB}$=16.5 Hz, —OCH$_2$CO—), 4.37 (1H, d, J=7.6 Hz, H-1'), 4.72 (1H, d, J$_{AB}$=11.7 Hz, —CH$_2$Ph), 4.75 (1H, d, J$_{AB}$=11.7 Hz, —CH$_2$Ph), 4.79 (1H, d, J=11.2 Hz, —CH$_2$Ph), 4.94 (1H, d, J=11.2 Hz, —CH$_2$Ph), 5.55 (1H, dd, J=15.3 and 7.9 Hz, H-4), 5.68 (1H, dd, J=7.9 and 3.2 Hz, H-3), 5.88 (1H, dt, J=15.3 and 6.8 Hz, H-5), 7.24–7.40, 7.44–7.48, 7.56–7.60 and 8.07–8.09 (13H, 4 sets of m, aromatic H).

E. (2S,3R,4E)-2-Hexadecanoylamino-3-benzoyloxy-1-(4,6-di-O-tert-butyloxycarbonylmethyl-2,3-di-O-benzyl-α-D-galactopyranosyloxy)-4-octadecene

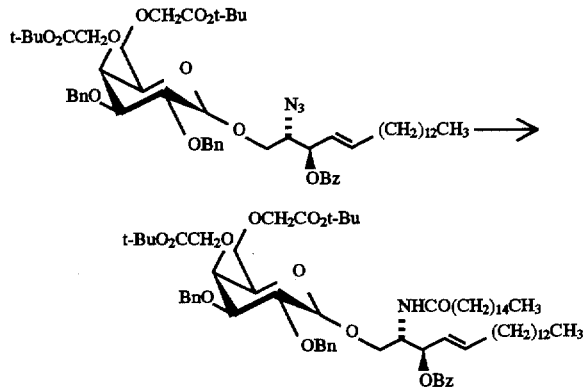

(2S,3R,4E)-2-Azido-3-benzoyloxy-1-(4,6-di-O-tert-butyloxycarbonylmethyl-2,3-di-O-benzyl-α-D-galactopyranoside)-4-octadecene (0.390 g, 0.39 mmol) was reacted by the general procedure as described in Example 1-G and afforded the title compound (0.405 g, 86%) as a white solid.

IR (CH$_2$Cl$_2$) ν$_{max}$ (cm$^{-1}$): 3060, 2930, 2860 (C—H), 1745, 1720, 1675 (C=O).

$^1$H NMR 400 MHz (CDCl$_3$) δ(ppm): 0.89 (6H, br t, 2×—CH$_3$), 1.22–1.41 (46H, m, —(CH$_2$)$_{11}$— and —(CH$_2$)$_{12}$—), 1.44 and 1.47 (18H, 2s, 2×tert-butyl), 1.53–1.66 (2H, m, —CH$_2$—), 1.97 (2H, qa, J=6.9 Hz, =CH—CH$_2$—), 2.11 (2H, m, —CH$_2$CONH—), 3.67 (1H, dd, J=11.6 and 3.1 Hz, H-1), 3.74 (1H, dd, J=7.5 and 9.8 Hz, H-6'), 3.86 (1H, dd, J=10.1 and 2.5 Hz, H-3'), 3.92–4.01 (4H, m, H-6', H-1 and —OCH$_2$CO—), 4.03 (1H, br t, H-4'), 4.07 (1H, dd, J=10.1 and 3.6 Hz, H-2'), 4.13 (1H, br dd, H-5'), 4.28 (1H, d, J$_{AB}$=16.6 Hz, —OCH$_2$CO—), 4.31 (1H, d, J$_{AB}$=16.6 Hz, —OCH$_2$CO—), 4.42 (1H, m, H-2), 4.65 (1H, d, J$_{AB}$=11.7 Hz, —OCH$_2$CO—), 4.67 (1H, d, J$_{AB}$=11.4 Hz, —OCH$_2$CO—), 4.71 (1H, d, J$_{AB}$=11.7 Hz, —OCH$_2$CO—), 4.77 (1H, d, J$_{AB}$=11.4 Hz, —OCH$_2$CO—), 4.78 (1H, d, J=3.6 Hz, H-1'), 5.49 (1H, dd, J=15.3 and 7.9 Hz, H-4), 5.63 (1H, t, J=7.9 Hz, H-3), 5.82 (1H, dt, J=15.3 and 6.9 Hz, H-5), 6.37 (1H, d, J=9.4 Hz, —NH—), 7.21–7.45, 7.54–7.58 and 8.02–8.04 (15H, 3 sets of m, 3×—C$_6$H$_5$).

EXAMPLE 5

(2S,3R,4E)-2-Hexadecanoylamino-3-benzoyloxy-1-(4,6-di-O-carboxymethyl-2,3-di-O-benzyl-α-D-galactopyranosyloxy)-4-octadecene

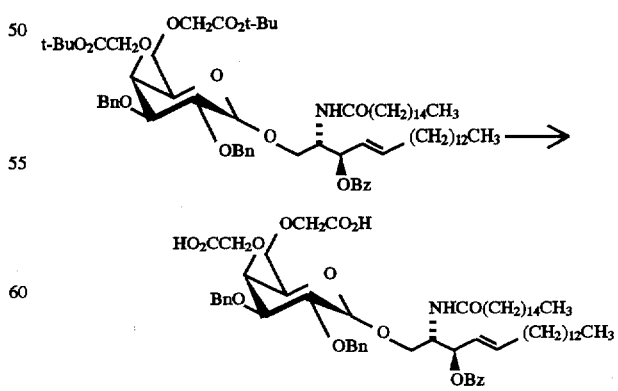

(2S,3R,4E)-2-Hexadecanoylamino-3-benzoyloxy-1-(4,6-di-O-tert-butyloxycarbonylmethyl-2,3-di-O-benzyl-α-D- galactopyranoside)-4-octadecene (0.405 g, 0.33 mmol) was reacted by the general procedure as described in Example 2 and afforded the title compound (0.295 g, 81%) as a white solid.

IR (nujol) $v_{max}$ (cm$^{-1}$): 3200 (NH), 2920, 2860 (C—H), 1725, 1640 (C=O).

$^1$H NMR 400 MHz (pyridine-d$_5$) δ(ppm): 0.86 (6H, t, 2x—CH$_3$), 1.21-1.46 (46H, m, —(CH$_2$)$_{11}$— and —(CH$_2$)$_{12}$—), 1.87 (2H, m, —CH$_2$—), 2.04 (2H, qa, J=6.8 Hz, =CH—CH$_2$—), 2.51 (2H, m, —CH$_2$CONH—), 4.12 (1H, dd, J=10.6 and 5.5 Hz, H-1), 4.26 (1H, dd, J=10.1 and 2.7 Hz, H-3'), 4.32-4.37 (2H, m, H-6' and H-1), 4.41 (1H, br s, H-4'), 4.49 (1H, dd, J=10.1 and 3.6 Hz, H-2'), 4.55 (1H, d, J$_{AB}$=9.2 Hz, —OCH$_2$CO—), 4.57 (1H, d, J$_{AB}$=9.2 Hz, —OCH$_2$CO—), 4.58-4.63 (2H, m, H-6' and H-5'), 4.75 (2H, s, —OCH$_2$CO—), 4.81 (1H, d, J$_{AB}$=11.7 Hz, —CH$_2$Ph), 4.87 (1H, d, J$_{AB}$=11.7 Hz, —CH$_2$Ph), 4.88 (2H, s, —OCH$_2$CO—), 5.20 (1H, m, H-2), 5.34 (1H, d, J=3.6 Hz, H-1'), 5.94 (1H, dd, J=15.4 and 7.2 Hz, H-4), 6.07 (1H, dt, J=15.4 and 6.8 Hz, H-5), 6.30 (1H, t, J=7.2 Hz, H-3), 7.25-7.36, 7.40-7.46, 7.48-7.56 and 8.24-8.26 (16H, 4 sets of m, 3x—C$_6$H$_5$ and —NH—).

EXAMPLE 6

(2S,3R,4E)-3-Benzoyloxy-2-azido-1-(2,3-di-O-benzoyl-4,6-di-O-tert-butyloxycarbonylmethyl-α-D-galactopyranosyloxy)-4-undecene A. (2S,3R,4E)-1,3-O-Benzylidene-4-undecene-1,2,3-triol

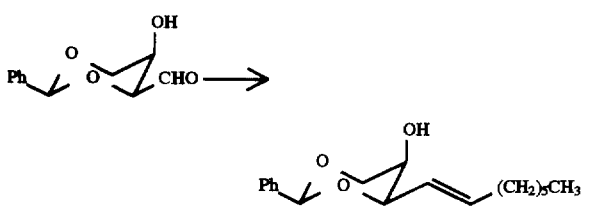

Reaction of 2,4-O-benzylidene-D-threose [P. Zimmermann and R. R. Schmidt, Liebigs Ann. Chem. 1988, 663-667] (23.5 g, 0.112 mol) with n-heptyltriphenylphosphonium bromide [C. F. Hauser, T. W. Brooks, M. L. Miles, M. A. Raymond and G. B. Butler, J. Org. Chem., 28, 372 (1963)] (64 g, 0.145 mol) and phenyllithium (0.393 mol) using the methodology described by R. R. Schmidt gave 15.14 g (46%) of the title material as a white solid after chromatography.

m.p.=50°-52° C.

[α]$_D^{22}$: -2° (c=0.5, CHCl$_3$).

IR (KBr) $v_{max}$ (cm$^{-1}$): 3380 (OH).

$^1$H NMR 400 MHz (CDCl$_3$) δ(ppm): 0.89 (3H, t, J=6.9 Hz, —CH$_3$), 1.2-1.45 (8H, m, —(CH$_2$)$_4$—), 2.09 (2H, m, =CHCH$_2$—), 2.64 (1H, d, J=10.4 Hz, —OH), 3.54 (1H, m, H-2), 4.09 (1H, dd, J=1.3 and 11.8 Hz, H-1), 4.25 (1H, dd, J=1.9 and 11.8 Hz, H-1), 4.42 (1H, br d, J=6 Hz, H-3), 5.63 (1H, s, —O—CH—O—), 5.67 (1H, m, J=15.6 Hz, H-4), 5.88 (1H, m, J=15.6 Hz, H-5), 7.38 and 7.53 (3H and 2H, 2m, —C$_6$H$_5$).

Anal. Calcd. for C$_{18}$H$_{26}$O$_3$: C, 74.45; H, 9.02. Found: C, 74.47; H, 8.87.

B. (2S,3R,4E)-2-Azido-1,3-O-benzylidene-4-undecene-1,3diol

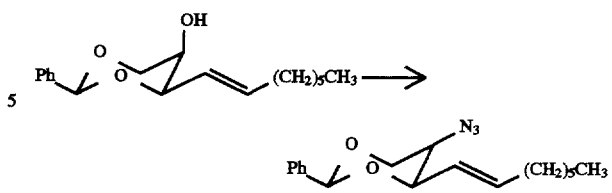

A solution of (2S,3R,4E)-1,3-O-benzylidene-4-undecene-1,2,3-triol (9.20 g, 31.7 mmol) in dichloromethane (90 mL) was cooled to -15° C. and treated successively with pyridine (6.3 mL, 77.9 mmol) and triflic anhydride (6.57 mL, 39.01 mmol). After 15 minutes at -15° C., a suspension of powdered sodium azide (9.5 g, 146 mmol) in N,N-dimethylformamide (310 mL) was added and the resulting mixture was stirred at 22° C. for 5 hours. The reaction mixture was then diluted with hexane (300 mL) and cold water (200 mL). The aqueous phase was extracted with hexane (2×100 mL) and the combined organic extracts were washed with brine and dried over anhydrous magnesium sulfate. Evaporation of the solvent gave an oil which was diluted in dry methanol (150 mL), treated with p-toluenesulfonic acid (0.250 g) and stirred at 5° C. for 1 hour. p-Toluenesulfonic acid (0.100 g) was added again and the mixture was stirred for another hour. Solid sodium bicarbonate (~2 g) was added and after 15 minutes, the solution was filtered and concentrated under vacuum. Chromatography of the residual oil on silica gel (5×12 cm, hexane/toluene 1:1) gave the title compound (5.32 g, 53%) as an oil.

[α]$_D^{22}$: -17° (c=1.0, CHCl$_3$).

IR (NaCl, film) $v_{max}$ (cm$^{-1}$): 2105 (N$_3$).

$^1$H NMR 200 MHz (CDCl$_3$) δ(ppm): 0.89 (3H, t, J=6.5 Hz, —CH$_3$), 1.2-1.5 (8H, m, —(CH$_2$)$_4$—), 2.11 (2H, m, =CHCH$_2$—) 3.46 (1H, ddd, J=4.7 Hz, 9.0 and 10.7 Hz, H-2), 3.62 (1H, dd, J=10.7 and 10.7 Hz, H-1), 4.05 (1H, dd, J=7.4 and 9.0 Hz, H-3), 4.34 (1H, dd, J=4.7 and 10.7 Hz, H-1), 5.49 (1H, s, —O—CH—O—), 5.59 (1H, ddt, J=7.4, 15.5 and 1.3 Hz, H-4), 6.00 (1H, dt, J=6.8 and 15.5 Hz, H-5), 7.3-7.5 (5H, m, —C$_6$H$_5$).

Anal. Calcd. for C$_{18}$H$_{25}$N$_3$O$_2$: C, 68.54; H, 7.99; N, 13.32. Found: C, 68.59; H, 7.49; N, 13.41.

C. (2S,3R,4E)-2-Azido-4-undecene-1,3-diol

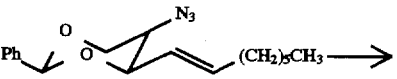

A solution of (2S,3R,4E)-2-azido-1,3-O-benzylidene-4-undecene-1,3-diol (5.32 g, 16.86 mmol) in a mixture of methylene chloride (50 mL) and methanol (200 mL) was treated with p-toluenesulfonic acid (0.170 g) and the resulting mixture was stirred at 22° C. for 36 hours. The resulting mixture was then stirred with sodium bicarbonate (0.5 g) filtered and evaporated. Chromatography of the residue on silica gel (5×11 cm, toluene/ethyl acetate 7:3) gave the title material (3.48 g, 91%) as a white solid.

m.p.=29°-30° C. (hexane). [α]$^{22}_D$: -51° (c=1.0, CHCl$_3$).

IR (NaCl, film) $v_{max}$ (cm$^{-1}$): 3350 (OH), 2100 (N$_3$).

$^1$H NMR 200 MHz (CDCl$_3$) δ(ppm): 0.88 (3H, t, J=6.5 Hz, —CH$_3$), 1.2-1.7 (8H, m, —(CH$_2$)$_4$—), 2.1 (4H, m, =CHC$\underline{H}_2$— and 2×—OH), 3.51 (1H, dt, J=5.3 and 5.3 Hz, H-2), 3.78 (2H, br d, CH$_2$-1), 4.25 (1H, br t, H-3), 5.53 (1H, ddt, J=15.4, 7.2 and 1.3 Hz, H-4), 5.82 (1H, dt, J=15.4 and 6.6 Hz, H-5).

Anal. calcd. for C$_{11}$H$_{21}$N$_3$O$_2$: C, 58.12; H, 9.31; N, 18.49. Found: C, 58.21; H, 9.22; N, 18.27.

D. (2S,3R,4E)-2-Azido-1-O-t-butyldimethylsilyl-4-undecene-1,3-diol

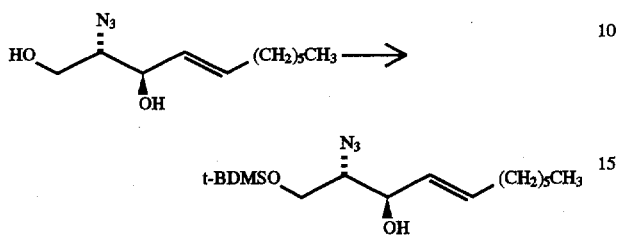

A solution of (2S,3R,4E)-2-azido-4-undecene-1,3-diol (2.74 g, 12.06 mmol) in pyridine (30 mL) was treated with tert-butyldimethylsilyl chloride (2.18 g, 14.4 mmol) and the resulting mixture was stirred at 22° C. for 18 hours. Methanol (2 mL) was added and the solvent was evaporated under vacuum. The residue was diluted with ethyl acetate (300 mL) and this solution was washed with cold 0.1N hydrochloric acid and saturated aqueous sodium bicarbonate. The organic layer was dried over anhydrous magnesium sulfate, filtered and concentrated. The residue was purified by silica gel chromatography (5×11 cm, 0–2% ethyl acetate/toluene) and gave the title compound (3.96 g, 96%) as an oil.

$[\alpha]_D^{22}$: −3.5° (c=1.0, CHCl$_3$).

IR (NaCl, film) $v_{max}$ (cm$^{-1}$): 3440 (OH), 2100 (N$_3$).

$^1$H NMR 200 MHz (CDCl$_3$) δ(ppm): 0.09 (6H, s, —SiCH$_3$), 0.9 (12H, br s, —Si-t-Bu and —CH$_3$), 1.2–1.5 (8H, m, —(CH$_2$)$_4$—), 2.06 (2H, m, =CHC$\underline{H}_2$—), 2.32 (1H, d, J=5.0 Hz, —OH), 3.42 (1H, m, H-2), 3.80 (2H, m, CH$_2$-1), 4.21 (1H, m, H-3), 5.49 (1H, ddt, J=15.4, 7.0 and 1.3 Hz, H-4), 5.78 (1H, m, H-5).

Anal. calcd. for C$_{17}$H$_{35}$N$_3$O$_2$Si: C, 59.78, H, 10.33; N, 12.30. Found: C, 59.71; H, 10.24; N, 12.16.

E. (2S,3R,4E)-2-Azido-3-benzoyloxy-1-O-t-butyldimethylsilyl-4-undecene-1-ol

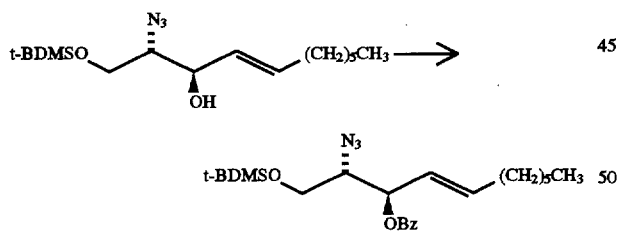

A solution of (2S,3R,4E)-2-azido-1-O-t-butyldimethylsilyl-4-undecene-1,3-diol (3.96 g, 11.6 mmol) in a mixture of toluene (30 mL) and pyridine (30 mL) was treated at 0°–5° C. with benzoyl chloride (2.7 mL, 23.2 mmol) and a crystal of 4-dimethylaminopyridine and the resulting mixture was stirred at 22° C. for 5 hours and at 0°–5° C. for 18 hours. Methanol (3 mL) was added and the solvent was evaporated under vacuum. The residue was diluted with ethyl acetate (400 mL), washed with cold 0.1N hydrochloric acid, saturated sodium bicarbonate, brine and dried over magnesium sulfate. Evaporation of the solvent gave an oil (6.02 g) which was used as such for the next step.

IR (NaCl, film) $v_{max}$ (cm$^{-1}$): 2100 (N$_3$), 1725 (C=O ester).

$^1$H NMR 200 MHz (CDCl$_3$) δ(ppm): 0.07 (6H, s, —SiCH$_3$), 0.86 (3H, t, J=6.7 Hz, —CH$_3$), 0.91 (9H, s, —Si-t-Bu), 1.2–1.5 (8H, m, —(CH$_2$)$_4$—), 2.08 (2H, m, =CHC$\underline{H}_2$—), 3.6–3.9 (3H, m, CH$_2$-1 and H-2), 5.5–5.7 (2H, m, H-3 and H-4), 5.92 (1H, dt, J=6.7 and 14.4 Hz, H-5), 7.45, 7.56 and 8.06 (2H, 1H and 2H, 3 m, —C$_6$H$_5$).

F. (2S,3R,4E)-2-Azido-3-benzoyloxy-4-undecene-1-ol

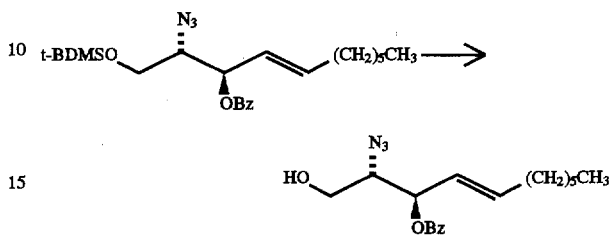

A solution of crude (2S,3R,4E)-2-azido-3-benzoyloxy-1-O-t-butyl dimethylsilyl-4-undecene-1-ol (6.02 g) in tetrahydrofuran (100 mL) cooled to 0°–5° C. and treated successively with acetic acid (4 mL) and a 1M solution of tetrabutylammonium fluoride (34.8 mL, 34.8 mmol) in tetrahydrofuran.

After 6 hours at 22° C., the reaction mixture was diluted with ethyl acetate (400 mL), washed with a saturated solution of sodium bicarbonate, brine and dried over anhydrous magnesium sulfate. Evaporation of the solvent under vacuum gave an oil which was purified by silica gel chromatography (5×12 cm, 10% ethyl acetate/toluene) to afford the title compound (3.26 g, 95%) as an oil.

$[\alpha]_D^{22}$: −65° (c=1.0, CHCl$_3$).

IR (NaCl, film) $v_{max}$ (cm$^{-1}$): 2105 (N$_3$), 1720 (C=O of ester). $^1$H NMR 400 MHz (CDCl$_3$) δ(ppm): 0.87 (3H, t, J=6.8 Hz, —CH$_3$), 1.2–1.4 (8H, m, —(CH$_2$)$_4$—), 2.09 (2H, m, =CHC$\underline{H}_2$—), 3.63 (1H, dd, J=11.7 and 7.1 Hz, H-1), 3.76 (1H, dd, J=11.7 and 4.0 Hz, H-1), 3.81 (1H, m, H-2), 5.58–5.65 (2H, m, H-3 and H-4), 5.95 (1H, m, H-5), 7.44, 7.59 and 8.06 (2H, 1H and 2H, 3 m, —C$_6$H$_5$).

Anal. Calcd. for C$_{18}$H$_{25}$N$_3$O$_3$.0.5 H$_2$O: C, 63.51; H, 7.70; N, 12.34. Found: C, 63.45; H, 7.45; N, 12.29.

G. (2S,3R,4E)-3-Benzoyloxy-2-azido-1-(2,3-di-O-para-methoxybenzyl-4,6-di-O-tert-butyloxycarbonylmethyl-α-D-galactopyranosyloxy)-4-undecene and (2S,3R,4E)-3-benzoyloxy-2-azido-1-(2,3-di-O-para-methoxybenzyl-4,6-di-O-tert-butyloxycarbonylmethyl-β-D-galactopyranosyloxy)-4-undecene

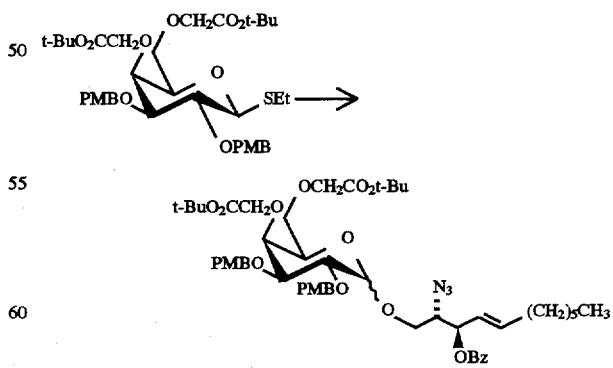

Ethyl 4,6-di-O-tert-butyloxycarbonylmethyl-2,3-di-O-para-methoxybenzyl-1-thio-β-D-galactopyranoside described in Example 1-C (7.5 g, 10.82 mmol) and (2S,3R,4E)-3-benzoyloxy-2-azido-4-undecene-1-ol (3.0 g, 9.04 mmol) were reacted by the general procedure as described in Example 1-D and afforded the title compound (8.90 g, 100%) as a (~1:1 evaluated by NMR) mixture of α and β-anomers.

IR (neat) $v_{max}$ (cm$^{-1}$): 3100–2800 (C—H), 2100 (N3), 1745 and 1720 (C=O), 1610 and 1510 (aromatic C=C).

$^1$H NMR 400 MHz (CDCl$_3$) δ(ppm): 0.86 (3H, t, J=6.6 Hz, —CH$_3$), 1.25–1.38 (8H, m, —(CH$_2$)$_4$—), 1.44, 1.46, 1.46 and 1.49.(18H, 4s, 2×tert-butyl), 2.05 (2H, m, =CH—CH$_2$—), 3.46 (0.5H, dd, J=9.7 and 2.6 Hz, H-1), 3.53 (0.5H, dd, J=10.9 and 8.0 Hz, H-1), 3.66 (0.5H, dd, J=9.2 and 6.2 Hz, H-6'), 3.72 (0.5H, dd, J=9.7 and 6.0 Hz, H-1), 3.55–3.64, 3.84–3.89 and 3.92–4.06 (7H, 3 sets of m, H-2', H-3', H-4', H-5', H-2, H-6' and H-1), 3.77, 3.79 and 3.82 (6H, 3s, 2×—OCH$_3$), 3.99 and 4.11 (2H, 2s, —OCH$_2$CO—), 4.25–4.37 (2H, m, —OCH$_2$CO—), 4.36 (0.5H, d, J=9.5 Hz, H-1'α), 4.58–4.74 (3.5H, m, —CH$_2$Ph), 4.81 (0.5H, d, J=3.6 Hz, H-1'β), 4.85 (0.5H, d, J=10.6 Hz, —CH$_2$Ph), 5.53–5.60 (1H, m, H-4), 5.63 (0.5H, dd, J=7.8 and 4.1 Hz, H-3), 5.69 (0.5H, dd, J=7.9 and 3.4 Hz, H-3), 5.86–5.95 (1H, m, H-5), 6.81–6.89, 7.24–7.35, 7.44–7.48, 7.56–7.59 and 8.06–8.08 (13H, 5 sets of m, aromatic H).

H. (2S,3R,4E)-3-Benzoyloxy-2-azido-1-(4,6-di-O-tert-butyloxycarbonylmethyl-α-D-galactopyranosyloxy)-4-undecene and (2S,3R,4E)-3-benzoyloxy-2-azido-1-(4,6-di-O-tert-butyloxycarbonylmethyl-α-D-galactopyranosyloxy)-4-undecene

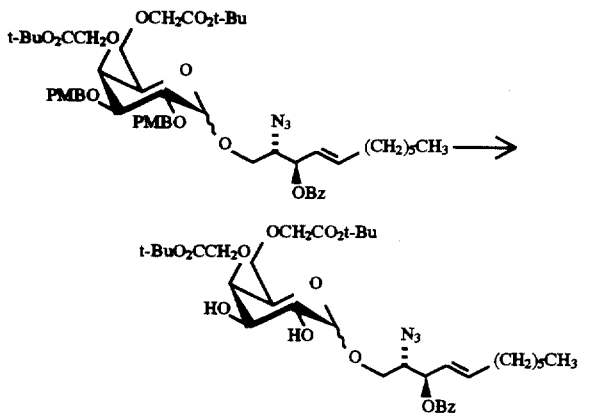

(2S,3R,4E)-3-Benzoyloxy-2-azido-1-(2,3-di-O-para-methoxybenzyl-4,6-di-O-tert-butyloxycarbonylmethyl-α-D-galactopyranosyloxy)-4-undecene and (2S,3R,4E)-3-benzoyloxy-2-azido-1-(2,3-di-O-para-methoxybenzyl-4,6-di-O-tert-butyloxycarbonylmethyl-β-D-galactopyranosyloxy)-4-undecene (~1:1 mixture, 8.69 g, 9.04 mmol) was reacted by the general procedure as described in Example 1-E and afforded the pure α-anomer (1.96 g, 30%), a mixture of anomers α and β (0.92 g, 14%) and the pure β-anomer (1.64 g, 25%) of the title compound as syrups.

α-anomer:

$[α]_D^{22}$: +45° (c=1.0, CHCl$_3$).

IR (neat) $v_{max}$ (cm$^{-1}$): 3700–3100 (OH), 3100–2800 (C—H), 2100 (N3), 1735 (broad, C=O).

$^1$H NMR 400 MHz (CDCl$_3$) δ(ppm): 0.87 (3H, t, J=6.7 Hz, —CH$_3$), 1.26–1.45 (8H, m, —(CH$_2$)$_4$—), 1.48 (18H, s, 2×tert-butyl), 2.08 (2H, qa, J=7.0 Hz, =CH—CH$_2$—), 2.30 (1H, d, J=8.4 Hz, —OH), 3.56 (1H, dd, J=10.4 and 7.3 Hz, H-1), 3.61 (1H, dd, J=9.3 and 5.9 Hz, H-6'), 3.76–3.86 (3H, m, H-2', H-3' and H-6'), 3.84 (1H, d, J=3.3 Hz, H-4'), 3.89 (1H, dd, J=10.4 and 4.0 Hz, H-1), 3.93–3.97 (1H, m, H-2), 3.99 (1H, d, J$_{AB}$=16.3 Hz, —OCH$_2$CO—), 4.04 (1H, d, J$_{AB}$=16.3 Hz, —OCH$_2$CO—), 4.05–4.09 (1H, m, H-5'), 4.09 (1H, d, J=17.2 Hz, —OCH$_2$CO—), 4.36 (1H, d, J=17.2 Hz, —OCH$_2$CO—), 4.66 (1H, d, J=8.4 Hz, —OH), 4.92 (1H, d, J=3.7 Hz, H-1'), 5.59 (1H, dd, J=15.0 and 8.0 Hz, H-4), 5.65 (1H, dd, J=8.0 and 4.7 Hz, H-3), 5.95 (1H, dt, J=15.0 and 7.0 Hz, H-5), 7.44–7.48, 7.56–7.60 and 8.05–8.07 (5H, 3 sets of m, C$_6$H$_5$).

Anal. Calcd. for C$_{36}$H$_{55}$N$_3$O$_{12}$: C, 59.90; H, 7.68; N, 5.82. Found: C, 59.69; H, 7.49; N, 5.73.

β-anomer:

$[α]_D^{22}$: -2° (C=1.0, CHCl$_3$).

IR (neat) $v_{max}$ (cm$^{-1}$): 3700–3100 (OH), 3100–2800 (C—H), 2100 (N$_3$), 1725 (broad, C=O).

$^1$H NMR 400 MHz (CDCl$_3$) δ(ppm): 0.87 (3H, t, J=6.7 Hz, —CH$_3$), 1.27–1.40 (8H, m, —(CH$_2$)$_4$—), 1.49 (18H, s, 2×tert-butyl), 2.08 (2H, m, =CH—CH$_2$—), 2.63 (1H, d, J=1.6 Hz. —OH—2'), 3.51 (1H, dd, J=9.3 and 3.3 Hz, H-3'), 3.61 (1H, dd, J=8.4 and 4.9 Hz, H-6'), 3.66–3.80 (4H, m, H-2', H-6', H-5' and H-1), 3.79 (1H, br d, H-4'), 3.90 (1H, dd, J=10.4 and 7.1 Hz, H-1), 4.00 (2H, s, —OCH$_2$CO—), 4.00–4.05 (1H, m, H-2), 4.07 (1H, d, J=17.3 Hz, —OCH$_2$CO—), 4.28 (1H, d, J=7.7 Hz, H-1'), 4.37 (1H, d, J=17.3 Hz, —OCH$_2$CO—), 5.16 (1H, d, J=8.9 Hz, —OH-3'), 5.57 (1H, dd, J=15.2 and 8.0 Hz, H-4), 5.66 (1H, dd, J=8.0 and 4.3 Hz, H-3), 5.96 (1H, dt, J=15.2 and 6.7 Hz, H-5), 7.44–7.48, 7.56–7.60 and 8.06–8.08 (5H, 3 sets of m, —C$_6$H$_5$).

Anal. Calcd. for C$_{36}$H$_{55}$N$_3$O$_{12}$: C, 59.90; H, 7.68; N, 5.82. Found: C, 59.55; H, 7.45; N, 5.76.

I. (2S,3R,4E)-3-Benzoyloxy-2-azido-1-(2,3-di-O-benzoyl-4,6-di-O-tert-butyloxycarbonylmethyl-α-D-galactopyranosyloxy)-4-undecene

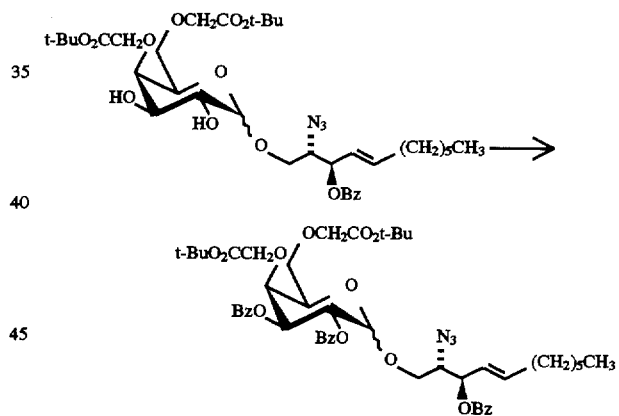

(2S,3R,4E)-3-Benzoyloxy-2-azido-1-(4,6-di-O-tert-butyloxycarbonylmethyl-α-D-galactopyranosyloxy)-4-undecene (2.66 g, 3.65 mmol) was reacted by the general procedure as described in Example 1-F and afforded the title compound (3.10 g, 90%) as a clear oil.

$[α]_D^{22}$: +45° (c=1.0, CHCl$_3$).

IR (neat) $v_{max}$ (cm$^{-1}$): 3100–2800 (C—H), 2100 (N3), 1745, 1720 (broad, C=O).

$^1$H NMR 400 MHz (CDCl$_3$) δ(ppm): 0.86 (3H, t, J=6.7 Hz, —CH$_3$), 1.26–1.39 (8H, m, —(CH$_2$)$_4$—), 1.42 and 1.49 (18H, 2s, 2×tert-butyl), 2.06 (2H, qa, =CH—CH$_2$), 3.51 (1H, m, H-1), 3.82 (1H, dd, J=9.6 and 6.6 Hz, H-6'), 3.95–4.09 (3H, m, H-6', H-2 and H-1), 4.03 (2H, AB qa, —OCH$_2$CO—), 4.07 (1H, d, J=16.1 Hz, —OCH$_2$CO—), 4.24 (1H, br s, H-4'), 4.28–4.32 (1H, m overlapping —OCH$_2$CO—, H-5'), 4.30 (1H, d, J=16.1 Hz, —OCH$_2$CO—), 5.33 (1H, d, J=3.2 Hz, H-1'), 5.51–5.58 (2H, m, H-4 and H-3), 5.75 (1H, dd, J=10.8 and 3.2 Hz, H-2'), 5.79 (1H, dd, J=10.8 and 2.4 Hz, H-3'), 5.90 (1H, dt, J=14.2 and 6.7 Hz, H-5), 7.32–7.58 and 7.98–8.02 (15H, 2 sets of m, 3×—C₆H₅).

Anal. Calcd. for $C_{50}H_{63}N_3O_{14}$: C, 64.57; H, 6.83; N, 4.52. Found: C, 64.47; H, 6.73; N, 4.53.

J. (2S,3R,4E)-3-Benzoyloxy-2-decanoylamino-1-(2,3-di-O-benzoyl-4,6-di-O-tert-butyloxycarbonylmethyl-α-D-galactopyranosyloxy)-4-undecene

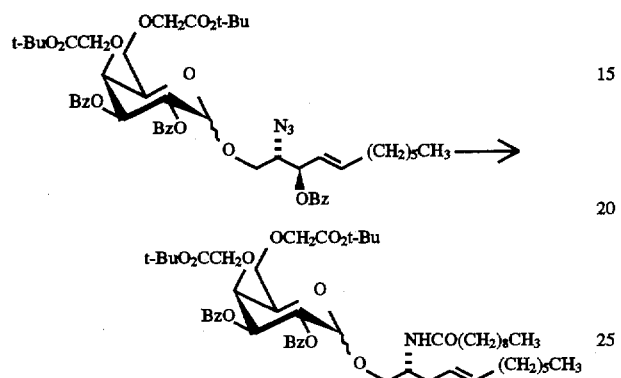

(2S,3R,4E)-3-Benzoyloxy-2-azido-1-(2,3-di-O-benzoyl-4,6-di-O-tert-butyloxycarbonylmethyl-α-D-galactopyranosyloxy)-4-undecene (1.48 g, 1.59 mmol) was reacted by the general procedure as described in Example 1-G, except that decanoyl chloride was used as acylating agent, and afforded the title compound (1.274 g, 76%) as a white solid.

m.p.: 106°–107° C.

$[\alpha]_D^{22}$: +59° (c=1.0, CHCl₃).

IR (KBr) $v_{max}$ (cm⁻¹): 3290 (NH), 2960, 2930 and 2850 (C—H), 1755, 1750, 1720 and 1655 (C=O).

¹H NMR 400 MHz (CDCl₃) δ(ppm): 0.86 (3H, t, J=7.0 Hz, —CH₃), 0.89 (3H, t, J=6.6 Hz, —CH₃), 1.23–1.26 (20H, m, —(CH₂)₄— and —(CH₂)₆—), 1.41 and 1.4 (18H, 2s, 2×tert-butyl), 1.57–1.65 (2H, m, —CH₂—), 1.97 (2H, qa, J=6.9 Hz, =CH—CH₂—), 2.15 (2H, m, —NHCOCH₂—), 3.80–3.89 (3H, m, H1 and H-6'), 4.01 (1H, d, $J_{AB}$=16.4 Hz, —OCH₂CO—), 4.01 (1H, dd, J=9.5 and 5.4 Hz, H-6'), 4.40 (1H, $J_{AB}$=16.4 Hz, —OCH₂CO—), 4.07 (1H, d, J=16.0 Hz, —OCH₂CO—), 4.23 (1H, br s, H-4'), 4.29 (1H, d, J=16.0 Hz, —OCH₂CO—) 4.35 (1H, br t, H-5'), 4.42–4.48 (1H, m, H-2), 5.24 (1H, d, J=3.0 Hz, H-1'), 5.49 (1H, dd, J=15.2 and 7.6 Hz, H-4), 5.58 (1H, t, J=7.6 Hz, H-3), 5.70–5.79 (3H, m, H-5, H-2' and H-3'), 6.08 (1H, d, J=9.3 Hz, —NH—), 7.29–7.33, 7.39–7.49, 7.52–7.56 and 7.91–8.02 (15H, 4 sets of m, 3×—C₆H₅).

Anal. Calcd. for $C_{60}H_{83}NO_{15}$: C, 68.08; H, 7.91; N, 1.32. Found: C, 68.21; H, 7.73; N, 1.51

EXAMPLE 7

(2S,3R,4E)-3-Benzoyloxy-2-decanoylamino-1-(2,3-di-O-benzoyl-4,6-di-O-carboxymethyl-α-D-galactopyranosyloxy)-4-undecene

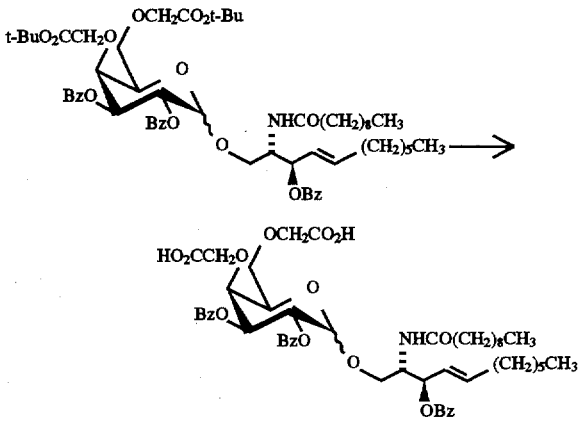

(2S,3R,4E)-3-Benzoyloxy-2-decanoylamino-1-(2,3-di-O-benzoyl-4,6-di-O-tert-butyloxycarbonylmethyl-α-D-galactopyranosyloxy)-4-undecene (0.566 g, 0.535 mmol) as prepared in Example 6 was reacted by the general procedure as described in Example 2 and afforded the title compound (0.256 g, 51%) as a white amorphous solid.

$[\alpha]_D^{22}$: +59° (c=1.0, CHCl₃).

IR (KBr) $v_{max}$ (cm⁻¹): 3700–2500 (broad, NH, OH and C—H), 1725 and 1635 (broad, C=O).

¹H NMR 400 MHz (CDCl₃) δ(ppm): 0.81 (3H, t, J=7.0 Hz, —CH₃), 0.83 (3H, t, J=6.7 Hz, —CH₃), 1.14–1.42 (22H, m, —(CH₂)₂— and —(CH₂)₇—), 1.83–2.02 (4H, m, =CH—CH₂— and —NHCOCH₂—), 3.57 (1H, dd, J=10.3 and 7.0 Hz, H-1), 3.66 (1H, dd, J=9.9 and 6.5 Hz, H-6'), 3.80 (1H, dd, J=10.3 and 4.3 Hz, H-1), 3.85 (1H, dd, J=9.9 and 5.9 Hz, H-6'), 4.03 (1H, d, $J_{AB}$=20.9 Hz, —OCH₂CO—), 4.07 (1H, d, $J_{AB}$=10.9 Hz, —OCH₂CO—), 4.19 (1H, d, $J_{AB}$=16.3 Hz, —OCH₂CO—), 4.20–4.27 (2H, m, H-4' and H-5'), 4.24 (1H, d, $J_{AB}$=16.3 Hz, —OCH₂CO—), 4.35 (1H, m, H-2), 5.19 (1H, d, J=3.6 Hz, H-1'), 5.47–5.58 (3H, m, H-4, H-3 and H-2'), 5.90 (1H, dd, J=10.8 and 2.7 Hz, H-3'), 5.76 (1H, dt, J=15.0 and 6.7 Hz, H-5), 7.36–7.40, 7.44–7.48, 7.54–7.63 and 7.79–7.91 (15H, 4 sets of m, 3×—C₆H₅), 7.96 (1H, d, J=8.6 Hz, —NH—).

Anal. Calcd. for $C_{52}H_{67}NO_{15} \cdot 0.5\ H_2O$: C, 65.39; H, 7.18; N, 1.47. Found: C, 65.40; H, 7.08; N, 1.47

EXAMPLE 8

(2S,3R,4E)-3-Benzoyloxy-2-(9-methoxycarbonyl-nonanoylamino)-1-(2,3-di-O-benzoyl-4,6-di-O-carboxymethyl-α-D-galactopyranosyloxy)-4-undecene A. (2S,3R,4E)-3-Benzoyloxy-2-(9-methoxycarbonyl-nonanoylamino)-1-(2,3-di-O-benzoyl-4,6-di-O-tert-butyloxycarbonylmethyl-α-D-galactopyranosyloxy)-4-undecene

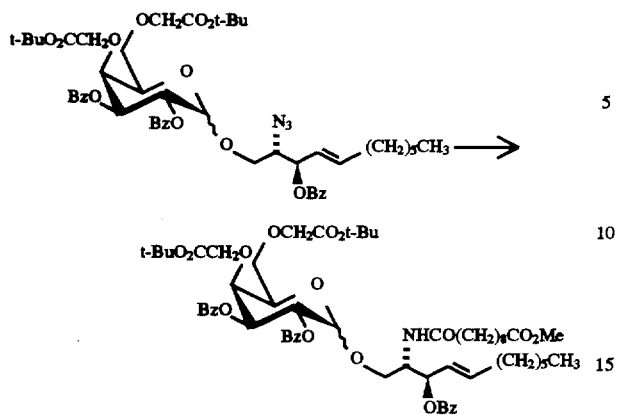

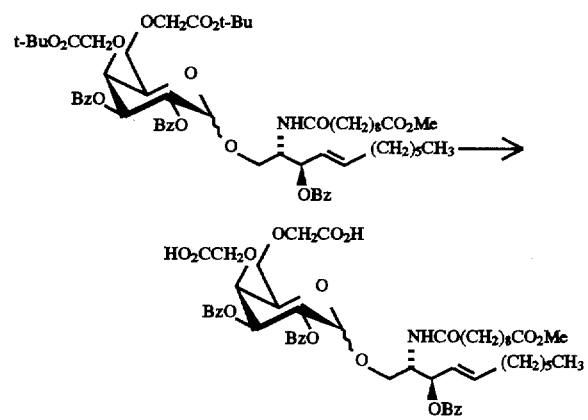

A solution of (2S,3R,4E)-3-benzoyloxy-2-azido-1-(4,6-di-O-tert-butyloxycarbonylmethyl-α-D-galactopyranosyloxy)-4-undecene described in Example 6I (1.52 g, 1.63 mmol) in pyridine (75 mL) and water (10 mL) was saturated with a stream of hydrogen sulfide. The mixture was stirred at 22° C. for ~72 hours then concentrated under vacuum and co-evaporated with toluene (2×). The residue was dissolved in dichloromethane (125 mL) and this solution was treated with 9-methoxycarbonyl nonanoic acid (0.71 g, 3.28 mmol) followed by 1-ethyl-3-(3-dimethylaminopropyl)carbodiimide hydrochloride (0.95 g, 4.96 mmol). The mixture was stirred at 22° C. for 2 hours. The organic phase was washed with water and brine, dried over anhydrous magnesium sulfate, filtered and concentrated. The residue was purified by silica gel chromatography (3.5×13 cm, 0 to 20% ethyl acetate/toluene) and afforded the title compound (1.62 g, 90 %) as a white solid.

m.p.: 124°–125° C. (ethyl acetate/hexane); $[\alpha]_D^{22}$: +44° (c=1.0, CHCl$_3$).

IR (KBr) $v_{max}$ (cm$^{-1}$): 3300 (NH), 2930, 2850 (C—H), 1745, 1720, 1650 (C=O).

$^1$H NMR 400 MHz (CDCl$_3$) δ(ppm): 0.86 (3H, t, J=6.8 Hz, —CH$_3$), 1.23–1.29 (18H, m, —(CH$_2$)$_4$— and —(CH$_2$)$_5$—), 1.41 and 1.49 (18H, 2s, 2×tert-butyl), 1.57–1.64 (2H, m, —CH$_2$—), 1.97 (2H, qa, J=6.9 Hz, =CH—CH$_2$—), 2.14 (2H, m, —NHCOCH$_2$—), 2.30 (2H, t, J=7.5 Hz, —CH$_2$CO$_2$Me), 3.67 (3H, s, —OCH$_3$), 3.80–3.89 and 3.98–4.02 (4H, 2 sets of m, H-6' and H-1), 4.01 (1H, d, J$_{AB}$=16.4 Hz, —OCH$_2$CO—), 4.03 (1H, d, J$_{AB}$=16.4 Hz, —OCH$_2$CO—), 4.07 (1H, d, J=16.1 Hz, —OCH$_2$CO—), 4.23 (1H, br s, H-4'), 4.29 (1H, d, J=16.1 Hz, —OCH$_2$CO—), 4.35 (1H, br t, J=6.2 Hz, H-5'), 4.51 (1H, m, H-2), 5.24 (1H, d, J=3.0 Hz, H-1'), 5.49 (1H, dd, J=15.2 and 7.6 Hz, H-4), 5.58 (1H, t, J=7.6 Hz, H-3), 5.70–5.79 (3H, m, H-5, H-2' and H-3'), 6.09 (1H, d, J=9.2 Hz, —NH—), 7.29–7.33, 7.39–7.48, 7.52–7.56 and 7.90–8.02 (15H, 3 sets of m, 3×—C$_6$H$_5$).

Anal. Calcd. for C$_{61}$H$_{83}$NO$_{17}$: C, 66.47; H, 7.59; N, 1.27. Found: C, 66.44; H, 7.54; N, 1.39.

B. (2S,3R,4E)-3-Benzoyloxy-2-(9-methoxycarbonyl-nonanoylamino)-1-(2,3-di-O-benzoyl-4,6-di-O-carboxymethyl-α-D-galactopyranosyloxy)-4-undecene (2S,3R,4E)-3-Benzoyloxy-2-(9-methoxycarbonyl-nonanoylamino)-1-(2,3-di-O-benzoyl-4,6-di-O-tert-butyloxycarbonylmethyl-α-D-galactopyranosyloxy)-4-undecene (0.862 g, 0.782 mmol) was reacted by the general procedure as described in Example 2 and afforded the title compound (0.734 g, 94%) as a white amorphous solid.

$[\alpha]_D^{22}$: +59° (c=1.0, CHCl$_3$). IR (KBr) $v_{max}$ (cm$^{-1}$): 3700–2700 (OH and NH), 2930, 2850 (C—H), 1735, 1635 (broad, C=O).

$^1$H NMR 400 MHz (CDCl$_3$) δ(ppm): 0.80 (3H, t, J=6.6 Hz, —CH$_3$), 1.13–1.46 (20H, m, —(CH$_2$)$_4$— and —(CH$_2$)$_6$—), 1.82–2.01 (4H, m, —NHCOCH$_2$— and =CH—CH$_2$—), 2.24 (2H, t, J=7.4 Hz, —CHCO$_2$Me), 3.55–3.59 (1H, m, H-1), 3.56 (3H, s overlapping H-1, —OCH$_3$), 3.66 (1H, dd, J=10.0 and 6.5 Hz, H-6'), 3.80 (1H, dd, J=10.4 and 4.4 Hz, H-1), 3.85 (1H, dd, J=10.0 and 5.9 Hz, H-6'), 4.03 (1H, d, J$_{AB}$=16.7 Hz, —OCH$_2$CO—), 4.06 (1H, d, J$_{AB}$=16.7 Hz, —OCH$_2$CO—), 4.16–4.22 (2H, m, H-4' and H-5'), 4.19 (1H, d overlapping H-4' and H-5', J$_{AB}$=16.5 Hz, —OCH$_2$CO—), 4.24 (1H, d, J$_{AB}$=16.5 Hz, —OCH$_2$CO—), 4.34 (1H, m, H-2), 5.19 (1H, d, J=3.6 Hz, H-1'), 5.23–5.65 (3H, m, H-4, H-3 and H-2'), 5.70 (1H, dd, J=10.6 and 2.8 Hz, H-3'), 5.75 (1H, dt, J=14.9 and 6.8 Hz, H-5), 7.35–7.48, 7.54–7.62, 7.79–7.83 and 7.88–7.90 (15H, 4 sets of m, 3×—C$_6$H$_5$), 7.96 (1H, d, J=8.7 Hz, —NH—).

Anal. Calcd. for C$_{53}$H$_{67}$NO$_{17}$·H$_2$O: C, 63.15; H, 6.90; N, 1.39. Found: C, 63.18; H, 6.65; N, 1.52.

EXAMPLE 9

(2S,3R,4E)-2-Hexadecanoylamino-3-benzoyloxy-1-(3,4-di-O-tert-butyloxycarbonylmethyl-2,6-di-O-benzoyl-α-D-galactopyranosyloxy)-4-octadecene A. Ethyl 3,4-O-isopropylidene-1-thio-β-D-galactopyranoside

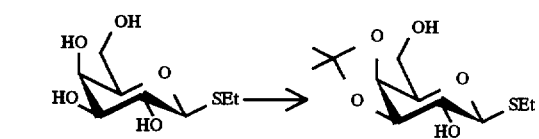

A mixture of ethyl 1-thio-β-D-galactopyranoside [R. U. Lemieux, Can.J. Chem, 29, 1079 (1951)] (24.86 g, 0.111 mol) and 2,2-dimethoxypropane (500 mL) was treated with p-toluenesulfonic acid (0.625 g) and stirred at 22° C. for 24 hours. Water (80 mL) was added and after 15 minutes the reaction mixture was cooled in an ice water bath and stirred for another 30 minutes. Then triethylamine (5 mL) was added and the mixture was stirred for 20 minutes. The solvent was evaporated under vacuum and the residue was purified by silica gel chromatography (9×12 cm, 50% to 70% ethyl acetate/toluene) to give the title material (25.50 g, 87%) as a white solid. Recrystallization from ethyl acetate and hexane gave white prisms.

m.p. =90°–93° C. $[\alpha]_D^{22}$: +20.8° (c=2.8, $CHCl_3$).

IR (KBr) $v_{max}$ ($cm^{-1}$): 3200 (broad, OH).

$^1$H NMR 400 MHz ($CDCl_3$) δ(ppm): 1.33 (3H, t, J=7.3 Hz, —$SCH_2CH_3$), 1.36 and 1.52 (2×3H, 2s, —$CH_3$ of isopropylidene), 2.2 and 2.5 (broad, OH), 2.75 (2H, m, —$SCH_2CH_3$), 3.57 (1H, dd, J=10.2 and 7.0 Hz, H-2), 3.81 (1H, dd, J=11.5 and 4.0 Hz, H-6), 3.89 (1H, m, H-5), 3.98 (1H, J=11.5 and 7.2 Hz, H-6), 4.09 (1H, dd, J=7.0 and 5.6 Hz, H-3), 4.21 (1H, dd, J=5.6 and 2.2 Hz, H-4), 4.27 (1H, d, J=10.2 Hz, H-1).

Anal. Calcd. for $C_{11}H_{20}O_5S$: C, 49.98; H, 7.63; S,12.13. Found: C, 49.89; H, 7.49; S, 12.33.

B. Ethyl 3,4-O-isopropylidene-2,6-di-O-para-methoxybenzyl-1-thio-β-D-galactopyranoside

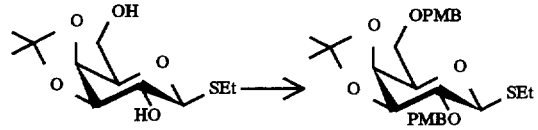

Ethyl 3,4-O-isopropylidene-1-thio-β-D-galactopyranoside (1.00 g, 3.78 mmol) was added to a stirred suspension of sodium hydride (0.680 g, 80% in mineral oil) in dry dimethylformamide (20 mL, kept on molecular sieves 4 Å) at 23° C. The mixture was stirred for 2 hours then cooled to 0°–5° C. and treated with potassium iodide (2.43 g, 14.6 mmol) and dropwise with para-methoxybenzyl chloride (1.54 mL, 11.35 mmol). The resulting mixture was stirred for another 1.5 hours, cooled again to 0°–5° C., treated with water (50 mL) and extracted with diethyl ether (3×50 mL). The combined organic extracts were washed with brine, dried over anhydrous magnesium sulfate, filtered and concentrated. The residue was purified on silica gel chromatography (10 ×18 cm, 10 to 20% ethyl acetate/toluene) and gave the title material (1.87 g, 97%).

$[\alpha]_D^{22}$: –6.9° (c=0.39, $CH_2Cl_2$).

IR (KBr) $v_{max}$ ($cm^{-1}$): 2980, 2935, 2900, 2860, 2840 (C—H), 1610, 1515 (aromatic C=C).

$^1$H NMR 400 MHz ($CDCl_3$) δ(ppm): 1.31 (3H, t, J=7.4 Hz, —$CH_3$), 1.36, 1.45 (6H, 2s, —$C(CH_3)_2$), 2.73 (2H, m, —$SCH_2$—), 3.44 (1H, rid, J=9.7 and 6.0 Hz, H-2), 3.74 (2H, d, J=6.0 Hz, H-6), 3.80 and 3.81 (6H, 2s, 2×—$OCH_3$), 3.88 (1H, br t, H-5), 4.18–4.22 (2H, m, H-3 and H-4), 4.42 (1H, d, J=9.7 Hz, H-1), 4.48 (1H, d, $J_{AB}$=11.5 Hz, —$OCH_2Ar$), 4.56 (1H, d, $J_{AB}$=11.5 Hz, —$OCH_2Ar$), 4.69 (1H, d, $J_{AB}$=11.0 Hz, —$OCH_2Ar$), 4.77 (1H, d, $J_{AB}$=11.0 Hz, —$OCH_2Ar$), 6.86–6.89, 7.25–7.27 and 7.34–7.36 (8H, 3 sets of m, aromatic H).

Anal. Calcd. for $C_{27}H_{36}O_7S$: C, 64.26; H, 7.19; S, 6.35. Found: C, 64.53; H, 7.15; S, 5.97.

C. Ethyl 2,6-di-O-para-methoxybenzyl-1-thio-β-D-galactopyranoside

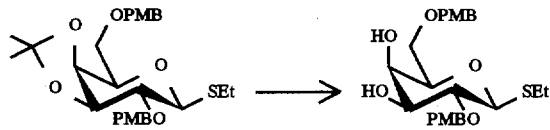

A solution of ethyl 3,4-O-isopropylidene-2,6-di-O-para-methoxybenzyl-1-thio-β-D-galactopyranoside (17.0 g, 33.7 mmol) in 80% aqueous acetic acid (200 mL) was heated to 60° C. for 1.5 hours. The cooled mixture was then evaporated under vacuum and last traces of acetic acid were removed by co-evaporation with toluene. The residue was purified by silica gel column chromatography (10×20 cm, 15 to 50% ethyl acetate/toluene) and afforded the title compound (12.2 g, 78%).

$[\alpha]_D^{22}$: +1.3° (c=0.39, $CH_2Cl_2$).

IR (KBr) $v_{max}$ ($cm^{-1}$): 3600–3100 (broad, OH), 2970, 2920, 2880, 2840 (C—H), 1610, 1512 (aromatic C=C).

$^1$H NMR 400 MHz ($CDCl_3$) δ(ppm): 1.35 (3H, t, J=7.4 Hz, —$CH_3$), 2.45 (1H, d, J=5.4 Hz, —OH), 2.64 (1H, d, J=3.5 Hz, —OH), 2.79 (2H, m, —$SCH_2$—), 3.52 (1H, t, J=9.2 Hz, H-2), 3.58–3.64 (2H, m, H-3 and H-5), 3.72 (1H, dd, $J_{AB}$=10.1 and $J_{AX}$=5.2 Hz, H-6), 3.75 (1H, d, $J_{AB}$=10.1 and $J_{BX}$=5.6 Hz, H-6), 3.82 (6H, s, 2×—$OCH_3$), 4.03 (1H, t, J=3.1 Hz, H-4), 4.42 (1H, d, J=9.5 Hz, H-1), 4.52 (2H, br s, —$OCH_2Ar$), 4.64 (1H, d, J=10.8 Hz, —$OCH_2Ar$), 4.89 (1H, d, J=10.8 Hz, —$OCH_2Ar$), 6.87–6.92, 7.25–7.28 and 7.34–7.37 (8H, 3 sets of m, aromatic H).

Anal. Calcd. for $C_{24}H_{32}O_7S$: C, 62.05; H, 6.94; S, 6.90. Found: C, 62.15; H, 6.95; S, 6.93.

D. Ethyl 2,6-di-O-para-methoxybenzyl-3,4-di-O-tert-butyloxy-carbonylmethyl-1-thio-β-D-galactopyranoside

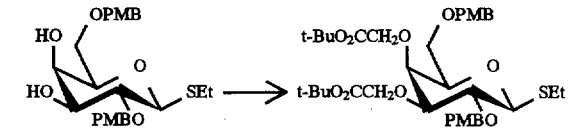

Ethyl 2,6-di-O-para-methoxybenzyl-1-thio-β-D-galactopyranoside (9.2 g, 19.8 mmol) was reacted by the general procedure as described in Example 1-C procedure 1 and gave the title compound (8.16 g, 60%).

$[\alpha]_D^{22}$: –29.5° (c=0.735, $CH_2Cl_2$).

IR (film) $v_{max}$ ($cm^{-1}$): 2970, 2930, 2870, 2840 (C—H), 1745 (C=O), 1611, 1586 (aromatic C=C).

$^1$H NMR 400 MHz ($CDCl_3$) δ(ppm): 1.32 (3H, t, J=7.4 Hz, —$CH_3$), 1.46 and 1.48 (18H, 2s, 2×tert-butyl), 2.76 (2H, m, —$SCH_2$—), 3.39 (1H, dd, J=9.3 and 2.7 Hz, H-3), 3.57 (1H, br t, H-5), 3.74 (1H, dd, J=10.0 and 6.2 Hz, H-6), 3.79–3.84 (1H, m, H-2), 3.81 (6H, s overlapping H-2, 2×—$OCH_3$), 3.95 (1H, dd, J=10.0 and 5.7 Hz, H-6), 4.14 (1H, d, J=2.7 Hz, H-4), 4.20 (1H, d, $J_{AB}$=16.5 Hz, —$OCH_2CO$—), 4.24 (1H, d, $J_{AB}$=16.5 Hz, —$OCH_2CO$—), 4.34 (1H, d, $J_{AB}$=16.6 Hz, —$OCH_2CO$—), 4.36 (1H, d, J=9.7 Hz, H-1), 4.38 (1H, d, $J_{AB}$=16.6 Hz, —$OCH_2CO$—), 4.51 (2H, br s, —$OCH_2Ar$), 4.64 (1H, d, J=9.8 Hz, —$OCH_2Ar$), 4.84 (1H, d, J=9.8 Hz, —$OCH_2Ar$), 6.86–6.90, 7.26–7.29 and 7.35–7.38 (8H, 3 sets of m, aromatic H).

Anal. Calcd. for $C_{36}H_{52}O_{11}S.0.15$ $H_2O$: C, 62.16; H, 7.58; S, 4.61. Found: C, 61.70; H, 7.39; S, 4.69.

E. (2S,3R,4E)-2-Azido-3-benzoyloxy-1-(3,4-di-O-tert-butyloxycarbonylmethyl-2,6-di-O-para-methoxybenzyl-α-D-galactopyranosyloxy)-4-octadecene and (2S,3R,4E)-2-azido-3-benzoyloxy-1-(3,4-di-O-tert-butyloxycarbonylmethyl-2,6-di-O-para-methoxybenzyl-β-D-galactopyranosyloxy)-4-octadecene

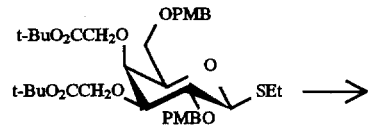

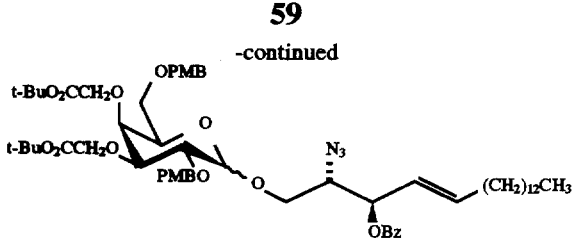

Ethyl 2,6-di-O-para-methoxybenzyl-3,4-di-O-tert-butyloxycarbonylmethyl-1-thio-β-D-galactopyranoside (3.87 g, 5.58 mmol) and (2S,3R,4E)-2-azido-3-benzoyloxy-4-octadecen-1-ol (2.00 g, 4.65 mmol) were reacted by the general procedure as described in Example 1-D and gave the title compounds (4.70 g, 95%) as a mixture of α and β-anomers (55:45, evaluated by NMR). Aliquots of the two anomers were separated by silica gel plates.

α-anomer:

$[\alpha]_D^{22}$: +3.5° (c=0.42, $CH_2Cl_2$).

IR (film) $v_{max}$ (cm$^{-1}$): 2930, 2850 (C—H), 2100 ($N_3$), 1745, 1725 (C=O), 1611, 1585 (aromatic C=C).

$^1$H NMR 400 MHz (CDCl$_3$) δ(ppm): 0.89 (3H, t, J=6.8 Hz, —CH$_3$), 1.24–1.35 (22H, m, —(CH$_2$)$_{11}$—), 1.47 (18H, s, 2×tert-butyl), 2.03 (2H, qa, J=6.9 Hz, =CH—CH$_2$—), 3.51 (1H, dd, J=10.9 and 7.9 Hz, H-1), 3.68 (1H, dd, J=9.9 and 6.9 Hz, H-6'), 3.73 (1H, dd, J=10.1 and 2.8 Hz, H-3'), 3.75–3.79 and 3.95–4.0 (4H, 2 sets of m, H-5', H-2', H-1 and H-2), 3.78 and 3.79 (6H, 2s, 2×—OCH$_3$), 3.87 (1H, dd, J=9.9 and 5.2 Hz, H-6'), 4.11 (1H, br d, H-4'), 4.24 (1H, d, J$_{AB}$16.9 Hz, —OCH$_2$CO—), 4.25 (1H, d, J$_{AB}$=16.9 Hz, —OCH$_2$CO—), 4.31 (1H, d, J$_{AB}$=16.7 Hz, —OCH$_2$CO—), 4.38 (1H, d, J$_{AB}$=16.7 Hz, —OCH$_2$CO—), 4.47 (1H, d, J$_{AB}$=11.5 Hz, —OCH$_2$Ar), 4.50 (1H, d, J$_{AB}$=11.5 Hz, —OCH$_2$Ar), 4.57 (1H, d, J$_{AB}$=11.5 Hz, —OCH$_2$Ar), 4.63 (1H, d, J$_{AB}$=11.5 Hz, —OCH$_2$Ar), 4.80 (1H, d, J=3.6 Hz, H-1'), 5.51 (1H, dd, J=15.1 and 7.8 Hz, H-4), 5.58 (1H, dd, J=7.8 and 4.4 Hz, H-3), 5.87 (1H, dt, J=15.1 and 6.9 Hz, H-5), 6.82–6.87, 7.24–7.30, 7.43–7.47, 7.56–7.60 and 8.05–8.07 (13H, 5 sets of m, aromatic H).

Anal. Calcd. for $C_{59}H_{85}N_3O_{14}$·0.3 $H_2O$: C, 66.49; H, 8.10; N, 3.94. Found: C, 66.16; H, 7.98; N, 4.20.

$[\alpha]_D^{22}$: −37.1° (C=0.38, $CH_2Cl_2$).

IR (film) $v_{max}$ (cm-1): 2930, 2850 (C—H), 2100 ($N_3$), 1745, 1725 (C=O), 1611, 1585 (aromatic C=C).

$^1$H NMR 400 MHz (CDCl$_3$) δ(ppm): 0.89 (3H, t, J=6.8 Hz, —CH$_3$), 1.2–1.35 (22H, m, —(CH$_2$)$_{11}$—), 1.45 and 1.47 (18H, 2s, 2×tert-butyl), 2.03 (2H, qa, J=6.9 Hz, =CH—CH$_2$—), 3.36 (1H, dd, J=9.7 and 2.7 Hz, H-3'), 3.55 (1H, br t, H-5'), 3.58 (1H, dd, J=10.1 and 4.4 Hz, H-1), 3.73 (1H, dd, J=10.0 and 6.3 Hz, H-6'), 3.77–3.83 and 3.96–4.03 (4H, 2 sets of m, H-2', H-6', H-1 and H-2), 3.79 and 3.80 (6H, 2s, 2×—OCH$_3$), 4.10 (1H, d, J=2.7 Hz, H-4—), 4.18 (1H, d, J$_{AB}$=16.7 Hz, —OCH$_2$CO—), 4.23 (1H, d, J$_{AB}$=16.7 Hz, —OCH$_2$CO—), 4.31 (1H, d, J=7.8 Hz, H-2'), 4.32 (1H, d, J$_{AB}$=16.7 Hz, —OCH$_2$CO—), 4.39 (1H, d, J$_{AB}$=16.7 Hz, —OCH$_2$CO—), 4.50 (2H, s, —OCH$_2$Ar), 4.66 (1H, d, J=10.6 Hz, —OCH$_2$Ar), 4.86 (1H, d, J$_{AB}$=10.6 Hz, —OCH$_2$Ar), 5.56 (1H, dd, J=15.3 and 7.9 Hz, H-4), 5.69 (1H, dd, J=7.9 and 3.1 Hz, H-3), 5.90 (1H, dt, J=15.3 and 6.9 Hz, H-5), 6.82–6.89, 7.01–7.30, 7.32–7.35, 7.43–7.47, 7.53–7.59 and 8.05–8.08 (13H, 6 sets of m, aromatic H).

Anal. Calcd. for $C_{59}H_{85}N_3O_{14}$: C, 66.63; H, 8.08; N, 3.96. Found: C, 66.28; H, 7.86; N, 4.14.

F. (2S,3R,4E)-2-Azido-3-benzoyloxy-1-(3,4-di-O-tert-butyloxycarbonylmethyl-α-D-galactopyranosyloxy)-4-octadecene and (2S,3R,4E)-2-azido-3-benzoyloxy-1-(3,4-di-O-tert-butyloxycarbonylmethyl-β-D-galactopyranosyloxy)-4-octadecene

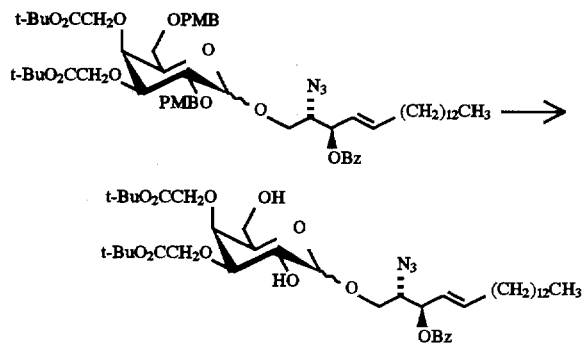

The mixture of (2S,3R,4E)-2-azido-3-benzoyloxy-1-(3,4-di-O-tert-butyloxycarbonylmethyl-2,6-di-O-para-methoxybenzyl-α-D-galactopyranosyloxy)-4-octadecene and (2S,3R,4E)-2-azido-3-benzoyloxy-1-(3,4-di-O-tert-butyloxycarbonylmethyl-2,6-di-O-para-methoxybenzyl-β-D-galactopyranosyloxy-4-octadecene (3.70 g, 3.49 mmol) was reacted by the general procedure as described in Example 1-E and afforded the title compound (2.46 g, 86%). Aliquots of the two isomers were separated by silica gel plates.

α-anomer:

$[\alpha]_D^{22}$: +19.7° (c=0.63, $CH_2Cl_2$).

IR (film) $v_{max}$ (cm$^{-1}$): 3480 (OH), 2930, 2855 (C—H), 2105 ($N_3$), 1725 (C=O).

$^1$H NMR 400 MHz (CDCl$_3$) δ(ppm): 0.88 (3H, t, J=6.8 Hz, —CH$_3$), 1.24–1.45 (22H, m, —(CH$_2$)$_{11}$—), 1.47 and 1.48 (18H, 2s, 2×tert-butyl), 2.08 (2H, qa, J=6.9 Hz, =CH—CH$_2$—), 3.00 (1H, d, J=8.3 Hz, —OH-2'), 3.56–3.60 (1H, m, H-1), 3.61 (1H, dd, J=10.0 and 2.6 Hz, H-3'), 3.68 (1H, ddd, J=11.1, 8.3 and 4.6 Hz, H-6'), 3.84–4.00 (4H, m, H-1, H-2, H-5' and H-6'), 4.09 (1H, ddd, J=10.0, 8.3 and 3.8 Hz, H-2'), 4.20 (1H, d, J$_{AB}$=16.7 Hz, —OCH$_2$CO—), 4.22 (1H, br s, H-4'), 4.26 (1H, d, J$_{AB}$=16.7 Hz, —OCH$_2$CO—), 4.28 (1H, d, J=17.8 Hz, —OCH$_2$CO—), 4.50 (1H, dd, J=8.3 and 6.6 Hz, —OH-6'), 4.63 (1H, d, J=17.8 Hz, —OCH$_2$CO—), 4.90 (1H, d, J=3.8 Hz, H-1'), 5.57 (1H, dd, J=15.0 and 8.0 Hz, H-4), 5.64 (1H, dd, J=8.0 and 4.7 Hz, H-3), 5.94 (1H, dt, J=15.0 and 6.9 Hz, H-5), 7.43–7.47, 7.56–7.60 and 8.03–8.05 (5H, 3 sets of m, —$C_6H_5$).

Anal. Calcd. for $C_{43}H_{69}N_3O_{12}$·0.5 $H_2O$: C, 62.30; H, 8.51; N, 5.07. Found: C, 61.78; H, 8.23; N, 5.08.

β-anomer $[\alpha]_D^{22}$: −40.0° (c=0.23, $CH_2Cl_2$).

IR (film) $v_{max}$ (cm$^{-1}$): 3480 (OH), 2930, 2855 (C—H), 2100 ($N_3$), 1730 (C=O).

$^1$H NMR 400 MHz (CDCl$_3$) δ(ppm): 0.88 (3H, t, J=6.8 Hz, —CH$_3$), 1.24–1.39 (22H, m, —(CH$_2$)$_{11}$—), 1.46 and 1.48 (18H, 2s, 2×tert-butyl), 2.06 (2H, ap qa, =CH—CH$_2$—), 3.34 (1H, dd, J=9.8 and 2.7 Hz, H-3'), 3.45 (1H, d, J=1.1 Hz, —OH-2'), 3.49 (1H, dd, J=8.8 and 5.5 Hz, H-1), 3.65–3.71 and 3.86–4.01 (6H, 2 sets of m, H-6', H-5', H-2', H-1 and H-2), 4.14 (1H, brd, H-4'), 4.18 (1H, d, J$_{AB}$=17.0 Hz, —OCH$_2$CO—), 4.23 (1H, d, J$_{AB}$=17.0 Hz, —OCH$_2$CO—), 4.26 (1H, d, J=17.7 Hz, —OCH$_2$CO—), 4.27 (1H, d, J=7.6 Hz, H-1'), 4.53 (1H, dd, J=9.1 and 6.2 Hz, —OH-6'), 4.59 (1H, d, J=17.7 Hz, —OCH$_2$CO—), 5.56 (1H, dd, J=15.2 and 8.0 Hz, H-4), 5.64 (1H, dd, J=8.0 and 4.3 Hz, H-3), 5.95 (1H, dt, J=15.2 and 6.8 Hz, H-5), 7.43–7.46, 7.55–7.58 and 8.04–8.06 (5H, 3 sets of m, —$C_6H_5$).

Anal. Calcd. for $C_{43}H_{69}N_3O_{12}·0.4\ H_2O$: C, 62.43; H, 8.51; N, 5.08. Found: C, 62.14; H, 8.21; N, 5.04.

G. (2S,3R,4E)-2-Azido-3-benzoyloxy-1-(3,4-di-O-tert-butylocycarbonylmethyl-2,6-di-O-benzoyl-α-D-galactopyranosyloxy)-4-octadecene and (2S,3R,4E)-2-azido-3-benzoyloxy-1-(3,4-di-O-tert-butyloxycarbonylmethyl-2,6-di-O-benzoyl-β-D-galactopyranosyloxy)-4-octadecene

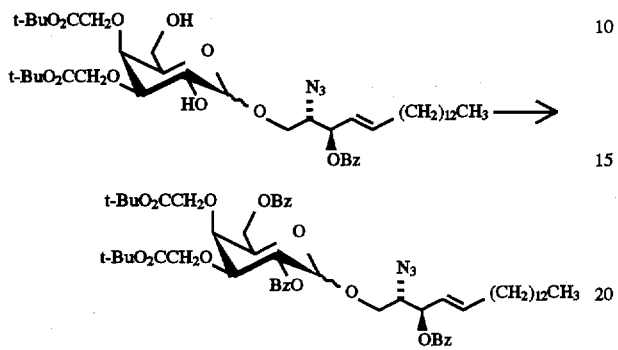

The mixture of (2S,3R,4E)-2-azido-3-benzoyloxy-1-(3,4-di-O-tert-butyloxycarbonylmethyl-α-D-galactopyranosyloxy)-4-octadecene and (2S,3R,4E)-2-azido-3-benzoyloxy-1-(3,4-di-O-tert-butyloxycarbonylmethyl-β-D-galactopyranosyloxy)-4-octadecene (2.43 g, 2.96 mmol) was reacted by the general method as described in Example 1-F except that triethylamine was used instead of pyridine, and afforded the α-anomer (1.49 g, 49%) and the β-anomer (1.15 g, 38%) of the title material.

α-anomer:

$[\alpha]_D^{22}$: +25.0° (c=1.42, $CH_2Cl_2$).

IR (film) $v_{max}$ ($cm^{-1}$): 2930, 2855 (C—H), 2100 ($N_3$), 1725 (C=O). $^1H$ NMR 400 MHz ($CDCl_3$) δ(ppm): 0.89 (3H, t, J=6.8 Hz, —$CH_3$), 1.21–1.31 (22H, m, —$(CH_2)_{11}$—), 1.48 (18H, 2s, 2×tert-butyl), 1.93 (2H, qa, J=7.0 Hz, =CH—$CH_2$—), 3.44 (1H, dd, J=10.2 and 8.0 Hz, H-1), 3.83 (1H, dd, J=10.2 and 3.6 Hz, H-1), 3.84–3.88 (1H, m, H-2), 4.03 (1H, dd, J=10.4 and 2.7 Hz, H-3'), 4.13 (1H, d, $J_{AB}$=16.8 Hz, —$OCH_2CO$—), 4.25 (1H, d, $J_{AB}$=16.8 Hz, —$OCH_2CO$—), 4.29 (1H, dd, J=7.8 and 4.2 Hz, H-5'), 4.38 (1H, d, $J_{AB}$=16.9 Hz, —$OCH_2CO$—), 4.45 (1H, br s, H-4'), 4.56 (1H, d, $J_{AB}$=16.9 Hz, —$OCH_2CO$—), 4.73 (1H, dd, J=11.8 and 7.8 Hz, H-6'), 4.86 (1H, d, $J_{AB}$=11.8 and 4.2 Hz, —$OCH_2CO$—), 5.27 (1H, d, J=3.7 Hz, H-1'), 5.41 (1H, dd, J=14.1 and 8.1 Hz, H-4), 5.38–5.44 (1H, m, H-3), 5:53 (1H, dd, J=10.4 and 3.7 Hz, H-2'), 5.66–5.73 (1H, m, H-5), 7.39–7.47, 7.54–7.59, 7.95–7.97 and 8.07–8.09 (15H, 4 sets of m, 3×—$C_6H_5$).

Anal. Calcd. for $C_{57}H_{77}N_3O_{14}$: C, 66.58; H, 7.55; N, 4.09. Found: C, 66.70; H, 7.53; N, 4.13.

β-anomer:

$[\alpha]_D^{22}$: -39° (C=1.0, $CH_2Cl_2$).

IR (film) $v_{max}$ ($cm^{-1}$): 2930, 2855 (C—H), 2100 ($N_3$), 1725 (C=O).

$^1H$ NMR 400 MHz ($CDCl_3$) δ(ppm): 0.89 (3H, t, J=6.8 Hz, —$CH_3$), 1.21–1.31 (22H, m, —$(CH_2)_{11}$—), 1.43 and 1.48 (18H, 2s, 2×tert-butyl), 1.89 (2H, ap qa, =CH—$CH_2$—), 3.59 (1H, dd, J=9.9 and 6.0 Hz, H-1), 3.71 (1H, dd, J=9.9 and 2.6 Hz, H-3'), 3.88 (1H, dd, J=9.9 and 6.8 Hz, H-1), 3.86–3.93 (2H, m, H-2 and H-5'), 3.96 (1H, d, $J_{AB}$=16.7 Hz, —$OCH_2CO$—), 4.16 (1H, d, $J_{AB}$=17.0 Hz, —$OCH_2CO$—), 4.36 (1H, d, $J_{AB}$=17.0 Hz, —$OCH_2CO$—), 4.39 (1H, br s, H-4'), 4.58 (1H, d, $J_{AB}$=17.0 Hz, —$OCH_2CO$—), 4.58 (1H, d, J=8.0 Hz, H-1'), 4.71 (1H, dd, J=11.8 and 7.5 Hz, H-6'), 4.96 (1H, dd, J=11.8 and 4.5 Hz, H-6'), 5.43 (1H, dd, J=15.3 and 8.0 Hz, H-4), 5.53 (1H, dd, J=8.0 and 3.6 Hz, H-3), 5.62 (1H, dd, J=9.9 and 8.0 Hz, H-2'), 5.68 (1H, dt, J=15.3 and 6.8 Hz, H-5), 7.40–7.48, 7.53–7.59 and 8.00–8.10 (15H, 3 sets of m, 3×—$C_6H_5$).

Anal. Calcd. for $C_{57}H_{77}N_3O_{14}$: C, 66.58; H, 7.55; N, 4.09. Found: C, 66.48; H, 7.32; N, 4.10.

H. (2S,3R,4E)-2-Hexadecanoylamino-3-benzoyloxy-1-(3,4-di-O-tert-butyloxycarbonylmethyl-2,6-di-O-benzoyl-α-D-galactopyranosyloxy)-4-octadecene

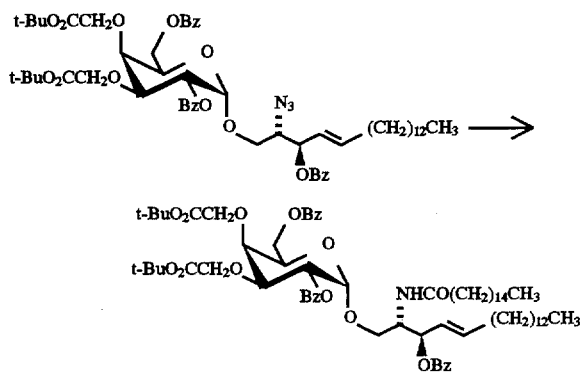

(2S,3R,4E)-2-Azido-3-benzoyloxy-1-(3,4-di-O-tert-butyloxycarbonylmethyl-2,6-di-O-benzoyl-α-D-galactopyranosyloxy)-4-octadecene (0.600 g, 0.58 mmol) was reacted by the general procedure as described in Example 1-G and afforded the title material (0.536 g, 74%).

$[\alpha]_D^{22}$: +32.7° (c=0.63, $CH_2Cl_2$).

IR (film) $v_{max}$ ($cm^{-1}$): 2930, 2855 (C—H), 1722, 1655 (C=O).

$^1H$ NMR 400 MHz ($CDCl_3$) δ(ppm): 0.89 (6H, t, J=6.7 Hz, 2×—$CH_3$), 1.2–14 (48H, m, —$(CH_2)_{11}$— and —$(CH_2)_{13}$—), 1.49 (18H, 2s, 2×tert-butyl), 1.89–1.94 (4H, m, —$NHCOCH_2$— and =CH—$CH_2$—), 3.63 (1H, dd, J=10.8 and 6.0 Hz, H-1), 3.77 (1H, dd, J=10.8 and 3.7 Hz, H-1), 4.00 (1H, dd, J=10.3 and 2.7 Hz, H-3'), 4.10 (1H, d, $J_{AB}$=16.7 Hz, —$OCH_2CO$—), 4.23 (1H, d, $J_{AB}$=16.7 Hz, —$OCH_2CO$—), 4.29 (1H, br dd, H-5'), 4.38 (1H, d, $J_{AB}$=16.9 Hz, —$OCH_2CO$—), 4.43 (1H, br s, H-4'), 4.45 (1H, m, H-2), 4.56 (1H, d, $J_{AB}$=16.9 Hz, —$OCH_2CO$—), 4.70 (1H, dd, J=11.7 and 7.4 Hz, H-6'), 4.84 (1H, dd, J=11.7 and 4.7 Hz, H-6'), 5.23 (1H, d, J=3.7 Hz, H-1'), 5.39 (1H, dd, J=15.3 and 7.3 Hz, H-4), 5.47 (1H, dd, J=10.3 and 3.7 Hz, H-2'), 5.45–5.52 (1H, m, H-3), 5.67–5.74 (1H, m, H-5), 5.69 (1H, d, J=9.2 Hz, —NH—), 7.37–7.44, 7.53–7.57, 7.92–7.97 and 8.05–8.07 (15H, 4 sets of m, 3×—$C_6H_5$).

Anal. Calcd. for $C_{73}H_{109}NO_{15}·0.3\ H_2O$: C, 70.37; H, 8.87; N, 1.12. Found: C, 70.25; H, 8.51; N, 1.17.

EXAMPLE 10

(2S,3R,4E)-2-Hexadecanoylamino-3-benzoyloxy-1-
[3,4-di-O-carboxy-methyl-2,6-di-O-benzoyl-α-D-
galactopyranosyloxy]-4-octadecene

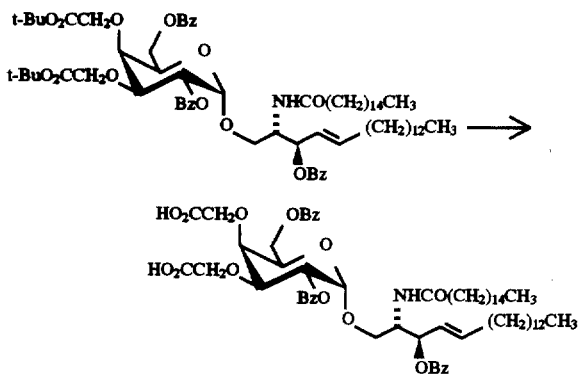

A solution of (2S,3R,4E)-2-hexadecanoylamino-3-benzoyloxy-1-(3,4-di-O-tert-butyloxycarbonylmethyl-2,6-di-O-benzoyl-α-D-galactopyranosyloxy)-4-octadecene (0.400 g, 0.32 mmol) was treated with aqueous trifluoroacetic acid (90%, 11 mL) at 22° C. The mixture was stirred for 15 minutes, then toluene was added and the solvents were evaporated in vacuo. This process was repeated 4 times to give a glass. The crude material was precipitated in acetonitrile (~12 mL) and afforded the diacid of the title compound (0.360 g, 98%) as a white solid.

$[\alpha]_D^{22}$: +46.1° (c=0.77, $CH_2Cl_2$).

IR (KBr) $v_{max}$ ($cm^{-1}$): 3320 (OH), 2920, 2850 (C—H), 1758, 1722, 1645 (C=O).

$^1$H NMR 400 MHz (pyridine-$d_5$) δ(ppm): 0.86 (6H, br t, 2×—$CH_3$), 1.1–1.4 (46H, m, —$(CH_2)_{11}$— and —$(CH_2)_{12}$—), 1.6–1.85 (2H, m, —$CH_2$—), 1.94 (2H, qa, J=6.5 Hz, =CH—$CH_2$—), 2.15–2.3 (2H, m, —NHCO$CH_2$—), 3.98 (1H, dd, J=10.5 and 7.8 Hz, H-1), 4.43 (1H, dd, J=10.5 and 3.0 Hz, H-1), 4.66 (1H, d, $J_{AB}$=16.7 Hz, —OCH$_2$CO—), 4.70 (1H, dd, J=10.3 and 2.6 Hz, H-3'), 4.71 (1H, d, $J_{AB}$=16.7 Hz, —OCH$_2$CO—), 4.76 (1H, dd, J=7.4 and 4.6 Hz, H-5'), 4.96 (1H, d, J=17.0 Hz, —OCH$_2$CO—), 5.10 (1H, br, s, H-4'), 5.22 (1H, m, H-2), 5.29–5.39 (2H, m, H-6'), 5.37 (1H, d overlapping H-6', J=17.0 Hz, —OCH$_2$CO—), 5.71 (1H, dd, J=3.7 Hz, H-1'), 5.83 (1H, dd, J=15.4 and 7.2 Hz, H-4), 5.96 (1H, dt, J=15.4 and 6.5 Hz, H-5), 6.12 (1H, dd, J=10.3 and 3.7 Hz, H-2'), 6.16 (1H, br t, H-3), 7.33–7.37, 7.44–7.57, 8.11–8.13 and 8.33–8.39 (15H, 4 sets of m, 3×—$C_6H_5$), 8.79 (1H, d, J=8.8 Hz, —NH—).

Anal. Calcd. for $C_{65}H_{93}NO_{15}$·0.3 $H_2O$: C, 68.85; H, 8.32; N, 1.24. Found: C, 68.85; H, 8.00; N, 1.29.

Preparation of Sodium Salt of Title compound

Part of this diacid (0.325 g, 0.288 mmol) was dissolved in freshly distilled dioxane (17 mL) and this solution was treated with sodium bicarbonate (47.5 mg, 0.565 mmol) in water (15 mL). The milky solution was warmed (~50° C., ~3 minutes) and became clear. Lyophilization gave the sodium salt of the title compound (0.265 g) as a white powder.

$[\alpha]_D^{22}$: +68.3° (c=0.63, $CH_2Cl_2$).

IR (KBr) $v_{max}$ ($cm^{-1}$): 2930, 2855 (C—H), 1722, 1650–1600 (C=O).

$^1$H NMR 400 MHz (DMSO-$d_6$) δ(ppm): 0.83 (6H, t, J=6.7 Hz, 2×—$CH_3$), 1.09–1.33 (48H, m, —$(CH_2)_{11}$—' and —$(CH_2)_{13}$—), 1.70–1.77 and 1.84–1.90 (4H, 2 sets of m, —NHCOC$H_2$— and =CH—$CH_2$—), 3.52 (1H, dd, J=10.1 and 6.6 Hz, H-1), 3.74–3.77 (2H, m, —OCH$_2$CO— and H-1), 3.90 (1H, d, $J_{AB}$=13.7 Hz, —OCH$_2$CO—), 3.95 (1H, d, $J_{AB}$=13.7 Hz, —OCH$_2$CO—), 4.08 (1H, dd, J=10.4 and 2.8 Hz, H-3'), 4.13 (1H, d, J=12.0 Hz, —OCH$_2$CO—), 4.15 (1H, br s, H-4'), 4.23 (1H, br dd, H-5'), 4.32–4.35 (1H, m, H-2), 4.43 (1H, dd, J=11.0 and 3.6 Hz, H-6'), 4.54 (1H, dd, J=11.0 and 8.5 Hz, H-6'), 5.15 (1H, d, J=3.4 Hz, H-1'), 5.26 (1H, dd, J=10.4 and 3.4 Hz, H-2'), 5.34–5.40 (2H, m, H-4 and H-3), 5.64 (1H, dt, J=14.0 and 6.7 Hz, H-5), 7.34–7.43, 7.49–7.58, 7.80–7.82, 7.90–7.91 and 7.95–7.97 (15H, 5 sets of m, 3×—$C_6H_5$), 7.75 (1H, d, J=8.8 Hz, —NH—).

EXAMPLE 11

(2S,3R,4E)-2-Hexadecanoylamino-3-benzoyloxy-1-
(3,4-di-O-tert-butyloxycarbonylmethyl-2,6-di-O-
benzoyl-β-D-galactopyranosyloxy)-4-octadecene

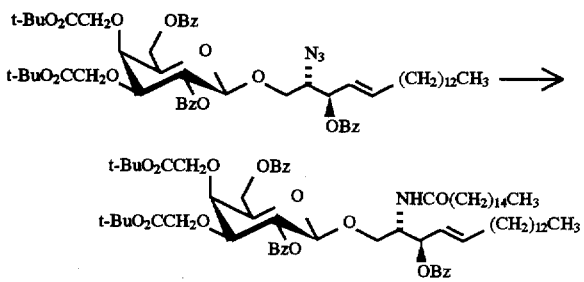

(2S,3R,4E)-2-Azido-3-benzoyloxy-1-(3,4-di-O-tert-butyloxycarbonylmethyl-2,6-di-O-benzoyl-β-D-galactopyranosyloxy)-4-octadecene described in Example 9-G (0.510 g, 0.496 mmol) was reacted by the general procedure as described in Example 1-G and afforded the title compound (0.506 g, 82%).

$[\alpha]_D^{22}$: −11.9° (c=0.47, $CH_2Cl_2$).

IR (film) $v_{max}$ ($cm^{-1}$): 3700–3000 (NH), 2925, 2855 (C—H), 1745, 1722, 1655 (C=O).

$^1$H NMR 400 MHz (CDCl$_3$) δ(ppm): 0.88–0.91 (6H, m, 2×—$CH_3$), 1.1–1.3 (48H, m, —$(CH_2)_3$— and —$(CH_2)_{11}$—), 1.43 and 1.48 (18H, 2s, 2×tert-butyl), 1.78 (2H, t, J=7.7 Hz, —NHCOC$H_2$—), 1.96 (2H, m, =CH—$CH_2$—), 3.65 (1H, dd, J=10.2 and 4.0 Hz, H-1), 3.70 (1H, dd, J=9.9 and 2.6 Hz, H-3'), 3.89 (1H, br, dd, H-5'), 3.96 (1H, d, J=16.7 Hz, —OCH$_2$CO—), 4.11 (1H, dd, J=10.2 and 3.6 Hz, H-1), 4.15 (1H, d, J=16.7 Hz, —OCH$_2$CO—), 4.36 (1H, d, J=16.7 Hz, —OCH$_2$CO—), 4.38 (1H, br d, H-4'), 4.3–4.4 (1H, m, H-2), 4.51 (1H, d, J=7.8 Hz, H-1'), 4.57 (1H, d, J=16.7 Hz, —OCH$_2$CO—), 4.61 (1H, dd, J=11.8 and 7.4 Hz, H-6'), 4.92 (1H, dd, J=11.8 and 4.5 Hz, H-6'), 5.46 (1H, dd, J=15.2 and 7.0 Hz, H-4), 5.53 (1H, br t, H-3), 5.58 (1H, dd, J=9.9 and 7.8 Hz, H-2'), 5.76 (1H, d, J=9.2 Hz, —NH—), 5.75–5.85 (1H, m, H-5), 7.39–7.61 and 8.01–8.03 (15H, 2 sets of m, 3×—$C_6H_5$).

Anal. Calcd. for $C_{73}H_{109}NO_{15}$·0.7 $H_2O$: C, 69.96; H, 8.88; N, 1.12. Found: C, 69.97; H, 8.68; N, 1.11.

EXAMPLE 12

(2S,3R,4E)-2-Hexadecanoylamino-3-benzoyloxy-1-[3,4-di-O-carboxy-methyl-2,6-di-O-benzoyl-β-D-galactopyranosyloxy]-4-octadecene

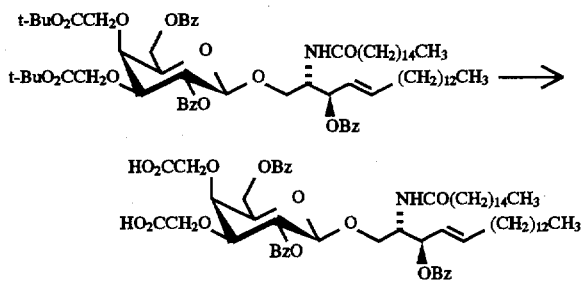

(2S,3R,4E)-2-Hexadecanoylamino-3-benzoyloxy-1-(3,4-di-O-tert-butyloxycarbonylmethyl-2,6-di-O-benzoyl-β-D-galactopyranosyloxy)-4-octadecene (0.330 g, 0.266 mmol) was reacted by the general procedure as described in Example 10 and afforded (2S,3R,4E)-2-hexadecanoylamino-3-benzoyloxy-1-(3,4-di-O-carboxymethyl-2,6-di-O-benzoyl-β-D-galactopyranosyloxy-4-octadecene (0.252 g, 84%).

Diacid:

$[\alpha]_D^{22}$: +9.1° (c=0.38, $CH_2Cl_2$).

IR (KBr) $v_{max}$ ($cm^{-1}$): 3700–3000 (NH), 2920, 2850 (C—H), 1725, 1645 (C=O).

$^1$H NMR 400 MHz (pyridine-$d_5$) δ(ppm): 0.85 (6H, t, J=6.7 Hz, 2×—$CH_3$), 1.1–1.4 (46H, m, —$(CH_2)_{11}$— and —$(CH_2)_{12}$—), 1.6–1.8 (2H, m, —$CH_2$—), 1.91 (2H, m, =CH—$CH_2$—), 2.07–2.14 and 2.17–2.25 (2H, 2 sets of m, —NHCO$CH_2$—), 4.32 (1H, dd, J=10.8 and 4.7 Hz, H-1), 4.40 (1H, dd, J=9.9 and 2.7 Hz, H-3'), 4.37–4.44 (2H, m, H-1 and H-5'), 4.60 (1H, d, $J_{AB}$=16.7 Hz, —O$CH_2$CO—), 4.66 (1H, d, $J_{AB}$=16.7 Hz, —O$CH_2$CO—), 4.89 (1H, d, J=17.1 Hz, —O$CH_2$CO—), 5.11 (1H, br d, H-4'), 5.11–5.19 (1H, m, H-2), 5.15 (1H, dd, J=11.6 and 6.9 Hz, H-6'), 5.18 (1H, d, J=8.0 Hz, H-1'), 5.35 (1H, d, J=17.1 Hz, —O$CH_2$CO—), 5.50 (1H, dd, J=11.6 and 4.6 Hz, H-6'), 5.80 (1H, dd, J=15.5 and 7.1 Hz, H-4), 5.92 (1H, dt, J=15.5 and 6.5 Hz, H-5), 6.15 (1H, br dd, H-3), 6.34 (1H, dd, J=9.9 and 8.0 Hz, H-2'), 7.35–7.56, 8.18–8.20, 8.24–8.26 and 8.33–8.35 (15H, 4 sets of m, 3×—$C_6H_5$), 8.49 (1H, d, J=8.4 Hz, —NH—).

Anal. Calcd. for $C_{65}H_{93}NO_{15}$·0.6 $H_2O$: C, 68.53; H, 8.33; N, 1.23. Found: C, 68.51; H, 8.26; N, 1.22.

Preparation of Sodium Salt of Title Compound

The above diacid (0.223 g, 0.198 mmol) was converted to the sodium salt by the general procedure as described in Example 10 and gave the sodium salt of the title compound (0.206 g, 89%) as a white powder.

$[\alpha]_D^{22}$: +27.8° (c=0.54, $CH_2Cl_2$).

IR (film) $v_{max}$ ($cm^{-1}$): 3700–3000 (NH), 2920, 2850 (C—H), 1720, 1645, 1615 (C=O).

$^1$H NMR 400 MHz (DMSO-$d_6$) δ(ppm): 0.84 (6H, t, J=6.8 Hz, 2×—$CH_3$), 1.1–1.4 (48H, m, —$(CH_2)_{11}$— and —$(CH_2)_{13}$—), 1.80 and 1.87–1.94 (4H, 2 sets of m, =CH—$CH_2$— and —NHCO$CH_2$—), 3.59 (1H, dd, J=10.1 and 6.2 Hz, H-1), 3.70–3.84 (2H, m, H-3' and H-1), 3.72 (1H, d, $J_{AB}$=14.1 Hz, —O$CH_2$CO—), 3.80 (1H, br d, H-4'), 3.82 (1H, d, $J_{AB}$=14.1 Hz, —O$CH_2$CO—), 3.95 (1H, br dd, H-5'), 4.22 (2H, br s, —O$CH_2$CO—), 4.28–4.35 (1H, m, H-2), 4.47 (1H, dd, J=11.7 and 7.5 Hz, H-6'), 4.53 (1H, dd, J=11.7 and 5.2 Hz, H-6'), 4.65 (1H, d, J=7.7 Hz, H-1'), 5.27 (1H, dd, J=9.6 and 7.7 Hz, H-2'), 5.33–5.41 (2H, m, H-4 and H-3), 5.54 (1H, dt, J=14.1 and 6.7 Hz, H-5), 7.37–7.60, 7.86–7.91 and 7.96–7.98 (16H, 3 sets of m, 3×—$C_6H_5$ and —NH—).

EXAMPLE 13

(2S,3R,4E)-3-Benzoyloxy-2-hexadecanoylamino-1-(2-O-benzoyl-4,6-di-O-tert-butyloxycarbonylmethyl-α-D-galactopyranosyloxy)-4-octadecene A. (2S,3R,4E)-3-Benzoyloxy-2-azido-1-(2-O-benzoyl-4,6-di-O-tert-butyloxycarbonylmethyl-α-galactopyranosyloxy)-4-octadecene

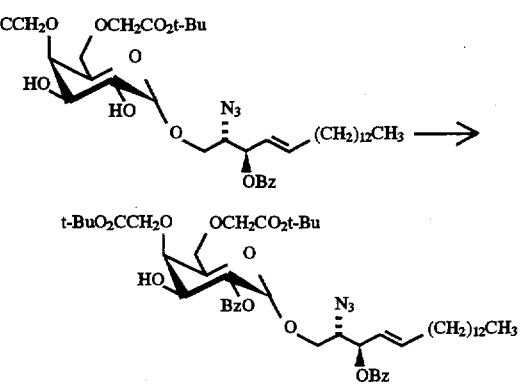

A solution of (2S,3R,4E)-3-benzoyloxy-2-azido-1-(4,6-di-O-tert-butyloxycarbonylmethyl-α-D-galactopyranosyloxy)-4-octadecene prepared as described in Example 1-E (0.422 g, 0.51 mmol) in pyridine (12 mL) and methylene chloride (12 mL) was treated with benzoyl chloride (80 μL, 0.69 mmol) at −15° C. The mixture was stirred for 30 minutes at −15° C. then methanol (10 mL) was added and the mixture was stirred for another 18 hours at room temperature. The solvents were evaporated and the residue was co-evaporated with toluene (2×5 mL) and diluted with ethyl acetate (100 mL). This organic phase was washed with 1M aqueous sodium bicarbonate (2×100 mL), water (2×100 mL) and brine (2×100 mL), dried over anhydrous magnesium sulfate, filtered and concentrated. The residue was purified by silica gel column chromatography (60g, 5 to 20% ethyl acetate/hexane) and afforded the title compound (0.420 g, 90%) along with (2S,3R,4E)-3-benzoyloxy-2-azido-1-(2,3-di-O-benzoyl-4,6-di-O-tert-butyloxycarbonylmethyl-α-D-galactopyranosyloxy)-4-octadecene (0.028g).

IR ($CH_2Cl_2$) $v_{max}$ ($cm^{-1}$): 3600–3300 (OH), 2105 ($N_3$), 1722 (C=O).

$^1$H NMR 400 MHz ($CDCl_3$) δ(ppm): 0.89 (3H, t, J=6.8 Hz, m —$CH_3$), 1.24–1.37 (22H, m, —$(CH_2)_{11}$—), 1.48 and 1.51 (18H, 2s, 2×tert-butyl), 2.04 (2H, m, =CH—$CH_2$—), 3.48 (1H, dd, J=10.6 and 8.0 Hz, H-1), 3.63 (1H, dd, J=9.2 and 5.8 Hz, H-6'), 3.82–3.86 (2H, m, H-1 and H-6'), 3.9 (1H, dd, J=7.8 and 3.9 Hz, H-2), 3.94 (1H, d, J=3.1 Hz, H-4'), 4.02 (1H, d, $J_{AB}$=16.2 Hz, —O$CH_2$CO—), 4.06 (1H, d, $J_{AB}$=16.2 Hz, —O$CH_2$CO—), 4.12 (1H, d, J=17.2 Hz, —O$CH_2$CO—), 4.14–4.17 (1H, m, H-5'), 4.19 (1H, br td, H-3'), 4.42 (1H, d, J=17.2 Hz, —O$CH_2$CO—), 4.93 (1H, d, J=9.8 Hz, —OH), 5.20 (1H, d, J=3.7 Hz, H-1'), 5.28 (1H, dd, J=10.4 and 3.7 Hz, H-2'), 5.50–5.57 (2H, m, H3 and H-4), 5.89 (1H, dt, J=14.2 and 6.8 Hz, H-5), 7.40–7.46, 7.51–7.58, 8.00–8.02 and 8.12–8.15 (10H, 4 sets of m, 2×—$C_6H_5$).

Anal. Calcd. for $C_{50}H_{73}N_3O_{13}$: C, 64.98; H, 7.96; N, 4.55. Found: C, 64.99; H, 7.84; N, 4.59.

B. (2S,3R,4E)-3-Benzoyloxy-2-hexadecanoylamino-1-(2-O-benzoyl-4,6-di-O-tert-butyloxycarbonylmethyl-α-D-galactopyranosyloxy)-4-octadecene

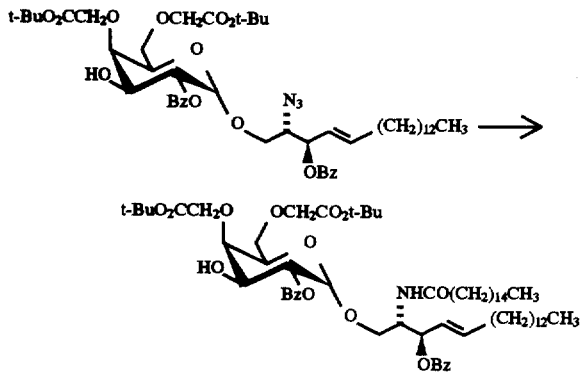

(2S,3R,4E)-3-Benzoyloxy-2-azido-1-(2-O-benzoyl-4,6-di-O-tert-butyloxy-carbonylmethyl-α-D-galactopyranosyloxy)-4-octadecene (0.57 g, 0.62 mmol) was reacted by the general procedure as described in Example 1-G except that the acylation reaction was performed at 0° C. This gave the title compound (0.571 g, 81%) as a white solid.

$^1$H NMR 400 MHz (CDCl$_3$) δ(ppm): 0.89 (6H, t, J=6.7 Hz, 2×—CH$_3$), 1.23–1.31 (48H, m, —(CH$_2$)$_{11}$— and —(CH$_2$)$_{13}$—), 1.48 and 1.50 (18H, 2s, 2×tert-butyl), 1.97 (2H, m, =CH—CH$_2$—), 2.08 (2H, m, —NHCOCH$_2$—), 3.65 (1H, dd, J=9.1 and 6.2 Hz, H-1), 3.74 (1H, dd, J=11.0 and 4.6 Hz, H-6'), 3.78 (1H, dd, J=11.0 and 3.6 Hz, H-6'), 3.82 (1H, dd, J=9.1 and 7.7 Hz, H-1), 3.92 (1H, d, J=3.0 Hz, H-4'), 3.98 (1H, d, J$_{AB}$=16.2 Hz, —OCH$_2$CO—), 4.06 (1H, d, J$_{AB}$=16.2 Hz, —OCH$_2$CO—), 4.10 (1H, d, J=17.5 Hz, —OCH$_2$CO—), 4.13–4.19 (2H, m, H-3' and H-5'), 4.41 (1H, d, J=17.2 Hz, —OCH$_2$CO—), 4.46 (1H, m, H-2), 4.90 (1H, d, J=9.6 Hz, —OH), 5.14 (1H, d, J=3.7 Hz, H-1'), 5.27 (1H, dd, J=10.4 and 3.7 Hz, H-2'), 5.47 (1H, dd, J=15.2 and 7.5 Hz, H-4), 5.55 (1H, br t, H-3), 5.75 (1H, dt, J=15.2 and 6.9 Hz, H-5), 5.84 (1H, d, J=9.2 Hz, —NH—), 7.37–7.45, 7.51–7.57, 7.98–8.00 and 8.07–8.09 (10H, 4 sets of m, 2×—C$_6$H$_5$).

Anal. Calcd. for C$_{66}$H$_{105}$NO$_{14}$: C, 69.75; H, 9.31; N, 1.23. Found: C, 68.76; H, 9.05; N, 1.28.

EXAMPLE 14

(2S,3R,4E)-3-Benzoyloxy-2-hexadecanoylamino-1-[2-O-benzoyl-4,6-di-O-carboxymethyl-α-D-galactopyranosyloxy]-4-octadecene

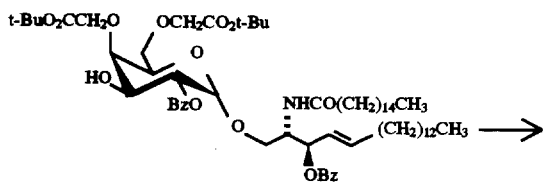

-continued

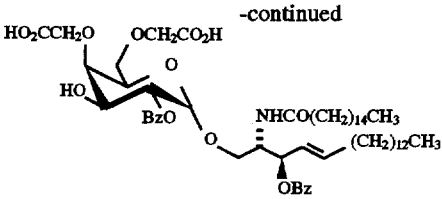

(2S,3R,4E)-3-Benzoyloxy-2-hexadecanoylamino-1-(2-O-benzoyl-4,6-di-O-tert-butyloxycarbonylmethyl-α-D-galactopyranosyloxy)-4-octadecene (0.466 g, 0.41 mmol) was reacted by the general procedure as described in Example 2 and afforded (2S,3R,4E)-3-benzoyloxy-2-hexadecanoylamino-1-(2-O-benzoyl-4,6-di-O-carboxymethyl-α-D-galactopyranosyloxy)-4-octadecene (0.145 g, 34%) as a beige solid.

IR (Nujol) ν$_{max}$ (cm$^{-1}$): 3300 (OH, NH), 2920, 2850 (C—H), 1718, 1645 (C=O).

$^1$H NMR 400 MHz (DMSO-d$_6$) δ(ppm): 0.85 (6H, t, J=6.7 Hz, 2×—CH$_3$), 1.16–1.39 (48H, m, —(CH$_2$)$_{11}$— and —(CH$_2$)$_{13}$—), 1.80–1.99 (4H, m, =CH—CH$_2$— and —NHCOCH$_2$—), 3.45 (1H, dd, J=10.2 and 6.9 Hz, H-1), 3.58 (1H, dd, J=9.9 and 6.7 Hz, H-6'), 3.68 (1H, dd, J=10.2 and 4.2 Hz, H-1), 3.79 (1H, dd, J=9.9 and 5.6 Hz, H-6'), 3.82 (1H, br d, H-4'), 3.97–4.06 (1H, m overlapped by —OCH$_2$CO—, H-5—), 4.00 (1H, d, J$_{AB}$=16.8 Hz, —OCH$_2$CO—), 4.03 (1H, d, J$_{AB}$=16.8 Hz, —OCH$_2$CO—), 4.18 (1H, dd, J=10.4 and 2.6 Hz, H-3'), 4.26–4.38 (1H, m overlapped by —OCH$_2$CO—, H-2), 4.98 (1H, d, J=3.5 Hz, H-1'), 5.08 (1H, dd, J=10.4 and 3.5 Hz, H-2'), 5.44 (1H, t, J=7.3 Hz, H-3), 5.49 (1H, dd, J=14.7 and 7.4 Hz, H-4), 5.73 (1H, dt, J=14.7 and 6.9 Hz, H-5), 7.44–7.48, 7.59–7.64, 7.86–7.88 and 7.93–7.95 (1 OH, 4 sets of m, 2×—C$_6$H$_5$), 7.82 (1H, d, J=8.9 Hz, —NH—).

Preparation of Sodium Salt of Title Compound

This diacid was dissolved in dioxane (9 mL) and the resulting solution was filtered on a filter Millex LCR 0.5 μm and treated dropwise with a sodium bicarbonate solution (23 mg, 0.274 mmol) in water (2 mL). The solution became unclear and dioxane (~30 mL) was added. This was heated to ~40° C., stirred at room temperature for 2 hours and lyophilized to afford the sodium salt of the title material (0.125 g, 82%) as a white fluffy solid.

IR (Nujol) ν$_{max}$ (cm$^{-1}$): 3700–3000 (broad, OH, NH), 2930, 2850 (C—H), 1710, 1648 (C=O).

$^1$H NMR 400 MHz (DMSO-d$_6$/CDCl$_3$) δ(ppm): 0.85 (6H, t, J=6.8 Hz, 2×—CH$_3$), 1.16–1.42 (48H, m, —(CH$_2$)$_{11}$— and —(CH$_2$)$_{13}$—), 1.85–1.97 (4H, m, =CH—CH$_2$— and —NHCOCH$_2$—), 3.43 (1H, dd, J=10.3 and 6.8 Hz, H-1), 3.50 (1H, dd, J=9.3 and 6.1 Hz, H-6'), 3.55–3.68 (5H, m, H-1, H-6' and —OCH$_2$CO—), 3.70 (1H, d, J=3.0 Hz, H-4'), 3.83 (1H, d, J=16.0 Hz, —OCH$_2$CO—), 3.96 (1H, br t, H-5'), 3.98 (1H, dd, J=10.2 and 3.0 Hz, H-3'), 4.28 (1H, m, H-2), 4.90 (1H, d, J=3.6 Hz, H-1'), 5.02 (1H, dd, J=10.2 and 3.6 Hz, H-2'), 5.44 (1H, t, J=7.5 Hz, H-3), 5.48 (1H, dd, J=14.2 and 7.5 Hz, H-4), 5.72 (1H, dt, J=14.2 and 7.0 Hz, H-5), 7.42–7.47, 7.57–7.61, 7.87–7.89 and 7.92–7.94 (10H, 4 sets of m, 2×—C$_6$H$_5$), 7.83 (1H, d, J=8.9 Hz, —NH—).

EXAMPLE 15

(2S,3R,4E)-2-Hexadecanoylamino-3-benzoyloxy-1-(4,6-di-O-tert-butyloxycarbonylmethyl-2,3-di-O-benzoyl-β-D-galactopyranoside)-4-octadecene A. (2S,3R,4E)-2-Azido-3-benzoyloxy-1-(4,6-di-O-tert-butyloxycarbonylmethyl-β-D-galactopyranoside)-4-octadecene

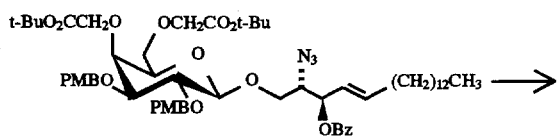

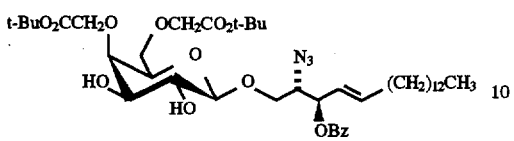

(2S,3R,4E)-2-Azido-3-benzoyloxy-1-(4,6-di-O-tert-butyloxycarbonylmethyl-2,3-di-O-para-methoxybenzyl-β-D-galactopyranoside)-4-octadecene described in Example 1-D (0.932 g, 0.88 mmol) was reacted by the general procedure as described in Example 1-E and afforded the title material (0.468 g, 65%) as a colorless oil.

IR (CH$_2$Cl$_2$) $v_{max}$ (cm$^{-1}$): 3570, 3380 (broad, OH), 3040, 2910, 2840 (C—H), 2090 (N$_3$), 1715 (C=O).

$^1$H NMR 400 MHz (CDCl$_3$) δ(ppm): 0.89 (3H, t, J=6.8 Hz, —CH$_3$), 1.25–1.40 (22H, m, —(CH$_2$)$_{11}$—), 1.49 (18H, s, 2×tert-butyl), 2.08 (2H, qa, J=6.8 Hz, =CH—CH$_2$—), 2.63 (1H, d, J=1.9 Hz, —OH-2'), 3.51 (1H, td, J=9.3 Hz and 3.3 Hz, H-3'), 3.61 (1H, dd, J=8.4 and 4.8 Hz, H-1), 3.66–3.73 (3H, m, H-6', H-5' and H-2'), 3.76 (1H, d, J=8.4 Hz, H-1), 3.79 (1H, br d, H-4'), 3.90 (1H, dd, J=10.5 and 7.1 Hz, H-6'), 3.99–4.02 (3H, m, H-2 and —OCH$_2$CO—), 4.07 (1H, d, J=17.3 Hz, —OCH$_2$CO—), 4.28 (1H, d, J=7.7 Hz, H-1'), 4.37 (1H, d, J=17.3 Hz, —OCH$_2$CO—), 5.15 (1H, d, J=9.0 Hz, —OH-3'), 5.67 (1H, dd, J=15.2 and 8.0 Hz, H-4), 5.66 (1H, dd, J=8.0 and 4.3 Hz, H-3), 5.97 (1H, dt, J=15.2 and 6.8 Hz, H-5), 7.44–7.48, 7.56–7.60 and 8.05–8.08 (5H, 3 sets of m, —C$_6$H$_5$).

B. (2S,3R,4E)-2-Azido-3-benzoyloxy-1-(4,6-di-O-tert-butyloxycarbonylmethyl-2,3-di-O-benzoyl-β-D-galactopyranoside)-4-octadecene

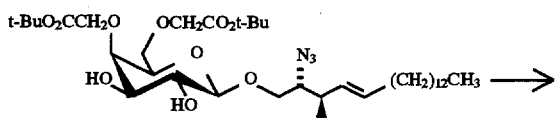

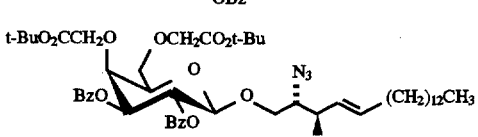

(2S,3R,4E)-2-Azido-3-benzoyloxy-1-(4,6-di-O-tert-butyloxycarbonylmethyl-β-D-galactopyranoside)-4-octadecene (55 mg, 0.067 mmol) was reacted by the general procedure as described in Example 1-F and afforded the title material (54 mg, 78%) as a colorless oil.

IR (CH$_2$Cl$_2$) $v_{max}$ (cm$^{-1}$): 3040, 2910, 2840 (C—H), 2090 (N$_3$), 1715 (C=O).

$^1$H NMR 400 MHz (CDCl$_3$) δ(ppm): 0.89 (3H, t, J=6.8 Hz, —CH$_3$), 1.22–1.34 (22H, m, —(CH$_2$)$_{11}$—), 1.40 and 1.49 (18H, 2s, 2×tert-butyl), 1.92 (2H, qa, J=6.7 Hz, =CH—CH$_2$—), 3.63 (1H, dd, J=12.8 and 8.7 Hz, H-1), 3.84 (1H, dd, J=9.4 and 6.0 Hz, H-6'), 3.92–3.96 (3H, m, H-1, H-2 and H-5'), 4.05 (2H, br s, —OCH$_2$CO—), 4.06 (1H, d, J=16.0 Hz, —OCH$_2$CO—), 4.11 (1H, dd, J=9.4 and 6.2 Hz, H-6'), 4.19 (1H, d, J=2.4 Hz, H-4'), 4.30 (1H, d, J=16.0 Hz, —OCH$_2$CO—), 4.72 (1H, d, J=7.9 Hz, H-1'), 5.39 (1H, dd, J=10.4 and 2.7 Hz, H-3'), 5.46 (1H, dd, J=15.2 and 8.1 Hz, H-4), 5.53 (1H, dd, J=8.1 and 3.4 Hz, H-3), 5.72 (1H, dt, J=15.2 and 6.7 Hz, H-5), 5.81 (1H, dd, J=10.4 and 7.9 Hz, H-2'), 7.33–7.57 and 7.95–8.08 (15H, 2 sets of m, 3×—C$_6$H$_5$).

C. (2S,3R,4E)-2-Hexadecanoylamino-3-benzoyloxy-1-(4,6-di-O-tert-butyloxycarbonylmethyl-2,3-di-O-benzoyl-β-D-galactopyranoside)-4-octadecene

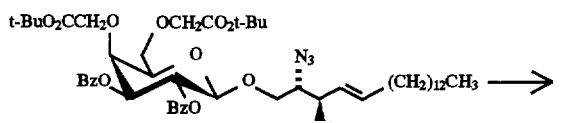

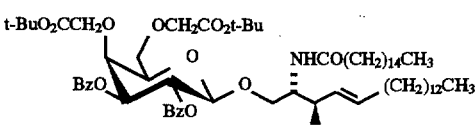

(2S,3R,4E)-2-Azido-3-benzoyloxy-1-(4,6-di-O-tert-butyloxycarbonylmethyl-2,3-di-O-benzoyl-β-D-galactopyranoside)-4-octadecene (0.333 g, 0.32 mmol) was reacted by the general procedure as described in Example 1-G and afforded the title material (0.322 g, 81%) as a white solid.

IR (CH$_2$Cl$_2$) $v_{max}$ (cm$^{-1}$): 3030, 2920, 2850 (C—H), 1725, 1670 (C=O).

$^1$H NMR 400 MHz (CDCl$_3$) δ(ppm): 0.89 (6H, t, J=6.7 Hz, 2×—CH$_3$), 1.24–1.31 (46H, m, —(CH$_2$)11— and —(CH$_2$)$_{12}$—), 1.41 and 1.48 (18H, 2s, 2×tert-butyl), 1.51–1.67 (2H, m, —CH$_2$—), 1.83 (2H, t, J=7.4 Hz, —NHCOCH$_2$—), 2.00 (2H, qa, J=6.8 Hz, =CH—CH$_2$—), 3.69 (1H, dd, J=9.6 and 3.9 Hz, H-1), 3.71 (1H, dd, J=9.6 and 5.8 Hz, H-6'), 3.91 (1H, br t, H-5'), 3.97 (2H, br d, —OCH$_2$CO—), 4.02 (1H, dd, J=9.6 and 6.8 Hz, H-6'), 4.07 (1H, d, J=16.1 Hz, —OCH$_2$CO—), 4.16 (1H, dd, J=9.6 and 3.6 Hz, H-1), 4.17 (1H, br d, H-4—), 4.30 (1H, d, J=16.1 Hz, —OCH$_2$CO—), 4.41 (1H, m, H-2), 4.65 (1H, d, J=7.9 Hz, H-1'), 5.41 (1H, dd, J=10.5 and 2.8 Hz, H-3'), 5.47 (1H, dd, J=15.2 and 7.2 Hz, H-4), 5.54 (1H, br t, H-3), 5.76 (1H, dd, J=10.5 and 7.9 Hz, H-2'), 5.80 (1H, d, J=8.9 Hz, —NH—), 5.74–5.85 (1H, m overlapped by —NH— and H-2', H-5), 7.27–7.57, 7.91–7.93, 7.97–7.99 and 8.03–8.05 (15H, 4 sets of m, 3×—C$_6$H$_5$).

EXAMPLE 16

(2S,3R,4E)-2-Hexadecanoylamino-3-benzoyloxy-1-(4,6-di-O-carboxymethyl-2,3-di-O-benzoyl-β-D-galactopyranoside)-4-octadecene

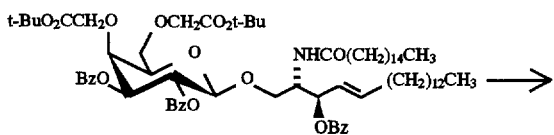

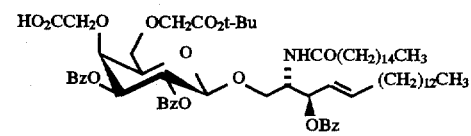

(2S,3R,4E)-2-Hexadecanoylamino-3-benzoyloxy-1-(4,6-di-O-tert-butyloxycarbonylmethyl-2,3-di-O-benzoyl-β-D-galactopyranoside)-4-octadecene (0.160 g, 0.13 mmol) was reacted by the general procedure as described in Example 1-H and afforded the title material (0.114 g, 78%) as a beige solid.

IR (nujol) ν$_{max}$ (cm$^{-1}$): 3500–2500 (broad, OH, NH, C—H), 1720, 1645 (C=O).

$^1$H NMR 400 MHz (pyridine-d$_5$) δ(ppm): 0.85 (6H, t, J=6.6 Hz, 2×—CH$_3$), 1.22–1.24 (46H, m, —(CH$_2$)$_{11}$— and —(CH$_2$)$_{12}$—), 1.67 and 1.75 (2H, 2 sets of m, —CH$_2$—), 1.96 (2H, m, =CH—CH$_2$—), 2.20 (2H, m, —NHCOC H$_2$—), 4.23 (1H, dd, J=9.5 and 6.0 Hz, H-6'), 4.33 (1H, dd, J=10.4 and 4.7 Hz, H-1), 4.43 (1H, br t, H-5'), 4.49 (2H, br d, —OCH$_2$CO—), 4.52 (1H, dd, J=10.4 and 3.1 Hz, H-1), 4.62 (1H, dd, J=9.5 and 6.9 Hz, H-6'), 4.74 (1H, d, J$_{AB}$=16.2 Hz, —OCH$_2$CO—), 4.79 (1H, d, J=2.7 Hz, H-4'), 4.86 (1H, d, J$_{AB}$=16.2 Hz, —OCH$_2$CO—), 5.12 (1H, m, H-2), 5.29 (1H, d, J=7.9 Hz, H-1—), 5.83 (1H, dd, J=15.5 and 7.1 Hz, H-4), 5.95 (1H, dt J=15.5 and 6.5 Hz, H-5), 6.05 (1H, dd, J=10.4 and 2.7 Hz, H-3'), 6.17 (1H, br t, H-3), 6.47 (1H, dd, J=10.4 and 7.9 Hz, H-2'), 7.19–7.51, 8.14–8.16 and 8.21–8.24 (15H, 3 sets of m, 3×—C$_6$H$_5$), 8.50 (1H, d, J=8.5 Hz, —NH—).

Anal. Calcd. for C$_{65}$H$_{93}$NO$_{15}$: C, 69.18; H, 8.31; N, 1.24. Found: C, 68.95; H, 8.22; N, 1.32.

EXAMPLE 17

(2S,3R,4E)-3-Benzoyloxy-2-hexadecanoylamino-1-(3-O-benzoyl-4,6-di-O-tert-butyloxycarbonylmethyl-β-D-galactopyranosyloxy)-4-octadecene A. (2S,3R,4E)-3-Benzoyloxy-2-azido-1-(3-O-benzoyl-4,6-di-O-tert-butyloxycarbonylmethyl-β-D-galactopyranosyloxy)-4-octadecene

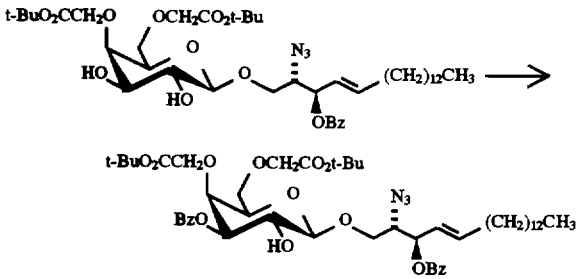

A solution of (2S,3R,4E)-2-azido-3-benzoyloxy-1-(4,6-di-O-tert-butyloxycarbonylmethyl-β-D-galactopyranosyloxy)-4-octadecene described in Example 15-A (1.34 g 1.63 mmol) in a mixture of pyridine/methylene chloride (1:1, 70 mL) was treated with benzoyl chloride (210 μL, 1.81 mmol) at −78° C. The mixture was stirred at −78° C. for 1 hour, then methanol (10 mL) was added and the resulting mixture was stirred at 22° C. for 20 more hours. The solvents were evaporated and the residue was dissolved in ethyl acetate (200 mL). This solution was washed with water (4×75 mL), saturated aqueous sodium bicarbonate (2×100 mL) and brine (2×100 mL), dried over anhydrous magnesium sulfate, filtered and concentrated. The residue was purified by silica gel chromatography (150 g, 5 to 50 % ethyl acetate/hexane) and gave the title compound (0.275 g, 20%), along with the starting material (0.839 g, 63%), the 2-benzoate (0.124 g, 8%) and the bis-benzoate (0.030 g, 2%).

IR (CH$_2$Cl$_2$) ν$_{max}$ (cm$^{-1}$): 3600 (OH), 3055, 2930, 2850 (C—H), 2120 (N$_3$), 1745 and 1720 (C=O).

$^1$H NMR 400 MHz (CDCl$_3$) δ(ppm): 0.89 (3H, t, J=6.8 Hz, —CH$_3$), 1.25–1.31 (20H, m, —(CH$_2$)$_{11}$—), 1.40 and 1.48 (18H, 2s, 2×tert-butyl), 2.09 (2H, qa, J=6.8 Hz, =CH—CH$_2$—), 2.54 (1H, d, J=3.2 Hz, —OH), 3.67 (1H, m, H-1), 3.76 (1H, dd, J=9.4 and 6.0 Hz, H-6'), 3.85 (1H, br t, J=6.2 Hz, H-5'), 3.97–4.03 (5H, m, —OCH$_2$CO—, H-6', H-1 and H-2), 4.06 (1H, d, J=2.8 Hz, H-4'), 4.11 (1H, d, J$_{AB}$=16.1 Hz, —OCH$_2$CO—), 4.12–4.17 (1H, m, H-2'), 4.23 (1H, d, J$_{AB}$=16.1 Hz, —OCH$_2$CO—), 4.43 (1H, d, J=7.6 Hz, H-1'), 5.18 (1H, dd, J=10.2 and 2.9 Hz, H-3'), 5.59 (1H, dd, J=15.2 and 8.0 Hz, H-4), 5.68 (1H, dd, J=8.0 and 3.8 Hz, H-3), 5.97 (1H, dt, J=15.2 and 6.8 Hz, H-5), 7.45–7.50, 7.57–7.63 and 8.06–8.13 (10H, 3 sets of m, 2×—C$_6$H$_5$).

B. (2S,3R,4E)-3-Benzoyloxy-2-hexadecanoylamino-1-(3-O-benzoyl-4,6-di-O-tert-butyloxycarbonylmethyl-β-D-galactopyranosyloxy)-4-octadecene

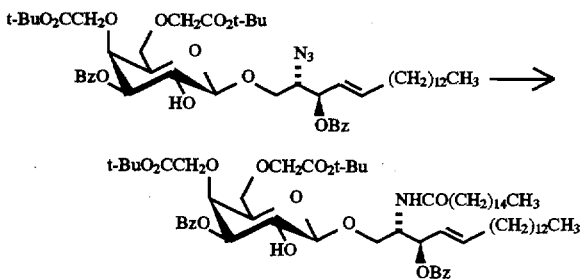

(2S,3R,4E)-3-Benzoyloxy-2-azido-1-(3-O-benzoyl-4,6-di-O-tert-butyloxycarbonylmethyl-β-D-galactopyranosyloxy)-4-octadecene (0.444 g, 0.48 mmol) was reacted by the general procedure as described in Example 1-G and gave the title compound (0.486 g, 89%) as a white solid.

IR (CH$_2$Cl$_2$) ν$_{max}$ (cm$^{-1}$): 3600–3300 (OH, NH), 3055, 2925, 2855 (C—H), 1745, 1720 and 1668 (C=O).

$^1$H NMR 400 MHz (CDCl$_3$) δ(ppm): 0.89 (6H, t, J=6.8 Hz, 2×—CH$_3$), 1.17–1.36 (44H, m, —(CH$_2$)$_{11}$— and —(CH$_2$)$_{12}$—), 1.39 and 1.48 (18H, 2s, 2×tert-butyl), 1.55–1.65 (4H, m, 2×—CH$_2$—), 2.05 (2H, m, =CH—C H$_2$—), 2.19 (2H, m, —NHCOCH$_2$—), 3.50 (1H, br s, —OH), 3.75 (1H, dd, J=9.3 and 6.0 Hz, H-6'), 3.84 (1H, br t, H-5'), 3.86 (1H, dd, J=11.3 and 3.6 Hz, H-1), 3.98 (1H, dd, J=9.3 and 6.2 Hz, H-6'), 4.00 (2H, s, —OCH$_2$CO—), 4.05–4.11 (3H, m, H-4', H-2' and H-1), 4.10 (1H, d, J$_{AB}$= 16.0 Hz, —OCH$_2$CO—), 4.21 (1H, d, J$_{AB}$=16.0 Hz, —OCH$_2$CO—), 4.42 (1H, d, J=7.6 Hz, H-1'), 4.53 (1H, m, H-2), 5.16 (1H, dd, J=10.2 and 2.8 Hz, H-3'), 5.50 (1H, dd, J=15.2 and 7.2 Hz, H-4), 5.57 (1H, br t, H-3), 5.88 (1H, dt, J=15.2 and 6.9 Hz, H-5), 6.09 (1H, d, J=9.3 Hz, —NH—), 7.45–7.50, 7.57–7.63, 8.04–8.10 and 8.10–8.12 (10H, 4 sets of m, 2×—C$_6$H$_5$).

EXAMPLE 18

(2S,3R,4E)-3-Benzoyloxy-2-hexadecanoylamino-1-[3-O-benzoyl-4,6-di-O-carboxymethyl-β-D-galactopyranosyloxy]-4-octadecene

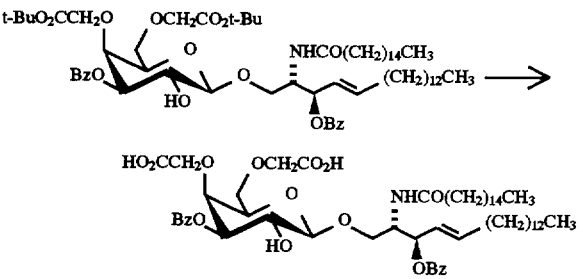

(2S,3R,4E)-3-Benzoyloxy-2-hexadecanoylamino-1-(3-O-benzoyl-4,6-di-O-tert-butyloxycarbonylmethyl-β-D- galactopyranosyloxy)-4-octadecene (0.274 g, 0.242 mmol) was reacted by the general procedure as described in Examples 2 and 14. This afforded the sodium salt of the title compound (0.144 g, 56%) as a white fluffy solid.

Diacid:

IR (Nujol) $v_{max}$ (cm$^{-1}$): 3650–2600 (broad, OH, NH, C—H), 1720 and 1640 (C=O).

$^1$H NMR 400 MHz (DMSO-d$_6$) δ(ppm): 0.84 (6H, t, J=6.7 Hz, 2×—CH$_3$), 1.14–1.5 (48H, m, —(CH$_2$)$_{11}$— and —(CH$_2$)$_{13}$—), 2.00 (2H, m, =CH—C$\underline{H}_2$—), 2.08 (2H, m, —NHCOC$\underline{H}_2$—), 3.50–3.62 (2H, m, H-1 and H-6'), 3.71–3.78 (2H, m, H-2' and H-6'), 3.83 (1H, t, J=6.2 Hz, H-5'), 3.87–3.91 (2H, m, H-1 and H-4'), 3.97 (1H, d, J$_{AB}$=16.8 Hz, —OCH$_2$CO—), 4.00 (1H, d, J$_{AB}$=16.8 Hz, —OCH$_2$CO—), 4.08 (1H, d, J$_{AB}$=16.4 Hz, —OCH$_2$CO—), 4.13 (1H, d, J$_{AB}$=16.4 Hz, —OCH$_2$CO—), 4.37 (1H, d, J=7.4 Hz, H-1'), 4.37 (1H, m, H-2), 5.03 (1H, dd, J=10.1 and 2.8 Hz, H-3'), 5.44–5.55 (3H, m, —OH, H-4 and H-3), 5.80 (1H, dt, J=14.4 and 6.8 Hz, H-5), 7.48–7.56, 7.62–7.69, 7.95–7.96 and 8.01–8.03 (10H, 4 sets of m, 2×—C$_6$H$_5$), 7.78 (1H, d, J=9.0 Hz, —NH—), 12.54 (1H, br s, —OH).

Sodium salt:

IR (Nujol) $v_{max}$ (cm$^{-1}$): 3700–3100 (broad, OH, NH), 2930, 2850 (C—H), 1718 and 1650–1600 (C=O).

$^1$H NMR 400 MHz (DMSO-d$_6$) δ(ppm): 0.74 (6H, t, J=6.6 Hz, —CH$_3$), 0.80–1.4 (48H, m, —(CH$_2$)$_{11}$— and —(CH$_2$)$_{13}$—), 1.88 (2H, m, =CH—C$\underline{H}_2$—), 1.97 (2H, m, —NHCOC$\underline{H}_2$—), 3.2–3.66 (7H, m, H-1, H-2', H-5', H-6' and —OCH$_2$CO—), 3.73 (2H, br d, —OCH$_2$CO—), 3.79 (1H, dd, J=9.6 and 5.8 Hz, H-1), 3.88 (1H, br s, H-4'), 4.26 (1H, d, J=7.3 Hz, H-1'), 4.26 (1H, m overlapped by H-1', H-2), 4.89 (1H, br d, J=11.6 Hz, H-3'), 5.36–5.45 (3H, m, H-4, H-3 and —OH), 5.69 (1H, dt, J=14.0 and 6.9 Hz, H-5), 7.39–7.46, 7.51–7.59 and 7.84–8.87 (10H, 3 sets of m, 2×—C$_6$H$_5$), 7.74 (1H, d, J=8.8 Hz, —NH—).

EXAMPLE 19

(2S,3R,4E)-3-Benzoyloxy-2-hexadecanoylamino-1-(2,3-di-O-benzoyl-4,6-di-O-methyloxycarbonylmethyl-α-D-galactopyranosyloxy)-4-octadecene

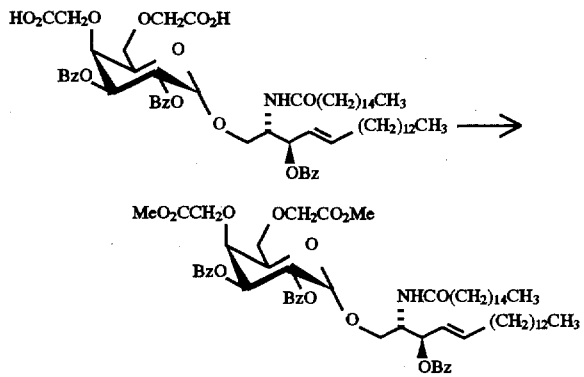

A solution of (2S,3R,4E)-3-benzoyloxy-2-hexadecanoylamino-1-(2,3-di-O-benzoyl-4,6-di-O-carboxymethyl-α-D-galactopyranosyloxy)-4-octadecene described in Example 2 (0.452 g, 0.4 mmol) in toluene (20 mL, dried over molecular sieves) and methanol (4 mL) was treated with (trimethylsilyl)diazomethane (2.0M in hexanes, 0.52 mL, 1.04 mmol) at 22° C. This mixture was stirred for 1 hour at 22° C. and then concentrated under vacuum. The residue was purified by silica gel column chromatography (0% to 25% ethyl acetate/toluene) and afforded the title compound (0.410 g, 89%) as a white amorphous solid.

$[α]_D^{22}$: +57.5° (c=1.0, CHCl$_3$).

IR (film) $v_{max}$ (cm$^{-1}$): 3300 (NH), 2920,2850 (C—H), 1755, 1720 and 1650 (C=O).

$^1$H NMR 400 MHz (CDCl$_3$) δ(ppm): 0.89 (6H, t, J=6.8 Hz, 2×—CH$_3$), 1.22–1.31 (46H, m, —(CH$_2$)$_{11}$— and —(CH$_2$)$_{12}$—), 1.56–1.60 (2H, m, —CH$_2$—), 1.97 (2H, qa, J=6.7 Hz, =CH—C$\underline{H}_2$—), 2.14 (2H, m, —NHCOC$\underline{H}_2$—), 3.66 and 3.75 (6H, 2s, 2×—OCH$_3$), 3.82 (1 H, dd, J=9.6 and 6.9 Hz, H-6'), 3.83 (2H, br d, H-1), 4.01 (1H, dd, J=9.6 and 5.7 Hz, H-6'), 4.12 (1H, d, J$_{AB}$=16.5 Hz, —OCH$_2$CO—), 4.17 (1H, d, J$_{AB}$=16.5 Hz, —OCH$_2$CO—), 4.21 (1H, d, J=16.3 Hz, —OCH$_2$CO—), 4.24 (1H, br s, H-4'), 4.34 (1H, br t, H-5'), 4.41 (1H, d, J=16.3 Hz, —OCH$_2$CO—), 4.47 (1H, m, H-2), 5.24 (1H, br s, H-1'), 5.49 (1H, dd, J=15.1 and 7.6 Hz, H-4), 5.56 (1H, t, J=7.5 Hz, H-3), 5.74 (1H, dt, J=15.1 and 6.7 Hz, H-5), 5.74 (2H, br d, H-2' and H-3'), 6.00 (1H, d, J=9.3 Hz, —NH—), 7.29–7.49, 7.52–7.56 and 7.91–8.00 (15H, 3 sets of m, 3×—C$_6$H$_5$).

Anal. Calcd. for C$_{67}$H$_{97}$NO$_{15}$: C, 69.58; H, 8.45; N, 1.21. Found: C, 69.58; H, 8.37; N, 1.35.

EXAMPLE 20

(2S,3R,4E)-3-Benzoyloxy-2-hexadecanoylamino-1-(2,3-di-O-benzoyl-4,6-di-O-[(2,2-dimethylpropanoyloxymethyl)oxycarbonylmethyl]-α-D-galacto-pyranosyloxy)-4-octadecene

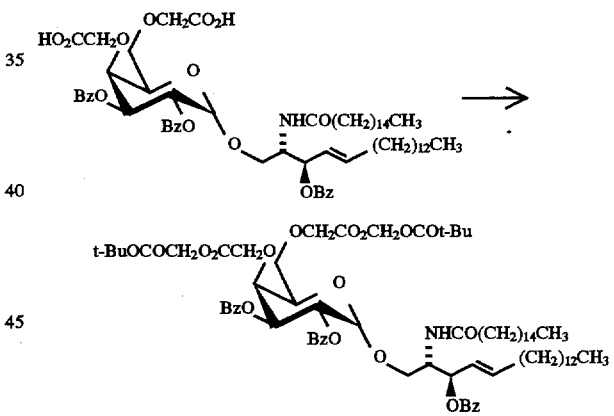

A stirred solution of (2S,3R,4E)-3-benzoyloxy-2-hexadecanoyiamino-1-(2,3-di-O-benzoyl-4,6-di-O-carboxymethyl-α-D-galactopyranosyloxy)-4-octadecene described in Example 2 (1.0 g, 0.92 mmol) in dioxane (20 mL) was treated with water (20 mL) and then with an aqueous solution of cesium carbonate (0.60 g, 1.84 mmol in 10 mL of water) until the pH reached ~8.5. The solution was lyophilized to give a white solid (~1.4 g) which was used for the next reaction. A part of this salt (0.95 g, 0.682 mmol) was dissolved in toluene (40 mL) and the resulting solution was evaporated under vacuum. This was repeated two times. Dimethylformamide (40 mL, dry) was added to this solid followed by chloromethyl pivalate (393 μL, 2.73 mmol) and sodium iodide (~10 mg). The mixture was stirred for 24 hours at 22° C. then chloromethyl pivalate (200 μL, 1.39 mmol) was added again. The mixture was stirred for another 24 hours, concentrated under vacuum, diluted with ethyl acetate (~100 mL) and washed with cold water (100 mL), diluted brine (~100 mL) and brine (~100 mL). It was then dried over anhydrous magnesium sulfate, filtered and concentrated. The residue was purified by silica gel column chromatography (4.4×15 cm, 0 to 20% ethyl acetate/toluene) and afforded the title compound (0.738 g, 80%).

$[\alpha]_D^{22}$: +47.1° (c=1.0, CHCl$_3$).

IR (film) $v_{max}$ (cm$^{-1}$): 3300 (NH), 2920,2850 (C—H), 1755, 1722 and 1650 (C=O).

$^1$H NMR 400 MHz (CDCl$_3$) δ(ppm): 0.89 (6H, t, J=6.8 Hz, 2×—CH$_3$), 1.18 and 1.23 (18H, 2s, 2×tert-butyl), 1.26–1.31 (46H, m, —(CH$_2$)$_{11}$— and —(CH$_2$)$_{12}$—), 1.56–1.59 (2H, m, —CH$_2$—), 1.97 (2H, qa, J=6.8 Hz, =CH—CH$_2$—), 2.14 (2H, m, —NHCOCH$_2$—), 3.78–3.87 (3H, m, H-1 and H-6'), 4.03 (1H, dd J=9.5 and 5.9 Hz, H-6'), 4.17 (1H, d, J$_{AB}$=17.0 Hz, —OCH$_2$CO—), 4.21 (1 H, d, J$_{AB}$=17.0 Hz, —OCH$_2$CO—), 4.23 (1H, d, J=1.3 Hz, H-4'), 4.24 (1H, d, J=16.9 Hz, —OCH$_2$CO—), 4.32 (1 H, br t, H-5'), 4.46 (1H, d, J=16.9 Hz, —OCH$_2$CO—), 4.48 (1H, m, H-2), 5.24 (1H, d, J=3.0 Hz, H-1'), 5.49 (1H, dd, J=14.9 and 7.6 Hz, H-4), 5.56 (1H, br t, H-3), 5.70–5.77 (5H, m, H-5 and 2×—OCH$_2$O—), 5.80 and 5.81 (2H, 2d, J$_{AB}$=5.6 Hz, H-2' and H-3'), 5.93 (1H, d, J=9.3 Hz, —NH—), 7.30–7.49, 7.52–7.57 and 7.92–7.99 (15H, 3 sets of m, 3×—C$_6$H$_5$).

Anal. Calcd. for C$_{77}$H$_{113}$NO$_{19}$: C, 68.17; H, 8.40; N, 1.03. Found: C, 68.16; H, 8.27; N, 1.11.

EXAMPLE 21

(2S,3R,4E)-3-Benzoyloxy-2-hexadecanoylamino-1-(2,3-di-O-benzoyl-4,6-di-O[(tert-butyloxycarbonylmethyl)oxycarbonylmethyl]-α-D-galactopyranosyloxy)-4-octadecene

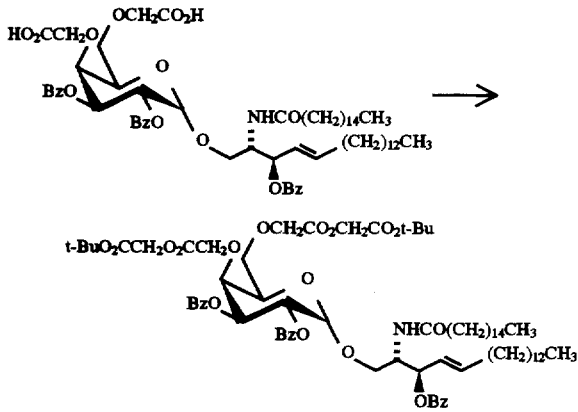

(2S,3R,4E)-3-Benzoyloxy-2-hexadecanoylamino-1-(2,3-di-O-benzoyl-4,6-di-O-carboxymethyl-α-D-galactopyranosyloxy)-4-octadecene described in Example 2 (0.32 g, 0.287 mmol) was reacted as described in Example 20 except that tert-butyl bromoacetate was used instead of chloromethyl pivalate. The reaction time was 4 hours. The title material was obtained (0.357 g, 92%) as a white amorphous solid.

$[\alpha]_D^{22}$: +48.6° (c=1.0, CHCl$_3$).

IR (film) $v_{max}$ (cm$^{-1}$): 3350 (NH), 2920,2850 (C—H), 1750, 1725 and 1655 (C=O).

$^1$H NMR 400 MHz (CDCl$_3$) δ(ppm): 0.88 (6H, t, J=6.7 Hz, 2×—CH$_3$), 1.21–1.25 (46H, m, —(CH$_2$)$_{11}$— and —(CH$_2$)$_{12}$—), 1.44 and 1.47 (18H, 2s, 2×tert-butyl), 1.51–1.63 (2H, m, —CH$_2$—), 1.95 (2H, qa, J=6.8 Hz, =CH—CH$_2$—), 2.12 (2H, m, —NHCOCH$_2$—), 3.70–3.85 (2H, m, H-1), 3.83 (1H, dd, J=9.6 and 6.6 Hz, H-6'), 4.04 (1H, dd, J=9.6 and 6.0 Hz, H-6'), 4.24 (2H, s, —OCH$_2$CO—), 4.26 (1H, br s, H-4'), 4.30 (1H, d, J=16.5 Hz, —OCH$_2$CO—), 4.33 (1H, br t, H-5'), 4.48 (1H, m overlapped by —OCH$_2$CO—, H-2), 4.48 (2H, s, —OCH$_2$CO—) 4.51 (1H, d, J=16.5 Hz, —OCH$_2$CO—), 4.56 (2H, s, —OCH$_2$CO—), 5.23 (1H, d, J=3.3 Hz, H-1'), 5.47 (1H, dd, J=15.1 and 7.6 Hz, H-4), 5.53 (1H, t, J=7.6 Hz, H-3), 5.68–5.77 (1H, m overlapped by H-2' and H-3', H-5), 5.72 (1H, dd, J$_{AB}$=10.9 and J$_{AX}$=3.3 Hz, H-2'), 5.75 (1H, dd, J$_{AB}$=10.9 and J$_{BX}$=2.4 Hz, H-3'), 5.99 (1H, d, J=9.3 Hz, —NH—), 7.28–7.54, 7.89–7.99 (15H, 2 sets of m, 3×—C$_6$H$_5$).

Anal. Calcd. for C$_{77}$H$_{113}$NO$_{19}$: C, 68.17; H, 8.40; N, 1.03. Found: C, 68.19; H, 8.31; N, 1.12.

EXAMPLE 22

(2S,3R,4E)-1-(2,3-di-O-Benzoyl-4,6-di-O-ethyloxycarbonylmethyl-α-D-galactopyranosyloxy)-3-benzoyloxy-2-hexadecanoylamino-4-octadecene A. Ethyl 4,6-di-O-carboxymethyl-2,3-di-O-para-methoxybenzyl-1-thio-β-D-galactopyranoside

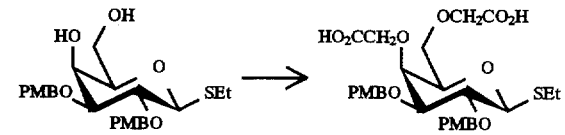

A suspension of sodium hydride (7.5 g, 0.25 mol, 80% dispersion in mineral oil) in dry N,N-dimethylformamide (75 ml) treated dropwise with a solution of ethyl 2,3-di-O-para-methoxybenzyl-1-thio-β-D-galactopyranoside described in Example 1-B (5.05 g, 10.87 mmol) in N,N-dimethylformamide (75 ml). After 45 min, the resulting mixture was cooled to 0°–5° C. and treated with bromoacetic acid (7.5 g, 54.0 mmol) and the mixture was slowly warmed up to 25° C. and stirred for 18 h. After careful addition of water (100 ml), the pH of the solution was adjusted to 3 with 2N HCl. The aqueous solution was then extracted with CH$_2$Cl$_2$ and the combined organic extracts washed with brine and dried (MgSO$_4$). Evaporation of the solvent under vacuum gave an oil which was filtered on a silica gel pad (5×11 cm) using a mixture of chloroform and methanol (95:5). The oil obtained (4.77 g, 75%) was used as such for the next step.

IR (NaCl) $v_{max}$ (cm$^{-1}$): 1755, 1730 (C=O of carboxylate).

$^1$H NMR 400 MHz (DMSO-d$_6$) δ(ppm): 1.21 (3H, t, J=7.4 —CH$_3$), 2.64 (2H, m, —SCH$_2$—), 3.52 (1H, m, H-6), 3.6 (2, m, H-2 and H-3 overlapping), 3.69 (1H, br t, H-5), 3.73 and 3.74 (2×3H, 2s, —OCH$_3$), 3.76 (1H, dd, J=5.0 and J=10.1 Hz, H-6), 3.95 (1H, br d, H-4), 4.03 (2H, ABq, J$_{AB}$=16.7 Hz, Δv=10.2 Hz, —OCH$_2$CO—), 4.26 (3H, s, —OCH$_2$CO—), 4.45 (1H, d, J=9.48 Hz, H-1), 4.59 (2H, s, —OCH$_2$Ar), 4.60 (2H, ABq, J$_{AB}$=11.3 Hz, Δv=49.9 Hz, —OCH$_2$Ar), 6.85–6.9, 7.2–7.3 (2×4H, 2m, aromatic H).

B. Ethyl 4,6-di-O-ethyloxycarbonylmethyl-2,3-di-O-para-methoxybenzyl-1-thio-β-D-galactopyranoside

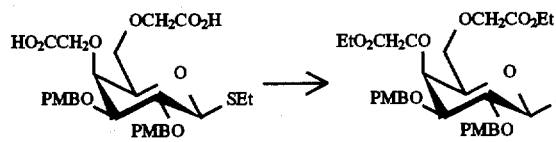

A mixture of dry acetonitrile (50 ml) and N,N-dimethylformamide (3.9 ml, 50.3 mmol) was cooled to −20° C. and then treated dropwise with oxalyl chloride (1.83 ml, 20.9 mmol). The resulting mixture with a white precipitate was stirred at −20° C. for 20 min and then treated with a solution of ethyl 4,6-di-O-carboxymethyl-2,3-di-O-para-methoxybenzyl-1-thio-β-D-galactopyranoside (2.43 g, 4.19 mmol) in acetonitrile (30 ml). After 20 min at −20° C. a mixture of pyridine (6.7 ml) and ethanol (5 ml) was added and the clear solution was warmed up to 20° C. and stirred for 30 min. The reaction mixture was quenched by the addition of water (20 ml) and ethyl acetate (200 ml). The aqueous phase was extracted a second time with ethyl acetate (200 ml) and the combined organic extracts were washed with brine and dried (MgSO$_4$). Evaporation of the solvent under reduced pressure and chromatography of the residue on silica gel (3.5×12 cm, elution toluene-AcOEt 9:1) gave 1.82 g (68%) of the title material as a clear oil.

$[α]_D^{22}$: 5.0° (c=1.0, CHCl$_3$).

IR (NaCl, film) $v_{max}$ (cm$^{-1}$): 1750 and 1730 (sh) (C=O of ester).

$^1$H NMR 400 MHz (CDCl$_3$) δ(ppm): 1.25–1.35 (9H, m, 3×—CH$_3$), 2.75 (2H, —SCH$_2$—), 3.52 (1H, dd, J=9.25 and 2.5 Hz, H-3), 3.62 (1H, br t, J=6 Hz, H-5), 3.76 (1H, dd, J=9.9 and J=6.1 Hz, H-6), 3.8–3.85 (1H, overlapping with —OCH$_3$, H-2), 3.81 and 3.82 (2×3H, 2s, —OCH$_3$), 3.89 (1H, br d, J=2.2 Hz, H-5), 4.00 (1H, dd, J=9.9 and J=5.8 Hz, H-6), 4.16 (2H, ABq overlapping with —OCH$_2$CH$_3$, —OCH$_2$CO—), 4.17 (2H, q, J=7.11 Hz, —OCH$_2$CH$_3$), 4.22 (2H, q, J=7.14, Hz, —OCH$_2$CH$_3$), 4.41 (1H, d, J=9.63 Hz, H-1), 4.42 (2H, ABq, J$_{AB}$=16.6 Hz, Δv=25.8 Hz, —OCH$_2$CO—), 4.66 (2H, ABq, J$_{AB}$=11.3 Hz, Δv=18.2 Hz, —CH$_2$Ar), 4.75 (2H, ABq, J$_{AB}$=9.8 Hz, Δv=48 Hz, —CH$_2$Ar), 6.8–6.90 and 7.24–7.34 (2×4H, 2m, aromatic H).

Anal. Calcd. for C$_{32}$H$_{44}$O$_{11}$S: C 60.36; H 6.97; S 5,04. Found: C 60.28; H 6.80; S 5.19.

C. (2S,3R,4E)-2-Azido-3-benzoyloxy-1-(4,6-di-O-ethyloxycarbonyl-methyl-2,3-di-O-para-methoxybenzyl-α-D-galactopyranosyloxy)-4-octadecene and (2S,3R,4E)-2-azido-3-benzoyloxy-1-(4,6-di-O-ethyloxycarbonylmethyl-2,3-di-O-para-methoxy-benzyl-β-D-galactopyranosyloxy)-4-octadecene

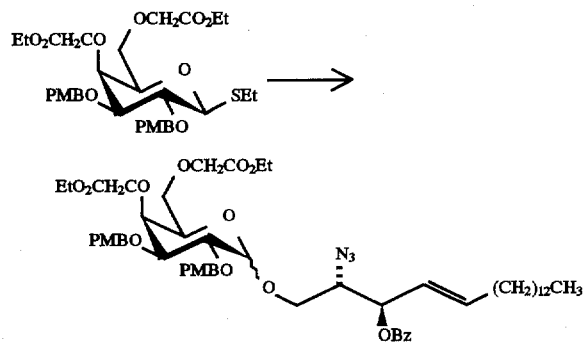

Ethyl 4,6-di-O-ethyloxycarbonylmethyl-2,3-di-O-para-methoxybenzyl-1-thio-β-D-galactopyranoside (1.80 g, 2.83 mmol) and (2S,3R,4E)-2-azido-3-benzoyloxy-4-octadecen-1-ol (1.06 g, 2.47 mmol) were coupled as described in Example 1-D to give 2.27 g (91%) of a 1:1 mixture of α and β anomers. Chromatography on silica gel (0–20% toluene/ethyl acetate) gave the pure anomers as oils.

α-anomer:

$[α]_D^{22}$: +3° (c=1.0, CHCl$_3$).

IR (NaCl, film) $v_{max}$ (cm$^{-1}$): 2001 (N$_3$), 1752 and 1722 (C=O of ester).

$^1$H NMR 400 MHz (CDCl$_3$) δ(ppm): 0.89 (3H, t, J=6.8 Hz, —CH$_3$), 1.2–1.4 (28H, m, —(CH$_2$)$_{11}$— and 2×CH$_3$), 2.07 (2H, m, =CH—CH$_2$—), 3.53 (1H, dd, J=10.8 and J=7.8 Hz, H-1), 3.69 (1H, dd, J=9.7 and J=6.6 Hz, H-6'), 3.78 and 3.82 (2×3H, 2s, —OCH$_3$), 3.86 (1H, br s, H-4), 3.89 (1H, dd, J=10.8 and J=2.55 Hz, H-1), 3.94 (1H, dd, J=9.7 and J=5.4 Hz, H-6'), 3.95–4.05 (4H, m, H-2, H-2', H-3' and H-5'), 4.09 (2H, ABq, J$_{AB}$=12.7 Hz, Δv=18.5 Hz, —OCH$_2$CO—), 4.15 (2H, q, J=7.01 Hz, —OCH$_2$CH$_3$), 4.18 (2H, q, J=7.11, OCH$_2$CH$_3$), 4.40 (2H, s, —OCH$_2$CO)—, 4.65 (2H, ABq, J$_{AB}$=11.5 Hz, Δv=41.3 Hz, —OCH$_2$Ar), 4.67 (2H, ABq, J$_{AB}$=11.2 Hz, Δv=53.3 Hz, —OCH$_2$Ar), 4.81 (1H, d, J=3.56 Hz, H-1'), 5.57 (1H, dd, J=14.8 and J=7.8 Hz, H-4), 5.63 (1H, dd, J=7.8 and J=4.2 Hz, H-3), 5.92 (1H, dt, J=14.8 and J=6.7 Hz, H-5), 6.8–6.9 and 7.23–7.33 (2×2H, 2m, CH of p-methoxybenzyl), 7.44–7.48, 7.56–7.60 and 8.05–8.08 (2H, 1H and 2H, 3m, CH of benzoate).

Anal. Calcd. for C$_{55}$H$_{77}$O$_{14}$: C 65.78; H 7.73; N 4.18. Found: C 65.86; H 7.84; N 4.17.

β-anomer:

$[α]_D^{22}$: 22.5° (c=1.0, CHCl$_3$).

IR (NaCl, film) $v_{max}$ (cm$^{-1}$): 2100 (N$_3$), 1750 and 1722 (C=O of ester).

$^1$H NMR 400 MHz (CDCl$_3$) δ(ppm): 0.89 (3H, t, J=7.0 Hz, —CH$_3$), 1.2–1.35 (28H, m, —(CH$_2$)$_{11}$— and 2×—CH$_3$), 2.04 (2H, m, =CH—CH$_2$—), 3.48 (1H, dd, J=9.8 and J=2.5 Hz, H-3'), 3.58 (1H, dd, J=9.8 and J=5.6 Hz, H-1), 3.60 (1H, br t, J=6 Hz, H-5'), 3.74 (1H, dd, J=9.9 and J=6.1 Hz, H-6'), 3.79 and 3.82 (2 ×3H, 2s, —OCH$_3$), 3.75–3.85 (1H, overlapping with —OCH$_3$, H-2 or H-1), 3.86 (1H, br d, H-4'), 3.96 (1H, dd, J=9.8 and J=7.7 Hz, H-2'), 4.03 (1H, dd, J=9.8 and J=5.9 Hz, H-6'), 3.95–4.05 (1H, overlapping with H-6', H-1 or H-2), 4.14 (2H, s, —OCH$_2$CO—), 4.17 (2H, q, J=7.17 Hz, —OCH$_2$CH$_3$), 4.21 (2H, q, J=7.19 Hz, —OCH$_2$CH$_3$), 4.35 (1H, d, J=7.7 Hz, H-1'), 4.42 (2H, ABq, J$_{AB}$=16.7 Hz and Δv=26.6 Hz, —OCH$_2$CO—), 4.65 (2H, ABq, J$_{AB}$=11.3 Hz, Δv=27.0 Hz, —CH$_2$Ar), 4.78 (2H, ABq, J$_{AB}$=10.5 Hz, Δv=61.4 Hz, —CH$_2$Ar), 5.57 (1H, dd, J=15.4 and 7.9 Hz, H-4), 5.70 (1H, dd, J=7.9 and J=3.67 Hz, H-3), 5.91 (1H, dt, J=15.4 and J=6.5 Hz, H-5), 6.85–6.88, 7.23–7.33 (2×2H, 2m, CH of p-methoxybenzyl), 7.44–7.48, 7.56–7.60 and 8.7–8.9 (2H, 1H and 2H, 3m, CH of benzoate).

Anal. Calcd. for C$_{55}$H$_{77}$N$_3$O$_{14}$: C 65.78; H 7.73; N 4.18. Found: C 65.71; H 7.69; N 4.23.

D. (2S,3R,4E)-2-Azido-3-benzoyloxy-1-(4,6-di-O-ethyloxycarbonylmethyl-α-D-galactopyranosyloxy)-4-octadecene

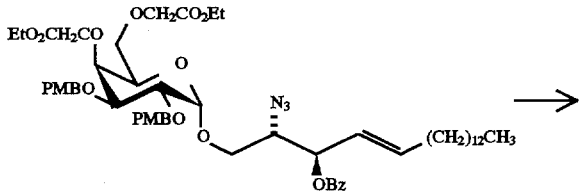

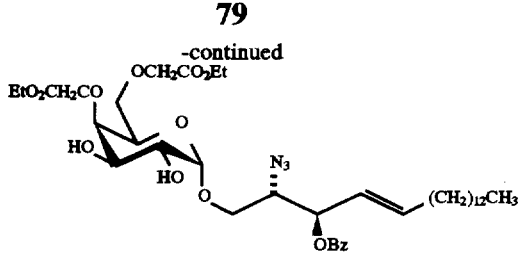

(2S,3R,4E)-2-Azido-3-benzoyloxy-1-(4,6-di-O-ethyloxycarbonylmethyl-2,3-di-O-para-methoxybenzyl-α-D-galactopyranosyloxy)-4-octadecene (0.705 g, 0.70 mmol) was treated as described in Example 1-E to give 0.418 g (78%) of the title material as an oil:

$[\alpha]_D^{22}$: +33° (c=1.0, CHCl$_3$).

IR (NaCl, film) $\nu_{max}$ (cm$^{-1}$): 2100 (N$_3$), 1750 and 1725 (C=O of ester).

$^1$H NMR 400 MHz (CDCl$_3$) δ(ppm): 0.89 (3H, t, J=6.8 Hz, —CH$_3$), 1.2–1.4 (28H, m, —(CH$_2$)$_{11}$— and 2×—CH$_3$), 2.08 (2H, m, =CH—CH$_2$—), 2.30 (1H, d, J=7.08 Hz, —OH, exchanged D$_2$O), 3.57 (1H, dd, J=10.3 and J=6.96 Hz, H-1), 3.62 (1H, dd, J=9.34 and J=5.95 Hz, H-6'), 3.80 (1H, m, +D$_2$O dd, J=10.2 and J=2.9 Hz, H-3'), 3.82–3.95 (5H, m, H-1, H-2, H-2', H-4' and H-6'), 4.08 (1H, br t, H-5), 4.13 (2H, ABq, J$_{AB}$=16.4 Hz, Δν=31.7 Hz, —OCH$_2$CO), 4.18–4.25 (4H, m, 2×—OCH$_2$CH$_3$), 4.29 (1H, d, J=7.74 Hz, —OH exchanged D$_2$O), 4.38 (2H, ABq, J$_{AB}$=17.3 Hz, Δν=87.7 Hz, —OCH$_2$CO—), 4.92 ( $^1$H, d, J=3.64 Hz, H-1'), 5.59 (1H, dd, J=15.1 and J=8.0 Hz, H-4), 5.66 (1H, dd, J=8.0 and J=4.76 Hz, H-3), 5.95 (1H, dt, J=15.1 and J=5.95 Hz, H-5), 7.44–7.48, 7.56–7.60 and 8.04–8.07 (2H, 1H and 2H, 3m, aromatic H).

Anal. Calcd. for C$_{39}$H$_{61}$N$_3$O$_{12}$: C 61.32; H 8.05; N 5.50.
Found: C 61.50; H 8.1; N 5.52.

E. (2S,3R,4E)-2-Azido-3-benzoyloxy-1-(2,3-di-O-benzoyl-4,6-di-O-ethyloxycarbonyl-methyl-α-D-galactopyranosyloxy)-4-octadecene

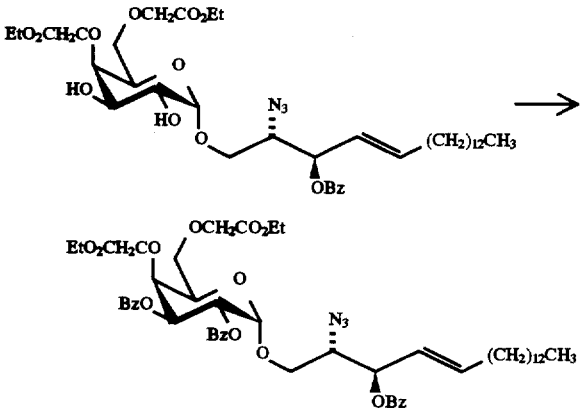

(2S,3R,4E)-2-Azido-3-benzoyloxy-1-(4,6-di-O-ethyloxycarbonylmethyl-α-D-galactopyranosyloxy)-4-octadecene (0.666 g, 0.87 mmol) was benzoylated as described in Example 1-F and gave 0.777 g (91%) of the title material as an oil.

$[\alpha]_D^{22}$: +45° (c=1.0, CHCl$_3$).

IR (NaCl, film) $\nu_{max}$ (cm$^{-1}$): 2100 (N$_3$), 1755 and 1720 (C=O of ester).

$^1$H NMR 400 MHz (CDCl$_3$) δ(ppm): 0.89 (3H, t, J=6.8 Hz, —CH$_3$), 1.2–1.4 (28H, m, —(CH$_2$)$_{11}$— and 2×—CH$_3$), 2.05 (2H, m, =CH—CH$_2$—), 3.52 (1H, dd, J=10.05 and J=7.88 Hz, H-1), 3.82 (1H, dd, J=9.67 and J=6.56 Hz, H-6'), 3.96 (1H, dd, J=10.05 and J=3.96 Hz, H-1), 4.00 (1H, m, H-2), 4.07 (1H, dd, J=9.67 and J=6.04 Hz, H-6'), 4.09–4.2 (4H, m, —OCH$_2$CH$_3$ and —OCH$_2$CO— overlapping), 4.21 (2H, q, J=7.12 Hz, —OCH$_2$CH$_3$), 4.26 (1H, br s, H-4'), 4.30 (2H, ABq, J$_{AB}$16.2 Hz, Δν=83.6 Hz, —OCH$_2$CO—), 4.33 (1H, br t, J=6.3 Hz, H-5'), 5.33 (1H, d, J=2.8 Hz, H-1'), 5.51–5.58 (2H, m, H-3 and H-4), 5.74–5.81 (2H, m, H-2' and H-3'), 5.91 (1H, dt, J=14.2 and J=6.7 Hz, H-5), 7.3–7.6 and 7.95–8.03 (9H and 6H, 2m, aromatic H).

Anal. Calcd. for C$_{53}$H$_{69}$N$_3$O$_{14}$: C 65.48; H 7.15; N 4.32.
Found: C 65.53; H 6.93; N 4.32.

F. (2S,3R,4E)-1-(2,3-di-O-Benzoyl-4,6-di-O-ethyloxycarbonylmethyl-α-D-galactopyranosyloxy)-3-benzoyloxy-2-hexadecanoylamino-4-octadecene.

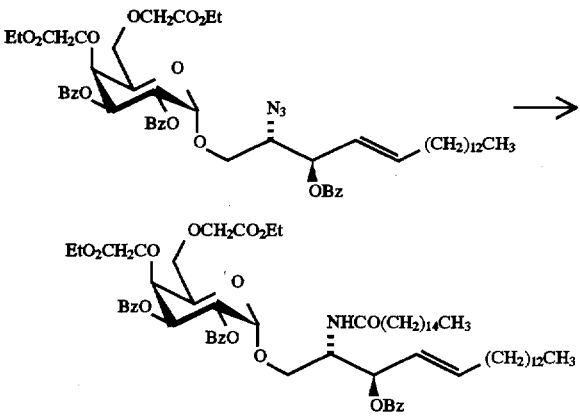

(2S,3R,4E)-2-Azido-3-benzoyloxy-1-(2,3-di-O-benzoyl-4,6-di-O-ethyloxycarbonyl-methyl-α-D-galactopyransyloxy)-4-octadecene (0.711 g, 0.73 mmol) was reacted as described in Example 1-G to give 0.744 g (86%) of the title material as a syrup.

$[\alpha]_D^{22}$: +54° (c=1.0, CHCl$_3$).

IR (NaCl, film) $\nu_{max}$ (cm$^{-1}$): 1752 and 1725 (C=O of ester), 1652 (C=O of amide).

$^1$H NMR 400 MHz (CDCl$_3$) δ(ppm): 0.89 (6H, t, J=6.7 Hz, 2×—CH$_3$), 1.1–1.5 (54H, m, 2×—CH$_3$, —(CH$_2$)$_{11}$— and —(CH$_2$)$_{13}$—), 1.97 (2H, m, =CH—CH$_2$—), 2.14 (2H, m, —CH$_2$CONH—), 3.83 (3H, m, H-1 and H-6'), 4.02 (1H, dd, J=9.7 and J=5.55 Hz, H-6'), 4.05–4.2 (4H, m, —OCH$_2$CH$_3$ and —OCH$_2$CO—), 4.21 (2H, q, J=7.15 Hz, —OCH$_2$CH$_3$), 4.24 (1H, br d, J=2 Hz, H-4'), 4.29 (2H, ABq, J$_{AB}$=16.3 Hz, Δν=81.3 Hz, —OCH$_2$CO—), 4.35 (1H, br, t, J=6.3 Hz, H-5), 4.47 (1H, m, H-2), 5.24 (1H, d, J=2.3 Hz, H-1'), 5.49 (1H, dd, J=15.1 and J=7.66 Hz, H-4), 5.56 (1H, ~t, J=7.6 Hz, H-3), 5.76 (2H, m, H-2' and H-3'), 5.76 (1H, dt, J=15.1 and J=6.7 Hz, H-5), 6.04 (1H, d, J=9.3 Hz, NH), 7.27–7.56 and 7.9–8.0 (9H and 6H, m, H aromatic).

Anal. Calcd. for C$_{69}$H$_{101}$NO$_{15}$: C 69.96; H 8.59; N 1.18.
Found: C 69.74; H 8.43; N 1.39.

EXAMPLE 23

(2S,3R,4E)-3-Benzoyloxy-2-hexadecanoylamino-1-(2,3-di-O-methoxymethyl-4,6-di-O-tert-butyloxycarbonylmethyl-β-D-galactopyranosyloxy)-4-octadecene A. Ethyl 4,6-benzylidene-2,3-di-O-methoxymethyl-1-thio-β-D-galactopyranoside

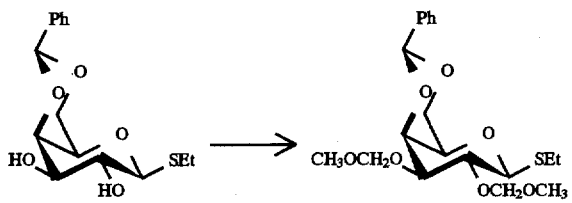

A cold (acetone/dry ice bath) solution of ethyl 4,6-O-benzylidene-1-thio-β-D-galactopyranoside [Nilsson et al., *J. Carbohy. Chem.* 10(6), 1023 (1991)] (2.0 g, 6.4 mmol) in THF (40 mL) was treated with 1.6M n-butyl lithium (10 mL) and the mixture was allowed to stir for 10 min. Bromomethylmethyl ether (2.5 mL, 1.6 g, 1.3 mmol) was added in and the temperature was allowed to reach 0° C. (ice bath). After a stirring period of 30 min, the mixture was poured over an ice cold saturated aqueous sodium bicarbonate solution and diluted with ethyl acetate (100 ml). The organic phase was washed with saturated aqueous sodium bicarbonate (2×50 ml), water (3×50 ml), saturated aqueous sodium bicarbonate (50 ml) and dried over anhydrous magnesium sulfate. Evaporation of the solvent gave a residue that crystallized from hexane (2.4 g, 94%).

$^1$H NMR 200 MHz (CDCl$_3$) δ(ppm): 1.33 (3H, t, J=7.3 Hz, —CH$_3$), 2.60–2.91 (2H, m, —SCH$_2$—), 3.415, 3.485 (6H, 2s, —OCH$_3$), 3.41–3.48 (1H, m, H-5), 3.678 (1H, dd, J=9.3 and 3.4 Hz, H-3), 3.959 (1H, t, J=9.4 Hz, H-2), 4.008 (1H, dd, J=12.4 and 1.8 Hz, H-6), 4.331 (1H, dd, J=12.3 and 1.5, H-6), 4.338 (1H, d, J=3.0 Hz, H-4), 4.420 (1H, d, J=9.6 Hz, H-1), 4.786, 4.811, 4.898, 4.930 (2H, ABq, J=6.4 Hz, —OCH$_2$O—), 4.811 (2H, s, —OCH$_2$O—), 5.516 (1H, s, —CH—), 7.31–7.38, 7.46–7.53 (5H, 2 sets of m, —C$_6$H$_5$).

B. (2S,3R,4E)-3-Benzoyloxy-2-hexadecanoylamino-1-(2,3-di-O-methoxymethyl-4,6-di-O-tert-butyloxycarbonylmethyl-α-D-galactopyransoyloxy)-4-octadecene Ethyl 4,6-O-benzylidene-2,3-di-O-methoxymethyl-1-thio-β-D-galactopyranoside (2.4 g, 6.0 mmol) was reacted by the general procedures as described in Examples 1-B, 1-C, 1-D, and 1-G to give title material (600 mg) as a solid.

IR (CH$_2$Cl$_2$) ν$_{max}$ (cm$^{-1}$): 3430 (—NH), 3050, 2980, 2920 and 2850 (—CH), 1745, 1715 and 1670 (C=O).

$^1$H NMR 400 MHz (CDCl$_3$) δ(ppm): 0.892 (6H, t, J=6.6 Hz, 2×—CH$_3$), 1.2–1.35 (46H, br s, —(CH$_2$)$_{11}$—, and —(CH$_2$)$_{12}$—), 1.470 (9H, s, 2×tert-butyl), 1.55–1.63 (2H, m, —CH$_2$—), 1.99–2.04 (2H, m, =CH—CH$_2$—), 2.12–2.2 (2H, m, —NHCOCH$_2$—), 3.398, 3.418 (6H, 2s, 2×—OCH$_3$), 3.620 (1H, dd, J=9.9 and 2.8 Hz, H-1), 3.61–3.67 (3H, m, H-3', H-5' and H-6'), 3.850 (1H, dd, J=9.8 and 7.5 Hz, H-1), 3.867 (1H, d, J=2.8 Hz, H-4'), 3.946, 1H, m, H-2), 3.970 (2H, br s, —OCH$_2$CO—), 4.159 (1H, dd, J=10.6 and 4.1 Hz, H-6'), 4.234, 4.275, 4.292, 4.332 (2H, ABq, J=16.4 Hz, —OCH$_2$CO—), 4.272 (H, d, J=7.6 Hz, H-1'), 4.44–4.48 (1H, m, H-2), 4.732, 4.749, 4.811, 4.825 (2H, ABq, J=6.2 Hz, —OCH$_2$O—), 4.764, 4.772, 4.779, 4.788 (2H, ABq, J=3.4 Hz, —OCH$_2$O—), 5.492 (1H, dd, J=15.3 and 7.4 Hz, H-4), 5.583 (1H, t, J=7.1 Hz, H-3), 5.863 (1H, dt, J=15.2 and 6.7 Hz, H-5), 6.412 (1H, d, J=8.9 Hz, —NH)—, 7.42–7.46, 7.53–7.57, 8.03–8.05 (5H, 3 sets of m, —C$_6$H$_5$).

EXAMPLE 24

(2S,3R,4E)-3-Benzoyloxy-1-(2,3-di-O-benzoyl-4,6-di-O-isopropyloxy-carbonyl-methyl-α-galactopyranosyloxy)-2-hexadecanoylamino-4-octadecene

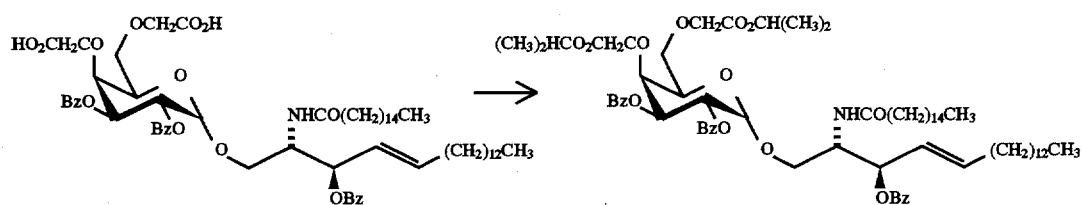

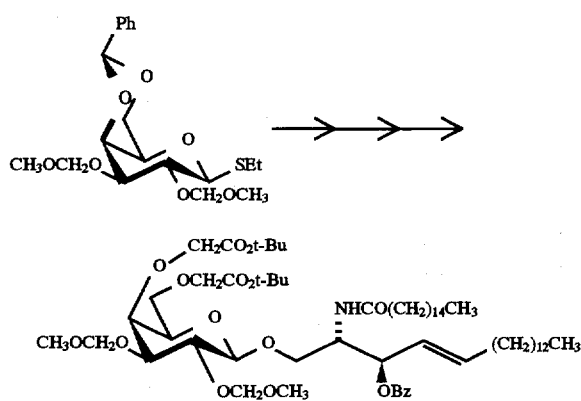

A mixture of dry acetonitrile (5 mL) and N,N-dimethylformamide treated with oxalyl chloride (0.1 ml, 1.1 mmol). After 20 min the resulting mixture was treated with a solution of (2S,3R,4E) 3-benzoyloxy-1-(2,3-di-O-benzoyl-4,6-di-O-carboxymethyl-α-D-galactopyranosyloxy)-2-hexadecanoylamino-4-octadecene described in Example 2 (0.24 g, 0.21 mmol) in chloroform (5 mL). After 20 min, a mixture of pyridine (0.35 ml) and isopropanol (0.2 ml) was added and the mixture was warmed up to 22° C. After 2 h the reaction mixture was diluted with ethyl acetate (100 ml), washed with saturated sodium bicarbonate, brine and dried over anhydrous magnesium sulfate. Evaporation of the solvent under reduced pressure and chromatography of the residue on silica gel (2.5×12 cm, elution toluene/ethyl acetate 0–20%) gave 0.058 g (27%) of the title material as a syrup.

[α]$_D^{22}$: +43° (c=1.0, CHCl$_3$).

IR (NaCl) ν$_{max}$ (cm$^{-1}$): 1752 and 1720 (C=O of ester) and 1646 (C=O of amide).

¹H NMR 400 MHz (CDCl₃) δ(ppm): 0.89 (6H, t, J=6.8 Hz, 2×—CH₃), 1.0–1.3 (60H, m, 4×—CH₃, —(CH₂)₁₁— and —(CH₂)₁₃—), 1.97 (2H, m, =CH—CH₂—), 2.14 (2H, m, —CH₂CONH—), 3.8–3.9 (3H, m, H-1 and H-6'), 4.03 (1H, dd, J=9.7 and J=5.38 Hz H-6'), 4.09 (2H, ABq, J$_{AB}$= 16.5 Hz, Δv=17.8 Hz, —OCH₂CO—), 4.23 (1H, br s, H-4'), 4.26 (2H, ABq, J$_{AB}$=16.2 Hz, Δv=85.9 Hz, —OCH₂CO—), 4.34 (1H, overlapping with —OCH₂CO—, H-5'), 4.47 (1H, m, H-2), 5.01 and 5.08 (2×1H, 2m, —CH(CH₃)₂), 5.24 (1H, d, J=2.7 Hz, H-1'), 5.49 (1H, dd, J=15.1 and J=7.7 Hz, H-4), 5.57 (1H, ~t, J=7.6 Hz, H-4), 5.74 (2H, m, H-2' and H-3'), 5.75 (1H, dd, J=15.1 and J=7.0 Hz, H-5), 6.06 (1H, d, J=9.3 Hz, —NH—), 7.28–7.55 and 7.83–8.0 (9H and 6H, 2m, H aromatic).

Anal. Calcd. for C₇₁H₁₀₅NO₁₅: C 70.33; H 8.73; N 1.16. Found: C 70.05; H 8.55; N 1.39.

EXAMPLE 25

(2S,3R,4E)-2-Azido-3-benzoyloxy-1-(2,3-di-O-benzoyl-4,6-di-O-carboxymethyl-β-D-galactopyranosyloxy)-4-octadecene

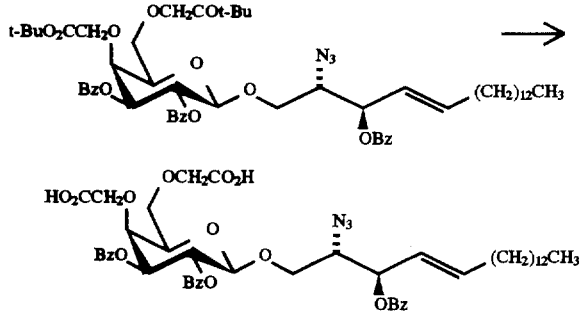

(2S,3R,4E)-2-Azido-3-benzoyloxy-1-(2,3-di-O-benzoyl-4,6-di-O-tert-butyloxy-carbonylmethyl-β-D-galactopyranosyloxy)-4-octadecene described in Example 15-B (191 mg, 0.19 mmol) was stirred at 22° C. with a 9/1 trifluoroacetic acid/water solution (2.5 mL) for 5 minutes. Toluene (5 mL) was added and the mixture was partially evaporated. This process was repeated again. Then toluene (5 mL) was added and the solvent was evaporated to dryness. The residue was purified by preparative TLC (MeOH/CHCl₃/H₂O: 20/80/2 and 25/75/2) twice and treated in dichloromethane/methanol (1:1, 10 mL) at 0° C. (ice bath) with Dowex 50W8 (H⁺) resin for 30 min to give title material as the free carboxylic acid (41 mg, 24%).

IR (CH₂Cl₂) v$_{max}$ (cm⁻¹): 3200–2500 (OH), 2105 (N₃) and 1730 (C=O).

¹H NMR 400 MHz (pyridine-d₅) δ(ppm): 0.846 (3H, t, J=6.7 Hz, —CH₃), 1.23 (22H, br s, —(CH₂)₁₁—), 1.91–1.94 (2H, m, =CH—CH₂—), 4.04–4.10 (1H, m, H-2), 4.31–4.38 (3H, m, H-5', H-6' and H-1), 4.48–4.57 (1H, m, H-1), 4.488, 4.529, 4.533, 4.575 (2H, ABq, J=16.5 Hz, —OCH₂CO), 4.682 (1H, dd, J=9.7 and 6.5 Hz, H-6'), 4.721, 4.761, 4.842, 4.883 (2H, ABq, J=16.3 Hz, —OCH₂CO), 4.682 (1H, dd, J=9.7 and 6.5 Hz, H-6'), 4.721, 4.761, 4.842, 4.883 (2H, ABq, J=16.3 Hz, —OCH₂CO), 4.812 (1H, d, J=2.6 Hz, H-4'), 5.296 (1H, d, J=7.9 Hz, H-1'), 5.740 (1H, dd, J=15.4 and 7.9 Hz, H-4), 5.923 (1H, dt, J=15.5 and 6.7 Hz, H-4), 5.923 (1H, dt, J=15.5 and 6.7 Hz, H-5), 6.001 (1H, dd, J=7.7 and 3.2 Hz, H-3), 6.096 (1H, dd, J=10.5 and 2.9 Hz, H-3'), 6.509 (1H, dd, J=10.4 and 7.9 Hz, H-2'), 7.18–7.51, 8.16–8.23 (15H, 5 sets of m, aromatic H).

EXAMPLE 26

(2S,3R,4E)-1-(2,3-di-O-Benzoyl-4,6-di-O-tert-butyloxycarbonylmethyl-β-D-galactopyranosyloxy)-3-benzoyloxy-2-decanoylamino-4-undecene A. (2S,3R,4E)-2-Azido-3-benzoyloxy-1-(2,3-di-O-benzoyl-4,6-di-O-tert-butyloxycarbonylmethyl-β-D-galactopyranosyloxy)-4-undecene

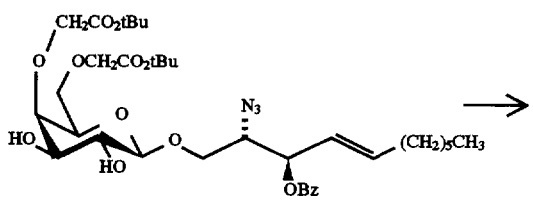

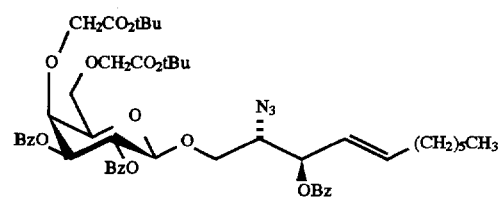

(2S,3R,4E)-2-Azido-3-benzoyloxy-1-(4,6-di-O-tert-butyloxycarbonylmethyl-β-D-galactopyranosyloxy)-4-undecene described in Example 6-H (2.00 g, 2.77 mmol) was benzoylated as described in Example 1-F and gave 2.36 g (91%) of the title material as an oil.

[α]$_D^{22}$: −12° (c=1.0, CHCl₃).

IR (NaCl, film) v$_{max}$ (cm⁻¹): 2100 (N₃), 1750 (sh) and 1725 (C=O of ester).

¹H NMR 400 MHz (CDCl₃) δ(ppm): 0.87 (3H, t, J=6.9 Hz, —CH₃), 1.2–1.3 (8H, m, —(CH₂)₄—), 1.4 and 1.49 (2×9H, 2s, 2×tert-butyl), 1.93 (2H, m, =CH—CH₂—), 3.63 (1H, dd, J=12.7 and J=8.8 Hz, H-1), 3.85 (1H, dd, J=9.4 and J=6.0 Hz, H-6'), 3.92–3.97 (2H, m, H-1 and H-5' overlapping), 4.05 (2H, s, —OCH₂CO—), 4.11 (1H, dd, J=9.4 and J=6.3 Hz, H-6'), 4.18 (2H, ABq, J$_{AB}$=16.1 Hz, Δv=94 Hz, —OCH₂CO—), 4.19 (1H, broad d, J=2.5 Hz, H-4'), 4.71 (1H, d, J=7.9 Hz, H-1'), 5.39 (1H, dd, J=10.5 and J=2.85 Hz, H-3'), 5.46 (1H, dd, 15.1 and J=8.1 Hz, H4), 5.53 (1H, dd, J=8.1 and J=3.3 Hz, H-3), 5.72 (1H, dt, J=15.1 and J=6.7 Hz, H-5), 5.82 (1H, dd, J=10.5 and J=7.9 Hz, H-2'), 7.33–7.58 and 7.92–8.04 (9H and 6H, 2m, aromatic H).

Anal. Calcd. for C₅₀H₆₃N₃O₁₄: C 64.57; H 6.83; S 4.52. Found: C 64.64; H 6.82; S 4.52.

B. (2S,3R,4E)-1-(2,3-di-O-Benzoyl-4,6-di-O-tert-butyloxycarbonylmethyl-β-D-galactopyranosyloxy)-3-benzoyloxy-2-decanoylamino-4-undecene

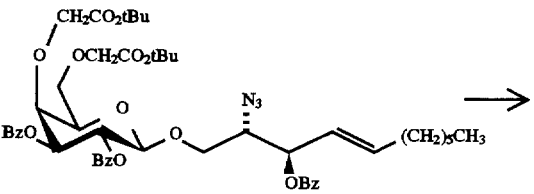

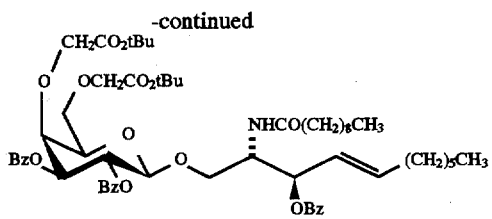

(2S,3R,4E)-2-Azido-3-benzoyloxy-1-(2,3-di-O-benzoyl-4,6-di-O-tert-butyloxycarbonylmethyl-β-D-galactopyranosyloxy)-4-undecene (1.06 g, 1.14 mmol) was reduced and acylated as described in Example 1-G except that decanoyl chloride was used as acylating agent and afforded 1.068 g (89%) of the title material as a syrup.

$[\alpha]_D^{22}$: +10° (c=1.0, CHCl$_3$).

IR (NaCl, film) $v_{max}$(cm$^{-1}$); 1740 (sh), and 1725 (C=O of ester) and 1670 (C=O of amide).

$^1$H NMR 400 MHz (CDCl$_3$) δ(ppm): 0.87 and 0.89 (2×3H, 2t, J=7.0 and J=6.7 Hz, 2×—CH$_3$), 1.14–1.5 (22H, m, —(CH$_2$)$_4$— and —(CH$_2$)$_7$—), 1.41 and 1.48 (2×9H, 2, 2×tert-butyl), 1.83 (2H, t, J=7.6 Hz, —NHCOCH$_2$—), 2.0 (2H, m, =CH—CH$_2$—), 3.70 (1H, dd, J=10.1 and J=3.97 Hz, H-1), 3.73 (1H, dd, J=9.5 and J=6.0 Hz, H-6'), 3.92 (1H, br t, J=6 Hz, H-5'), 3.97 (2H, ABq, J$_{AB}$=18.0 Hz, Δv=10.6 Hz, —OCH$_2$CO—), 4.04 (1H, dd, J=9.5 and J=6.0 Hz, H-6'), 4.17 (1H, dd, J=10.0 and J=3.6 Hz, H-1), 4.18 (1H, m overlapping with H-1, H-4'), 4.18 (2H, ABq, J$_{AB}$=16.1 Hz, Δv=85.6 Hz, —OCH$_2$CO—), 4.41 (1H, m, H-2), 4.65 (1H, d, J=7.8 Hz, H-1'), 5.41 (1H, dd, J=10.4 and J=2.9 Hz, H-3'), 5.47 (1H, dd, J=15.2 and J=7.2 Hz, H-4), 5.54 (1H, dd, J=7.2 and J=6.7 Hz, H-3), 5.75–5.85 (3H, m, H-2', H-5 and —NH— overlapping), 7.33–7.58 and 7.9–8.05 (9H and 6H, 2 m, aromatic H).

Anal. Calcd. for C$_{60}$H$_{83}$NO$_{15}$: C 68.09; H 7.91; N 1.32. Found: C 68.07; H 7.71; N 1.48.

EXAMPLE 27

(2S,3R,4E)-3-Benzoyloxy-1-(2,3-di-O-benzoyl-4,6-di-O-carboxymethyl-β-D-galactopyranosyloxy)-2-decanoylamino-4-undecene

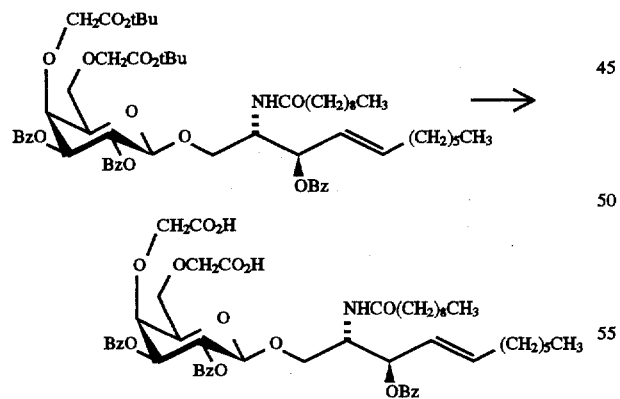

(2S,3R,4E)-1-(2,3-di-O-Benzoyl-4,6-di-O-tert-butyloxycarbonylmethyl-β-D-galactopyranosyloxy)-3-benzoyloxy-2-decanoylamino-4-undecene (0.980 g, 0.926 mmol) was deprotected as described in Example 2 to give 0.86 (98%) of the title diacid as a white glass.

$[\alpha]_D^{22}$: +2° (c=1.0, CHCl$_3$).

IR (KBr) $v_{max}$ (cm$^{-1}$): 1750 (sh) (C=O of ester), 1725 (C=O of acid) and 1635 (C=O of amide).

$^1$H NMR 400 MHz (DMSO-d$_6$) δ(ppm): 0.82 and 0.83 (2×3H, 2t, J=7.0 and J=6.7 Hz, 2×—CH$_3$), 1.1–1.37 (22H, m, —(CH$_2$)$_4$— and —(CH$_2$)$_7$—), 1.75–2.0 (4H, m, —NHCOCH$_2$— and =CH—CH$_2$—), 3.5–3.75 (4H, m, H-1 and H-6'), 3.77 (1H, dd, J=10.1 and J=6.8 Hz, H-1), 3.83 (1H, dd, J=9.8 and J=6.3 Hz, H-6'), 4.03 (2H, ABq, J$_{AB}$=16.7 Hz, Δv=10.9 Hz, —OCH$_2$CO—), 4.08 (1H, m, H-5'), 4.10 (1H, br d, J=2 Hz, H-4'), 4.19 (2H, ABq, J$_{AB}$=16.5, Hz, Δv=24.2 Hz, —OCH$_2$CO—), 4.31 (1H, m, H-2), 4.90 (1H, d, J=7.2 Hz, H-1'), 5.34 (1H, dd, J=7.3 and J=4.5 Hz, H-3), 5.44 (1H, dd, J=15.5 and J=7.3 Hz, H-4), 5.45–5.6 (3H, m, H-2', H-3' and H-5), 7.35–7.65 and 7.8–7.95 (9H and 6H, 2m, aromatic H), 7.7 (1H, d, J=8.8 Hz, —NH—).

Anal. Calcd. for C$_{52}$H$_{67}$NO$_{15}$.H$_2$O: C 64.78; H 7.21; N 1.45. Found: C 64.60; H 6.91; N 1.61.

Sodium salt of the title compound

The above diacid was converted to the sodium salt by the general procedure as described in Example 10.

IR (KBr) $v_{max}$ (cm$^{-1}$): 1725 (C=O of ester), 1780 (C=O of amide) and 1610 (C=O of carboxylate).

$^1$H NMR 400 MHz (DMSO-d$_6$) δ(ppm): 0.82 and 0.83 (2×3H, 2t, J=7.0 and J=6.7 Hz, 2×—CH$_3$), 1.1–1.4 (22H, m, —(CH$_2$)$_4$— and —(CH$_2$)$_7$—), 1.8–2.0 (4H m, —NHCOCH$_2$— and =CH—CH$_2$—), 3.39, 3.52, 3.63 and 3.99 (4×1H, 4 m, H-1 and H-6'), 3.7–3.8 (2H, m, —OCH$_2$CO—), 3.85 (2H, ABq, J$_{AB}$=14.5 Hz and Δv=63.5 Hz, —OCH$_2$CO—), 4.1 (1H, m, H-5'), 4.22 (1H, broad s, H-4'), 4.33 (1H, m, H-2), 4.90 (1H, d, J=7.1 Hz, H-1'), 5.34 (1H, dd, J=7.4 and J=4.6 Hz, H-3), 5.43 (1H, dd, J=15.2 and J=7.4 Hz, H-4), 5.45–5.55 (2H, m, H-2' and H-3'), 5.54 (1H, dt, J=15.2 and J=6.4 Hz, H-5'), 7.35–7.6 and 7.8–7.9 (9H and 6H, 2m, aromatic H), 7.75 (1H, d, J=8.8 Hz, —NH—).

EXAMPLE 28

(2S,3R,4E)-3-Benzoyloxy-2-hexadecanoylamino-1-(2-O-benzoyl-4-O-methyloxy-carbonylmethyl-6-O-carboxymethyl-α-D-galactopyranosyloxy)-4-octadecene

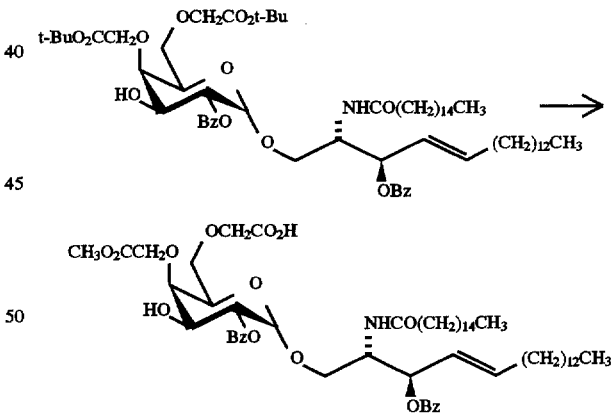

(2S,3R,4E)-3-Benzoyloxy-2-hexadecanoylamino-1-(2-O-benzoyl-4,6-di-O-tert-butyloxycarbonylmethyl-α-D-galactopyranosyloxy)-4-octadecene (466 mg, 0.41 mmol) was reacted by the general procedure as described in Example 2 to afford along with (2S,3R,4E)-3-benzoyloxy-2-hexadecanoylamino-1-(2-O-benzoyl-4,6-di-O-carboxymethyl-α-D-galactopyranosyloxy)-4-octadecene (see Example 14) the corresponding monomethylester (2S,3R,4E)-3-benzoyloxy-2-hexadecanoylamino-1-(2-O-benzoyl-4-O-methyloxycarbonylmethyl-6-carboxymethyl-α-D-galactopyranosyloxy)-4-octadecene (0.144 g, 34%) as a beige solid.

IR (CH$_2$Cl$_2$) $\nu_{max}$ (cm$^{-1}$): 3500–3100 (OH), 3300 (NH), 1715, 1650 and 1605 (C=O).

$^1$H NMR 400 MHz (DMSO-d$_6$) δ(ppm): 0.848 (6H, t, J=6.7H, 2×—CH$_3$), 1.19–1.39 (48H, m, —(CH$_2$)$_{11}$— and —(CH$_2$)$_{10}$—), 1.82–1.99 (4H, 2 sets of m, =CH—CH$_2$ and —CH$_2$CONH—), 3.447 (1H, dd, J=9.6 and 5.7 Hz, H-6′), 3.443, 3.479, 3.530, 3.568 (2H, ABq, J=15.4 Hz, —OCH$_2$CO—), 3.42–3.51 (1H, m, hidden H-1), 3.654 (3H, s, —OCH$_3$), 3.675 (1H, dd, J=12.1 and 6.1 Hz, H-1), 3.719 (1H, dd, J=9.6 and 6.8 Hz, H-6′), 3.840 (1H, br s, H-4′), 3.983 (1H, bt, J=6.3 Hz, H-5′), 4.143 (1H, dd, J=10.4 and 2.7 Hz, H-3′), 4.25–4.32 (1H, m, H-2) 4.477 (2H, part of ABq, —OCH$_2$CO—), 4.967 (1H, d, J=3.6 Hz, H-1′), 5.0922 (1H, dd, J=10.4 and 3.6 Hz, H-2′), 5.28 (1H, br s, —OH), 5.448 (1H, bt, J=7.4 Hz, H-3), 5.496 (1H, dd, J=14.8 and 7.5 Hz, H-4), 5.710 (1H, dt, J=14.7 and 6.8 Hz, H-5), 7.43–7.50, 7.58–7.63, 7.87–7.95 (10H, 3 sets of m, aromatic H), 7.91 (1H, part of —NH—).

Anal. Calcd. for C$_{59}$H$_{91}$NO$_{11}$·1.5H$_2$O: C 66.25; H 8.89; N 1.31. Found: C 66.42; H 8.43; N 1.41.

Preparation of the sodium salt of the title compound

The above monoacid (97 mg, 0.093 mmol) was dissolved in dioxane (8 ml). The solution was filtered on a Millex LCR 0.5 μm filter and treated with NaHCO$_3$ (7 mg, 0.083 mmol) in water (1 ml). The solution was lyophilized to afford the title material (94 mg, 85%) as a white fluffy solid.

IR (Nujol) $\nu_{max}$ (cm$^{-1}$): 3600–3300 (OH, NH), 3055, 2925, 2855 (C—H), 1745, 1720 and 1668 (C=O).

$^1$H NMR 400 MHz (CDCl$_3$) δ(ppm): 0.89 (6H, t, J=6.8 Hz, 2×—CH$_3$), 1.17–1.36 (44H, m, —(CH$_2$)$_{10}$— and —(CH$_2$)$_{12}$—), 1.39 and 1.48 (18H, 2s, 2×tert-butyl), 1.55–1.65 (4H, m, 2×—CH$_2$—), 2.05 (2H, m, =CH—CH$_2$—), 2.19 (2H, m, —NHCOCH$_2$—), 3.50 (1H, br s, —OH), 3.75 (1H, dd, J=9.3 and 6.0 Hz, H-6′), 3.84 (1H, br t, H-5′), 3.86 (1H, dd, J=11.3 and 3.6 Hz, H-1), 3.98 (1H, dd, J=9.3 and 6.2 Hz, H-6′), 4.00 (2H, s, —OCH$_2$CO—), 4.05–4.11 (3H, m, H-4′, H-2′ and H-1), 4.10 (1H, d, J$_{AB}$=16.0 Hz, —OCH$_2$CO—), 4.21 (1H, d, J$_{AB}$=16.0 Hz, —OCH$_2$CO—), 4.42 (1H, d, J=7.6 Hz, H-1′), 4.53 (1H, m, H-2), 5.16 (1H, dd, J=10.2 and 2.8 Hz, H-3′), 5.50 (1H, dd, J=15.2 and 7.2 Hz, H-4), 5.57 (1H, br t, H-3), 5.88 (1H, dt, J=15.2 and 6.9 Hz, H-5), 6.09 (1H, d, J=9.3 Hz, —NH—), 7.45–7.50, 7.57–7.63, 8.04–8.10 and 8.10–8.12 (10H, 4 sets of m, 2×—C$_6$H$_5$).

EXAMPLE 29

(2S,3R,4E)-Benzoyloxy-2-hexadecanoylamino-1-{2, 3-di-O-benzoyl-4,6-di-O-[(R and S)-(2,2-dimethyl-1,3-dioxolane-4-methyl)]-oxycarbonylmethyl-α-D-galactopyranosyloxy}-4-octadecene

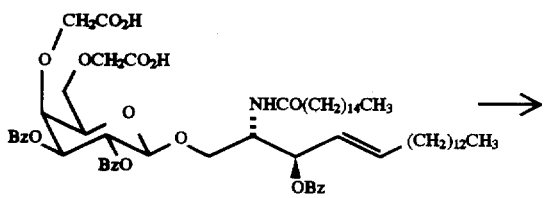

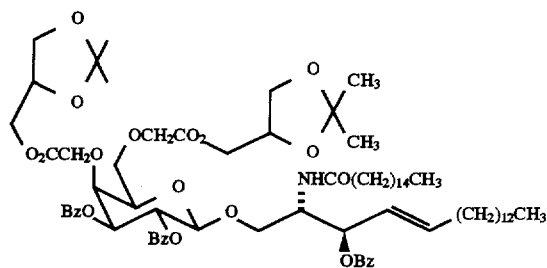

(2S,3R,4E)-3-Benzoyloxy-2-hexadecanoylamino-1-{2,3-di-O-benzoyl-4,6-di-O-carboxymethyl-α-D-galactopyranosyloxy}-4-octadecene described in Example 2 (0.113 g, 0.1 mmol)was reacted as described in Example 24-A except that (±) 2,2-dimethyl-1,3-dioxolane-4-methanol was used instead of 2-propanol. The title material was obtained (0.089 g, 70%) as an oil.

$[α]_D^{22}$: +38° (C=1.0, CHCl$_3$).

IR (film) $\nu_{max}$ (cm$^{-1}$): 2920, 2850 (C—H), 1760, 1725 and 1655 (C=O).

$^1$H NMR 400 MHz (CDCl$_3$) δ(ppm): 0.89 (6H, t, J=6.7 Hz, 2×—CH$_3$), 1.22–1.31 (46H, m, —(CH$_2$)$_{11}$— and —(CH$_2$)$_{12}$—), 1.33–1.44 (12H, m, 2×(CH$_3$)$_2$CH—), 1.57–1.60 (2H, m, —CH$_2$—), 1.96 (2H, qa, J=6.9 Hz, =CH—CH$_2$—), 2.17 (2H, m, —NHCOCH$_2$—), 3.6–4.5 (21H, m, H-6′, H-1, H5′, —OCH$_2$CO—, H-4′, H-2, —CO$_2$CH$_2$—CH—CH$_2$—O—), 5.24 (1H, br s, H-1′), 5.48 (1H, dd, J=15.1 and 7.6 Hz, H-4), 5.56 (1H, t, J=7.5 Hz, H-3), 5.74 (1H, dt, J=14.8 and 6.7 Hz, H-5), 5.74 (2H, br s, H-2′ and H-3′), 5.97 (1H, d, J=9.3 Hz, —NH—), 7.28–7.49, 7.52–7.57, 7.90–8.00 (15H, 3 sets of m, 3×—C$_6$H$_5$).

EXAMPLE 30

(2S,3R,4E)-3-Benzoyloxy-2-hexadecanoylamino-1-{2,3-di-O-benzoyl-4,6-di-O-[(R and S)-(2,3-dihydroxypropyl)]-oxycarbonylmethyl-α-D-galactopyranosyloxy}-4-octadecene

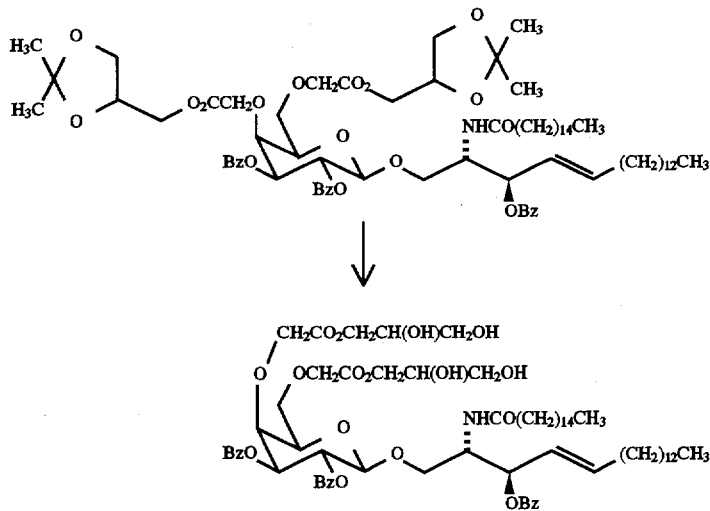

A solution of (2S,3R,4S)-3-Benzoyloxy-2-hexadecanoylamino-1-{2,3-di-O-benzoyl-4,6-di-O-[(R and S)-(2,2-dimethyl-1,3-dioxolane-4-methyl)]-oxycarbonylmethyl-α-D-galactopyranosyloxy}-4-octadecene (0.3 g, 0.221 mmol) in tetrahydrofuran (40 mL) was treated with a 1:1 trifluoroacetic acid/water solution (14 mL). The mixture was allowed to react at 22° C. for 5 minutes then diluted with toluene (50 mL). The solvent was removed under high vacuum. The last traces of trifluoroacetic acid were azeotropically removed with toluene (2×50 ml) under high vacuum and the residue was passed through a silica gel column (60 g, 0% to 8% methanol/dichloromethane) to give the title material. The residue upon solvent evaporation was dissolved in dioxane and lyophilized to afford the title compound (0.263 g, 77%) as a white fluffy solid.

$[\alpha]_D^{22}$: +45.2° (C=1.0, CHCl$_3$).

IR (film) $\nu_{max}$ (cm$^{-1}$): 3300 (OH and NH), 1750, 1720 and 1650 (C=O).

$^1$H NMR 400 MHz (CDCl$_3$) δ(ppm): 0.89 (6H, t, J=6.7 Hz, 2×—CH$_3$), 1.1–1.45 (46H, m, —(CH$_2$)$_{11}$— and —(CH$_2$)$_{12}$—), 1.57–1.60 (2H, m, —CH$_2$—), 1.99 (2H, qa, J=6.9 Hz, =CH—C$\underline{H}_2$—), 2.17 (2H, m, —NHCOC$\underline{H}_2$—), 2.4–3.5 (4H, 4 sets of m, 4×—OH), 3.5–4.5 (20H, m, H-6', H-1, H-5', —OCH$_2$CO—, H-4', —OC$\underline{H}_2$—CH—C$\underline{H}_2$—O—), 4.52 (1H, m, H-2), 5.24 (1H, br s, H-1'), 5.47 (1H, dd, J=15.2 and 7.5 Hz, H-4), 5.57 (1H, t, J=7.4 Hz, H-3), 5.74 (2H, br s, H-2' and H-3'), 5.79 (dt, J=14.9 and 6.8 Hz, H-5), 5.95 (1H, 2 sets of d, J=9 Hz, —NH—), 7.31–7.35, 7.4–7.58 and 7.91–8.00 (15H, 3 sets of m, 3×—C$_6$H$_5$).

Anal. Calcd. for C$_{71}$H$_{105}$NO$_{19}$: C 66.80; H 8.29; N 1.10. Found: C 66.22; H 8.09; N 1.23.

EXAMPLE 31

(2S,3R,4E)-3-Benzoyloxy-2-hexadecanoylamino-1-(3-O-benzoyl-4,6-di-O-tert-butyloxycarbonylmethyl-α-D-galactopyranosyloxy)-4-octadecene A. (2S,3R,4E)-2-Azido-3-benzoyloxy-1-(2-O-trichloroethoxycarbonyl-4,6-di-O-tert-butyloxycarbonylmethyl-α-D-galactopyranosyloxy)-4-octadecene

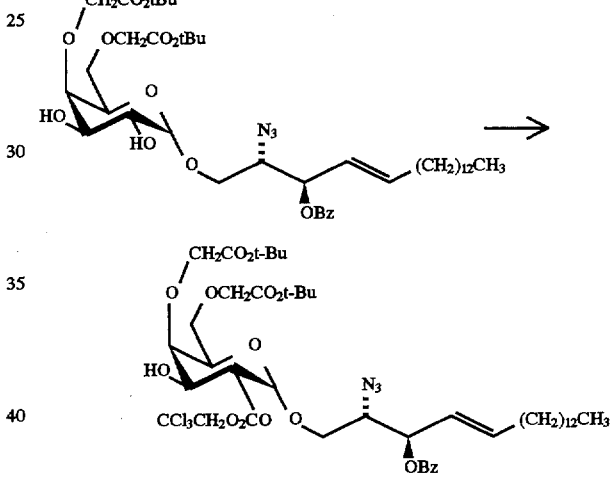

A cold solution (ice bath) of (2S,3R,4E)-2-azido-3-benzoyloxy-1-(4,6-di-O-tert-butyloxycarbonylmethyl-α-D-galactopyranosyloxy)-4-octadecene (0.973 mg, 1.19 mmol) in dichloromethane (30 mL) and pyridine (30 mL) was treated dropwise with trichloroethyl chloroformate (250 mL, 1.82 mmol). The mixture was stirred for 1 h, treated again with trichloroethyl chloroformate (75 mL, 0.54 mmol) and allowed to stir at 0° C. for 30 more min. It was then diluted with ethyl acetate (200 mL), washed with 1M aqueous NaHCO$_3$ (2×100 mL) water (2×100 mL), brine (100 mL) and dried over anhydrous magnesium sulfate. The residue upon solvent evaporation (1.5 g) was passed twice on a silica gel column (125 g, 60 g; 5 to 25% ethyl acetate/hexane) to give the title material (700 mg, 59.3%).

IR (CH$_2$Cl$_2$) $\nu_{max}$ (cm$^{-1}$): 3380 (OH), 2105 (N$_3$), 1760, 1745 and 1725 (C=O).

$^1$H NMR 400 MHz (CDCl$_3$) δ(ppm): 0.892 (3H, t, J=6.8 Hz, —CH$_3$), 1.253 (20H, s, —(CH$_2$)$_{10}$—), 1.35–1.40 (2H, m, —CH$_2$—), 1.487, 1.494 (18H, 2s, 2×tert-butyl), 2.05–2.11 (2H, m, =CH—C$\underline{H}_2$—), 3.524 (1H, dd, J=10.8 and 7.7 Hz, H-1), 3.610 (1H, dd, J=9.2 and 5.8 Hz, H-6'), 3.822 (1H, dd, J=10.8 and 4.1 Hz, H-1), 3.80 (1H, m, H-5'), 3.906 (1H, d, J=3.2 Hz, H-4'), 3.92–3.96 (1H, m, H-2), 3.965, 4.006, 4.027, 4.068 (2H, ABq, J=16.2 Hz, —OCH$_2$CO—), 4.079, 4.123, 4.369, 4.412 (2H, ABq, J=17.2 Hz, —OCH$_2$CO—), 4.06–4.12 (2H, m, H-3' and H-6'), 4.759, 4.789, 4.810, 4.839 (2H, ABq, J=11.8 Hz, —OCH$_2$CCl$_3$), 4.939 (1H, dd, J=10.4 and 3.7 Hz, H-2'), 4.951 (1H, d, J=9.5 Hz, —OH), 5.165 (1H, d, J=3.7 Hz, H-1'), 5.3–5.62 (2H, m, H-3 and H-4), 5.948 (1H, dt, J=14.2 and 6.6 Hz, H-5), 7.44–7.48, 7.56–7.60, 8.04–8.07 (5H, 3 sets of m, —C$_6$H$_5$).

Anal. Calcd. for C$_{46}$H$_{70}$N$_3$O$_{14}$Cl$_3$: C 55.50; H 7.09; N 4.22. Found: C 55.43; H 6.95; N 4.15.

B. (2S,3R,4E)-2-Azido-3-benzoyloxy-1-(3-O-benzoyl-2-O-trichloroethoxycarbonyl-4,6-di-O-tert-butyloxycarbonylmethyl-α-D-galactopyranosyloxy)-4-octadecene

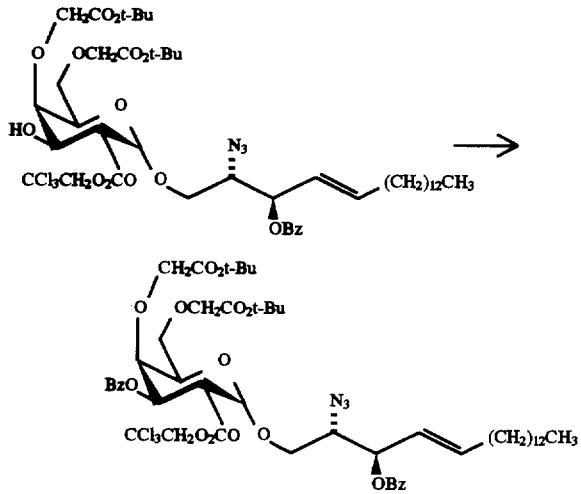

A solution of (2S,3R,4E)-2-azido-3-benzoyloxy-1-(2-O-trichloroethoxycarbonyl-4,6-di-O-tert-butyloxycarbonylmethyl-α-D-galactopyranosyloxy)-4-octadecene (0.7 g, 0.713 mmol) in dichloromethane (15 mL) and pyridine (15 mL) was treated with benzoyl chloride (130 μL, 1.12 mmol) and dimethylaminopyridine (325 mg, 2.66 mmol). The mixture was allowed to stir over a 2 h period, then treated with methanol and stirred for 18 more hours. The residue upon solvent evaporation was diluted with ethyl acetate (200 mL), washed with 1M aqueous NaHCO$_3$ (2×100 mL), water (2×100 mL) and brine (100 mL) and dried over anhydrous magnesium sulfate. Evaporation of the solvent afforded a residue (736 mg) that was passed through a silica gel column (60 g), 5 to 20% ethyl acetate/hexane) to give the title material (483 mg, 70%) as an oil.

IR (CH$_2$Cl$_2$) ν$_{max}$ (cm$^{-1}$): 3050–2350 (C—H), 2100 (N$_3$), 1760, 1745 and 1725 (C=O).

$^1$H NMR 400 MHz (CDCl$_3$) δ(ppm): 0.891 (3H, t, J=6.8 Hz, —CH$_3$), 1.25 (20H, br s, —(CH$_2$)$_{10}$—), 1.395 (11H, br s, —CH$_2$— and tert-butyl), 1.478 (9H, s, tert-butyl), 2.05–2.11 (2H, m, =CH—CH$_2$), 3.577 (1H, dd, J=10.8 and 7.8 Hz, H-1), 3.777 (1H, dd, J=9.6 and 6.5 Hz, H-6'), 3.950 (1H, dd, J=10.9 and 3.6 Hz, H-1), 3.990, 4.029, 4.200, 4.240 (2H, ABq, J=16.1 Hz, —OCH$_2$CO—), 4.000, 4.007 (2H, part of ABq, —OCH$_2$CO—), 3.97–4.05 (2H, m, H-2 and H-6'), 4.24–4.27 (2H, m, H-5' and H-4'), 4.620, 4.649, 4.824 and 4.854 (2H, ABq, J=11.8 Hz, —CH$_2$CCl$_3$), 2.618 (1H, d, J=3.6 Hz, H-1'), 5.475 1H, dd, J=10.7 and 3.6 Hz, H-2'), 5.575 (1H, dd, J=10.2 and 2.7 Hz, H-3'), 5.55–5.63 (2H, m, H-3 and H-4), 5.970 (1H, dt, J=14.4 and 6.7 Hz, H-5), 7.43–7.48, 7.56–7.61, 8.04–8.07 (10H, 3 sets of m, 2×—C$_6$H$_5$).

Anal. Calcd. for C$_{53}$H$_{74}$N$_3$O$_{15}$Cl$_3$: C 57.90; H 6.78; N 3.82. Found: C 57.99; H 6.70; N 3.84.

C. (2S,3R,4E)-3-Benzoyloxy-2-hexadecanoylamino-1-(3-O-benzoyl-2-O-trichloroethoxycarbonyl-4,6-di-O-tert-butyloxycarbonylmethyl-α-D-galactopyranosyloxy)-4-octadene

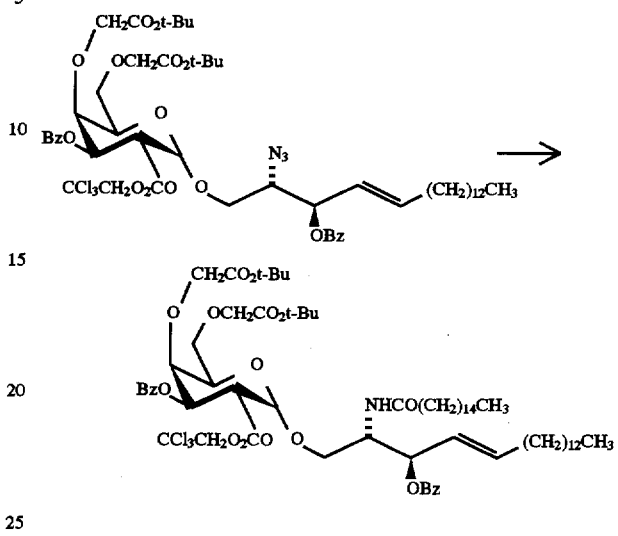

(2S,3R,4E)-2-Azido-3-benzoyloxy-1-(3-0-benzoyl-2-O-trichloroethoxycarbonyl-4,6-di-O-tert-butyloxycarbonylmethyl-α-D-galactopymnosyloxy)-4-octadecene (0.439 g, 0.40 mmol) was reacted by the general procedure as described in Example 1-G except that the acylation reaction was performed at 0° C. This gave title material (395 mg, 75%) as a colorless gum.

IR CH$_2$Cl$_2$) ν$_{max}$ (cm$^{-1}$): 3430 (NH), 3050, 2930 and 2865 (CH), 1765, 1745, 1720 and 1670 (C=O).

$^1$H NMR 400 MHz (CDCl$_3$) δ(ppm): 0.890 and 0.893 (6H, 2 sets of t, J=6.4 and 6.1 Hz, 2×—CH$_3$), 1.22–1.39 (46H, —(CH$_2$)$_{11}$— and —(CH$_2$)$_{12}$—), 1.388 and 1.476 (18H, 2s, 2×tert-butyl), 1.58–1.70 (2H, m, —CH$_2$—), 1.97–2.06 (2H, m, =CH—CH$_2$—), 2.15–2.31 (2H, m, —NHCOCH$_2$—), 3.754 (1H, dd, J=9.5 and 6.8 Hz, H-1), 3.806 (1H, dd, J=11.2 and 2.9 Hz, H-6'), 3.857 (1H, dd, J=11.3 and 2.9 Hz, H-6'), 3.957 (1H, dd, J=9.5 and 6.7, H-1), 3.979, 4.019, 4.194 and 4.233 (2H, ABq, J=15.9 Hz, —OCH$_2$CO—), 3.952, 3.989, 3.998 and 4.039 (2H, ABq, J=15.4 Hz, —OCH$_2$CO—), 4.255 (1H, bt, J=6.3 Hz, H-5'), 4.233 (1H, bs, H-4'), 4.45–4.53 (1H, m, H-2), 4.648, 4.678, 4.927 and 4.957 (2H, ABq, J=12.0 Hz, —OCH$_2$CCl$_3$), 5.058 (1H, d, J=3.6 Hz, H-1'), 5.470 (1H, dd, J=10.8 and 3.5 Hz, H-2'), 5.517 (1H, dd, J=15.2 and 7.3 Hz, H-4), 5.544 (1H, dd, J=10.8 and 2.8 Hz, H-3'), 5.627 (1H, br t, J=8.2 Hz, H-3), 5.896 (1H, dt, J=15.1 and 6.7 Hz, H-5), 6.294 (1H, d, J=9.5 Hz, —NH—), 7.42–7.48, 7.54–7.62, 8.00–8.06 (10H, 3 sets of m, 2×—C$_6$H$_5$).

D. (2S,3R,4E)-3-Benzoyloxy-2-hexanedecanoylamino-1-(3-O-benzoyl-4,6-di-O-tert-butyloxycarbonylmethyl-α-D-galactopyranosyloxy)-4-octadecene

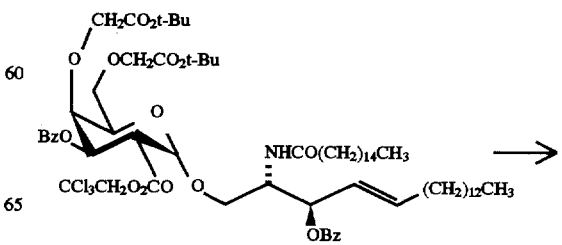

93 -continued

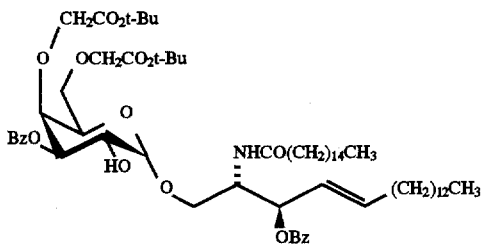

A solution of (2S,3R,4E)-3-benzoyloxy-2-hexadecanoylamino-1-(3-O-benzoyl-2-O-trichloroethoxycarbonyl-4,6-di-O-tert-butyloxycarbonylmethyl-α-D-galacto-pyranosyloxy)-4-octadecene (0.368 g, 0.28 mmol) in acetic acid (10 mL) and tetrahydrofuran (10 mL) was treated with zinc (574 mg). After a stirring period of 3 and 5 h respectively, more zinc was added in (486 mg and 202 mg). The mixture was stirred for 1 more hour and zinc was removed by filtration. The solution was diluted with ethyl acetate (100 mL), washed with water (4×50 mL) and brine (50 mL) and dried over anhydrous magnesium sulfate. The residue obtained upon solvent evaporation (337 mg) is passed through a silica gel column (25 g, 10 to 40% ethyl acetate/hexane to give the title material (271 mg, 85%) as a white solid.

IR (CH$_2$Cl$_2$) ν$_{max}$ (cm$^{-1}$): 3500, 3360 (OH), 3440 (NH), 3050, 2930 and 2860 (CH), 1745, 1720 and 1670 (C=O).

$^1$H NMR 400 MHz (CDCl$_3$) δ(ppm): 0.89 (6H, t, J=6.7 Hz, 2×—CH$_3$) 1.16–1.39 (46H, m, —(CH$_2$)$_{11}$— and —(CH$_2$)$_{12}$—), 1.418 and 1.480 (18H, 2s, 2×tert-butyl), 1.57–1.64 (2H, m, —CH$_2$—), 2.01–2.07 (2H, m, =CH—CH$_2$—), 2.15–2.30 (2H, m, —NHCOCH$_2$—), 2.468 (1H, d, J=10.8 Hz, —OH), 3.774 (1H, dd, J=9.8 and 6.9 Hz, H-1), 3.806 (1H, dd, J=10.9 and 4.0 Hz, H-6'), 3.898 (1H, dd, J=10.9 and 2.9 Hz, H-6'), 3.967 (1H, dd, J=9.8 and 5.6 Hz, H-1), 3.956, 3.997, 4.009, 4.050 (2H, ABq, J=16.4 Hz, —OCH$_2$CO—), 4.077 (1H, d, J=1.9 Hz, H-4'), 4.090, 4.130, 4.260, 4.300 (2H, ABq, J=16.1 Hz, —OCH$_2$CO—), 4.251 (1H, dd, J=10.4 Hz, and 3.6 Hz, H-2'), 4.221 (1H, t, J=6.2 Hz, H-5'), 4.47–4.55 (1H, m, H-2), 4.888 (1H, d, J=3.9 Hz, H-1'), 5.386 (1H, dd, J=10.5 and 2.8 Hz, H-3'), 5.562 (1H, dd, J=15.3 and 7.8 Hz, H-4), 5.723 (1H, br t J=7.9 Hz, H-3), 5.922 (1H, dt, J=15.3 and 6.7 Hz, H-5), 6.125 (1H, d, J=9.4 Hz, —NH—), 7.43–7.50, 7.55–7.63, 8.03–8.13 (10H, 3 sets of m, 2×—C$_6$H$_5$).

Anal. Calcd. for C$_{66}$H$_{105}$NO$_{14}$: C 69.75; H 9.31; N 1.23. Found: C 69.53; H 9.15; N 1.33.

EXAMPLE 32

(2S,3R,4E)-3-Benzoyloxy-2-hexadecanoylamino-1-(3-O-benzoyl-4,6-di-O-carboxymethyl-α-D-galactopyranosyloxy)-4-octadecene

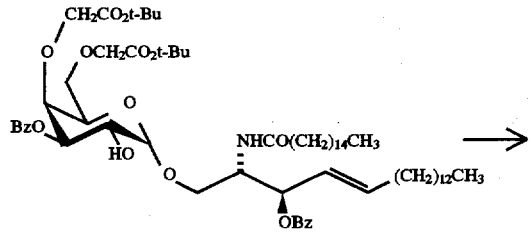

94 -continued

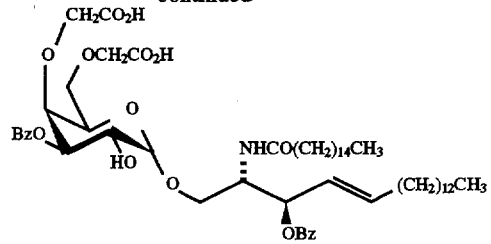

(2S,3R,4E)-3-Benzoyloxy-2-hexadecanoylamino-1-(3-O-benzoyl-4,6-di-O-tert-butyloxycarbonylmethyl-α-D-galactopyranosyloxy)-4-octadecene (246 mg, 0.22 mmol) was reacted by the general procedure as described in Example 2 and afforded the title compound (176 mg, 78%).

IR (Nujol) ν$_{max}$ (cm$^{-1}$): 3300 (OH), 1720 and 1745 (C=O).

$^1$H NMR 400 MHz (DMSO-d$_6$) δ(ppm): 0.849 (6H, t, J=6.6 Hz, 2×—CH$_3$) 1.16–1.39, 1.45–1.55 (48H, 3 sets of m, —(CH$_2$)$_{11}$— and (CH$_2$)$_{13}$—), 1.99–2.07 (2H, m, =CH—CH$_2$—), 2.08–2.17 (2H, m, —NHCOCH$_2$—), 3.550 (1H, dd, J=10.1 and 6.0 Hz, H-1), 3.574 (1H, dd, J=9.6 and 6.4 Hz, H-6'), 3.714 (1H, dd, J=10.2 and 5.7 Hz, H-1), 3.767 (1H, dd, J=9.7 and 6.3 Hz, H-6'), 3.96–4.06 (3H, m, H-2', H-4', H-5'), 4.003, 4.011 (2H, part of ABq, —OCH$_2$CO—), 4.112 (2H, ABq, J=16.4 Hz, —OCH$_2$CO—), 4.38–4.42 (1H, m, H-2), 4.763 (1H, br d, J=6.6 Hz, —OH), 4.819 (1H, d, J=3.5 Hz, H-1'), 5.238 (1H, dd, J=10.4 and 2.4 Hz, H-2'), 5.51–5.60 (2H, m, H-3 and H-4), 5.802 (1H, dt, J=14.0 and 6.7 Hz, H-5), 7.48–7.57, 7.62–7.70, 7.95–8.04 (10H, 3 sets of m, 2×—C$_6$H$_5$), 7.898 (1H, d, J=8.9 Hz, —NH—), 12.465 (2H, br s, —OH).

Anal. Calcd. for C$_{58}$H$_{89}$NO$_{14}$·H$_2$O: C 66.83; H 8.80; N 1.34. Found: C 66.53; H 8.53; N 1.41.

Preparation of the sodium salt of the title compound

The above diacid (163 mg, 0.15 mmol) was dissolved in water and dioxane and reacted as described in Example 14 to afford title material (161 mg, 69% from the ester).

IR (Nujol) ν$_{max}$ (cm$^{-1}$): 3600–3100 (broad, NH, OH), 1720, 1705, 1640 and 1600 (C=O).

$^1$H NMR 400 MHz (CD$_3$OD) δ(ppm): 0.892 (6H, t, J=7.0 Hz, 2×—CH$_3$), 1.15–1.4, 1.5–1.65 (48H, 3 sets of m, —(CH$_2$)$_{11}$— and —(CH$_2$)$_{13}$—), 2.05–2.11 (2H, m, =CH—CH$_2$—), 2.238 (2H, t, J=7.2 Hz, —NHCOCH$_2$—), 3.721 (1H, dd, J=10.8 and 5.3 Hz, H-1), 3.74–3.81 (2H, m, H-6'), 3.807, 3.846, 3.943, 3.983 (2H, ABq, J=16.0 Hz, —OCH$_2$CO—), 3.904 (1H, dd, J=10.8 and 3.5 Hz, H-1), 3.953, 3.989, 4.161, 4.197 (2H, ABq, J=14.7 Hz, —OCH$_2$CO—), 4.10–4.13 (2H, m, H-4' and H-5'), 4.342 (1H, dd, J=10.4 and 3.1 Hz, H-2'), 4.48–4.84 (1H, m, H-2), 4.927 (1H, d, J=3.1 Hz, H-1'), 5.399 (1H, bd, J=10.5 Hz, H-3'), 5.568 (1H, dd, J=15.1 and 7.8 Hz, H-4), 5.665 (1H, t, J=7.4 Hz, H-3), 5.931 (1H, dt, dd, J=15.1 and 6.6 Hz, H-5), 7.46–7.50, 7.58–7.62, 8.02–8.12 (10H, 3 sets of m, 2×—C$_6$H$_5$).

EXAMPLE 33

(2S,3R,4E)-2-Hexadecanoylamino-3-hydroxy-1-{4,6-di-O-carboxymethyl)-α-D-galactopyranosyloxy}-4-octadecene

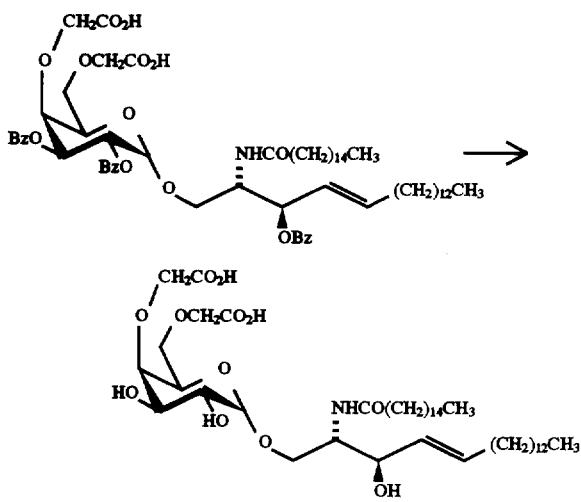

A solution of (2S,3R,4E)-3-benzoyloxy-2-hexadecanoylamino-1-(2,3-di-O-benzoyl-4,6-di-O-carboxymethyl-α-D-galactopyranosyloxy)-4-octadecene described in Example 2 (0.452 g, 0.4 mmol) in a mixture of methanol (68 ml, dried over molecular sieves) and dichloromethane (40 ml, dried over molecular sieves) was treated with a 0.2M solution of sodium methoxide in methanol (2.4 mmol, 12 ml) at 22° C. The mixture was stirred for 20 h at 22° C. then cooled to 5° C., neutralized with Dowex 50W×8 (H⁺) and stirred for 15 min. The resin was filtered and the filtrate was concentrated under vacuum and co-evaporated with chloroform (3×20 ml). The residual solid was crystallized from acetonitrile and chloroform at hot and afforded the title material (0.315 g, 96%) as a white solid.

m.p.: 117°–122° C.

$[\alpha]_D^{22}$: +61.4° (c=1.0, $CH_3OH$).

IR (film) $v_{max}$ ($cm^{-1}$): 3400, 3200 (OH and NH), 1760, 1740 and 1640 (C=O).

¹H NMR 400 MHz (DMSO-$d_6$) δ(ppm): 0.850 (6H, m, 2×—$CH_3$), 1.23–1.45 (48H, m, —($CH_2$)$_{13}$— and —($CH_2$)$_{11}$—), 1.93 (2H, m, =CH—$\underline{CH_2}$—), 2.01–2.05 (2H, m—$\underline{CH_2}$CONH—), 3.48–3.94 (11H, multiplets, H2', H-3', H-4', H-5', H-6', H-1, H2, H-3, -OH), 3.99 (1H, d, $J_{AB}$=16.7 Hz, —O$CH_2$CO—), 4.04 (1H, d, $J_{AB}$=16.7 Hz, —O$CH_2$CO—), 4.19 (1H, d, $J_{AB}$=17.09 Hz, —O$CH_2$CO—), 4.30 (1H, d, $J_{AB}$=17.07 Hz, —O$CH_2$CO—), 4.41 (1H, d, J=8.04 Hz, OH), 4.68 (1H, d, J=3.62 Hz, H-1'), 4.86 (1H, d, J=5.6 Hz, OH), 5.34 (1H, dd, J=15.4 and 6.9 Hz, H-4), 5.54 (1H, dt, J=15.3 and 6.7 Hz, H-5), 7.48 (1H, d, J=9.09 Hz, —NH—).

Preparation of the sodium salt of the title compound

The above diacid (0.2 g, 0.245 mmol) was dissolved in freshly distilled dioxane (5 ml) and water (5 ml) was added followed by solid sodium bicarbonate (0.040 g). This mixture was stirred for 15 minutes (pH ~7) and filtered. The filtrate was lyophilized to afford the title compound (0.210 g, 99.7%) as a white fluffy solid.

IR (film) $v_{max}$ ($cm^{-1}$), 3700–3100 (NH and OH), 1650–1600 (C=O).

¹H NMR 400 MHz (methanol-$d_4$) δ(ppm): 0.89 (6H, t, J=6.8 Hz, 2×—$CH_3$), 1.23–1.37 (46H, m, —($CH_2$)$_{11}$— and —($CH_2$)$_{12}$—), 1.56–1.57 (2H, m, —$CH_2$—), 2.01–2.05 (2H, m, —$\underline{CH_2}$—), 2.18 (2H, t, J=7.56 Hz, —$\underline{CH_2}$CONH—), 3.5–4.2 (14H, m, H-1, H-6', 2×—O$\underline{CH_2}$CO—, H-4', H-5', H-2, H-3, H-2', H-3'), 4.84 (1H, overlapped by HOD, H-1'), 5.43 (1H, dd, J=15.3 and 7.5 Hz, H-4), 5.71 (1H, dt, J=15.3 and 7.6 Hz, H-5).

EXAMPLE 34

(2S,3R,4E)-3-Benzoyloxy-2-hexadecanoylamino-1-(2,3-di-O-acetyl-4,6-di-O-carboxymethyl-α-D-galactopyranosyloxy)-4-octadecene A. (2S,3R,4E)-3-Benzoyloxy-2-hexadecanoylamino-1-(2,3-di-O-para-methoxybenzyl-4,6-di-O-tert-butyloxycarbonylmethyl-α-D-galactopyranosyloxy)-4-octadecene

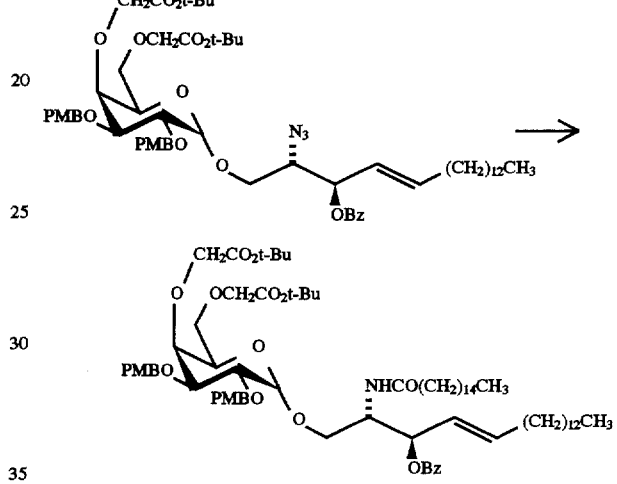

A solution of (2S,3R,4E)-2-azido-3-benzoyloxy-1-(2,3-di-O-para-methoxybenzyl-4,6-di-O-tert-butyloxycarbonylmethyl-α-D-galactopyranosyloxy)-4-octadecene (1.83 g, 1.73 mmol) in pyridine (140 mL) and water (30 mL) was treated with a stream of H2S gas over a 15 min period and then was allowed to stir for 66 h. The solvent was then evaporated and the residue obtained was dissolved in THF (140 mL). It was treated at 0° C. with a 50% aqueous solution of NaOAc (8.6 mL) and dropwise with palmitoyl chloride (575 µl, 1.88 mmol). The reaction mixture was allowed to stir for 30 min, diluted with ethyl acetate (300 mL), washed with water (1×200 mL), a 1M aqueous $NaHCO_3$ solution (2×200 mL) water (1×200 mL), brine (200 mL) and dried ($MgSO_4$). The residue obtained upon solvent evaporation (2.17 g) was passed through a silica gel flash column (250 g, 10%→25% ethyl acetate/hexane) to give the title compound (1.73 g, 79%) as a white solid.

IR ($CH_2Cl_2$) $v_{max}$ ($cm^{-1}$): 3430, 3360 (NH), 1755, 1720 and 1670 (C=O).

¹H NMR 400 MHz ($CDCl_3$) δ(ppm): 0.892 (6H t, J=6.8 Hz, 2×—$CH_3$), 1.228–1.31 (46H, bm, —($CH_2$)$_{11}$— and —($CH_2$)$_{12}$—), 1.447 and 1.4766 (18H, 2s, 2×tert-butyl), 1.55–1.65 (2H, m, —$CH_2$—), 1.95–2.01 (2H, m, =CH—($\underline{CH_2}$—), 2.05–2.2 (2H, m, —NHCO$\underline{CH_2}$—), 3.679 (1H, dd, J=11.4 and 2.9 Hz, H-6'), 3.738 (1H, dd, J=9.6 and 7.6 Hz, H-1), 3.779 (3H, s, —$OCH_3$), 3.79–3.84 (1H, m, H-2' or H-3'), 3.826 (3H, s, —$OCH_3$), 3.897 (1H, bs, H-4'), 3.930 (1H, dd, J=9.6 and 4.4 Hz, H-1), 3.936, 3.975, 3.991 and 4.032 (2H, ABq, J=16.1 Hz, —O$CH_2$CO—), 3.99–4.06 (2H, m, H-6' and H-3' or H-2'), 4.12 (1H, dd, J=6.9 and 4.6

Hz, H-5'), 4.230, 4.271, 4.289 and 4.330 (2H, ABq, J=16.5 Hz, —OCH$_2$CO—), 4.39–4.45 (1H, m, H-2), 4.561, 4.589, 4.625 and 4.654 (2H, ABq, J=11.3 Hz, —OCH$_2$Ar), 4.570, 4.598, 4.667, 4.695 (2H, ABq, J=11.1 Hz, —OCH$_2$Ar), 4.746 (1H, d, J=3.5 Hz, H-1'), 5.495 (1H, dd, J=15.3 and 7.7 Hz, H-4), 5.637 (1H, t, J=8.1 Hz, H-3), 5.840 (1H, dt, J=15.2 and 6.7 Hz, H-5), 6.463 (1H, bd, —NH), 6.789–6.89, 7.24–7.31, 7.42–7.58, 7.94–8.05 (13H, 5 sets of m, aromatic H).

Anal. Calcd. for C$_{75}$H$_{117}$NO$_{15}$: C, 70.78; H, 9.27; N, 1.10. Found: C, 70.10; H, 9.27; N, 1.10.

B. (2S,3R,4E)-3-Benzoyloxy-2-hexadecanoylamino-1-(4,6-di-O-tert-butyloxycarbonylmethyl-α-D-galactopyranosyloxy)-4-octadecene

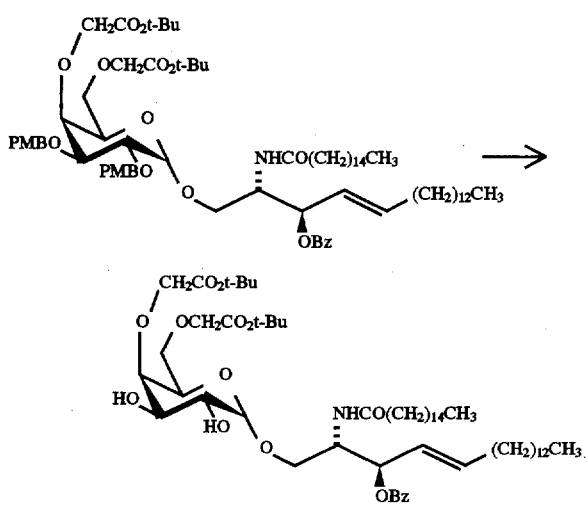

A solution of (2S,3R,4E)-3-benzoyloxy-2-hexadecanoylamino-1-(2,3-di-O-paramethoxybenzyl-4,6-di-O-tert-butyloxycarbonylmethyl-α-D-galactopyranosyloxy)-4-octadecene (1.53 g, 1.20 mmol) was reacted by the general procedure as described in Example 1-E and gave the title compound (1.08 g, 87%).

IR (CH$_2$Cl$_2$) ν$_{max}$ (cm$^{-1}$): 3580, 3500, 3440 and 3380 (OH and NH), 1755, 1725 and 1675 (C=O).

$^1$H NMR 400 MHz (CDCl$_3$) δ(ppm): 0.890 (6H t, J=6.8 Hz, 2×—CH$_3$), 1.24–1.41 (46H, bm, —(CH$_2$)$_{11}$— and —(CH$_2$)$_{12}$—), 1.483 and 1.487 (18H, 2s, 2×-tert-butyl), 1.58–1.62 (2H, m, —CH$_2$—), 2.00–2.11 (2H, m, =CH—CH$_2$—), 2.13–2.25 (2H, m, NHCOCH$_2$—), 3.616 (1H, dd, J=9.2 and 6.3 Hz, H-1), 3.740 (1H, dd, J=10.9 and 4.5 Hz, H-6), 3.779 (1H, dd, J=10.1 and 2.9 Hz, H-3'), 3.803 (1H, dd, J=9.3 and 2.9 Hz, H-1), 3.823 (1H, Hidden H-4'), 3.834 (1H, J=9.5 and 3.7 Hz, H-2'), 3.859 (1H, dd, J=10.0 and 3.7 Hz, H-6'), 3.948, 3.989, 4.013 and 4.057 (2H, ABq, J=16.3 Hz, —OCH$_2$CO—), 4.075 (1H, bt, J=7.0 Hz, H-5'), 4.057, 4.100, 4.328 and 4.371 (2H, ABq, J=17.1 Hz, —OCH$_2$CO), 4.458–4.496 (1H, m, H-2), 4.825 (1H, d, J=3.7 Hz, H-1'), 5.525 (1H, dd, J=15.3 and 7.6 Hz, H-4), 5.659 (1H, bt, J=7.6 Hz, H-2), 5.888 (1H, dt, J=15.9 and 6.7 Hz, H-5), 6.084 (1H, bd, J=3.6 Hz, —NH—), 7.43–7.47, 7.56–7.60 and 8.02–8.05 (5H, 3 sets of m, aromatic H).

Anal. Calcd. for C$_{59}$H$_{10}$NO$_{13}$: C, 68.64; H, 9.86; N, 1.36. Found: C, 68.01; H, 9.60; N, 1.49.

C. (2S,3R,4E)-3-Benzoyloxy-2-hexadecanoylamino-1-(2,3-di-O-acetyl-4,6-di-O-tert-butyloxycarbonylmethyl-α-D-galactopyranosyloxy)-4-octadecene

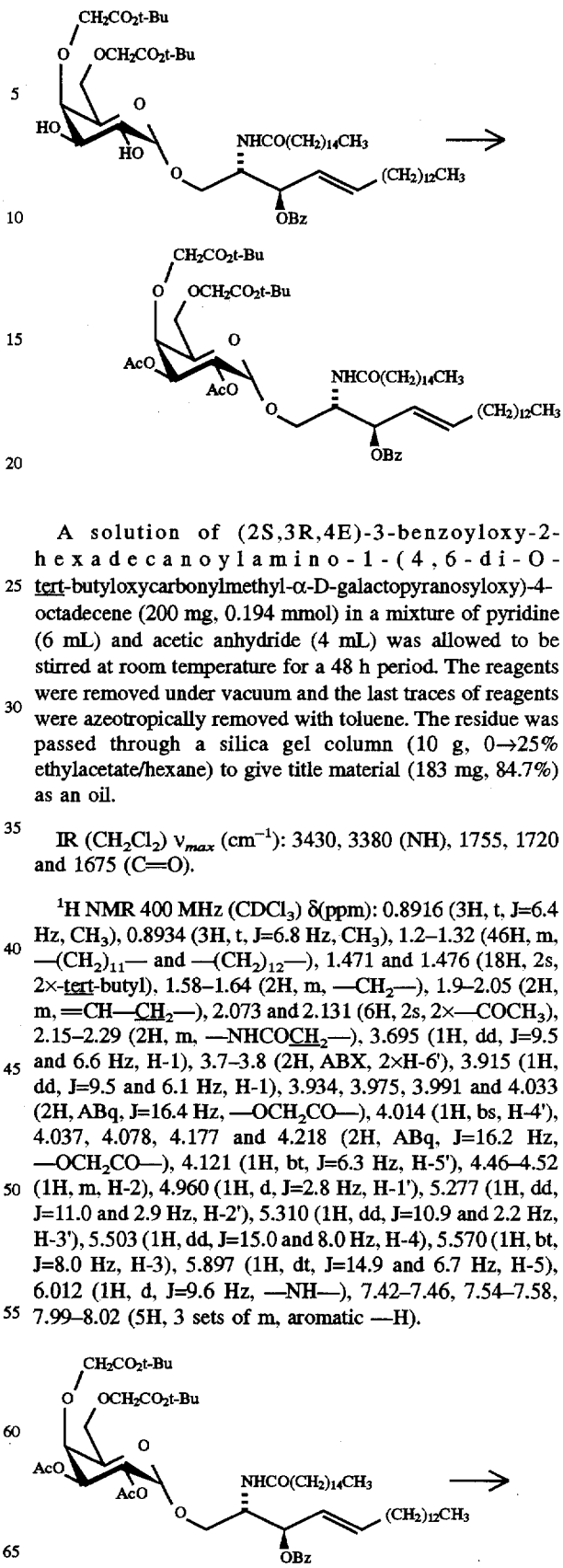

A solution of (2S,3R,4E)-3-benzoyloxy-2-hexadecanoylamino-1-(4,6-di-O-tert-butyloxycarbonylmethyl-α-D-galactopyranosyloxy)-4-octadecene (200 mg, 0.194 mmol) in a mixture of pyridine (6 mL) and acetic anhydride (4 mL) was allowed to be stirred at room temperature for a 48 h period. The reagents were removed under vacuum and the last traces of reagents were azeotropically removed with toluene. The residue was passed through a silica gel column (10 g, 0→25% ethylacetate/hexane) to give title material (183 mg, 84.7%) as an oil.

IR (CH$_2$Cl$_2$) ν$_{max}$ (cm$^{-1}$): 3430, 3380 (NH), 1755, 1720 and 1675 (C=O).

$^1$H NMR 400 MHz (CDCl$_3$) δ(ppm): 0.8916 (3H, t, J=6.4 Hz, CH$_3$), 0.8934 (3H, t, J=6.8 Hz, CH$_3$), 1.2–1.32 (46H, m, —(CH$_2$)$_{11}$— and —(CH$_2$)$_{12}$—), 1.471 and 1.476 (18H, 2s, 2×-tert-butyl), 1.58–1.64 (2H, m, —CH$_2$—), 1.9–2.05 (2H, m, =CH—CH$_2$—), 2.073 and 2.131 (6H, 2s, 2×—COCH$_3$), 2.15–2.29 (2H, m, —NHCOCH$_2$—), 3.695 (1H, dd, J=9.5 and 6.6 Hz, H-1), 3.7–3.8 (2H, ABX, 2×H-6'), 3.915 (1H, dd, J=9.5 and 6.1 Hz, H-1), 3.934, 3.975, 3.991 and 4.033 (2H, ABq, J=16.4 Hz, —OCH$_2$CO—), 4.014 (1H, bs, H-4'), 4.037, 4.078, 4.177 and 4.218 (2H, ABq, J=16.2 Hz, —OCH$_2$CO—), 4.121 (1H, bt, J=6.3 Hz, H-5'), 4.46–4.52 (1H, m, H-2), 4.960 (1H, d, J=2.8 Hz, H-1'), 5.277 (1H, dd, J=11.0 and 2.9 Hz, H-2'), 5.310 (1H, dd, J=10.9 and 2.2 Hz, H-3'), 5.503 (1H, dd, J=15.0 and 8.0 Hz, H-4), 5.570 (1H, bt, J=8.0 Hz, H-3), 5.897 (1H, dt, J=14.9 and 6.7 Hz, H-5), 6.012 (1H, d, J=9.6 Hz, —NH—), 7.42–7.46, 7.54–7.58, 7.99–8.02 (5H, 3 sets of m, aromatic —H).

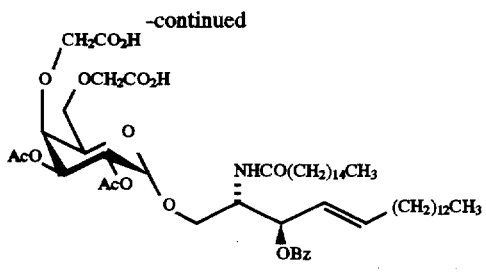

A solution of (2S,3R,4E)-3-benzoyloxy-2-hexadecanoylamino-1-(2,3-di-O-acetyl-4,6-di-O-tert-butyloxycarbonylmethyl-α-D-galactopyranosyloxy)-4-octadecene (172 mg, 0.150 mmol) was reacted according to the general procedure described in Example 2 and gave the diacid (128 mg, 85%) as a white solid.

IR (Nujol) $v_{max}$ (cm$^{-1}$): 3320 (NH), 1740, 1725 and 1680 (C=O).

$^1$H NMR 400 MHz (pyridine-d$_5$) δ(ppm): 0.856 (6H, t, J=6.8 Hz, 2×—CH$_3$), 1.2–1.4 (46H, m, —(CH$_2$)$_{11}$— and —(CH$_2$)$_{12}$—), 1.80–1.92 (2H, m, —CH$_2$—), 2.03–2.08 (2H, m, =CH—C$\underline{H}_2$—), 2.124 and 2.140 (6H, 2s, 2×—COCH$_3$), 2.40–2.55 (2H, m, —NHCOC$\underline{H}_2$—), 4.086 (1H, dd, J=10.8 and 5.8 Hz, H-1), 4.223 (1H, dd, J=9.3 and 6.8 Hz, H-6'), 4.334 (1H, dd, J=10.8 and 3.4 Hz, H-1), 4.447, 4.488, 4.504 and 4.545 (2H, ABq, J=16.4 Hz, —OCH$_2$CO—), 4.44–4.54 (1H, m, hidden H-6'), 4.545 (1H, bs, H-4'), 4.627 (1H, bt, J=6.3 Hz, H-5'), 4.666, 4.707, 4.732 and 4.773 (2H, ABq, J=16.2 Hz, —OCH$_2$CO—), 5.12–5.18 (1H, m, H-2), 5.546 (1H, d, J=2.4 Hz, H-1'), 5.830 and 5.862 (2H, part of AB, J=12.7 Hz, H-2' and H-3'), 5.917 (1H, dd, J=15.4 and 7.3 Hz, H-4), 6.094 (1H, dt, J=15.3 and 6.6 Hz, H-5), 6.208 (1H, bt, J=7.1 Hz, H-3), 7.38–7.51, 8.19–8.21 (5H, 3 sets of m, aromatic —H) and 8.884 (1H, d, J=8.9 Hz, —NH—).

Preparation of sodium salt of title compound

The diacid from the above procedure (122 mg, 0.121 mmol) was reacted by the general procedure as described in Example 2 to afford the sodium salt of the title compound (126 mg, 99%) as a white solid.

IR (Nujol) $v_{max}$ (cm$^{-1}$): 3300 (NH), 1740, 1645 and 1605 (C=O).

$^1$H NMR 400 MHz (Cd$_3$OD) δ(ppm): 0.888 (3H, t, J=6.8 Hz, 2×—CH$_3$), 1.2–1.4 (46H, m, —(CH$_2$)$_{11}$— and —(CH$_2$)$_{12}$—), 1.55–1.65 (2H, m, —CH$_2$—), 2.00 (3H, s, —COCH$_3$), 2.03–2.1 (2H, m, =CH—C$\underline{H}_2$—), 2.100 (3H, s, —COCH$_3$), 2.16–2.22 (2H, m, —NHCOC$\underline{H}_2$—), 3.626 (1H, dd, J=10.2 and 4.1 Hz, H-1), 3.75–3.82 (4H, m, H-5', H-4' and —OCH$_2$CO—), 3.92–3.97 (2H, m, H-6' and H-1), 4.069 (2H, bs, —OCH$_2$CO—), 4.220 (1H, bd, J=14.2 Hz, H-6'), 4.46 (1H, m, H-2), 5.078 (1H, bs, H-1'), 5.273 (1H, bd, J=10.7 Hz, H-3' or 2'), 5.345 (1H, bd, J=10.7 Hz, H-2' or 3'), 5.513 (1H, dd, J=14.8 and 8.1 Hz, H-4), 5.575 (1H, bt, J=7.8 Hz, H-3), 5.920 (1H, dt, J=14.8 and 6.5 Hz, H-5), 7.44–7.48, 7.57–7.61 and 7.84–8.01 (5H, 3 sets of m, aromatic —H).

EXAMPLE 35

(2S,3R,4E)-3-Benzoyloxy-2-hexadecanoylamino-1-(4,6-di-O-carboxymethyl-α-D-galactopyranosyloxy)-4-octadecene

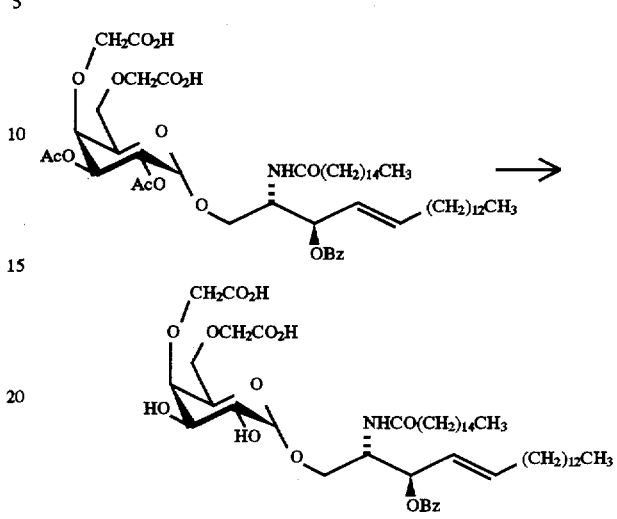

A cold (−78° C.) solution of (2S,3R,4E)-3-benzoyloxy-2-hexadecanoylamino-1-[2,3-di-O-acetyl-4,6-di-O-(sodium carboxylatomethyl)-α-D-galactopyranosyloxy)-4-octadecene (210 mg, 0.206 mmol) in methanol (10 mL) dichloromethane (10 mL) was treated with excess sodium methoxide (1 mmol) in methanol (1 mL). The mixture was allowed to warm up between −30° and −25° C. and stirring was continued until the reaction was complete as monitored by TLC. The mixture was acidified at −50° C. with 50W ion exchange resin. The resin was removed by filtration and the solution was immediately treated with pyridine. The solvent was evaporated and the residue (180 mg) was purified on preparative TLC (CHCl$_3$/MeOH/H$_2$O; 78/20/2) to give the diacid (161 mg, 85%) as a white fluffy solid.

IR (Nujol) $v_{max}$ (cm$^{-1}$): 3450, 3300 (OH and NH), 1720 and 1640 (C=O).

$^1$H NMR 400 MHz (pyridine-d$_5$) δ(ppm): 0.855 (6H t, J=6.8 Hz, 2×—CH$_3$), 1.23–1.46 (46H, m, —(CH$_2$)$_{11}$ and (CH$_2$)$_{10}$—), 1.78–1.92 (2H, m, —CH$_2$—), 2.03–2.12 (2H, m, =CH—C$\underline{H}_2$—), 2.472 (2H, t, J=7.4 Hz, —NHCOC$\underline{H}_2$—), 4.137 (1H, dd, J=10.7 and 6.6 Hz, H-1), 4.232 (1H, dd, J=9.4 and 6.3 Hz, H-6'), 4.319 (1H, d, J=2.9 Hz, H-4'), 4.390 (1H, dd, J=10.7 and 4.3 Hz, H-1), 4.476 (1H, dd, J=9.4 and 2.9 Hz, H-6'), 4.47–4.50 (1H, m, hidden H-3'), 4.489, 4.530, 4.556, 4.598, (2H, ABq, J=16.5 Hz, —OCH$_2$CO—), 4.609 (1H, dd, J=10.2 and 3.7 Hz, H-2'), 4.885, 4.928, 4.984 and 5.027 (2H, ABq, J=17.1 Hz, —OCH$_2$CO—), 5.15–5.22 (1H, m, H-2), 5.358 (1H, d, J=3.6 Hz, H-1'), 5.970 (1H, dd, J=15.5 and 7.1 Hz, H-4), 6.123 (1H, dt, J=15.3 and 6.5 Hz, H-5), 6.332 (1H, t, J=6.4 Hz, H-3), 7.39–7.49, 8.22–8.25 (5H, 3 sets of m, aromatic —H) and 8.789 (1H, d, J=8.7 Hz, —NH—).

Preparation of sodium salt of title compound

The diacid from the above procedure was reacted by the general procedure as described in Example 14 to afford the sodium salt of the title compound (159 mg, 94%).

IR (Nujol) $v_{max}$ (cm$^{-1}$): 3500–3200 (OH and NH), 1710, 1640 and 1600 (C=O).

$^1$H NMR 400 MHz (CD$_3$OD) δ(ppm): 0.888 (6H, t, J=6.8 Hz, —CH$_3$), 1.25–1.40 (46H, m, —(CH$_2$)$_{11}$— and —(CH$_2$)$_{12}$—), 1.56–1.70 (2H, m, —CH$_2$—), 2.03–2.10 (2H, m, =CH—CH₂—), 2.19–2.23 (2H, m, —NHCOCH₂—), 3.640 (1H, dd, J=10.8 and 5.2 Hz, H-1), 3.6–3.7 (1H, m, hidden H-6'), 3.77 (2H, bs, —OCH₂CO—), 3.7–3.85 (4H, m, H-4', H-6', H-3'), 3.88–3.92 (1H, m, H-1), 3.91 (2H, bs, —OCH₂CO—), 4.036 (1H, bs, H-5'), 4.151 (1H, bd, J=6.3 Hz, H-2'), 4.41–4.45 (1H, m, H-2), 4.747 (1H, bs, H-1'), 5.534 (1H, dd, J=15.2 and 7.8 Hz, H-4), 5.634 (1H, t, J=7.4 Hz, H-3), 5.901 (1H, dt, J=15.2 and 6.7 Hz, H-5), 7.45–7.48, 7.57–7.61 and 8.00–8.028 (5H, 3 sets of m, aromatic —H).

EXAMPLE 36

(2S,3R,4E)-2-Hexadecanoylamino-3-hydroxy-1-[(4,6-di-O-carboxymethyl)-β-D-galactopyranosyloxy]-4-octadecene

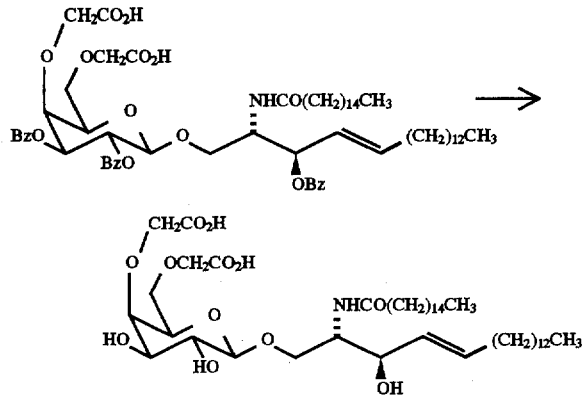

(2S,3R,4E)-3-Benzoyloxy-2-hexadecanoylamino-1-{2,3-di-O-benzoyl-4,6-di-O-carboxymethyl-α-D-galactopyranosyloxy}-4-octadecene described in Example 16 (0.50 g, 0.443 mmol) was reacted by the general procedure as described in Example 33 and gave the title material (0.336 g, 93%).

Preparation of the diacid of the title compound

IR (film) $v_{max}$ (cm⁻¹): 3600–3000 (OH and NH), 2920, 2850 (C—H), 1760, 1735 and 1630 (C=O).

¹H NMR 400 MHz (Pyridine-d₅) δ(ppm): 0.85 (6H, m, 2×—CH₃), 1.25–1.36 (46H, —(CH₂)₁₂— and —(CH₂)₁₁—), 1.81 (2H, m, —CH₂—), 2.05 (2H, qa, J=6.9 Hz, =CH—CH₂—), 2.41 (2H, m, —NHCOCH₂—), 4.11–4.4.24, 4.42–4.48 and 4.77–4.82 (9H, 3 sets of m, H-1', H-2, H-3, H-6', H-1, H-2' and H-3'), 4.32 (1H, d, J=3.1 Hz, H-4'), 4.47 (1H, d, J$_{AB}$=16.5 Hz, —OCH₂CO—), 4.53 (1H, d, J$_{AB}$=16.5 Hz, —OCH₂CO—), 4.73 (1H, t, J=6.4 Hz, H-5'), 4.93 (1H, d, J$_{AB}$=17.1 Hz, —OCH₂CO—), 5.01 (1H, d, J$_{AB}$=17.1 Hz, —OCH₂CO—), 5.87 (1H, dt, J=15.4 and 6.6 Hz, H-5), 5.99 (1H, dd, J=15.4 and 6.7 Hz, H-4), 8.29 (1H, d, J=8.0 Hz, —NH—).

Preparation of the sodium salt of the title compound

IR (film) $v_{max}$ (cm⁻¹): 3400 (OH and NH), 2920, 2850 (C—H), 1620 (C=O).

¹H NMR 400 MHz (CD₃OD) δ(ppm): 0.89 (6H, t, J=6.8 Hz, 2×—CH₃), 1.28–1.37 (46H, m, —(CH₂)₁₂— and —(CH₂)₁₁—), 1.57 (2H, m, —CH₂—), 2.01 (2H, m, qa, =CH—CH₂—), 2.16 (2H, t, J=7.5 Hz, —NHCOCH₂—), 3.46 (1H, dd, J=9.7 and 3.3 Hz, H-1), 3.54–3.59, 3.68–3.70, 3.76–3.79 (6H, 3 sets of m, H-1, H-6', H-4', H-2' and H-3'), 3.89 (1H, d, J=16.4 Hz, —OCH₂CO—), 3.90 (2H, br d, —OCH₂CO—), 3.92–3.96 (1H, m, H-3), 4.07 (1H, t, J=8.1 Hz, H-5'), 4.16 (1H, d, J=16.4 Hz, —OCH₂CO—), 4.16–4.19 (1H, m, H-2), 4.22 (1H, J=7.7 Hz, H-1'), 4.43 (1H, dd, J=15.3 and 7.7 Hz, H-4), 5.67 (1H, dt, J=15.4 and 6.8 Hz, H-5).

What is claimed is:

1. A compound of the formula

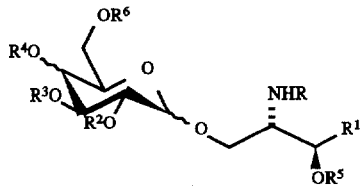

wherein

R is an acyl residue of a fatty acid;

R¹ is —(CH=CH)$_m$—(CH₂)$_n$—CH₃;

R², R³, R⁴ R⁵ and R⁶ each are independently hydrogen, unsubstituted or substituted alkanoyl, arylalkyl or arylcarbonyl wherein said substituent is selected from the group consisting of halogen, C$_{1-4}$ alkyl, trifluoromethyl, hydroxy and C$_{1-4}$ alkoxy, provided at least two of the R³, R⁴, and R⁶ substituent5 are —CH₂COOR⁷;

m is an integer of 0 or 1;

n is an integer of from 5 to 14, inclusive; and

R⁷ is hydrogen, a hydrolyzable ester group or a cation to form a non-toxic pharmaceutically acceptable salt;

or a solvate or hydrate thereof.

2. A compound of claim 1 having the formula

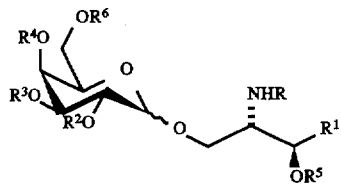

wherein

R is an acyl residue of a fatty acid;

R¹ is —(CH=CH)$_m$—(CH₂)$_n$—CH₃;

R², R³, R⁴ R⁵ and R⁶ each are independently hydrogen, unsubstituted or substituted alkanoyl, arylalkyl or arylcarbonyl wherein said substituent is selected from the group consisting of halogen, C$_{1-4}$ alkyl, trifluoromethyl, hydroxy and C$_{1-4}$ alkoxy, provided at least two of the R³, R⁴, and R⁶ substituents are —CH₂COOR⁷;

m is an integer of 0 or 1;

n is an integer of from 5 to 14, inclusive; and

R⁷ is hydrogen, a hydrolyzable ester group or a cation to form a non-toxic pharmaceutically acceptable salt;

or a solvate or hydrate thereof.

3. A compound of claim 1 having the formula

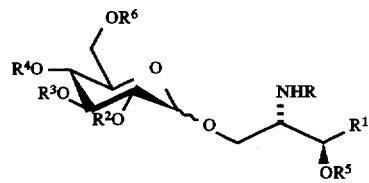

wherein

R is an acyl residue of a fatty acid;

R¹ is —(CH=CH)$_m$—(CH₂)$_n$—CH₃;

$R^2$, $R^3$, $R^4$ $R^5$ and $R^6$ each are independently hydrogen, unsubstituted or substituted alkanoyl, arylalkyl or arylcarbonyl wherein said substituent is selected from the group consisting of halogen, $C_{1-4}$ alkyl, trifluoromethyl, hydroxy and $C_{1-4}$ alkoxy, provided at least two of the $R^3$, $R^4$, and $R^6$ substituents are —$CH_2COOR^7$;

m is an integer of 0 or 1;

n is an integer of from 5 to 14, inclusive; and $R^7$ is hydrogen, a hydrolyzable ester group or a cation to form a non-toxic pharmaceutically acceptable salt;

or a solvate or hydrate thereof.

4. A compound of claim 2 having the formula

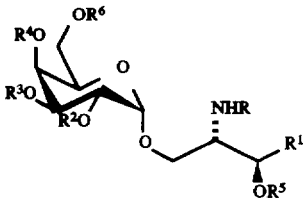

wherein

R is an acyl residue of a fatty acid;

$R^1$ is —$(CH=CH)_m$—$(CH_2)_n$—$CH_3$;

$R^2$, $R^3$, $R^4$ $R^5$ and $R^6$ each are independently hydrogen, unsubstituted or substituted alkanoyl, arylalkyl or arylcarbonyl wherein said substituent is selected from the group consisting of halogen, $C_{1-4}$ alkyl, trifluoromethyl, hydroxy and $C_{1-4}$ alkoxy, provided at least two of the $R^3$, $R^4$, and $R^6$ substituents are —$CH_2COOR^7$;

m is an integer of 0 or 1;

n is an integer of from 5 to 14, inclusive; and $R^7$ is hydrogen, a hydrolyzable ester group or a cation to form a non-toxic pharmaceutically acceptable salt;

or a solvate or hydrate thereof.

5. A compound of claim 2 having the formula

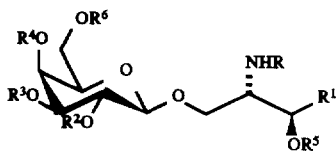

wherein

R is an acyl residue of a fatty acid;

$R^1$ is —$(CH=CH)_m$—$(CH_2)_n$—$CH_3$;

$R^2$, $R^3$, $R^4$ $R^5$ and $R^6$ each are independently hydrogen, unsubstituted or substituted alkanoyl, arylalkyl or arylcarbonyl wherein said substituent is selected from the group consisting of halogen, $C_{1-4}$ alkyl, trifluoromethyl, hydroxy and $C_{1-4}$ alkoxy, provided at least two of the $R^3$, $R^4$, and $R^6$ substituents are —$CH_2COOR^7$;

m is an integer of 0 or 1;

n is an integer of from 5 to 14, inclusive; and $R^7$ is hydrogen, a hydrolyzable ester group or a cation to form a non-toxic pharmaceutically acceptable salt;

or a solvate or hydrate thereof.

6. A compound of claim 1 wherein $R^4$ and $R^6$ are —$CH_2COOR^7$ and $R^2$, $R^3$ and $R^5$ each are independently hydrogen, unsubstituted or substituted alkanoyl, arylalkyl or arylcarbonyl wherein said substituent is selected from the group consisting of halogen, $C_{1-4}$ alkyl, trifluoromethyl, hydroxy and $C_{1-4}$ alkoxy; $R^7$ is hydrogen, a hydrolyzable ester group or a cation to form a non-toxic pharmaceutically acceptable salt; or a solvate or hydrate thereof.

7. A compound of claim 1 wherein $R^3$ and $R^6$ are —$CH_2COOR^7$ and $R^2$, $R^4$ and $R^5$ each are independently hydrogen, unsubstituted or substituted alkanoyl, arylalkyl or arylcarbonyl wherein said substituent is selected from the group consisting of halogen, $C_{1-4}$ alkyl, trifluoromethyl, hydroxy and $C_{1-4}$ alkoxy; $R^7$ is hydrogen, a hydrolyzable ester group or a cation to form a non-toxic pharmaceutically acceptable salt; or a solvate or hydrate thereof.

8. A compound of claim 1 wherein $R^3$ and $R^4$ are —$CH_2COOR^7$ and $R^2$, $R^5$ and $R^6$ each are independently hydrogen, unsubstituted or substituted alkanoyl, arylalkyl or arylcarbonyl wherein said substituent is selected from the group consisting of halogen, $C_{1-4}$ alkyl, trifluoromethyl, hydroxy and $C_{1-4}$ alkoxy; $R^7$ is hydrogen, a hydrolyzable ester group or a cation to form a non-toxic pharmaceutically acceptable salt; or a solvate or hydrate thereof.

9. A compound of claim 4 wherein $R^4$ and $R^6$ are —$CH_2COOR^7$ and $R^2$, $R^3$ and $R^5$ each are independently hydrogen or benzoyl.

10. A compound of claim 4 wherein $R^3$ and $R^6$ are —$CH_2COOR^7$ and $R^2$, $R^4$ and $R^5$ each are independently hydrogen or benzoyl.

11. A compound of claim 4 wherein $R^3$ and $R^4$ are —$CH_2COOR^7$ and $R^2$, $R^5$ and $R^6$ each are independently hydrogen or benzoyl.

12. A compound of claim 5 wherein $R^4$ and $R^6$ are —$CH_2COOR^7$ and $R^2$, $R^3$ and $R^5$ each are independently hydrogen or benzoyl.

13. A compound of claim 5 wherein $R^3$ and $R^6$ are —$CH_2COOR^7$ and $R^2$, $R^4$ and $R^5$ each are independently hydrogen or benzoyl.

14. A compound of claim 5 wherein $R^3$ and $R^4$ are —$CH_2COOR^7$ and $R^2$, $R^5$ and $R^6$ each are independently hydrogen or benzoyl.

15. A compound of claim 1 wherein R is the acyl residue of palmitic acid, lignoceric acid, nervonic acid or stearic acid; $R^7$ is hydrogen or a cation to form a non-toxic pharmaceutically acceptable salt; or a solvate or hydrate thereof.

16. A compound of claim 2 wherein R is the acyl residue of palmitic acid, lignoceric acid, nervonic acid or stearic acid; $R^7$ is hydrogen or a cation to form a non-toxic pharmaceutically acceptable salt; or a solvate or hydrate thereof.

17. A compound of claim 9 wherein R is the acyl residue of palmitic acid, lignoceric acid, nervonic acid or stearic acid; $R^7$ is hydrogen or a cation to form a non-toxic pharmaceutically acceptable salt; or a solvate or hydrate thereof.

18. A compound of claim 10 wherein R is the acyl residue of palmitic acid, lignoceric acid, nervonic acid or stearic acid; $R^7$ is hydrogen or a cation to form a non-toxic pharmaceutically acceptable salt; or a solvate or hydrate thereof.

19. A compound of claim 11 wherein R is the acyl residue of palmitic acid, lignoceric acid, nervonic acid or stearic acid; $R^7$ is hydrogen or a cation to form a non-toxic pharmaceutically acceptable salt; or a solvate or hydrate thereof.

20. A compound of claim 12 wherein R is the acyl residue of palmitic acid, lignoceric acid, nervonic acid or stearic acid; $R^7$ is hydrogen or a cation to form a non-toxic pharmaceutically acceptable salt; or a solvate or hydrate thereof.

21. A compound of claim 13 wherein R is the acyl residue of palmitic acid, lignoceric acid, nervonic acid or stearic acid; $R^7$ is hydrogen or a cation to form a non-toxic pharmaceutically acceptable salt; or a solvate or hydrate thereof.

22. A compound of claim 14 wherein R is the acyl residue of palmitic acid, lignoceric acid, nervonic acid or stearic acid; $R^7$ is hydrogen or a cation to form a non-toxic pharmaceutically acceptable salt; or a solvate or hydrate thereof.

23. A compound of claim 1 wherein m is 1 and n is 12.

24. A compound of claim 9 wherein m is 1 and n is 12.

25. A compound of claim 12 wherein m is 1 and n is 12.

26. A compound of claim 16 wherein R is the acyl residue of nervonic acid.

27. A compound of claim 17 wherein R is the acyl residue of nervonic acid.

28. A compound of claim 20 wherein R is the acyl residue of nervonic acid.

29. A compound of claim 17 wherein said cation is sodium.

30. A compound of claim 20 wherein said cation is sodium.

31. The compound of claim 1 which is (2S,3R,4E)-3-benzoyloxy-2-hexadecanoylamino-1-[2,3-di-O-benzoyl-4,6-di-O-carboxymethyl-α-D-galactopyranosyloxy]-4-octadecene, or a non-toxic pharmaceutically acceptable salt, solvate or hydrate thereof.

32. The compound of claim 1 which is (2S,3R,4E)-2-hexadecanoylamino-3-benzoyloxy-1-(4,6-di-O-carboxymethyl-2,3-di-O-benzyl-α-D-galactopyranosyloxy)-4-octadecene, or a non-toxic pharmaceutically acceptable salt, solvate or hydrate thereof.

33. The compound of claim 1 which is (2S,3R,4E)-3-benzoyloxy-2-(9-methoxycarbonyl-nonanoylamino)-1-(2,3-di-O-benzoyl-4,6-di-O-carboxymethyl-α-D-galactopyranosyloxy)-4-undecene, or a non-toxic pharmaceutically acceptable salt, solvate or hydrate thereof.

34. The compound of claim 1 which is (2S,3R,4E)-2-hexadecanoyl-amino-3-benzoyloxy-1-[3,4-di-O-carboxymethyl-2,6-di-O-benzoyl-α-D-galactopyranosyloxy]-4-octadecene, or a non-toxic pharmaceutically acceptable salt, solvate or hydrate thereof.

35. The compound of claim 1 which is (2S,3R,4E)-3-benzoyloxy-2-hexadecanoylamino-1-[2-O-benzoyl-4,6-di-O-carboxymethyl-α-D-galactopyranosyloxy]-4-octadecene, or a non-toxic pharmaceutically acceptable salt, solvate or hydrate thereof.

36. The compound of claim 1 which is (2S,3R,4E)-3-benzoyloxy-2-hexadecanoylamino-1-[3-O-benzoyl-4,6-di-O-carboxymethyl-β-D-galactopyranosyloxy]-4-octadecene, or a non-toxic pharmaceutically acceptable salt, solvate or hydrate thereof.

37. The compound of claim 1 which is (2S,3R,4E)-3-benzoyloxy-2-hexadecanoylamino-1-(3-O-benzoyl-4,6-di-O-carboxymethyl-α-D-galactopyranosyloxy)-4-octadecene, or a non-toxic pharmaceutically acceptable salt, solvate or hydrate thereof.

38. A pharmaceutical composition comprising an amount of a compound as defined in claim 1 sufficient to inhibit selectin-mediated cellular adhesion, in association with a pharmaceutically acceptable carrier or diluent.

39. A pharmaceutical composition comprising an amount of a compound as defined in claim 4 sufficient to inhibit selectin-mediated cellular adhesion, in association with a pharmaceutically acceptable carrier or diluent.

40. A pharmaceutical composition comprising an amount of a compound as defined in claim 9 sufficient to inhibit selectin-mediated cellular adhesion, in association with a pharmaceutically acceptable carrier or diluent.

41. A method for the treatment of inflammatory diseases in a mammal in need thereof, which comprises administering to said mammal a therapeutically effective amount of a compound as defined in claim 1 or a pharmaceutical composition thereof.

42. A method for the treatment of inflammatory diseases in a mammal in need thereof, which comprises administering to said mammal a therapeutically effective amount of a compound as defined in claim 2 or a pharmaceutical composition thereof.

43. A method for the treatment of inflammatory diseases in a mammal in need thereof, which comprises administering to said mammal a therapeutically effective amount of a compound as defined in claim 9 or a pharmaceutical composition thereof.

44. A method for the treatment of inflammatory diseases in a mammal in need thereof, which comprises administering to said mammal a therapeutically effective amount of a compound as defined in claim 12 or a pharmaceutical composition thereof.

45. A method for the treatment of inflammatory diseases in a mammal in need thereof, which comprises administering to said mammal a therapeutically effective amount of a compound as defined in claim 31 or a pharmaceutical composition thereof.

* * * * *